(12) United States Patent
Kasai et al.

(10) Patent No.: US 8,853,215 B2
(45) Date of Patent: Oct. 7, 2014

(54) DERIVATIVES OF N-ACYL-N'-PHENYLPIPERAZINE USEFUL (INTER ALIA) FOR THE PROPHYLAXIS OR TREATMENT OF DIABETES

(75) Inventors: Shizuo Kasai, Kanagawa (JP); Kevin Francis McGee, Jr., New York, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 18 days.

(21) Appl. No.: 13/264,510

(22) PCT Filed: Apr. 16, 2010

(86) PCT No.: PCT/JP2010/057201
§ 371 (c)(1),
(2), (4) Date: Nov. 18, 2011

(87) PCT Pub. No.: WO2010/119992
PCT Pub. Date: Oct. 21, 2010

(65) Prior Publication Data
US 2012/0071489 A1    Mar. 22, 2012

Related U.S. Application Data

(60) Provisional application No. 61/202,886, filed on Apr. 16, 2009.

(51) Int. Cl.
*A61K 31/495* (2006.01)
*C07D 295/00* (2006.01)
*C07D 207/416* (2006.01)
*C07D 335/02* (2006.01)
*C07D 231/18* (2006.01)
*C07D 295/215* (2006.01)
*C07D 261/18* (2006.01)
*C07D 209/24* (2006.01)
*C07D 209/18* (2006.01)
*C07D 295/185* (2006.01)
*C07D 213/75* (2006.01)
(Continued)

(52) U.S. Cl.
CPC ........ *C07D 295/185* (2013.01); *C07D 207/416* (2013.01); *C07D 335/02* (2013.01); *C07D 231/18* (2013.01); *C07D 295/215* (2013.01); *C07D 261/18* (2013.01); *C07D 209/24* (2013.01); *C07D 209/18* (2013.01); *C07D 213/75* (2013.01); *C07D 211/88* (2013.01); *C07D 263/34* (2013.01); *C07D 513/04* (2013.01); *C07D 213/70* (2013.01); *C07D 213/65* (2013.01); *C07D 235/28* (2013.01); *C07D 233/72* (2013.01); *C07D 233/64* (2013.01); *C07D 307/24* (2013.01); *C07D 211/76* (2013.01); *C07D 231/14* (2013.01); *C07D 211/58* (2013.01); *C07D 233/90* (2013.01); *C07D 257/04* (2013.01); *C07D 211/46* (2013.01); *C07D 213/61* (2013.01); *C07D 261/12* (2013.01); *C07D 209/42* (2013.01); *C07D 207/16* (2013.01); *C07D 211/22* (2013.01); *C07D 307/30* (2013.01); *C07D 233/34* (2013.01); *C07D 309/38* (2013.01); *C07D 249/10* (2013.01); *C07D 211/34* (2013.01); *C07D 213/81* (2013.01); *C07D 207/26* (2013.01)
USPC ...................................... 514/252.13; 544/391

(58) Field of Classification Search
CPC ..................................................... C07D 241/04
USPC ................. 514/252.12, 252.13; 544/391, 374
See application file for complete search history.

(56) References Cited

U.S. PATENT DOCUMENTS 2,922,788 A * 1/1960 Parcell ......................... 544/394
2002/0147198 A1   10/2002 Chen et al.
(Continued)

FOREIGN PATENT DOCUMENTS

CN           1717390         1/2006
CN         101048405         10/2007
(Continued)

OTHER PUBLICATIONS

Testa, B. "Prodrug research: futile or fertile?" Biochem. Pharm. vol. 68 (2004), pp. 2097-2106.*

(Continued)

*Primary Examiner* — Andrew D Kosar
*Assistant Examiner* — John S Kenyon
(74) *Attorney, Agent, or Firm* — Wenderoth, Lind & Ponack, L.L.P.

(57) ABSTRACT

The present invention relates to a compound represented by the formula wherein each symbol is as defined in the present specification, which has a superior RBP4-lowering action and is useful as a pharmaceutical composition for the prophylaxis or treatment of a disease or condition mediated by an increase in RBP4.

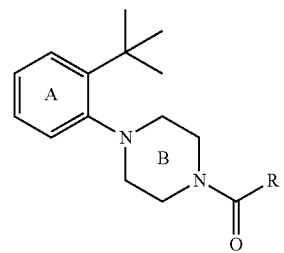

8 Claims, No Drawings

(51) Int. Cl.

| | | |
|---|---|---|
| *C07D 211/88* | (2006.01) |
| *C07D 263/34* | (2006.01) |
| *C07D 513/04* | (2006.01) |
| *C07D 213/70* | (2006.01) |
| *C07D 213/65* | (2006.01) |
| *C07D 235/28* | (2006.01) |
| *C07D 233/72* | (2006.01) |
| *C07D 233/64* | (2006.01) |
| *C07D 307/24* | (2006.01) |
| *C07D 211/76* | (2006.01) |
| *C07D 231/14* | (2006.01) |
| *C07D 211/58* | (2006.01) |
| *C07D 233/90* | (2006.01) |
| *C07D 257/04* | (2006.01) |
| *C07D 211/46* | (2006.01) |
| *C07D 213/61* | (2006.01) |
| *C07D 261/12* | (2006.01) |
| *C07D 209/42* | (2006.01) |
| *C07D 207/16* | (2006.01) |
| *C07D 211/22* | (2006.01) |
| *C07D 307/30* | (2006.01) |
| *C07D 233/34* | (2006.01) |
| *C07D 309/38* | (2006.01) |
| *C07D 249/10* | (2006.01) |
| *C07D 211/34* | (2006.01) |
| *C07D 213/81* | (2006.01) |
| *C07D 207/26* | (2006.01) |

(56) References Cited

U.S. PATENT DOCUMENTS

| | | |
|---|---|---|
| 2003/0125339 A1 | 7/2003 | Chen et al. |
| 2003/0134836 A1 | 7/2003 | Elbaum et al. |
| 2003/0195230 A1 | 10/2003 | Chen et al. |
| 2003/0225106 A1 | 12/2003 | Askew et al. |
| 2004/0087568 A1 | 5/2004 | Huang et al. |
| 2004/0180880 A1 | 9/2004 | Lauffer et al. |
| 2004/0204437 A1 | 10/2004 | Elbaum et al. |
| 2005/0153960 A1 | 7/2005 | Elbaum et al. |
| 2005/0261313 A1 | 11/2005 | Askew et al. |
| 2006/0009456 A1 | 1/2006 | Hutchinson et al. |
| 2006/0040956 A1 | 2/2006 | Chen et al. |
| 2009/0270413 A1 | 10/2009 | Galemmo, Jr. et al. |
| 2010/0292206 A1 | 11/2010 | Kasai et al. |
| 2011/0251187 A1 | 10/2011 | Kasai et al. |
| 2012/0065185 A1 | 3/2012 | Chen et al. |
| 2013/0273004 A1 | 10/2013 | Chen et al. |

FOREIGN PATENT DOCUMENTS

| | | | |
|---|---|---|---|
| EP | 2 295 406 | | 3/2011 |
| GB | 794239 | * | 4/1958 |
| WO | 02/068406 | | 9/2002 |
| WO | 03/009850 | | 2/2003 |
| WO | 2004/005279 | | 1/2004 |
| WO | 2004/007481 | | 1/2004 |
| WO | 2009/042444 | | 4/2009 |
| WO | 2009/051244 | | 4/2009 |
| WO | 2009/145286 | | 12/2009 |

OTHER PUBLICATIONS

Han, Hyo-Kyung. "Targeted Prodrug Design to Optimize Drug Delivery." AAPS Pharmsci 2000; 2 (1) article 6, pp. 1-11.*

Ettmayer, P., et al. "Lessons Learned from Marketed and Investigational Prodrugs." J. Med. Chem. (May 6, 2004), vol. 47, No. 10, pp. 2393-2404.*

Kotnik, P., et al. "RBP4: a controversial adipokine." European Journal of Endocrinology. (2011), 165, pp. 703-711.*

WebMD. "Diabetes Health Center." Available at: < http://diabetes.webmd.com/guide/diabetes_treatment_care >.*

IUPAC Gold Book. "Acyl Groups." © 2007. < http://goldbook.iupac.org/A00123.html >.*

International Search Report issued Aug. 31, 2010 in International (PCT) Application No. PCT/JP2010/057201.

A. Motani et al., "Identification and Characterization of a Non-Retinoid Ligand for Retinol-Binding Protein 4 which Lowers Serum Retinol-Binding Protein 4 Levels in Vivo", The Journal of Biological Chemistry, vol. 284, No. 12, pp. 7673-7680, Mar. 20, 2009.

Chinese Office Action issued Jun. 19, 2013 in corresponding Chinese Patent Application No. 2010800325361.

* cited by examiner

SEQUENCE LISTING

```
<160> NUMBER OF SEQ ID NOS: 9

<210> SEQ ID NO 1
<211> LENGTH: 34
<212> TYPE: DNA
<213> ORGANISM: Artificial
<220> FEATURE:
<223> OTHER INFORMATION: PCR primer (RBPU)

<400> SEQUENCE: 1
atatggatcc accatgaagt gggtgtgggc gctc                             34

<210> SEQ ID NO 2
<211> LENGTH: 38
<212> TYPE: DNA
<213> ORGANISM: Artificial
<220> FEATURE:
<223> OTHER INFORMATION: PCR primer (RBPL)

<400> SEQUENCE: 2
atatgcggcc gcctacaaaa ggtttctttc tgatctgc                         38

<210> SEQ ID NO 3
<211> LENGTH: 35
<212> TYPE: DNA
<213> ORGANISM: Artificial
<220> FEATURE:
<223> OTHER INFORMATION: PCR primer (TTRU)

<400> SEQUENCE: 3
atatggatcc accatggctt ctcatcgtct gctcc                            35

<210> SEQ ID NO 4
```

```
<211> LENGTH: 35
<212> TYPE: DNA
<213> ORGANISM: Artificial
<220> FEATURE:
<223> OTHER INFORMATION: PCR primer (TTRL)

<400> SEQUENCE: 4
atatgcggcc gctcattcct tgggattggt gacga                              35

<210> SEQ ID NO 5
<211> LENGTH: 26
<212> TYPE: DNA
<213> ORGANISM: Artificial
<220> FEATURE:
<223> OTHER INFORMATION: PCR primer (CMVP)

<400> SEQUENCE: 5
tgggaggtct atataagcag agctcg                                        26

<210> SEQ ID NO 6
<211> LENGTH: 28
<212> TYPE: DNA
<213> ORGANISM: Artificial
<220> FEATURE:
<223> OTHER INFORMATION: PCR primer (RBPECO)

<400> SEQUENCE: 6
atatgaattc ttccttggga ttggtgac                                      28

<210> SEQ ID NO 7
<211> LENGTH: 30
<212> TYPE: DNA
<213> ORGANISM: Artificial
<220> FEATURE:
<223> OTHER INFORMATION: PCR primer (TTRECO)

<400> SEQUENCE: 7
atatgaattc caaaaggttt ctttctgatc                                    30

<210> SEQ ID NO 8
<211> LENGTH: 28
<212> TYPE: DNA
<213> ORGANISM: Artificial
<220> FEATURE:
<223> OTHER INFORMATION: oligonucleotide for preparation of synthetic
      gene fragment containing His tag sequence (HISENU)

<400> SEQUENCE: 8
aattccatca tcatcatcat cactaggc                                      28

<210> SEQ ID NO 9
<211> LENGTH: 28
<212> TYPE: DNA
<213> ORGANISM: Artificial
<220> FEATURE:
<223> OTHER INFORMATION: oligonucleotide for preparation of synthetic
      gene fragment containing His tag sequence (HISENL)

<400> SEQUENCE: 9
ggccgcctag tgatgatgat gatgatgg                                      28
```

DERIVATIVES OF N-ACYL-N'-PHENYLPIPERAZINE USEFUL (INTER ALIA) FOR THE PROPHYLAXIS OR TREATMENT OF DIABETES

This application is a U.S. national stage of International Application No. PCT/JP2010/057201 filed Apr. 16, 2010, which claims the benefit of U.S. provisional application Ser. No. 61/202,886 filed Apr. 16, 2009.

TECHNICAL FIELD

The present invention relates to a novel heterocyclic compound useful as a pharmaceutical agent for the prophylaxis or treatment of diabetes, age-related macular degeneration and the like, and the like.

BACKGROUND OF THE INVENTION

Retinol binding protein 4 (hereinafter sometimes to be abbreviated as "RBP4") is known to be a sole blood retinol transport protein mainly produced in the liver. In recent years, moreover, RBP4 is suggested to be an insulin resistance-inducing factor from the following literatures and the like.
(1) Since RBP4 expression increases in the adipocytes of GLUT4 knockout mouse showing insulin resistance, RBP4 is suggested to be a potential adipocytokine inducing insulin resistance (see Nature 436, 356-362 (2005)).
(2) It has been reported that RBP4 overexpression mouse shows hyperglycemia and hyperinsulinemia, and RBP4 knockout mouse shows promotion of glucose tolerance and insulin sensitivity as phenotype (see Nature 436, 356-362 (2005)).
(3) It has been reported that mouse bred on a high-fat diet shows high blood RBP4 value, which is correlated with induction of insulin resistance (see Nature 436, 356-362 (2005)).
(4) It has been reported that disease model mouse showing diabetes and/or obesity pathology such as ob/ob mouse, 11β-HSD1 overexpression (adipose tissue specific) mouse, MC4R knockout mouse, GLUT4 knockout (adipose tissue•skeletal muscle specific) mouse and the like also shows high blood RBP4 value (see Nature 436, 356-362 (2005)).
(5) It has been reported that blood RBP4 concentration and insulin sensitivity and/or sugar disposal rate are inversely correlated in human. It has also been reported that the glucose infusion rate decreases as the blood RBP4 concentration increases in euglycemic hyperinsulinemic glucose clamp test (see Cell Metab., 6, 79-87 (2007)).
(6) While exercise is known to improve insulin sensitivity, an extremely high correlation between such an improving effect and lowering of blood RBP4 concentration has been reported recently (see N. Engl. J. Med., 354, 2552-2563 (2006)).
(7) WO2005-059564 describes that a compound that controls RBP4 activity is useful for the treatment of insulin resistance.

All these suggest that a compound capable of lowering blood RBP4 concentration can be a therapeutic drug for diabetes.

RBP4 is stably present in blood in the form of a complex resulting from the binding of retinol and TTR (transthyretin). When RBP4 is dissociated from TTR and becomes free, it is decomposed in and excreted from the kidney comparatively rapidly. It is unknown whether the binding of RBP4 and retinol is indeed essential for the formation of a complex with TTR. However, fenretinide, a retinol derivative, inhibits the binding of RBP4 and retinol, and consequently inhibits formation of a complex with TTR. It is known that administration of fenretinide to animal induces lowering of blood RBP4 (see Biochim. Biophys. Acta, 1294, 48-54 (1996)).

From the foregoing findings, a compound that inhibits formation of a complex of RBP4 and TTR by inhibiting the binding of RBP4 and retinol is expected to lower blood RBP4 concentration and consequently induce correction of hyperglycemia and improvement of insulin resistance.

In recent years, moreover, a report has documented that blood RBP4 value and blood TG (triglyceride) or LDL cholesterol value positively correlate in human, and blood RBP4 value negatively correlates with HDL cholesterol value (see J. Atheroscler. Thromb., 13, 209-215 (2006), N. Engl. J. Med., 355, 1392-1395 (2006), Diabetes, 56 (Supplement 1), A378 (1477-P) (2007)), thus suggesting relationship with lipid metabolism.

It has been reported the link between RBP4 and eye disease. For example, excess vitamin-A levels in target organs and tissues, such as the eye, may cause a variety of retinal diseases, including macular degeneration, and lowering RBP4 is effective to prevent or treat these eye diseases (see WO2009/042444).

Fenretinide is studied in patients with geographic atrophy (GA), the most advanced form of dry age-related macular degeneration (AMD). Fenretinide is suggested to halt the accumulation of retinol (vitamin A) toxin through affinity to RBP4. It is hypothesized that to slow the formation and accumulation of toxic byproducts, A2E (bis-retinoid pyridinium) for example, thought to be responsible for vision loss in condition such as GA. Sirion Therapeutics, Inc. has announced positive results from analysis of phase II trial evaluating fenretinide for the treatment of GA associated with AMD.

In view of the above, a pharmaceutical agent having an action to lower blood RBP4 value (concentration) (also referred to as "RBP4 lowering action" in the present specification) (also referred to as "RBP4 lowering agent" (agent for reducing RBP4) in the present specification) is expected to be widely applicable to lifestyle-related diseases.

WO02/068406 discloses that compounds such as a compound represented by the following formula has an inhibitory effect on VEGF and applications for preventing or treating of retinol-related diseases, cancer, diabetes and the like:

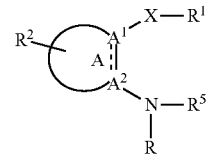

wherein $A^1$ and $A^2$ are each independently C, CH or N; ring A is a 5- or 6-membered partially saturated heterocycle, a 5- or 6-membered aromatic heterocycle and the like; X is

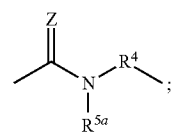

Z is O or S; R is an optionally substituted 4- to 6-membered heterocyclic group, a substituted aromatic ring group and the like; and $R^1$ is an optionally substituted 6- to 10-membered aromatic ring group, an optionally substituted 4- to 6-membered aromatic heterocyclic group and the like.

WO2004/007481 discloses that compounds such as a compound represented by the following formula has an inhibitory effect on VEGF and applications for preventing or treating of retinol-related diseases, cancer, diabetes and the like:

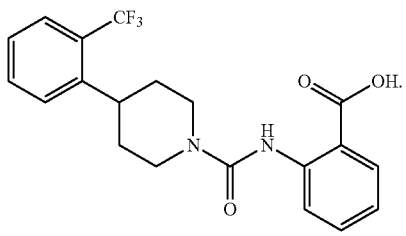

wherein R is an optionally substituted 6-indazolyl group, an optionally substituted 1-oxo-2,3-dihydro-1H-isoindol-4-yl group, an optionally substituted 2-oxo-2,3-dihydro-1H-benzimidazol-5-yl group or an optionally substituted 4-oxo-3,4-dihydroquinazolin-6-yl group; and $R^1$ is an optionally substituted aromatic ring group, optionally substituted 5- or 6-membered aromatic heterocyclic group and the like.

J. Biol. Chem., January 2009, vol. 284, p. 7673-7680 as Manuscript M809654200 discloses a compound represented by the following formula has a lowering effect on RBP4:

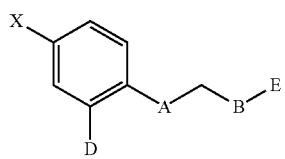

WO2009/042444 discloses that compounds such as a compound represented by the following formula has a lowering effect on RBP4 and applications for preventing or treating of retinol-related diseases, diabetes and the like:

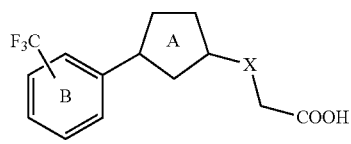

wherein A is O, NH, or S; B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, or —($C_3$-$C_8$)heterocycloalkenyl; D is isopropyl, isobutyl, sec-butyl, tert-butyl, neopentyl, sec-pentyl, isopentyl, cyclopropyl, cyclobutyl, cyclopentyl, methylenecyclopropyl, methylenecyclobutyl, or methylenecyclopentyl; E is (C=O)—OR, —O—(C=O)—R, —(C=O)—R, —OR, a carboxylic acid bioisostere, —(C=O)—$NR^1R$, (C=O)—R, —($C_1$-$C_7$)alkyl-(C=O)—OR, or —($C_1$-$C_7$)alkyl-(C=O)—$NR^1R$;

R is H or

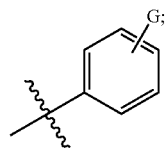

G is —$OR^1$, —($C_1$-$C_6$)alkyl, —($C_1$-$C_6$)alkyl-$OR^1$, halogen, —$CO_2R^1$, —($C_1$-$C_6$)alkyl-$CO_2R^1$, $NHR^1$, —($C_1$-$C_6$)alkyl-$NHR^1$, —(C=O)$NHR^1$, —($C_1$-$C_6$)alkyl-(C=O)$NHR^1$, —$NHR^1$(C=O)$R^1$ or —($C_1$-$C_6$)alkyl-$NHR^1$(C=O)$R^1$; $R^1$ is H or ($C_1$-$C_6$)alkyl; X is a halogen; or an active metabolite, or a pharmaceutically acceptable prodrug, salt, or solvate thereof; and a pharmaceutically acceptable excipient.

WO2009/051244 discloses that a compound represented by the following formula has a lowering effect on RBP4 and is useful for preventing or treating of diabetes and the like:

wherein ring A is benzene optionally further substituted; $R^1$ is an optionally substituted branched $C_{3-6}$ alkyl group; $X^1$ is O, S, SO, $SO_2$ or NH; $X^2$ is a bond or a $C_{1-3}$ alkylene group; ring B is azetidine, pyrrolidine or piperidine; $X^3$ is CO or $SO_2$; $R^2$ is a substituent; provided that (1) when —$X^1$—$X^2$— is —NH— and ring B is piperidine, then $X^3$ is CO; or (2) when $X^3$ is CO, then $R^2$ is not a tert-butoxy group, or a salt thereof.

WO2009/145286 discloses that a compound represented by the following formula has a lowering effect on RBP4 and is useful for preventing or treating of diabetes and the like:

wherein ring A is a 5-membered nonaromatic heterocyclic optionally further substituted with a substituent, ring B is an optionally further substituted benzene ring, and X is a bond, O, $CH_2$O, $OCH_2$, $CH_2$, $(CH_2)_2$, S, $CH_2$S, $SCH_2$, S(O), $CH_2$S(O), S(O)$CH_2$, $S(O)_2$, $CH_2S(O)_2$, or $S(O)_2CH_2$, with the proviso that {(3S,5R)-1-[4-(trifluoromethyl)benzyl]-5-[4-(trifluoromethyl)phenyl]pyrrolidin-3-yl}acetate, {(3S,5R)-1-[2,5-bis(trifluoromethyl)benzyl]-5-[4-(trifluoromethyl)phenyl]pyrrolidin-3-yl}acetate, {4-oxo-3-[3-(trifluoromethyl)phenyl]-1,3-thiazolidin-5-yl}acetate, {2-oxo-1-[3-(trifluoromethyl)phenyl]pyrrolidine-3-yl}acetate, {3-[4-fluoro-3-(trifluoromethyl)phenyl]-4-oxo-1,3-oxazolidine-5-yl}acetate, {4-oxo-3-[3-(trifluoromethyl)phenyl]-1,3-oxazolidine-5-yl}acetate, {3-[2-chloro-5-(trifluoromethyl)phenyl]-4-oxo-1,3-thiazolidine-5-yl}acetate, and {5-oxo-1-[3-(trifluoromethyl)phenyl]-4,5-dihydro-1H-pyrazole-3-yl}acetate is excluded, or the salt thereof.

SUMMARY OF THE INVENTION

The present inventors have found that a compound represented by the formula (I)

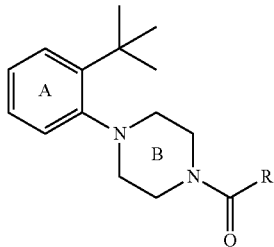

wherein
ring A is a benzene ring optionally further substituted;
ring B is a piperazine ring optionally further substituted; and
R is a substituent,
or a salt thereof (hereinafter sometimes to be referred to as compound (I)) has a superior RBP4 lowering action, which resulted in the completion of the present invention.

Accordingly, the present invention relates to
[1] a compound represented by the formula (I)

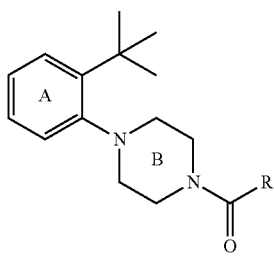

wherein
ring A is a benzene ring optionally further substituted;
ring B is a piperazine ring optionally further substituted; and
R is a substituent,
with the proviso that tert-butyl 4-[2-tert-butyl-5-({[2-(1H-indazol-6-ylamino)pyridin-3-yl]carbonyl}amino)phenyl]piperazine-1-carboxylate is excluded, or a salt thereof;
[2] the compound or salt of the above [1], wherein R is an optionally substituted hydrocarbon group, an optionally substituted heterocyclic group, an optionally substituted amino group or an acyl group;
[3] the compound or salt of the above [1] or [2], wherein ring A is a benzene ring optionally substituted by 1 to 3 substituents selected from (a) a halogen atom, and (b) a $C_{1-6}$ alkyl group;
[4] the compound or salt of the above [1] or [2], wherein ring A is a benzene ring;
[5] the compound or salt of the above [1], [2], [3] or [4], wherein ring B is a piperazine ring;
[5A] the compound or salt of the above [1], [3], [4] or [5], wherein R is
(1) a $C_{1-10}$ alkyl group optionally substituted by 1 to 3 substituents selected from
  (a) a carbamoyl group optionally mono- or di-substituted by
    (i) a $C_{1-6}$ alkylsulfonyl group, and
    (ii) a sulfamoyl group optionally substituted by a $C_{1-6}$ alkyl group optionally substituted by $C_{3-10}$ cycloalkyl,
  (b) a 5- or 6-membered aromatic heterocyclic group optionally substituted by 1 to 3 substituents selected from
    (i) a carboxy group, and
    (ii) a $C_{1-6}$ alkyl group,
  (c) a 5- or 6-membered nonaromatic heterocyclic group optionally substituted by 1 to 3 carboxy groups,
  (d) a carboxy group,
  (e) a $C_{3-10}$ cycloalkyl group, and
  (f) a hydroxy group;
(2) a $C_{3-10}$ cycloalkyl group optionally substituted by 1 to 3 carboxy groups;
(3) a $C_{6-14}$ aryl group optionally substituted by 1 to 3 substituents selected from
  (a) a carboxy group,
  (b) a $C_{1-6}$ alkoxy group optionally substituted by 1 to 3 substituents selected from
    (i) a carboxy group, and
    (ii) a 5- or 6-membered nonaromatic heterocyclic group optionally substituted by 1 to 3 substituents selected from
      (A) a carboxy-carbonyl group, and
      (B) a $C_{1-6}$ alkoxy-carbonyl-carbonyl group,
  (c) a 5- or 6-membered nonaromatic heterocyclic group optionally substituted by 1 to 3 carboxy groups, and
  (d) a $C_{6-14}$ aryl group optionally substituted by a carboxy-$C_{1-6}$ alkyl group;
(4) a 5- or 6-membered aromatic heterocyclic group optionally substituted by 1 to 3 substituents selected from
  (a) a $C_{1-6}$ alkyl group optionally substituted by 1 to 3 carboxy groups,
  (b) a $C_{1-6}$ alkoxy group optionally substituted by 1 to 3 carboxy groups, and
  (c) a $C_{1-6}$ alkylthio group optionally substituted by 1 to 3 carboxy groups;
(5) an amino group optionally mono- or di-substituted by substituents selected from
  (a) a $C_{6-14}$ aryl group optionally substituted by 1 to 3 carboxy-$C_{1-6}$ alkoxy groups,
  (b) a $C_{1-6}$ alkyl group optionally substituted by 1 to 3 carboxy groups, and
  (c) a 5- or 6-membered aromatic heterocyclic group optionally substituted by 1 to 3 substituents selected from
    (i) a hydroxy group, and
    (ii) a carbamoyl group;
(6) a carboxy group;
(7) a carbamoyl group optionally mono- or di-substituted by substituents selected from
  (a) a $C_{1-6}$ alkyl group optionally substituted by 1 to 3 substituents selected from
    (i) a $C_{6-14}$ aryl group optionally substituted by 1 to 3 substituents selected from
      (A) a carboxy group, and
      (B) a carboxy-$C_{1-6}$ alkyl group,
    (ii) a carboxy group, and
    (iii) a $C_{1-6}$ alkyl-sulfonyl group,
  (b) a $C_{6-14}$ aryl group optionally substituted by 1 to 3 substituents selected from
    (i) a carboxy-$C_{1-6}$ alkyl groups, and
    (ii) a carboxy-$C_{1-6}$ alkoxy groups,
  (c) a 5- or 6-membered nonaromatic heterocyclic group optionally substituted by 1 to 3 substituents selected from
    (i) a carboxy group,
    (ii) a carboxy-carbonyl group, and
    (iii) a carboxy-$C_{1-6}$ alkoxy group, and (d) a $C_{1-6}$ alkyl-sulfamoyl group optionally substituted by 1 to 3 $C_{3-10}$ cycloalkyl groups; or (8) a 5- or 6-membered nonaromatic heterocyclylcarbonyl group optionally substituted by 1 to 3 carboxy groups;

[6] the compound or salt of the above [1], [3], [4] or [5], wherein R is (1) a $C_{1-10}$ alkyl group optionally substituted by 1 to 3 substituents selected from (a) a carbamoyl group optionally mono- or di-substituted by
 (i) a $C_{1-6}$ alkylsulfonyl group, and
 (ii) a sulfamoyl group optionally substituted by a $C_{1-6}$ alkyl group optionally substituted by $C_{3-10}$ cycloalkyl, (b) a 5- or 6-membered aromatic heterocyclic group optionally substituted by 1 to 3 substituents selected from
 (i) a carboxy group, and
 (ii) a $C_{1-6}$ alkyl group, (c) a 5- or 6-membered nonaromatic heterocyclic group optionally substituted by 1 to 3 carboxy groups, and (d) a carboxy group;

(2) a $C_{6-14}$ aryl group optionally substituted by 1 to 3 substituents selected from
 (a) a carboxy group,
 (b) a $C_{1-6}$ alkoxy group optionally substituted by 1 to 3 carboxy groups,
 (c) a 5- or 6-membered nonaromatic heterocyclic group optionally substituted by 1 to 3 carboxy groups, and
 (d) a $C_{6-14}$ aryl group optionally substituted by a carboxy-$C_{1-6}$ alkyl group;

(3) a 5- or 6-membered aromatic heterocyclic group optionally substituted by 1 to 3 substituents selected from
 (a) a $C_{1-6}$ alkyl group optionally substituted by 1 to 3 carboxy groups, and
 (b) a $C_{1-6}$ alkoxy group optionally substituted by 1 to 3 carboxy groups;

(4) an amino group optionally mono- or di-substituted by substituents selected from
 (a) a $C_{6-14}$ aryl group optionally substituted by 1 to 3 carboxy-$C_{1-6}$ alkoxy groups,
 (b) a $C_{1-6}$ alkyl group optionally substituted by 1 to 3 carboxy groups, and
 (c) a 5- or 6-membered aromatic heterocyclic group optionally substituted by 1 to 3 substituents selected from
  (i) a hydroxy group, and
  (ii) a carbamoyl group;

(5) a carboxy group; or (6) a carbamoyl group optionally mono- or di-substituted by substituents selected from
 (a) a $C_{1-6}$ alkyl group optionally substituted by 1 to 3 substituents selected from
  (i) a $C_{6-14}$ aryl group optionally substituted by 1 to 3 substituents selected from
   (A) a carboxy group, and
   (B) a carboxy-$C_{1-6}$ alkyl group,
  (ii) a carboxy group, and
  (iii) a $C_{1-6}$ alkyl-sulfonyl group, and
 (b) a 5- or 6-membered nonaromatic heterocyclic group optionally substituted by 1 to 3 substituents selected from
  (i) a carboxy group,
  (ii) a carboxy-carbonyl group, and
  (iii) a carboxy-$C_{1-6}$ alkoxy group;

[7] the compound or salt of the above [1], wherein ring A is a benzene ring optionally substituted by 1 to 3 substituents selected from (a) a halogen atom, and (b) a $C_{1-6}$ alkyl group; ring B is a piperazine ring; and R is (1) a $C_{1-10}$ alkyl group optionally substituted by 1 to 3 substituents selected from (a) a carbamoyl group optionally mono- or di-substituted by
 (i) a $C_{1-6}$ alkylsulfonyl group, and
 (ii) a sulfamoyl group optionally substituted by a $C_{1-6}$ alkyl group optionally substituted by $C_{3-10}$ cycloalkyl, (b) a 5- or 6-membered aromatic heterocyclic group optionally substituted by 1 to 3 substituents selected from
 (i) a carboxy group, and
 (ii) a $C_{1-6}$ alkyl group, (c) a 5- or 6-membered nonaromatic heterocyclic group optionally substituted by 1 to 3 carboxy groups, and (d) a carboxy group;

(2) a $C_{6-14}$ aryl group optionally substituted by 1 to 3 substituents selected from
 (a) a carboxy group,
 (b) a $C_{1-6}$ alkoxy group optionally substituted by 1 to 3 carboxy groups,
 (c) a 5- or 6-membered nonaromatic heterocyclic group optionally substituted by 1 to 3 carboxy groups, and
 (d) a $C_{6-14}$ aryl group optionally substituted by a carboxy-$C_{1-6}$ alkyl group;

(3) a 5- or 6-membered aromatic heterocyclic group optionally substituted by 1 to 3 substituents selected from
 (a) a $C_{1-6}$ alkyl group optionally substituted by 1 to 3 carboxy groups, and
 (b) a $C_{1-6}$ alkoxy group optionally substituted by 1 to 3 carboxy groups;

(4) an amino group optionally mono- or di-substituted by substituents selected from
 (a) a $C_{6-14}$ aryl group optionally substituted by 1 to 3 carboxy-$C_{1-6}$ alkoxy groups,
 (b) a $C_{1-6}$ alkyl group optionally substituted by 1 to 3 carboxy groups, and
 (c) a 5- or 6-membered aromatic heterocyclic group optionally substituted by 1 to 3 substituents selected from
  (i) a hydroxy group, and
  (ii) a carbamoyl group;

(5) a carboxy group; or (6) a carbamoyl group optionally mono- or di-substituted by substituents selected from
 (a) a $C_{1-6}$ alkyl group optionally substituted by 1 to 3 substituents selected from
  (i) a $C_{6-14}$ aryl group optionally substituted by 1 to 3 substituents selected from
   (A) a carboxy group, and
   (B) a carboxy-$C_{1-6}$ alkyl group,
  (ii) a carboxy group, and
  (iii) a $C_{1-6}$ alkyl-sulfonyl group, and
 (b) a 5- or 6-membered nonaromatic heterocyclic group optionally substituted by 1 to 3 substituents selected from
  (i) a carboxy group,
  (ii) a carboxy-carbonyl group, and
  (iii) a carboxy-$C_{1-6}$ alkoxy group;

[8] N-{[4-(2-tert-Butylphenyl)piperazin-1-yl]carbonyl}glycine or a salt thereof;

[9] 3-[4-(2-tert-Butylphenyl)piperazin-1-yl]-3-oxopropanoic acid or a salt thereof;

[10] [4-(2-tert-Butyl-4-chlorophenyl)piperazin-1-yl](oxo)acetic acid or a salt thereof;

[11] a prodrug of the compound or salt of the above [1];

[12] a pharmaceutical composition comprising the compound or salt of the above [1] or a prodrug thereof;

[13] the pharmaceutical composition of the above [13], which is a composition for the prophylaxis or treatment of a retinol binding protein 4 associated disease;

[14] a retinol binding protein 4-lowering agent comprising a compound represented by the formula (I)

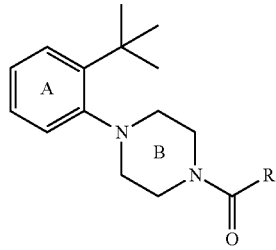

wherein
ring A is a benzene ring optionally further substituted;
ring B is a piperazine ring optionally further substituted; and
R is a substituent,
or a salt thereof or a prodrug thereof;
[15] an agent for the prophylaxis or treatment of diabetes, comprising a compound represented by the formula (I)

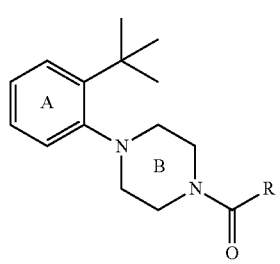

wherein
ring A is a benzene ring optionally further substituted;
ring B is a piperazine ring optionally further substituted; and
R is a substituent,
or a salt thereof or a prodrug thereof;
[15A] an agent for the prophylaxis or treatment of age-related macular degeneration, comprising a compound represented by the formula (I)

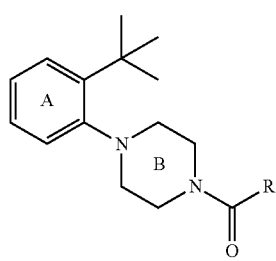

wherein
ring A is a benzene ring optionally further substituted;
ring B is a piperazine ring optionally further substituted; and
R is a substituent,
or a salt thereof or a prodrug thereof;
[16] a method of lowering retinol binding protein 4 in a mammal, comprising administering an effective amount of a compound represented by the formula (I)

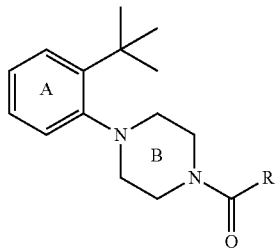

wherein
ring A is a benzene ring optionally further substituted;
ring B is a piperazine ring optionally further substituted; and
R is a substituent,
or a salt thereof or a prodrug thereof to the mammal;
[17] a method for the prophylaxis or treatment of diabetes in a mammal, comprising administering an effective amount of a compound represented by the formula (I)

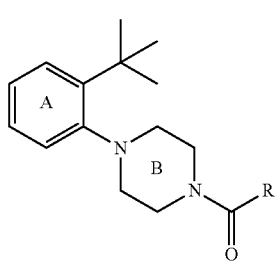

wherein
ring A is a benzene ring optionally further substituted; ring B is a piperazine ring optionally further substituted; and
R is a substituent,
or a salt thereof or a prodrug thereof to the mammal;
[17A] a method for the prophylaxis or treatment of age-related macular degeneration in a mammal, comprising administering an effective amount of a compound represented by the formula (I)

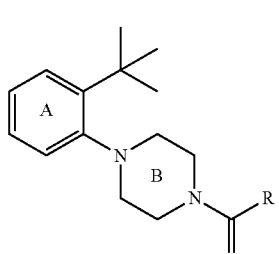

wherein
ring A is a benzene ring optionally further substituted;
ring B is a piperazine ring optionally further substituted; and
R is a substituent,
or a salt thereof or a prodrug thereof to the mammal;

[18] use of a compound represented by the formula (I)

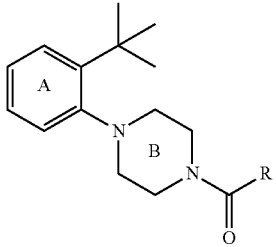

wherein
ring A is a benzene ring optionally further substituted;
ring B is a piperazine ring optionally further substituted; and
R is a substituent,
or a salt thereof or a prodrug thereof, for manufacturing a retinol binding protein 4 lowering agent;

[19] use of a compound represented by the formula (I)

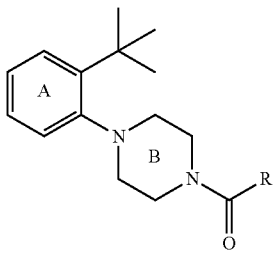

wherein
ring A is a benzene ring optionally further substituted;
ring B is a piperazine ring optionally further substituted; and
R is a substituent,
or a salt thereof or a prodrug thereof, for manufacturing a pharmaceutical composition for the prophylaxis or treatment of diabetes;

[19A] use of a compound represented by the formula (I)

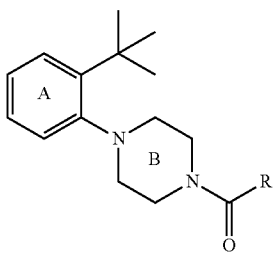

wherein
ring A is a benzene ring optionally further substituted;
ring B is a piperazine ring optionally further substituted; and
R is a substituent,
or a salt thereof or a prodrug thereof, for manufacturing a pharmaceutical composition for the prophylaxis or treatment of age-related macular degeneration;
and the like.

Effect of the Invention

The present invention provides a prophylactic or therapeutic agent for a disease or condition mediated by an increase in RBP4, such as diabetes, obesity, age-related macular degeneration and the like.

DETAILED DESCRIPTION OF THE INVENTION

The definition of each symbol or term used for compound (I) is described in detail in the following.

In the present specification, the "halogen atom" means, unless otherwise specified, a fluorine atom, a chlorine atom, a bromine atom or an iodine atom.

In the present specification, the "$C_{1-6}$ alkyl group" means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

In the present specification, the "$C_{1-10}$ alkyl group" means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

In the present specification, the "$C_{2-10}$ alkenyl group" means, unless otherwise specified, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

In the present specification, the "$C_{2-10}$ alkynyl group" means, unless otherwise specified, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

In the present specification, the "$C_{3-10}$ cycloalkyl group" means, unless otherwise specified, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

In the present specification, the "$C_{3-10}$ cycloalkenyl group" means, unless otherwise specified, 2-cyclopenten-1-yl, 3-cyclopenten-1-yl, 2-cyclohexen-1-yl, 3-cyclohexen-1-yl and the like.

In the present specification, the "$C_{4-10}$ cycloalkadienyl group" means, unless otherwise specified, 2,4-cyclopentadien-1-yl, 2,4-cyclohexadien-1-yl, 2,5-cyclohexadien-1-yl and the like.

The above-mentioned $C_{3-10}$ cycloalkyl group, $C_{3-10}$ cycloalkenyl group and $C_{4-10}$ cycloalkadienyl group may each form a fused ring group with a benzene ring. Examples of the fused ring group include indanyl, dihydronaphthyl, tetrahydronaphthyl, fluorenyl and the like.

In the present specification, the "$C_{6-14}$ aryl group" means, unless otherwise specified, phenyl, naphthyl, anthryl, phenanthryl, acenaphthyl, biphenylyl and the like.

In the present specification, the "$C_{7-13}$ aralkyl group" means, unless otherwise specified, benzyl, phenethyl, naphthylmethyl, biphenylylmethyl and the like.

In the present specification, the "$C_{8-13}$ arylalkenyl group" means, unless otherwise specified, styryl and the like.

In the present specification, the "$C_{1-3}$ alkylenedioxy group" means, unless otherwise specified, methylenedioxy, ethylenedioxy and the like.

In the present specification, the "$C_{1-6}$ alkoxy group" means, unless otherwise specified, methoxy, ethoxy, propoxy, isopropoxy, butoxy, isobutoxy, sec-butoxy, tert-butoxy and the like.

In the present specification, the "$C_{1-6}$ alkoxy-carbonyl group" means, unless otherwise specified, methoxycarbonyl, ethoxycarbonyl, propoxycarbonyl, tert-butoxycarbonyl and the like.

In the present specification, the "$C_{1-6}$ alkyl-carbonyl group" means, unless otherwise specified, acetyl, propanoyl, butanoyl, isobutanoyl, pentanoyl, isopentanoyl, hexanoyl and the like.

In the present specification, the "$C_{6-14}$ aryl-carbonyl group" means, unless otherwise specified, benzoyl, naphthylcarbonyl, biphenylcarbonyl and the like.

In the present specification, "heterocyclic group" means an aromatic heterocyclic group and a nonaromatic heterocyclic group.

In the present specification, the "aromatic heterocyclic group" means, unless otherwise specified, a 4- to 7-membered (preferably 5- or 6-membered) monocyclic aromatic heterocyclic group containing, as a ring constituting atom besides carbon atom, 1 to 4 hetero atoms selected from an oxygen atom, a sulfur atom and a nitrogen atom and a condensed aromatic heterocyclic group. Examples of the condensed aromatic heterocyclic group include a group derived from a ring obtained by condensation of a ring corresponding to such 4- to 7-membered monocyclic aromatic heterocyclic group and 1 or 2 selected from a 5- or 6-membered aromatic heterocycle (e.g., pyrrole, imidazole, pyrazole, pyrazine, pyridine, pyrimidine) containing 1 or 2 nitrogen atoms, a 5-membered aromatic heterocycle (e.g., thiophene) containing one sulfur atom and a benzene ring, and the like.

Preferable examples of the aromatic heterocyclic group include a 5- or 6-membered monocyclic aromatic heterocyclic group such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

a 8- to 14-membered condensed aromatic heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisooxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazothiazolyl (e.g., imidazo[2,1-b]thiazol-6-yl), thienopyridinyl (e.g., thieno[2,3-b]pyridin-3-yl), thienopyrazinyl (e.g., thieno[2,3-b]pyrazin-6-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like;

and the like.

In the present specification, the "nonaromatic heterocyclic group" means, unless otherwise specified, a 4- to 7-membered (preferably 5- or 6-membered) monocyclic nonaromatic heterocyclic group containing, as a ring constituting atom besides carbon atom, 1 to 4 hetero atoms selected from an oxygen atom, a sulfur atom and a nitrogen atom and a condensed nonaromatic heterocyclic group. Examples of the condensed nonaromatic heterocyclic group include a group derived from a ring obtained by condensation of a ring corresponding to such 4- to 7-membered monocyclic nonaromatic heterocyclic group and 1 or 2 rings selected from a 5- or 6-membered aromatic heterocycle (e.g., pyrrole, imidazole, pyrazole, pyrazine, pyridine, pyrimidine, thiophene) containing 1 or 2 nitrogen atoms or one sulfur atom, and a benzene ring, a group obtained by partial saturation of the group and the like.

Preferable examples of the nonaromatic heterocyclic group include a 5- or 6-membered monocyclic nonaromatic heterocyclic group such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl, thiazolidin-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuranyl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl, tetrahydropyrimidin-4-yl, tetrahydropyrimidin-5-yl), hexahydropyrimidinyl (e.g., hexahydropyrimidin-4-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;

a 8- to 14-membered condensed nonaromatic heterocyclic group such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), 5H-[1,3]thiazolo[3,2-a]pyrimidinyl (e.g., 5H-[1,3]thiazolo[3,2-a]pyrimidin-6-yl, 2-oxabicyclo[2,2,1]heptan-1-yl) and the like;
and the like.

In the present specification, the "fused ring group" means the aforementioned a 8- to 14-membered condensed aromatic heterocyclic group or a 8- to 14-membered condensed non-aromatic heterocyclic group and the like.

In the present specification, the "aromatic heterocyclylcarbonyl group" means, unless otherwise specified, a 4- to 7-membered (preferably 5- or 6-membered) monocyclic aromatic heterocyclylcarbonyl group such as pyridylcarbonyl and the like.

In the present specification, the "nonaromatic heterocyclylcarbonyl" means, unless otherwise specified, a 4- to 7-membered (preferably 5- or 6-membered) monocyclic nonaromatic heterocyclylcarbonyl group such as piperidinylcarbonyl, pyrrolidinylcarbonyl and the like.

Ring A is a benzene ring optionally further substituted. The benzene ring optionally has 1 to 4 substituents at substitutable position(s), in addition to the tert-butyl group and ring B.

Examples of the substituent include the following Substituent group A and the like. When two or more substituents are present, the substituents may be the same or different.

Substituent Group A
(1) a halogen atom;
(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;
(3) a $C_{2-10}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by a $C_{1-6}$ alkyl group, and
  (g) a 4- to 7-membered nonaromatic heterocyclic group (e.g., tetrahydrofuranyl, morpholinyl, thiomorpholinyl, piperidinyl, pyrrolidinyl, piperazinyl, thiazolidinyl) optionally substituted by 1 to 3 substituents selected from
    (i) a $C_{1-6}$ alkyl group optionally substituted by 1 to 3 halogen atoms,
    (ii) a hydroxy group,
    (iii) a $C_{1-6}$ alkoxy group optionally substituted by 1 to 3 halogen atoms,
    (iv) a halogen atom, and
    (v) an oxo group;
(4) a $C_{3-10}$ cycloalkyl group (e.g., cyclopropyl, cyclohexyl);
(5) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(6) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(7) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(8) a 4- to 7-membered nonaromatic heterocyclic group (e.g., tetrahydrofuranyl, morpholinyl, thiomorpholinyl, piperidinyl, pyrrolidinyl, piperazinyl, dihydrooxadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom,
  (e) an oxo group, and
  (f) a carboxy group;
(9) a $C_{1-6}$ alkoxy group optionally substituted by 1 to 3 substituents selected from
  (a) a halogen atom,
  (b) a carboxy group,
  (c) a hydroxy group,
  (d) a $C_{1-6}$ alkoxy-carbonyl group optionally substituted by 1 to 3 $C_{6-14}$ aryl groups (e.g., phenyl),
  (e) a $C_{1-6}$ alkoxy group,
  (f) an amino group optionally mono- or di-substituted by substituent(s) selected from a $C_{1-6}$ alkyl group and a $C_{1-6}$ alkoxy-carbonyl group, and
  (g) a 4- to 7-membered nonaromatic heterocyclic group (e.g., piperidinyl) optionally substituted by 1 to 3 substituents selected from
    (i) a carboxy group,
    (ii) a $C_{1-6}$ alkyl-carbonyl group, and
    (iii) a $C_{1-6}$ alkoxy-carbonyl group (e.g., tert-butoxycarbonyl);
(10) a $C_{2-6}$ alkenyloxy group (e.g., ethenyloxy) optionally substituted by 1 to 3 halogen atoms;
(11) a $C_{7-13}$ aralkyloxy group (e.g., benzyloxy);
(12) a $C_{6-14}$ aryloxy group (e.g., phenyloxy, naphthyloxy);
(13) a $C_{1-3}$ alkylenedioxy group (e.g., ethylenedioxy);
(14) a $C_{1-6}$ alkyl-carbonyloxy group (e.g., acetyloxy, tert-butylcarbonyloxy);
(15) a $C_{1-6}$ alkyl-carbonyl group optionally substituted by 1 to 3 substituents selected from
  (a) a halogen atom
  (b) a $C_{1-6}$ alkoxy group, and
  (c) a $C_{6-14}$ aryl group;
(16) a carboxy group;
(17) a $C_{1-6}$ alkoxy-carbonyl group optionally substituted by 1 to 3 substituents selected from
  (a) a halogen atom,
  (b) a $C_{1-6}$ alkoxy group, and
  (c) a $C_{6-14}$ aryl group (e.g., phenyl);

(18) a $C_{6-14}$ aryl-carbonyl group optionally substituted by 1 to 3 substituents selected from
  (a) a halogen atom, and
  (b) a $C_{1-6}$ alkyl group optionally substituted by 1 to 3 halogen atoms;
(19) a 4- to 7-membered nonaromatic heterocyclylcarbonyl group (e.g., pyrrolidinylcarbonyl, morpholinylcarbonyl) optionally substituted by 1 to 3 $C_{1-6}$ alkyl groups optionally substituted by 1 to 3 halogen atoms;
(20) a 4- to 7-membered aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from $C_{1-6}$ alkyl groups optionally substituted by 1 to 3 halogen atoms;
(21) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{6-14}$ aryl-carbonyl group optionally substituted by 1 to 3 halogen atoms,
  (d) a $C_{1-6}$ alkoxy-carbonyl group optionally substituted by 1 to 3 halogen atoms,
  (e) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
  (f) a carbamoyl group optionally mono- or di-substituted by a $C_{1-6}$ alkyl group optionally substituted by 1 to 3 halogen atoms, and
  (g) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl);
(22) a carbamoyl group optionally mono- or di-substituted by substituent(s) selected from
  (a) a $C_{1-6}$ alkyl group optionally substituted by 1 to 3 halogen atoms,
  (b) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
  (c) a $C_{6-14}$ arylsulfonyl group (e.g., phenylsulfonyl) optionally substituted by a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl), and
  (d) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl);
(23) a thiocarbamoyl group optionally mono- or di-substituted by a $C_{1-6}$ alkyl group optionally substituted by 1 to 3 halogen atoms;
(24) a sulfamoyl group optionally mono- or di-substituted by a $C_{1-6}$ alkyl group optionally substituted by 1 to 3 halogen atoms;
(25) a mercapto group;
(26) a $C_{1-6}$ alkylthio group (e.g., methylthio, ethylthio) optionally substituted by 1 to 3 substituents selected from
  (a) a halogen atom,
  (b) a $C_{1-6}$ alkoxy-carbonyl group
  (c) a carboxy group,
  (d) a hydroxy group, and
  (e) a $C_{1-6}$ alkoxy group;
(27) a $C_{7-13}$ aralkylthio group (e.g., benzylthio);
(28) a $C_{6-14}$ arylthio group (e.g., phenylthio, naphthylthio);
(29) a $C_{1-6}$ alkylsulfonyl group (e.g., methylsulfonyl, ethylsulfonyl, isopropylsulfonyl) optionally substituted by 1 to 3 halogen atoms;
(30) a cyano group;
(31) a nitro group;
(32) a hydroxy group;
(33) a formyl group,
and the like.

Preferable examples of the substituent of the "benzene ring optionally further substituted" for ring A include
(1) a halogen atom (e.g., chlorine atom, bromine atom);
(2) a $C_{1-6}$ alkyl group (e.g., methyl, isopropyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;
(3) a $C_{1-6}$ alkoxy group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group
(4) a cyano group
(5) a $C_{6-14}$ aryl group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(6) a 4- to 7-membered aromatic heterocyclic group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(7) a 4- to 7-membered nonaromatic heterocyclic group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(8) a $C_{2-10}$ alkenyl group (e.g., ethenyl, 1-propenyl, isopropenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by a $C_{1-6}$ alkyl group, and
  (g) a 4- to 7-membered nonaromatic heterocyclic group (e.g., tetrahydrofuranyl, morpholinyl, thiomorpholinyl, piperidinyl, pyrrolidinyl, piperazinyl, thiazolidinyl) optionally substituted by 1 to 3 substituents selected from
  (i) a $C_{1-6}$ alkyl group optionally substituted by 1 to 3 halogen atoms,
  (ii) a hydroxy group,
  (iii) a $C_{1-6}$ alkoxy group optionally substituted by 1 to 3 halogen atoms,
  (iv) a halogen atom, and
  (v) an oxo group,
and the like.

Ring A is preferably a benzene ring optionally substituted by 1 to 3 substituents selected from
(1) a halogen atom (e.g., chlorine atom, bromine atom);
(2) an optionally substituted $C_{1-6}$ alkyl group (e.g., methyl, isopropyl);
(3) an optionally substituted $C_{2-10}$ alkenyl group (e.g., ethenyl, 1-propenyl, isopropenyl);
(4) an optionally substituted $C_{1-6}$ alkoxy group;
(5) a cyano group;
(6) an optionally substituted $C_{6-14}$ aryl group;
(7) an optionally substituted 4- to 7-membered aromatic heterocyclic group;
(8) an optionally substituted 4- to 7-membered nonaromatic heterocyclic group
and the like.

Ring A is more preferably a benzene ring optionally substituted by 1 to 3 substituents selected from
(1) a halogen atom (e.g., chlorine atom, bromine atom);
(2) a $C_{1-6}$ alkyl group (e.g., methyl, isopropyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;
(3) a $C_{2-10}$ alkenyl group (e.g., ethenyl, 1-propenyl, isopropenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by a $C_{1-6}$ alkyl group, and
  (g) a 5- or 6-membered nonaromatic heterocyclic group (e.g., tetrahydrofuranyl, morpholinyl, thiomorpholinyl, piperidinyl, pyrrolidinyl, piperazinyl, thiazolidinyl) optionally substituted by 1 to 3 substituents selected from
    (i) a $C_{1-6}$ alkyl group optionally substituted by 1 to 3 halogen atoms,
    (ii) a hydroxy group,
    (iii) a $C_{1-6}$ alkoxy group optionally substituted by 1 to 3 halogen atoms,
    (iv) a halogen atom, and
    (v) an oxo group;
(4) a $C_{1-6}$ alkoxy group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;
(5) a cyano group;
(6) a $C_{6-14}$ aryl group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(7) a 5- or 6-membered aromatic heterocyclic group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(8) a 5- or 6-membered nonaromatic heterocyclic group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group,
and the like.

Ring A is more preferably a benzene ring optionally substituted by 1 to 3 substituents selected from a halogen atom (e.g., chlorine atom, bromine atom), a $C_{1-6}$ alkyl group (e.g., methyl, isopropyl) optionally substituted by 1 to 3 substituents selected from a hydroxy group, a $C_{2-10}$ alkenyl group (e.g., ethenyl, 1-propenyl, isopropenyl) and a cyano group and the like.

Ring A is more preferably a benzene ring optionally substituted by 1 to 3 substituents selected from a halogen atom or a $C_{1-6}$ alkyl group and the like.

Ring B is a piperazine ring optionally further substituted. The piperazine ring optionally has 1 to 4 substituents at substitutable position(s), in addition to ring A and —CO—R group.

Examples of such substituent include the aforementioned Substituent group A, an oxo group, and the like. When two or more substituents are present, the substituents may be the same or different.

The substituent of the "piperazine ring optionally further substituted" for ring B is preferably
(1) a halogen atom;
(2) a $C_{1-6}$ alkyl group optionally substituted by 1 to 3 halogen atoms;
(3) a $C_{1-6}$ alkoxy group optionally substituted by 1 to 3 halogen atoms
and the like.

Ring B is preferably a piperazine ring optionally further substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms, and the like.

Ring B is more preferably a piperazine ring.

R is a substituent.

Examples of the "substituent" for R include "optionally substituted hydrocarbon group", "optionally substituted heterocyclic group", "optionally substituted hydroxy group", "optionally substituted mercapto group", "optionally substituted amino group", "cyano group", "nitro group", "acyl group", "halogen atom" and the like.

Examples of the "hydrocarbon group" of the "optionally substituted hydrocarbon group" for R include $C_{1-10}$ alkyl group, $C_{2-10}$ alkenyl group, $C_{2-10}$ alkynyl group, $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group, $C_{8-13}$ arylalkenyl group and the like.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group exemplified as the "hydrocarbon group" optionally have 1 to 3 substituents at substitutable position(s).

Examples of the substituent include the aforementioned Substituent group A and the like. When two or more substituents are present, the substituents may be the same or different.

The $C_{1-10}$ alkyl group, $C_{2-10}$ alkenyl group and $C_{2-10}$ alkynyl group exemplified for the "hydrocarbon group" optionally have 1 to 3 substituents at substitutable position(s).

Examples of the substituent include the following Substituent group B and the like. When two or more substituents are present, the substituents may be the same or different.

Substituent Group B (1) a halogen atom;
(2) a $C_{3-10}$ cycloalkyl group (e.g., cyclopropyl, cyclobutyl, cyclopentyl, cyclohexyl) optionally substituted by 1 to 3 substituents selected from
   (a) $C_{1-6}$ alkyl group,
   (b) $C_{1-6}$ alkyl-carbonyl group, and
   (c) an oxo group
(the $C_{3-10}$ cycloalkyl group may form a fused ring group with a benzene ring optionally substituted by a $C_{1-6}$ alkoxy group);
(3) a $C_{6-14}$ aryl group (e.g., phenyl, naphthyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(4) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) a carboxy group;
(5) a 4- to 7-membered nonaromatic heterocyclic group (e.g., tetrahydrofuranyl, morpholinyl, thiomorpholinyl, piperidinyl, pyrrolidinyl, piperazinyl, imidazolidinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom,
   (e) an oxo group, and
   (f) a carboxy group;
(6) a $C_{1-6}$ alkoxy group optionally substituted by 1 to 3 substituents selected from
   (a) a halogen atom,
   (b) a carboxy group,
   (c) a $C_{1-6}$ alkoxy group,
   (d) a $C_{1-6}$ alkoxy-carbonyl group optionally substituted by 1 to 3 $C_{6-14}$ aryl groups (e.g., phenyl), and
   (e) an amino group optionally mono- or di-substituted by substituent(s) selected from a $C_{1-6}$ alkyl group and a $C_{1-6}$ alkoxy-carbonyl group;
(7) a $C_{2-6}$ alkenyloxy group (e.g., ethenyloxy) optionally substituted by 1 to 3 halogen atoms;
(8) a $C_{7-13}$ aralkyloxy group (e.g., benzyloxy);
(9) a $C_{6-14}$ aryloxy group (e.g., phenyloxy, naphthyloxy);
(10) a $C_{1-6}$ alkyl-carbonyloxy group (e.g., acetyloxy, tert-butylcarbonyloxy);
(11) a $C_{1-3}$ alkylenedioxy group;
(12) a $C_{1-6}$ alkyl-carbonyl group optionally substituted by 1 to 3 halogen atoms;
(13) a $C_{1-6}$ alkoxy-carbonyl group optionally substituted by 1 to 3 substituents selected from
   (a) a halogen atom,
   (b) a $C_{1-6}$ alkoxy group, and
   (c) a $C_{6-14}$ aryl group (e.g., phenyl);
(14) a $C_{6-14}$ aryl-carbonyl group optionally substituted by 1 to 3 substituents selected from
   (a) a halogen atom, and
   (b) $C_{1-6}$ alkyl groups optionally substituted by 1 to 3 halogen atoms;
(15) a 4- to 7-membered aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from $C_{1-6}$ alkyl groups optionally substituted by 1 to 3 halogen atoms;
(16) a 4- to 7-membered nonaromatic heterocyclylcarbonyl group (e.g., pyrrolidinylcarbonyl, morpholinylcarbonyl) optionally substituted by 1 to 3 substituents selected from $C_{1-6}$ alkyl groups optionally substituted by 1 to 3 halogen atoms;
(17) a $C_{7-13}$ aralkyloxy-carbonyl group (e.g., benzyloxycarbonyl);
(18) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 halogen atoms,
   (c) a $C_{6-14}$ aryl-carbonyl group optionally substituted by 1 to 3 halogen atoms,
   (d) a $C_{1-6}$ alkoxy-carbonyl group optionally substituted by 1 to 3 halogen atoms,
   (e) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
   (f) a carbamoyl group optionally mono- or di-substituted by a $C_{1-6}$ alkyl group optionally substituted by 1 to 3 halogen atoms, and
   (g) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl);
(19) a carbamoyl group optionally mono- or di-substituted by substituent(s) selected from
   (a) a $C_{1-6}$ alkyl group optionally substituted by 1 to 3 substituents selected from
     (i) a halogen atom,
     (ii) a hydroxy group, and
     (iii) a carboxy group,
   (b) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms, (c) a $C_{6-14}$ arylsulfonyl group (e.g., phenylsulfonyl) optionally substituted by a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl), (d) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl), (e) a sulfamoyl group optionally substituted by a $C_{1-6}$ alkyl group optionally substituted by a $C_{3-10}$ cycloalkyl group (e.g., cyclopropyl), (f) a carboxy group, (g) a $C_{6-14}$ aryl group, and (h) a 4- to 7-membered nonaromatic heterocyclic group (e.g., pyrrolidinyl, piperidinyl) optionally substituted by a carboxy group;

(20) a thiocarbamoyl group optionally mono- or di-substituted by a $C_{1-6}$ alkyl group optionally substituted by 1 to 3 halogen atoms;

(21) a sulfamoyl group optionally mono- or di-substituted by a $C_{1-6}$ alkyl group optionally substituted by 1 to 3 halogen atoms;

(22) a $C_{1-6}$ alkylsulfonyl group (e.g., methylsulfonyl, ethylsulfonyl, isopropylsulfonyl) optionally substituted by 1 to 3 halogen atoms;

(23) a carboxy group;

(24) a hydroxy group;

(25) a mercapto group;

(26) a $C_{1-6}$ alkylthio group (e.g., methylthio, ethylthio) optionally substituted by 1 to 3 substituents selected from
  (a) a halogen atom, and
  (b) a $C_{1-6}$ alkoxy-carbonyl group;

(27) a $C_{7-13}$ aralkylthio group (e.g., benzylthio);

(28) a $C_{6-14}$ arylthio group (e.g., phenylthio, naphthylthio) optionally substituted by a hydroxy group;

(29) a $C_{6-14}$ arylthio group (e.g., phenylthio) optionally substituted by a hydroxy group;

(30) a $C_{6-14}$ arylsulfinyl group (e.g., phenylsulfinyl) optionally substituted by a hydroxy group;

(31) a $C_{6-14}$ arylsulfonyl group (e.g., phenylsulfonyl) optionally substituted by a hydroxy group;

(32) a 4- to 7-membered aromatic heterocyclylthio group (e.g., triazolylthio, tetrazolylthio, pyrazolylthio) optionally substituted by 1 to 3 substituents selected from
  (a) a $C_{1-6}$ alkyl group optionally substituted by a carboxy group,
  (b) a carboxy group, and
  (c) a $C_{6-14}$ aryl group;

(33) a 4- to 7-membered aromatic heterocyclylsulfinyl group (e.g., triazolylsulfinyl);

(34) a 4- to 7-membered aromatic aromatic heterocyclylsulfonyl group (e.g., triazolylsulfonyl);

(35) a sulfoxy group;

(36) a cyano group;

(37) a nitro group, and the like.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group exemplified as the aforementioned "hydrocarbon group" optionally have 1 to 3 substituents at substitutable position(s).

Examples of the substituent include the aforementioned Substituent group A and the like. When two or more substituents are present, the substituents may be the same or different.

The "optionally substituted hydrocarbon group" for R is preferably (1) a $C_{1-10}$ alkyl group (e.g., methyl, ethyl, propyl, isopropyl, tert-butyl, isobutyl, pentyl) optionally substituted by 1 to 3 substituents selected from
  (a) a carbamoyl group optionally mono- or di-substituted by substituent(s) selected from
    (i) a carboxy group,
    (ii) a $C_{1-6}$ alkyl group (e.g., methyl) optionally substituted by 1 to 3 substituents selected from
      (A) a carboxy group, and
      (B) a $C_{6-14}$ aryl group (e.g., phenyl) optionally substituted by a carboxy group,
    (iii) a $C_{1-6}$ alkylsulfonyl group (e.g., methyl sulfonyl),
    (iv) a $C_{6-14}$ aryl group,
    (v) a 4- to 7-membered aromatic heterocyclic group, and
    (vi) a sulfamoyl group optionally substituted by a $C_{1-6}$ alkyl group (e.g., methyl) optionally substituted by a $C_{3-10}$ cycloalkyl (e.g., cyclopropyl),
  (b) a 4- to 7-membered aromatic heterocyclylthio group (e.g., pyrazolylthio (e.g., pyrazol-5-ylthio), tetrazolylthio (e.g., tetrazol-5-ylthio), benzimidazolylthio (e.g., benzimidazol-2-ylthio)) optionally substituted by 1 to 3 substituents selected from
    (i) a carboxy group,
    (ii) a $C_{1-6}$ alkyl group (e.g., methyl) optionally substituted by a carboxy group, and
    (iii) a $C_{6-14}$ aryl group,
  (c) a 4- to 7-membered aromatic heterocyclic group (e.g., tetrazolyl (e.g., tetrazol-5-yl, tetrazol-1-yl), imidazolyl) optionally substituted by 1 to 3 substituents selected from
    (i) a carboxy group,
    (ii) a $C_{1-6}$ alkyl group, and
    (iii) a $C_{1-6}$ alkylthio group (e.g., methylthio) optionally substituted by a carboxy group,
  (d) a 4- to 7-membered nonaromatic heterocyclic group (e.g., imidazolidinyl (e.g., imidazolidin-5-yl), piperidinyl (e.g., piperidin-4-yl)) optionally substituted by 1 to 3 substituents selected from
    (i) a carboxy group,
    (ii) a $C_{1-6}$ alkyl group (e.g., methyl) optionally substituted by 1 to 3 substituents selected from
      (A) a carboxy group,
      (B) a $C_{1-6}$ alkoxy-carbonyl group (e.g., methoxycarbonyl) optionally substituted by a $C_{6-14}$ aryl group (e.g., phenyl), and
      (C) a $C_{6-14}$ aryl group (e.g., phenyl) optionally substituted by a $C_{1-6}$ alkoxy-carbonyl group (e.g., methoxycarbonyl),
    (iii) an oxo group, and
    (iv) a $C_{7-13}$ aralkyl group (e.g., benzyl) optionally substituted by a carboxy group,
  (e) a halogen atom,
  (f) a cyano group,
  (g) a hydroxy group,
  (h) a carboxy group,
  (i) a $C_{1-6}$ alkoxy group (e.g., methoxy, ethoxy) optionally substituted by 1 to 3 substituents selected from
    (i) a halogen atom,
    (ii) a carboxy group,
    (iii) a $C_{1-6}$ alkoxy group,
    (iv) a $C_{1-6}$ alkoxy-carbonyl group, and
    (v) a $C_{6-14}$ aryl group (e.g., phenyl)
  (j) an amino group optionally mono- or di-substituted by substituent(s) selected from
    (i) a $C_{1-6}$ alkyl group,
    (ii) a $C_{1-6}$ alkyl-carbonyl group (e.g., acetyl), (iii) a $C_{6-14}$ aryl-carbonyl group (e.g., benzoyl),
(iv) a $C_{1-6}$ alkoxy-carbonyl group (e.g., tert-butoxycarbonyl),
(v) a $C_{1-6}$ alkylsulfonyl group,
(vi) a carbamoyl group optionally mono- or di-substituted by a $C_{1-6}$ alkyl group, and
(vii) a 4- to 7-membered aromatic heterocyclic group,
(k) a $C_{1-6}$ alkyl-carbonyl group (e.g., acetyl) optionally substituted by 1 to 3 substituents selected from
(i) a halogen atom,
(ii) a $C_{1-6}$ alkoxy group, and
(iii) a $C_{6-14}$ aryl group,
(l) a $C_{1-6}$ alkoxy-carbonyl group (e.g., ethoxycarbonyl) optionally substituted by 1 to 3 substituents selected from
(i) a halogen atom,
(ii) a $C_{1-6}$ alkoxy group, and
(iii) a $C_{6-14}$ aryl group,
(m) a $C_{6-14}$ aryloxy group (e.g., phenyloxy),
(n) a $C_{6-14}$ aryl group (e.g., phenyl) optionally substituted by 1 to 3 substituents selected from
(i) a $C_{1-6}$ alkyl group,
(ii) a hydroxy group,
(iii) a $C_{1-6}$ alkoxy group (e.g., methoxy), and
(iv) a halogen atom (e.g., chlorine atom), and
(o) a $C_{3-10}$ cycloalkyl group (e.g., cyclobutyl, cyclopentyl) optionally substituted by 1 to 3 substituents selected from
(i) a $C_{1-6}$ alkyl group (e.g., methyl),
(ii) a $C_{1-6}$ alkyl-carbonyl group (e.g., acetyl), and
(iii) an oxo group
(the $C_{3-10}$ cycloalkyl group may form a fused ring group with a benzene ring optionally substituted by a $C_{1-6}$ alkoxy group (e.g., methoxy));
(2) a $C_{3-10}$ cycloalkyl group (e.g., cyclopropyl, cyclobutyl, adamantyl) optionally substituted by 1 to 3 substituents selected from
(a) a carboxy group,
(b) a $C_{1-6}$ alkyl group (e.g., methyl),
(c) a hydroxy group, and
(d) a $C_{1-6}$ alkoxy-carbonyl group (e.g., methoxycarbonyl),
(3) a $C_{2-10}$ alkenyl group (e.g., ethenyl) optionally substituted by 1 to 3 substituents selected from
(a) a carbamoyl group optionally mono- or di-substituted by substituent(s) selected from
(i) a $C_{1-6}$ alkyl group (e.g., methyl),
(ii) a $C_{6-14}$ aryl group, and
(iii) a 4- to 7-membered aromatic heterocyclic group,
(b) a carboxy group, and
(c) a hydroxy group,
(4) a $C_{6-14}$ aryl group (e.g., phenyl) optionally substituted by 1 to 3 substituents selected from
(a) a carboxy group,
(b) a $C_{1-6}$ alkyl group (e.g., methyl) optionally substituted by 1 to 3 substituents selected from
(i) a halogen atom (e.g., chlorine atom),
(ii) a 4- to 7-membered nonaromatic heterocyclic group (e.g., pyrrolidinyl) optionally substituted by 1 to 3 substituents selected from
(A) a hydroxy group, and
(B) an oxo group, and
(iii) an amino group optionally mono- or di-substituted by substituent(s) selected from
(A) a $C_{1-6}$ alkyl group, and
(B) a 4- to 7-membered nonaromatic heterocyclic group (e.g., tetrahydrothiopyranyl) optionally substituted by an oxo group,
(c) a $C_{1-6}$ alkoxy group (e.g., methoxy, ethoxy) optionally substituted by 1 to 3 substituents selected from
(i) a carboxy group,
(ii) a hydroxy group,
(iii) a $C_{6-14}$ aryl group (e.g., phenyl),
(iv) a 4- to 7-membered nonaromatic heterocyclic group (e.g., piperidinyl, dihydrooxadiazolyl) optionally substituted by 1 to 3 substituents selected from
(A) an oxo group,
(B) a carboxy-carbonyl group optionally substituted by $C_{1-6}$ alkyl (e.g., methyl),
(C) $C_{1-6}$ alkyl (e.g., methyl), and
(D) a $C_{1-6}$ alkoxy-carbonyl group (e.g., tert-butoxycarbonyl),
(v) a $C_{1-6}$ alkoxy-carbonyl group (e.g., methoxycarbonyl),
(vi) an amino group optionally mono- or di-substituted by substituent(s) selected from
(A) a $C_{1-6}$ alkyl group (e.g., methyl),
(B) a carboxy-carbonyl group, and
(C) a $C_{1-6}$ alkylsulfonyl group (e.g., methylsulfonyl),
(vii) a 4- to 7-membered aromatic heterocyclic group (e.g., tetrazolyl), and
(viii) a carbamoyl group optionally mono- or di-substituted by substituent(s) selected from
(A) a $C_{1-6}$ alkylsulfonyl group (e.g., pentylsulfonyl),
(B) a $C_{3-10}$ cycloalkyl group, and
(C) a methylaminosulfonyl group optionally substituted by $C_{3-10}$ cycloalkyl (e.g., cyclopropyl),
(d) a halogen atom (e.g., fluorine atom),
(e) a 4- to 7-membered nonaromatic heterocyclic group (e.g., dihydrooxadiazolyl, imidazolidinyl) optionally substituted by 1 to 3 substituents selected from
(i) a carboxy group,
(ii) a $C_{1-6}$ alkyl group,
(iii) an oxo group, and
(iv) a $C_{1-6}$ alkyl group (e.g., methyl) optionally substituted by 1 to 3 substituents selected from
(A) a carboxy group, and
(B) a $C_{1-6}$ alkoxy-carbonyl group (e.g., tert-butoxycarbonyl),
(f) a cyano group,
(g) a hydroxy group,
(h) a $C_{1-6}$ alkoxy-carbonyl group (e.g., methoxycarbonyl),
(i) a 4- to 7-membered nonaromatic heterocycleoxy group (e.g., piperazinyloxy) optionally substituted by 1 to 3 substituents selected from
(i) a carboxy-carbonyl group, and
(ii) a $C_{1-6}$ alkyl group (e.g., methyl), and
(j) a $C_{6-14}$ aryl group (e.g., phenyl) optionally substituted by a $C_{1-6}$ alkyl group (e.g., methyl) optionally substituted by a carboxy group,
and the like.

The "optionally substituted hydrocarbon group" for R is more preferably
(1) a $C_{1-10}$ alkyl group (e.g., methyl, ethyl) optionally substituted by 1 to 3 substituents selected from
(a) a carbamoyl group optionally mono- or di-substituted by substituent(s) selected from
(i) a carboxy group,
(ii) a $C_{1-6}$ alkyl group,
(iii) a $C_{1-6}$ alkylsulfonyl group (e.g., methylsulfonyl),
(iv) a $C_{6-14}$ aryl group, and
(v) a 4- to 7-membered aromatic heterocyclic group,
(b) a 4- to 7-membered aromatic heterocyclylthio group (e.g., pyrazol-5-ylthio) optionally substituted by 1 to 3 substituents selected from
(i) a carboxy group,
(ii) a $C_{1-6}$ alkyl group, and
(iii) a $C_{6-14}$ aryl group, (c) a 4- to 7-membered aromatic heterocyclic group (e.g., tetrazolyl) optionally substituted by 1 to 3 substituents selected from
  (i) a carboxy group, and
  (ii) a $C_{1-6}$ alkyl group,
(d) a 4- to 7-membered nonaromatic heterocyclic group (e.g., imidazolidinyl, piperidinyl) optionally substituted by 1 to 3 substituents selected from
  (i) a carboxy group,
  (ii) a $C_{1-6}$ alkyl group, and
  (iii) an oxo group, and
(e) a hydroxy group;
(2) a $C_{3-10}$ cycloalkyl group (e.g., cyclopropyl, adamantyl) optionally substituted by 1 to 3 substituents selected from
  (a) a carboxy group,
  (b) a $C_{1-6}$ alkyl group, and
  (c) a hydroxy group;
(3) a $C_{6-14}$ aryl group (e.g., phenyl) optionally substituted by 1 to 3 substituents selected from
  (a) a carboxy group,
  (b) a $C_{1-6}$ alkyl group,
  (c) a $C_{1-6}$ alkoxy group (e.g., methoxy) optionally substituted by 1 to 3 substituents selected from
    (i) a carboxy group, and
    (ii) a hydroxy group,
  (d) a halogen atom (e.g., fluorine atom), and
  (e) a 4- to 7-membered nonaromatic heterocyclic group (e.g., dihydrooxadiazolyl) optionally substituted by 1 to 3 substituents selected from
    (i) a carboxy group,
    (ii) a $C_{1-6}$ alkyl group, and
    (iii) an oxo group
and the like.

The "optionally substituted hydrocarbon group" for R is more preferably
(1) a $C_{1-10}$ alkyl group optionally substituted by 1 to 3 substituents selected from
  (a) a carbamoyl group optionally mono- or di-substituted by
    (i) a $C_{1-6}$ alkylsulfonyl group, and
    (ii) a sulfamoyl group optionally substituted by a $C_{1-6}$ alkyl group optionally substituted by $C_{3-10}$ cycloalkyl,
  (b) a 5- or 6-membered aromatic heterocyclic group (e.g., tetrazolyl) optionally substituted by 1 to 3 substituents selected from
    (i) a carboxy group, and
    (ii) a $C_{1-6}$ alkyl group,
  (c) a 5- or 6-membered nonaromatic heterocyclic group (e.g., imidazolidinyl, piperidinyl) optionally substituted by 1 to 3 substituents selected from
    (i) a carboxy group, and
    (ii) an oxo group,
  (d) a carboxy group,
  (e) a $C_{1-6}$ alkoxy-carbonyl group,
  (f) a $C_{3-10}$ cycloalkyl group, and
  (g) a hydroxy group;
(2) a $C_{3-10}$ cycloalkyl group optionally substituted by 1 to 3 carboxy groups,
(3) a $C_{6-14}$ aryl group optionally substituted by 1 to 3 substituents selected from
  (a) a carboxy group,
  (b) a $C_{1-6}$ alkyl group optionally substituted by 1 to 3 amino groups optionally mono- or di-substituted by substituent(s) selected from
    (i) a $C_{1-6}$ alkyl group, and
    (ii) a 5- or 6-membered nonaromatic heterocyclic group (e.g., tetrahydrothiopyranyl) optionally substituted by an oxo group,
  (c) a $C_{1-6}$ alkoxy group optionally substituted by 1 to 3 substituents selected from
    (i) a carboxy group, and
    (ii) a 5- or 6-membered nonaromatic heterocyclic group optionally substituted by a carboxy-carbonyl group or a $C_{1-6}$ alkoxy-carbonyl-carbonyl group,
  (d) a 5- or 6-membered nonaromatic heterocyclic group optionally substituted by 1 to 3 substituents selected from
    (i) a carboxy group,
    (ii) an oxo group, and
    (iv) a $C_{1-6}$ alkyl group (e.g., methyl) optionally substituted by 1 to 3 substituents selected from a carboxy group and a $C_{1-6}$ alkoxy-carbonyl group (e.g., tert-butoxycarbonyl), and
  (e) a $C_{6-14}$ aryl group optionally substituted by a carboxy-$C_{1-6}$ alkyl group
and the like.

The "optionally substituted hydrocarbon group" for R is more preferably
(1) a $C_{1-10}$ alkyl group optionally substituted by 1 to 3% substituents selected from
  (a) a carbamoyl group optionally mono- or di-substituted by
    (i) a $C_{1-6}$ alkylsulfonyl group, and
    (ii) a sulfamoyl group optionally substituted by a $C_{1-6}$ alkyl group optionally substituted by $C_{3-10}$ cycloalkyl,
  (b) a 5- or 6-membered aromatic heterocyclic group (e.g., imidazolidinyl, piperidinyl) optionally substituted by 1 to 3 substituents selected from
    (i) a carboxy group, and
    (ii) a $C_{1-6}$ alkyl group,
  (c) a 5- or 6-membered nonaromatic heterocyclic group (e.g., tetrazolyl) optionally substituted by 1 to 3 carboxy groups, and
  (d) a carboxy group;
(2) a $C_{6-14}$ aryl group optionally substituted by 1 to 3 substituents selected from
  (a) a carboxy group,
  (b) a $C_{1-6}$ alkoxy group optionally substituted by 1 to 3 carboxy groups, and
  (c) a 5- or 6-membered nonaromatic heterocyclic group optionally substituted by 1 to 3 carboxy groups, and
  (d) a $C_{6-14}$ aryl group optionally substituted by a carboxy-$C_{1-6}$ alkyl group
and the like.

Examples of the "heterocyclic group" of the "optionally substituted heterocyclic group" include the aromatic heterocyclic group and the nonaromatic heterocyclic group.

The "heterocyclic group" of the aforementioned "optionally substituted heterocyclic group" optionally has 1 to 3 substituents at substitutable position(s). Examples of the substituent include the aforementioned Substituent group A and the like. When the heterocyclic group is a "nonaromatic heterocyclic group", the substituent further includes an oxo group. When two or more substituents are present, the substituents may be the same or different.

The "optionally substituted heterocyclic group" for R is preferably
(1) a 4- to 7-membered aromatic heterocyclic group (e.g., pyrazolyl, tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
- (a) a halogen atom (e.g., chlorine atom),
- (b) a hydroxy group,
- (c) a $C_{1-6}$ alkyl group (e.g., methyl, ethyl) optionally substituted by 1 to 3 substituents selected from
  - (i) a carboxy group,
  - (ii) a halogen atom (e.g., chlorine atom, fluorine atom),
  - (iii) a 4- to 7-membered nonaromatic heterocyclic group (e.g., pyrrolidinyl) optionally substituted by a hydroxy group,
  - (iv) an amino group optionally mono- or di-substituted by substituent(s) selected from
    - (A) a $C_{1-6}$ alkyl group, and
    - (B) a 4- to 7-membered nonaromatic heterocyclic group (e.g., tetrahydrothiopyranyl) optionally substituted by an oxo group, and
  - (v) a $C_{1-6}$ alkoxy-carbonyl group (e.g., methoxycarbonyl, tert-butoxycarbonyl),
- (d) a $C_{3-10}$ cycloalkyl group (e.g., cyclohexyl),
- (e) a $C_{6-14}$ aryl group (e.g., phenyl) optionally substituted by 1 to 3 substituents selected from
  - (i) a $C_{1-6}$ alkyl group,
  - (ii) a hydroxy group,
  - (iii) a $C_{1-6}$ alkoxy group, and
  - (iv) a halogen atom,
- (f) a $C_{1-6}$ alkylthio group (e.g., methylthio) optionally substituted by 1 to 3 substituents selected from
  - (i) a carboxy group,
  - (ii) a hydroxy group,
  - (iii) a $C_{1-6}$ alkoxy group (e.g., methoxy), and
  - (iv) a $C_{1-6}$ alkoxy-carbonyl group (e.g., methoxycarbonyl, ethoxycarbonyl, tert-butoxycarbonyl),
- (g) a $C_{7-13}$ aralkyloxy group (e.g., benzyloxy),
- (h) a mercapto group,
- (i) a $C_{1-6}$ alkoxy group (e.g., methoxy, ethoxy) optionally substituted by 1 to 3 substituents selected from
  - (i) a halogen atom,
  - (ii) a carboxy group,
  - (iii) a $C_{1-6}$ alkoxy group,
  - (iv) a $C_{1-6}$ alkoxy-carbonyl group (e.g., methoxycarbonyl, tert-butoxycarbonyl),
  - (v) a 4- to 7-membered nonaromatic heterocyclic group (e.g., piperidinyl, dihydrooxadiazolyl) optionally substituted by 1 to 3 substituents selected from
    - (A) an oxo group,
    - (B) a carboxy-carbonyl group, and
    - (C) a $C_{1-6}$ alkyl group (e.g., methyl),
  - (vi) an amino group optionally mono- or di-substituted by substituent(s) selected from
    - (A) a $C_{1-6}$ alkyl group (e.g., methyl),
    - (B) a carboxy-carbonyl group, and
    - (C) a $C_{1-6}$ alkylsulfonyl group (e.g., methylsulfonyl),
  - (vii) a 4- to 7-membered aromatic heterocyclic group (e.g., tetrazolyl),
  - (viii) a carbamoyl group optionally mono- or di-substituted by substituent(s) selected from
    - (A) a $C_{1-6}$ alkylsulfonyl group (e.g., pentylsulfonyl),
    - (B) a $C_{3-10}$ cycloalkyl group, and
    - (C) a methylaminosulfonyl group optionally substituted by $C_{3-10}$ cycloalkyl (e.g., cyclopropyl), and
  - (ix) a $C_{6-14}$ aryl group (e.g., phenyl),
- (j) a $C_{1-6}$ alkyl-carbonyl group (e.g., acetyl) optionally substituted by 1 to 3 substituents selected from
  - (i) a halogen atom,
  - (ii) a $C_{1-6}$ alkoxy group, and
  - (iii) a $C_{6-14}$ aryl group,
- (k) a $C_{1-6}$ alkoxy-carbonyl group (e.g., tert-butoxycarbonyl) optionally substituted by 1 to 3 substituents selected from
  - (i) a halogen atom,
  - (ii) a $C_{1-6}$ alkoxy group, and
  - (iii) a $C_{6-14}$ aryl group,
- (l) a 4- to 7-membered nonaromatic heterocycleoxy group (e.g., piperazinyloxy) optionally substituted by 1 to 3 substituents selected from
  - (i) a carboxy-carbonyl group, and
  - (ii) a $C_{1-6}$ alkyl group (e.g., methyl), and
  - (iii) a $C_{1-6}$ alkoxy-carbonyl group (tert-butoxycarbonyl),
- (m) a 4- to 7-membered nonaromatic heterocyclic group (e.g., imidazolidinyl, piperidinyl) optionally substituted by 1 to 3 substituents selected from
  - (i) a $C_{1-6}$ alkyl group (e.g., methyl) optionally substituted by a carboxy group,
  - (ii) a $C_{1-6}$ alkoxy-carbonyl group (e.g., tert-butoxycarbonyl) and
  - (iii) an oxo group, and
- (n) an amino group optionally mono- or di-substituted by substituent(s) selected from
  - (i) a carboxy-carbonyl group, and
  - (ii) a $C_{1-6}$ alkyl group, and the like, (2) a 4- to 7-membered nonaromatic heterocyclic group (e.g., pyrrolidinyl (e.g., 2-pyrrolidinyl), tetrahydrofuranyl (e.g., tetrahydrofuran-3-yl, tetrahydrofuran-2-yl), thiazolidinyl (e.g., thiazolidin-4-yl), piperidinyl (e.g., 1-piperidinyl, 2-piperidinyl, 4-piperidinyl), pyranyl (e.g., 2-pyranyl), tetrahydropyrimidinyl (e.g., tetrahydropyrimidin-4-yl, tetrahydropyrimidin-5-yl), hexahydropyrimidinyl (e.g., hexahydropyrimidin-4-yl), 5H-[1,3]thiazolo[3,2-a]pyrimidinyl (e.g., 5H-[1,3]thiazolo[3,2-a]pyrimidin-6-yl), 2-oxabicyclo[2,2,1]heptan-1-yl, dihydrobenzofuran, indolinyl, morpholinyl) optionally substituted by 1 to 3 substituents selected from
- (a) a halogen atom (e.g., chlorine atom),
- (b) a hydroxy group,
- (c) a $C_{1-6}$ alkyl group (e.g., methyl) optionally substituted by 1 to 3 substituents selected from
  - (i) a carboxy group, and
  - (ii) a halogen atom (e.g., chlorine atom),
  - (iii) a $C_{6-14}$ aryl group (e.g., phenyl), and
  - (iv) a $C_{1-6}$ alkoxy-carbonyl group (e.g., methoxycarbonyl),
- (d) a $C_{6-14}$ aryl group (e.g., phenyl) optionally substituted by 1 to 3 substituents selected from
  - (i) a $C_{1-6}$ alkyl group,
  - (ii) a hydroxy group,
  - (iii) a $C_{1-6}$ alkoxy group, and
  - (iv) a halogen atom,
- (e) a $C_{1-6}$ alkylthio group (e.g., methylthio) optionally substituted by 1 to 3 substituents selected from
  - (i) a carboxy group,
  - (ii) a hydroxy group,
  - (iii) a $C_{1-6}$ alkoxy group (e.g., methoxy), and
  - (iv) a $C_{1-6}$ alkoxy-carbonyl group (e.g., methoxycarbonyl, tert-butoxycarbonyl),
- (f) a $C_{7-13}$ aralkyloxy group (e.g., benzyloxy),
- (g) a mercapto group,
- (h) a $C_{1-6}$ alkoxy group (e.g., methoxy) optionally substituted by 1 to 3 substituents selected from
  - (i) a halogen atom,
  - (ii) a carboxy group,
  - (iii) a $C_{1-6}$ alkoxy group, and
  - (iv) a $C_{1-6}$ alkoxy-carbonyl group (e.g., methoxycarbonyl, tert-butoxycarbonyl);

(i) a $C_{1-6}$ alkyl-carbonyl group (e.g., acetyl) optionally substituted by 1 to 3 substituents selected from
  (i) a halogen atom,
  (ii) a $C_{1-6}$ alkoxy group,
  (iii) a $C_{6-14}$ aryl group, and
  (iv) a carboxy group,
(j) a $C_{1-6}$ alkoxy-carbonyl group (e.g., tert-butoxycarbonyl) optionally substituted by 1 to 3 substituents selected from
  (i) a halogen atom,
  (ii) a $C_{1-6}$ alkoxy group, and
  (iii) a $C_{6-14}$ aryl group,
(k) an oxo group, and
(l) a carboxy group,
and the like,
and the like.

The "optionally substituted heterocyclic group" for R is more preferably
(1) a 4- to 7-membered aromatic heterocyclic group (e.g., triazolyl, oxazolyl, pyridyl) optionally substituted by 1 to 3 substituents selected from
  (a) a $C_{1-6}$ alkyl group (e.g., methyl) optionally substituted by 1 to 3 substituents selected from
    (i) a carboxy group,
    (ii) a $C_{1-6}$ alkoxy-carbonyl group, and
    (iii) a halogen atom (e.g., chlorine atom),
  (b) a $C_{6-14}$ aryl group (e.g., phenyl),
  (c) a $C_{1-6}$ alkoxy group (e.g., methoxy) optionally substituted by 1 to 3 substituents selected from
    (i) a halogen atom,
    (ii) a $C_{1-6}$ alkoxy-carbonyl group,
    (iii) a carboxy group, and
    (iv) a $C_{6-14}$ aryl group,
  (d) a hydroxy group,
  (e) a $C_{3-10}$ cycloalkyl group,
  (f) a 4- to 7-membered nonaromatic heterocyclic group optionally substituted by 1 to 3 $C_{1-6}$ alkoxycarbonyl groups,
and the like,
(2) a 4- to 7-membered nonaromatic heterocyclic group (e.g., piperidinyl, 5H-[1,3]thiazolo[3,2-a]pyrimidinyl) optionally substituted by 1 to 3 substituents selected from
  (a) a $C_{1-6}$ alkyl-carbonyl group (e.g., acetyl),
  (b) an oxo group,
  (c) a $C_{6-14}$ aryl group,
and the like,
and the like.

The "optionally substituted heterocyclic group" for R is more preferably a 5- or 6-membered aromatic heterocyclic group optionally substituted by 1 to 3 substituents selected from
  (a) a $C_{1-6}$ alkyl group optionally substituted by 1 to 3 carboxy groups,
  (b) a $C_{1-6}$ alkoxy group optionally substituted by 1 to 3 carboxy groups, and
  (c) a $C_{1-6}$ alkylthio group optionally substituted by 1 to 3 carboxy groups
and the like.

The "optionally substituted heterocyclic group" for R is more preferably a 5- or 6-membered aromatic heterocyclic group optionally substituted by 1 to 3 substituents selected from
  (a) a $C_{1-6}$ alkyl group optionally substituted by 1 to 3 carboxy groups, and
  (b) a $C_{1-6}$ alkoxy group optionally substituted by 1 to 3 carboxy groups
and the like.

Examples of the "optionally substituted hydroxy group" for R include a hydroxy group optionally substituted by a substituent selected from $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group, 4- to 7-membered heterocyclic group etc., each of which is optionally substituted.

The aforementioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and 4- to 7-membered heterocyclic group each optionally have 1 to 3 substituents at substitutable position(s). When two or more substituents are present, the substituents may be the same or different.

Here, examples of the substituent of the $C_{1-10}$ alkyl group, $C_{2-10}$ alkenyl group and $C_{1-6}$ alkyl-carbonyl group include the aforementioned Substituent group B and the like.

Examples of the substituent of the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include the aforementioned Substituent group A and the like.

Examples of the substituent of the 4- to 7-membered heterocyclic group include the aforementioned Substituent group A and the like. When the 4- to 7-membered heterocyclic group is a "nonaromatic 4- to 7-membered heterocyclic group", the substituent further includes an oxo group.

The "optionally substituted hydroxy group" for R is preferably a hydroxy group optionally substituted by substituent selected from
(1) a $C_{1-6}$ alkyl group optionally substituted by 1 to 3 halogen atoms;
(2) a $C_{3-10}$ cycloalkyl group;
(3) a $C_{6-14}$ aryl group;
(4) a $C_{7-13}$ aralkyl group
and the like, and the like.

The "optionally substituted hydroxy group" for R is more preferably a hydroxy group optionally substituted by substituent selected from
  (a) a $C_{1-6}$ alkyl group (e.g., ethyl, isopropyl, tert-butyl) optionally substituted by 1 to 3 halogen atoms (e.g., chlorine atom), and
  (b) a $C_{6-14}$ aryl group (e.g., phenyl).

Examples of the "optionally substituted mercapto group" for R include a mercapto group optionally substituted by substituent selected from $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group, 4- to 7-membered heterocyclic group and the like, each of which are optionally substituted.

Examples of the substituent include those similar to the substituent of the aforementioned "optionally substituted hydroxy group".

The "optionally substituted mercapto group" for R is preferably a mercapto group optionally substituted by substituent selected from
(1) a $C_{1-8}$ alkyl group;
(2) a $C_{3-10}$ cycloalkyl group;
(3) a $C_{8-14}$ aryl group;
(4) a $C_{7-13}$ aralkyl group
and the like, and the like.

Examples of the "optionally substituted amino group" for R include an amino group optionally mono- or di-substituted by substituent(s) selected from $C_{1-10}$ alkyl group, $C_{2-10}$ alkenyl group, $C_{3-10}$ cycloalkyl group, $C_{3-10}$ cycloalkenyl group, $C_{8-14}$ aryl group, $C_{7-13}$ aralkyl group, $C_{8-13}$ arylalkenyl group and 4- to 7-membered heterocyclic group, each of which are optionally substituted, an acyl group, and the like.

The $C_{1-10}$ alkyl group, $C_{2-10}$ alkenyl group, $C_{3-10}$ cycloalkyl group, $C_{3-10}$ cycloalkenyl group, $C_{8-14}$ aryl group, $C_{7-13}$ aralkyl group, $C_{8-13}$ arylalkenyl group and 4- to 7-membered heterocyclic group each optionally have 1 to 3 substituents at substitutable position(s). When two or more substituents are present, the substituents may be the same or different.

Here, examples of the substituent of the $C_{1-10}$ alkyl group and $C_{2-10}$ alkenyl group include the aforementioned Substituent group B and the like.

Examples of the substituent of the $C_{3-10}$ cycloalkyl group, $C_{3-10}$ cycloalkenyl group, $C_{8-14}$ aryl group, $C_{7-13}$ aralkyl group and $C_{8-13}$ arylalkenyl group include the aforementioned Substituent group A and the like.

Examples of the substituent of the 4- to 7-membered heterocyclic group include the aforementioned Substituent group A and the like. When the 4- to 7-membered heterocyclic group is a "4- to 7-membered nonaromatic heterocyclic group", the substituent further includes an oxo group.

Examples of the "acyl group" exemplified as the substituent of the "optionally substituted amino group" for R include groups represented by the formulas: —$COR^{A1}$, —CO—$OR^{A1}$, $SO_3R^{A1}$, —$SO_2R^{A1}$, $SOR^{A1}$, —CO—$NR^{A2}R^{B2}$, —CS—$NR^{A2}R^{B2}$ and —$SO_2NR^{A2}R^{B2}$ wherein $R^{A1}$ is a hydrogen atom, an optionally substituted hydrocarbon group, or an optionally substituted heterocyclic group. $R^{A2}$ and $R^{B2}$ are each independently a hydrogen atom, a sulfamoyl group optionally mono- or di-substituted by a $C_{1-6}$ alkyl group, a sulfonyl group optionally mono- or di-substituted by a $C_{1-6}$ alkyl group, an optionally substituted hydrocarbon group or an optionally substituted heterocyclic group, or $R^{A2}$ and $R^{B2}$ form an optionally substituted nitrogen-containing heterocycle together with the adjacent nitrogen atom, and the like.

Examples of the "optionally substituted hydrocarbon group" and "optionally substituted heterocyclic group" for $R^{A1}$, $R^{A2}$ or $R^{B2}$ include those similar to the "optionally substituted hydrocarbon group" and "optionally substituted heterocyclic group" exemplified as the "substituent" for R.

Examples of the "nitrogen-containing heterocycle" of the "optionally substituted nitrogen-containing heterocycle" formed by $R^{A2}$ and $R^{B2}$ together with the adjacent nitrogen atom include a 5- to 7-membered nitrogen-containing heterocycle containing, as a ring constituting atom besides carbon atom, at least one nitrogen atom, and optionally further containing 1 or 2 hetero atoms selected from an oxygen atom, a sulfur atom and a nitrogen atom. Preferable examples of the 5- or 6-membered nitrogen-containing heterocycle include pyrrolidine, imidazolidine, pyrazolidine, piperidine, piperazine, morpholine, thiomorpholine and the like.

The nitrogen-containing heterocycle optionally has 1 to 3 substituents at substitutable position(s). Examples of the substituent include the aforementioned Substituent group A and the like. When two or more substituents are present, the substituents may be the same or different.

The "optionally substituted amino group" for R is preferably an amino group optionally mono- or di-substituted by substituent(s) selected from
(1) $C_{3-10}$ cycloalkyl group,
(2) a $C_{6-14}$ aryl group (e.g., phenyl group) optionally substituted by 1 to 3 substituents selected from
  (i) a hydroxy group,
  (ii) a carbamoyl group,
  (iii) a $C_{1-6}$ alkyl group, and
  (iv) a $C_{1-6}$ alkoxy group (e.g., methoxy) optionally substituted by 1 to 3 substituents selected from
    (A) a carboxy group,
    (B) a $C_{6-14}$ aryl group (e.g., phenyl), and
    (C) a $C_{1-6}$ alkoxy-carbonyl group (e.g., methoxycarbonyl);
(3) a $C_{1-6}$ alkyl group (e.g., methyl, ethyl) optionally substituted by 1 to 3 substituents selected from
  (i) a carboxy group,
  (ii) a $C_{1-6}$ alkoxy group, and
  (iii) a $C_{1-6}$ alkoxy-carbonyl group (e.g., ethoxycarbonyl),
(4) a $C_{7-13}$ aralkyl group,
(5) a 4- to 7-membered aromatic heterocyclic group (e.g., triazolyl, tetrazolyl, thiazolyl, pyridyl) optionally substituted by 1 to 3 substituents selected from
  (i) a hydroxy group,
  (ii) a carbamoyl group, and
  (iii) a $C_{1-6}$ alkyl group (e.g., methyl) optionally substituted by a carboxy group, and
(6) a 4- to 7-membered nonaromatic heterocyclic group (e.g., piperidinyl, morpholinyl) optionally substituted by 1 to 3 substituents selected from
  (i) a hydroxy group,
  (ii) a carbamoyl group,
  (iii) a $C_{1-6}$ alkyl group, and
  (iv) an oxo group,
and the like, and the like.

The "optionally substituted amino group" for R is more preferably an amino group optionally mono- or di-substituted by substituent(s) selected from
(1) a $C_{6-14}$ aryl group (e.g., phenyl group) optionally substituted by 1 to 3 substituents selected from
  (i) a hydroxy group, and
  (ii) a $C_{1-6}$ alkoxy group (e.g., methoxy) optionally substituted by 1 to 3 substituents selected from
    (A) a carboxy group,
    (B) a $C_{6-14}$ aryl group, and
    (C) a $C_{1-6}$ alkoxy-carbonyl group;
(2) a $C_{1-6}$ alkyl group (e.g., methyl, ethyl) optionally substituted by 1 to 3 substituents selected from
  (i) a carboxy group, and
  (ii) a $C_{1-6}$ alkoxy-carbonyl group (e.g., ethoxycarbonyl);
(3) a 5- or 6-membered aromatic heterocyclic group (e.g., triazolyl, tetrazolyl, pyridyl) optionally substituted by 1 to 3 substituents selected from
  (i) a hydroxy group, and
  (ii) a carbamoyl group;
(4) a 5- or 6-membered nonaromatic heterocyclic group (e.g., piperidinyl, morpholinyl) optionally substituted by 1 to 3 substituents selected from
  (i) a hydroxy group, and
  (ii) a carbamoyl group,
and the like, and the like.

The "optionally substituted amino group" for R is preferably an amino group optionally mono- or di-substituted by substituent(s) selected from
(a) a $C_{6-14}$ aryl group optionally substituted by 1 to 3 carboxy-$C_{1-6}$ alkoxy groups,
(b) a $C_{1-6}$ alkyl group optionally substituted by 1 to 3 carboxy groups, and
(c) a 5- or 6-membered aromatic heterocyclic group is optionally substituted by 1 to 3 substituents selected from
  (i) a hydroxy group, and
  (ii) a carbamoyl group
and the like.

Examples of the "acyl group" for R include those similar to the "acyl group" exemplified as the substituent of the abovementioned "optionally substituted amino group" for R.

The "acyl group" for R is preferably
(1) a formyl group,
(2) a carboxy group,
(3) a $C_{1-6}$ alkyl-carbonyl group (e.g., isobutylcarbonyl) optionally substituted by 1 to 3 substituents selected from (a) a halogen atom,
(b) a $C_{1-6}$ alkoxy-carbonyl group,
(c) a $C_{6-14}$ aryl group, and
(d) a $C_{1-6}$ alkoxy group,
(4) a $C_{1-6}$ alkoxy-carbonyl group (e.g., ethoxycarbonyl) optionally substituted by 1 to 3 substituents selected from
(a) a halogen atom,
(b) a $C_{6-14}$ aryl group, and
(c) a $C_{1-6}$ alkoxy group,
(5) a $C_{3-10}$ cycloalkyl-carbonyl group (e.g., cyclopropylcarbonyl, cyclopentylcarbonyl, cyclohexylcarbonyl),
(6) a $C_{6-14}$ aryl-carbonyl group (e.g., benzoyl) optionally substituted by 1 to 3 halogen atoms,
(7) a carbamoyl group optionally mono- or di-substituted by substituent(s) selected from
(a) a $C_{1-6}$ alkyl group (e.g., methyl, ethyl, isopropyl isobutyl, tert-butyl) optionally substituted by 1 to 3 substituents selected from
(i) a halogen atom,
(ii) a $C_{1-6}$ alkoxy-carbonyl group (e.g., methoxycarbonyl) optionally substituted by 1 to 3 $C_{6-14}$ aryl groups (e.g., phenyl),
(iii) a $C_{6-14}$ aryl group (e.g., phenyl) optionally substituted by 1 to 3 substituents selected from
(A) a $C_{1-6}$ alkoxy-carbonyl group (e.g., methoxycarbonyl) and
(B) a carboxy group,
(iv) a $C_{1-6}$ alkoxy group,
(v) a hydroxy group,
(vi) a 4- to 7-membered aromatic heterocyclic group,
(vii) a carboxy group,
(viii) a $C_{3-10}$ cycloalkyl group (e.g., cyclopropyl), and
(ix) a $C_{1-6}$ alkylsulfonyl group (e.g., methylsulfonyl),
(b) a $C_{3-10}$ cycloalkyl group,
(c) a $C_{6-14}$ aryl group (e.g., phenyl) optionally substituted by 1 to 3 substituents selected from
(i) a halogen atom,
(ii) a $C_{1-6}$ alkyl group (e.g., ethyl) optionally substituted by 1 to 3 substituents selected from
(A) a halogen atom,
(B) a carboxy group, and
(C) a $C_{1-6}$ alkoxy-carbonyl group (e.g., methoxycarbonyl), and
(iii) a $C_{1-6}$ alkoxy group (e.g., methoxy) optionally substituted by 1 to 3 substituents selected from
(A) a carboxy group,
(B) a $C_{1-6}$ alkoxy-carbonyl group (e.g., methoxycarbonyl), and
(C) a $C_{6-14}$ aryl group (e.g., phenyl),
(iv) a hydroxy group,
(d) a 4- to 7-membered aromatic heterocyclic group (e.g., pyridyl (e.g., 2-pyridyl), thiazolyl) optionally substituted by 1 to 3 substituents selected from
(i) a carboxy group, and
(ii) a $C_{1-6}$ alkyl group optionally substituted by a carboxy group,
(e) a sulfamoyl group optionally mono- or di-substituted by a $C_{1-6}$ alkyl group (e.g., methyl) optionally substituted by a $C_{3-10}$ cycloalkyl group (e.g., cyclopropyl),
(f) a sulfonyl group optionally mono- or di-substituted by a $C_{1-6}$ alkyl group (e.g., pentyl),
(g) a $C_{1-6}$ alkoxy group, and
(h) a 4- to 7-membered nonaromatic heterocyclic group (e.g., pyrrolidinyl, piperidinyl, tetrahydrothiopyranyl) optionally substituted by 1 to 3 substituents selected from
(i) a carboxy group,
(ii) a $C_{1-6}$ alkyl-carbonyl group (e.g., acetyl),
(iii) a $C_{1-6}$ alkoxy-carbonyl group (e.g., tert-butoxycarbonyl, ethoxycarbonyl),
(iv) a $C_{1-6}$ alkoxy-carbonyl-carbonyl group,
(v) a carboxy-carbonyl group,
(vi) a carboxy-carbonyl group (e.g., ethoxycarbonyl),
(vii) a carbamoyl group optionally mono- or di-substituted by $C_{1-6}$ alkyl groups (e.g., ethyl), and
(viii) a $C_{1-6}$ alkyl-sulfonyl group (e.g., methylsulfonyl), and
(ix) an oxo group;
(8) a $C_{1-6}$ alkylsulfonyl group optionally substituted by 1 to 3 substituents selected from
(a) a halogen atom, and
(b) a $C_{6-14}$ aryl group,
(9) a $C_{6-14}$ arylsulfonyl group optionally substituted by 1 to 3 halogen atoms,
(10) a sulfamoyl group optionally mono- or di-substituted by substituent(s) selected from $C_{1-6}$ alkyl groups optionally substituted by 1 to 3 substituents selected from
(a) a halogen atom, and
(b) a 4- to 7-membered nonaromatic heterocyclic group optionally substituted by an oxo group,
(11) a thiocarbamoyl group optionally mono- or di-substituted by substituent(s) selected from a $C_{1-6}$ alkyl group optionally substituted by 1 to 3 halogen atoms,
(12) a 4- to 7-membered heterocyclylcarbonyl group optionally substituted by 1 to 3 substituents selected from $C_{1-6}$ alkyl groups optionally substituted by 1 to 3 halogen atoms,
(13) a 4- to 7-membered nonaromatic heterocyclylcarbonyl group (e.g., piperidinylcarbonyl, pyrrolidinylcarbonyl) optionally substituted by 1 to 3 substituents selected from
(a) a carboxy group,
(b) a $C_{1-6}$ alkoxy group optionally substituted by a carboxy group,
(c) a $C_{1-6}$ alkyl group optionally substituted by 1 to 3 halogen atoms, and
(d) a $C_{1-6}$ alkoxy-carbonyl group (e.g., methoxycarbonyl), and the like.

The "acyl group" for R is more preferably
(1) a carboxy group;
(2) a $C_{1-6}$ alkyl-carbonyl group (e.g., isobutylcarbonyl);
(3) a $C_{1-6}$ alkoxy-carbonyl group (e.g., ethoxycarbonyl);
(4) a $C_{6-14}$ aryl-carbonyl group (e.g., benzoyl) optionally substituted by 1 to 3 halogen atoms;
(5) a carbamoyl group optionally mono- or di-substituted by substituent(s) selected from
(a) a $C_{1-6}$ alkyl group (e.g., methyl, ethyl, isopropyl) optionally substituted by 1 to 3 substituents selected from
(i) a halogen atom,
(ii) a $C_{6-14}$ aryl group (e.g., phenyl) optionally substituted by 1 to 3 substituents selected from
(A) a $C_{1-6}$ alkoxy-carbonyl group (e.g., methoxycarbonyl), and
(B) a carboxy group, and
(iii) a hydroxy group,
(b) a $C_{6-14}$ aryl group (e.g., phenyl) optionally substituted by 1 to 3 substituents selected from
(i) a halogen atom,
(ii) a $C_{1-6}$ alkyl group (e.g., ethyl) optionally substituted by 1 to 3 substituents selected from
(A) a halogen atom,
(B) a carboxy group, and
(C) a $C_{1-6}$ alkoxy-carbonyl group (e.g., methoxycarbonyl), and
(iii) a $C_{1-6}$ alkoxy group (e.g., methoxy) optionally substituted from (A) a carboxy group,
(B) a $C_{1-6}$ alkoxy-carbonyl group (e.g., methoxycarbonyl),
(C) a $C_{6-14}$ aryl group (e.g., phenyl), and
(D) a $C_{6-14}$ aryl group,
(iv) a hydroxy group,
(c) a 4- to 7-membered aromatic heterocyclic group (e.g., pyridyl) optionally substituted by 1 to 3 substituents selected from
(i) a carboxy group, and
(ii) a $C_{1-6}$ alkyl group optionally substituted by a carboxy group,
(d) a 4- to 7-membered nonaromatic heterocyclic group (e.g., pyrrolidinyl, piperidinyl, thiopyranyl) optionally substituted by 1 to 3 substituents selected from
(i) a carboxy group,
(ii) a $C_{1-6}$ alkyl-carbonyl group,
(iii) a $C_{1-6}$ alkoxy-carbonyl group (e.g., tert-butoxycarbonyl),
(iv) a $C_{1-6}$ alkoxy-carbonyl-carbonyl group,
(v) a carboxy-carbonyl group,
(vi) a carboxy-carbonyl group (e.g., ethoxycarbonyl),
(vii) a carbamoyl group optionally mono- or di-substituted by $C_{1-6}$ alkyl groups (e.g., ethyl),
(viii) a $C_{1-6}$ alkyl-sulfonyl group (e.g., methylsulfonyl), and
(ix) an oxo group,
(e) a sulfamoyl group optionally mono- or di-substituted by a $C_{1-6}$ alkyl group (e.g., methyl) optionally substituted by a $C_{3-10}$ cycloalkyl group (e.g., cyclopropyl), and
(f) a sulfonyl group optionally mono- or di-substituted by a $C_{1-6}$ alkyl group (e.g., pentyl);
(6) a 4- to 7-membered nonaromatic heterocyclylcarbonyl group (e.g., piperidinylcarbonyl, pyrrolidinylcarbonyl) optionally substituted by 1 to 3 substituents selected from
(a) a carboxy group,
(b) a $C_{1-6}$ alkoxy group optionally substituted by a carboxy group,
(c) a $C_{1-6}$ alkyl group optionally substituted by 1 to 3 halogen atoms, and
(d) a $C_{1-6}$ alkoxy-carbonyl group (e.g., methoxycarbonyl), and the like.
The "acyl group" for R is more preferably
(1) a carboxy group;
(2) a carbamoyl group optionally mono- or di-substituted by substituents selected from
(a) a $C_{1-6}$ alkyl group optionally substituted by 1 to 3 substituents selected from
(i) a $C_{6-14}$ aryl group optionally substituted by 1 to 3 substituents selected from
(A) a carboxy group,
(B) a carboxy-$C_{1-6}$ alkyl group, and
(C) a $C_{1-6}$ alkoxy-carbonyl group,
(ii) a carboxy group, and
(iii) a $C_{1-6}$ alkyl-sulfonyl group,
(b) a $C_{6-14}$ aryl group optionally substituted by 1 to 3 substituents selected from
(i) a carboxy-$C_{1-6}$ alkyl groups, and
(ii) carboxy-$C_{1-6}$ alkoxy groups,
(c) a 5- or 6-membered nonaromatic heterocyclic group optionally substituted by 1 to 3 substituents selected from
(i) a carboxy group,
(ii) a carboxy-carbonyl group, and
(iii) a carboxy-$C_{1-6}$ alkoxy group, and
(d) a $C_{1-6}$ alkyl-sulfamoyl group optionally substituted by 1 to 3 $C_{3-10}$ cycloalkyl groups, or (3) a 5- or 6-membered nonaromatic heterocyclylcarbonyl group optionally substituted by 1 to 3 carboxy groups,
and the like.
The "acyl group" for R is more preferably
(1) a carboxy group;
(2) a carbamoyl group optionally mono- or di-substituted by substituents selected from
(a) a $C_{1-6}$ alkyl group optionally substituted by 1 to 3 substituents selected from
(i) a $C_{6-14}$ aryl group optionally substituted by 1 to 3 substituents selected from
(A) a carboxy group, and
(B) a carboxy-$C_{1-6}$ alkyl group,
(ii) a carboxy group, and
(iii) a $C_{1-6}$ alkyl-sulfonyl group, and
(b) a 5- or 6-membered nonaromatic heterocyclic group optionally substituted by 1 to 3 substituents selected from
(i) a carboxy group,
(ii) a carboxy-carbonyl group, and
(iii) a carboxy-$C_{1-6}$ alkoxy group,
and the like.
R is preferably
(1) an optionally substituted hydrocarbon group,
(2) an optionally substituted heterocyclic group,
(3) an optionally substituted hydroxy group,
(4) an optionally substituted amino group, or
(5) an acyl group.
In addition, R is preferably
(1) an optionally substituted hydrocarbon group,
(2) an optionally substituted heterocyclic group,
(3) an optionally substituted amino group, or
(4) an acyl group.
R is more preferably
(1) a $C_{1-10}$ alkyl group (e.g., methyl, ethyl, propyl, isopropyl, tert-butyl, isobutyl, pentyl) optionally substituted by 1 to 3 substituents selected from
(a) a carbamoyl group optionally mono- or di-substituted by substituent(s) selected from
(i) a carboxy group,
(ii) a $C_{1-6}$ alkyl group (e.g., methyl) optionally substituted by 1 to 3 substituents selected from
(A) a carboxy group, and
(B) a $C_{6-14}$ aryl group (e.g., phenyl) optionally substituted by a carboxy group,
(iii) a $C_{1-6}$ alkylsulfonyl group (e.g., methylsulfonyl),
(iv) a $C_{6-14}$ aryl group,
(v) a 4- to 7-membered aromatic heterocyclic group, and
(vi) a sulfamoyl group optionally substituted by a $C_{1-6}$ alkyl group (e.g., methyl) optionally substituted by a $C_{3-10}$ cycloalkyl (e.g., cyclopropyl),
(b) a 4- to 7-membered aromatic heterocyclylthio group (e.g., pyrazolylthio (e.g., pyrazol-5-ylthio), tetrazolylthio (e.g., tetrazol-5-ylthio), benzimidazolylthio (e.g., benzimidazol-2-ylthio)) optionally substituted by 1 to 3 substituents selected from
(i) a carboxy group,
(ii) a $C_{1-6}$ alkyl group (e.g., methyl) optionally substituted by a carboxy group, and
(iii) a $C_{6-14}$ aryl group,
(c) a 4- to 7-membered aromatic heterocyclic group (e.g., tetrazolyl (e.g., tetrazol-5-yl, tetrazol-1-yl), imidazolyl) optionally substituted by 1 to 3 substituents selected from
(i) a carboxy group,
(ii) a $C_{1-6}$ alkyl group, and
(iii) a $C_{1-6}$ alkylthio group (e.g., methylthio) optionally substituted by a carboxy group, (d) a 4- to 7-membered nonaromatic heterocyclic group (e.g., imidazolidinyl (e.g., imidazolidin-5-yl), piperidinyl (e.g., piperidin-4-yl)) optionally substituted by 1 to 3 substituents selected from
  (i) a carboxy group,
  (ii) a $C_{1-6}$ alkyl group (e.g., methyl) optionally substituted by 1 to 3 substituents selected from
    (A) a carboxy group,
    (B) a $C_{1-6}$ alkoxy-carbonyl group (e.g., methoxycarbonyl) optionally substituted by a $C_{6-14}$ aryl group (e.g., phenyl), and
    (C) a $C_{6-14}$ aryl group (e.g., phenyl) optionally substituted by a $C_{1-6}$ alkoxy-carbonyl group (e.g., methoxycarbonyl),
  (iii) an oxo group, and
  (iv) a $C_{7-13}$ aralkyl group (e.g., benzyl) optionally substituted by a carboxy group,
(e) a halogen atom,
(f) a cyano group,
(g) a hydroxy group,
(h) a carboxy group,
(i) a $C_{1-6}$ alkoxy group (e.g., methoxy, ethoxy) optionally substituted by 1 to 3 substituents selected from
  (i) a halogen atom,
  (ii) a carboxy group,
  (iii) a $C_{1-6}$ alkoxy group,
  (iv) a $C_{1-6}$ alkoxy-carbonyl group, and
  (v) a $C_{6-14}$ aryl group (e.g., phenyl),
(j) an amino group optionally mono- or di-substituted by substituent(s) selected from
  (i) a $C_{1-6}$ alkyl group,
  (ii) a $C_{1-6}$ alkyl-carbonyl group (e.g., acetyl),
  (iii) $C_{6-14}$ aryl-carbonyl group (e.g., benzoyl),
  (iv) a $C_{1-6}$ alkoxy-carbonyl group (e.g., tert-butoxycarbonyl),
  (v) a $C_{1-6}$ alkylsulfonyl group,
  (vi) a carbamoyl group optionally mono- or di-substituted by a $C_{1-6}$ alkyl group, and
  (vii) a 4- to 7-membered aromatic heterocyclic group,
(k) a $C_{1-6}$ alkyl-carbonyl group (e.g., acetyl) optionally substituted by 1 to 3 substituents selected from
  (i) a halogen atom,
  (ii) a $C_{1-6}$ alkoxy group, and
  (iii) a $C_{6-14}$ aryl group,
(l) a $C_{1-6}$ alkoxy-carbonyl group (e.g., ethoxycarbonyl) optionally substituted by 1 to 3 substituents selected from
  (i) a halogen atom,
  (ii) a $C_{1-6}$ alkoxy group, and
  (iii) a $C_{6-14}$ aryl group,
(m) a $C_{6-14}$ aryloxy group (e.g., phenyloxy),
(n) a $C_{6-14}$ aryl group (e.g., phenyl) optionally substituted by 1 to 3 substituents selected from
  (i) a $C_{1-6}$ alkyl group,
  (ii) a hydroxy group,
  (iii) a $C_{1-6}$ alkoxy group (e.g., methoxy), and
  (iv) a halogen atom (e.g., chlorine atom), and
(o) a $C_{3-10}$ cycloalkyl group (e.g., cyclobutyl, cyclopentyl) optionally substituted by 1 to 3 substituents selected from
  (i) a $C_{1-6}$ alkyl group (e.g., methyl),
  (ii) a $C_{1-6}$ alkyl-carbonyl group (e.g., acetyl), and
  (iii) an oxo group
(the $C_{3-10}$ cycloalkyl group may form a fused ring group with a benzene ring optionally substituted by a $C_{1-6}$ alkoxy group (e.g., methoxy));
(2) a $C_{3-10}$ cycloalkyl group (e.g., cyclopropyl, cyclobutyl, adamantyl) optionally substituted by 1 to 3 substituents selected from
  (a) a carboxy group,
  (b) a $C_{1-6}$ alkyl group (e.g., methyl),
  (c) a hydroxy group, and
  (d) a $C_{1-6}$ alkoxy-carbonyl group (e.g., methoxycarbonyl),
(3) a $C_{2-10}$ alkenyl group (e.g., ethenyl) optionally substituted by 1 to 3 substituents selected from
  (a) a carbamoyl group optionally mono- or di-substituted by substituent(s) selected from
    (i) a $C_{1-6}$ alkyl group (e.g., methyl),
    (ii) a $C_{6-14}$ aryl group, and
    (iii) a 4- to 7-membered aromatic heterocyclic group,
  (b) a carboxy group, and
  (c) a hydroxy group,
(4) a $C_{6-14}$ aryl group (e.g., phenyl) optionally substituted by 1 to 3 substituents selected from
  (a) a carboxy group,
  (b) a $C_{1-6}$ alkyl group (e.g., methyl) optionally substituted by 1 to 3 substituents selected from
    (i) a halogen atom (e.g., chlorine atom),
    (ii) a 4- to 7-membered nonaromatic heterocyclic group (e.g., pyrrolidinyl) optionally substituted by 1 to 3 substituents selected from
      (A) a hydroxy group, and
      (B) an oxo group, and
    (iii) an amino group optionally mono- or di-substituted by substituent(s) selected from
      (A) a $C_{1-6}$ alkyl group, and
      (B) a 4- to 7-membered nonaromatic heterocyclic group (e.g., tetrahydrothiopyranyl) optionally substituted by an oxo group,
  (c) a $C_{1-6}$ alkoxy group (e.g., methoxy, ethoxy) optionally substituted by 1 to 3 substituents selected from
    (i) a carboxy group,
    (ii) a hydroxy group,
    (iii) a $C_{6-14}$ aryl group (e.g., phenyl),
    (iv) a 4- to 7-membered nonaromatic heterocyclic group (e.g., piperidinyl, dihydrooxadiazolyl) optionally substituted by 1 to 3 substituents selected from
      (A) an oxo group,
      (B) a carboxy-carbonyl group optionally substituted by $C_{1-6}$ alkyl (e.g., methyl),
      (C) $C_{1-6}$ alkyl (e.g., methyl), and
      (D) a $C_{1-6}$ alkoxy-carbonyl group (e.g., tert-butoxycarbonyl),
    (v) a $C_{1-6}$ alkoxy-carbonyl group (e.g., methoxycarbonyl),
    (vi) an amino group optionally mono- or di-substituted by substituent(s) selected from
      (A) a $C_{1-6}$ alkyl group (e.g., methyl),
      (B) a carboxy-carbonyl group, and
      (C) a $C_{1-6}$ alkylsulfonyl group (e.g., methylsulfonyl),
    (vii) a 4- to 7-membered aromatic heterocyclic group (e.g., tetrazolyl), and
    (viii) a carbamoyl group optionally mono- or di-substituted by substituent(s) selected from
      (A) a $C_{1-6}$ alkylsulfonyl group (e.g., pentylsulfonyl),
      (B) a $C_{3-10}$ cycloalkyl group, and
      (C) a methylaminosulfonyl group optionally substituted by $C_{3-10}$ cycloalkyl (e.g., cyclopropyl),
  (d) a halogen atom (e.g., fluorine atom),
  (e) a 4- to 7-membered nonaromatic heterocyclic group (e.g., dihydrooxadiazolyl, imidazolidinyl) optionally substituted by 1 to 3 substituents selected from
    (i) a carboxy group,
    (ii) a $C_{1-6}$ alkyl group,
    (iii) an oxo group, and
    (iv) a $C_{1-6}$ alkyl group (e.g., methyl) optionally substituted by (A) a carboxy group, and
(B) a $C_{1-6}$ alkoxy-carbonyl group (e.g., tert-butoxycarbonyl),
(f) a cyano group,
(g) a hydroxy group,
(i) a $C_{1-6}$ alkoxy-carbonyl group (e.g., methoxycarbonyl),
(h) a 4- to 7-membered nonaromatic heterocycleoxy group (e.g., piperazinyloxy) optionally substituted by 1 to 3 substituents selected from
  (i) a carboxy-carbonyl group, and
  (ii) a $C_{1-6}$ alkyl group (e.g., methyl), and
(j) a $C_{6-14}$ aryl group (e.g., phenyl) optionally substituted by a $C_{1-6}$ alkyl group (e.g., methyl) optionally substituted by a carboxy group,
(5) a 4- to 7-membered aromatic heterocyclic group (e.g., pyrazolyl, tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
  (a) a halogen atom (e.g., chlorine atom),
  (b) a hydroxy group,
  (c) a $C_{1-6}$ alkyl group (e.g., methyl, ethyl) optionally substituted by 1 to 3 substituents selected from
    (i) a carboxy group,
    (ii) a halogen atom (e.g., chlorine atom, fluorine atom),
    (iii) a 4- to 7-membered nonaromatic heterocyclic group (e.g., pyrrolidinyl) optionally substituted by a hydroxy group,
    (iv) an amino group optionally mono- or di-substituted by substituent(s) selected from
      (A) a $C_{1-6}$ alkyl group, and
      (B) a 4- to 7-membered nonaromatic heterocyclic group (e.g., tetrahydrothiopyranyl) optionally substituted by an oxo group, and
    (v) a $C_{1-6}$ alkoxy-carbonyl group (e.g., methoxycarbonyl, tert-butoxycarbonyl),
  (d) a $C_{3-10}$ cycloalkyl group (e.g., cyclohexyl),
  (e) a $C_{6-14}$ aryl group (e.g., phenyl) optionally substituted by 1 to 3 substituents selected from
    (i) a $C_{1-6}$ alkyl group,
    (ii) a hydroxy group,
    (iii) a $C_{1-6}$ alkoxy group, and
    (iv) a halogen atom,
  (f) a $C_{1-6}$ alkylthio group (e.g., methylthio) optionally substituted by 1 to 3 substituents selected from
    (i) a carboxy group,
    (ii) a hydroxy group,
    (iii) a $C_{1-6}$ alkoxy group (e.g., methoxy), and
    (iv) a $C_{1-6}$ alkoxy-carbonyl group (e.g., methoxycarbonyl, ethoxycarbonyl, tert-butoxycarbonyl),
  (g) a $C_{7-13}$ aralkyloxy group (e.g., benzyloxy),
  (h) a mercapto group,
  (i) a $C_{1-6}$ alkoxy group (e.g., methoxy, ethoxy) optionally substituted by 1 to 3 substituents selected from
    (i) a halogen atom,
    (ii) a carboxy group,
    (iii) a $C_{1-6}$ alkoxy group,
    (iv) a $C_{1-6}$ alkoxy-carbonyl group (e.g., methoxycarbonyl, tert-butoxycarbonyl),
    (v) a 4- to 7-membered nonaromatic heterocyclic group (e.g., piperidinyl, dihydrooxadiazolyl) optionally substituted by 1 to 3 substituents selected from
      (A) an oxo group,
      (B) a carboxy-carbonyl group, and
      (C) a $C_{1-6}$ alkyl group (e.g., methyl),
    (vi) an amino group optionally mono- or di-substituted by substituent(s) selected from
      (A) a $C_{1-6}$ alkyl group (e.g., methyl),
      (B) a carboxy-carbonyl group, and
      (C) a $C_{1-6}$ alkylsulfonyl group (e.g., methylsulfonyl),
    (vii) a 4- to 7-membered aromatic heterocyclic group (e.g., tetrazolyl),
    (viii) a carbamoyl group optionally mono- or di-substituted by substituent(s) selected from
      (A) a $C_{1-6}$ alkylsulfonyl group (e.g., pentylsulfonyl),
      (B) a $C_{3-10}$ cycloalkyl group, and
      (C) a methylaminosulfonyl group optionally substituted by $C_{3-10}$ cycloalkyl (e.g., cyclopropyl), and
    (ix) a $C_{6-14}$ aryl group (e.g., phenyl),
  (j) a $C_{1-6}$ alkyl-carbonyl group (e.g., acetyl) optionally substituted by 1 to 3 substituents selected from
    (i) a halogen atom,
    (ii) a $C_{1-6}$ alkoxy group, and
    (iii) a $C_{6-14}$ aryl group,
  (k) a $C_{1-6}$ alkoxy-carbonyl group (e.g., tert-butoxycarbonyl) optionally substituted by 1 to 3 substituents selected from
    (i) a halogen atom,
    (ii) a $C_{1-6}$ alkoxy group, and
    (iii) a $C_{6-14}$ aryl group,
  (l) a 4- to 7-membered nonaromatic heterocycleoxy group (e.g., piperazinyloxy) optionally substituted by 1 to 3 substituents selected from
    (i) a carboxy-carbonyl group,
    (ii) a $C_{1-6}$ alkyl group (e.g., methyl), and
    (iii) a $C_{1-6}$ alkoxy-carbonyl group (tert-butoxycarbonyl),
  (m) a 4- to 7-membered nonaromatic heterocyclic group (e.g., imidazolidinyl, piperidinyl) optionally substituted by 1 to 3 substituents selected from
    (i) a $C_{1-6}$ alkyl group (e.g., methyl) optionally substituted by a carboxy group,
    (ii) a $C_{1-6}$ alkoxy-carbonyl group (e.g., tert-butoxycarbonyl) and
    (iii) an oxo group, and
  (n) an amino group optionally mono- or di-substituted by substituent(s) selected from
    (i) a carboxy-carbonyl group, and
    (ii) a $C_{1-6}$ alkyl group,
(6) a 4- to 7-membered nonaromatic heterocyclic group (e.g., pyrrolidinyl (e.g., 2-pyrrolidinyl), tetrahydrofuranyl (e.g., tetrahydrofuran-3-yl, tetrahydrofuran-2-yl), thiazolidinyl (e.g., thiazolidin-4-yl), piperidinyl (e.g., 1-piperidinyl, 2-piperidinyl, 4-piperidinyl), pyranyl (e.g., 2-pyranyl), tetrahydropyrimidinyl (e.g., tetrahydropyrimidin-4-yl, tetrahydropyrimidin-5-yl), hexahydropyrimidinyl (e.g., hexahydropyrimidin-4-yl), 5H-[1,3]thiazolo[3,2-a]pyrimidinyl (e.g., 5H-[1,3]thiazolo[3,2-a]pyrimidin-6-yl), 2-oxabicyclo[2,2,1]heptan-1-yl, dihydrobenzofuran, indolinyl, morpholinyl) optionally substituted by 1 to 3 substituents selected from
  (a) a halogen atom (e.g., chlorine atom),
  (b) a hydroxy group,
  (c) a $C_{1-6}$ alkyl group (e.g., methyl) optionally substituted by 1 to 3 substituents selected from
    (i) a carboxy group,
    (ii) a halogen atom (e.g., chlorine atom),
    (iii) a $C_{6-14}$ aryl group (e.g., phenyl), and
    (iv) a $C_{1-6}$ alkoxy-carbonyl group (e.g., methoxycarbonyl),
  (d) a $C_{6-14}$ aryl group (e.g., phenyl) optionally substituted by 1 to 3 substituents selected from
    (i) a $C_{1-6}$ alkyl group,
    (ii) a hydroxy group,
    (iii) a $C_{1-6}$ alkoxy group, and
    (iv) a halogen atom, (e) a $C_{1-6}$ alkylthio group (e.g., methylthio) optionally substituted by 1 to 3 substituents selected from
  (i) a carboxy group,
  (ii) a hydroxy group,
  (iii) a $C_{1-6}$ alkoxy group (e.g., methoxy), and
  (iv) a $C_{1-6}$ alkoxy-carbonyl group (e.g., methoxycarbonyl, tert-butoxycarbonyl),
(f) a $C_{7-13}$ aralkyloxy group (e.g., benzyloxy),
(g) a mercapto group,
(h) a $C_{1-6}$ alkoxy group (e.g., methoxy) optionally substituted by 1 to 3 substituents selected from
  (i) a halogen atom,
  (ii) a carboxy group,
  (iii) a $C_{1-6}$ alkoxy group, and
  (iv) a $C_{1-6}$ alkoxy-carbonyl group (e.g., methoxycarbonyl, tert-butoxycarbonyl);
(i) a $C_{1-6}$ alkyl-carbonyl group (e.g., acetyl) optionally substituted by 1 to 3 substituents selected from
  (i) a halogen atom,
  (ii) a $C_{1-6}$ alkoxy group,
  (iii) a $C_{6-14}$ aryl group, and
  (iv) a carboxy group,
(j) a $C_{1-6}$ alkoxy-carbonyl group (e.g., tert-butoxycarbonyl) optionally substituted by 1 to 3 substituents selected from
  (i) a halogen atom,
  (ii) a $C_{1-6}$ alkoxy group, and
  (iii) a $C_{6-14}$ aryl group,
(k) an oxo group, and
(l) a carboxy group,
(7) an amino group optionally mono- or di-substituted by substituent(s) selected from
  (a) $C_{3-10}$ cycloalkyl group,
  (b) a $C_{6-14}$ aryl group (e.g., phenyl) optionally substituted by 1 to 3 substituents selected from
    (i) a hydroxy group,
    (ii) a carbamoyl group,
    (iii) a $C_{1-6}$ alkyl group, and
    (iv) a $C_{1-6}$ alkoxy group (e.g., methoxy) optionally substituted by 1 to 3 substituents selected from
      (A) a carboxy group,
      (B) a $C_{6-14}$ aryl group (e.g., phenyl), and
      (C) a $C_{1-6}$ alkoxy-carbonyl group (e.g., methoxycarbonyl);
  (c) a $C_{1-6}$ alkyl group (e.g., methyl, ethyl) optionally substituted by 1 to 3 substituents selected from
    (i) a carboxy group,
    (ii) a $C_{1-6}$ alkoxy group, and
    (iii) a $C_{1-6}$ alkoxy-carbonyl group (e.g., ethoxycarbonyl),
  (d) a $C_{7-13}$ aralkyl group,
  (e) a 4- to 7-membered aromatic heterocyclic group (e.g., triazolyl, tetrazolyl, thiazolyl, pyridyl) optionally substituted by 1 to 3 substituents selected from
    (i) a hydroxy group,
    (ii) a carbamoyl group, and
    (iii) a $C_{1-6}$ alkyl group (e.g., methyl) optionally substituted by a carboxy group, and
  (f) a 4- to 7-membered nonaromatic heterocyclic group (e.g., piperidinyl, morpholinyl) optionally substituted by 1 to 3 substituents selected from
    (i) a hydroxy group,
    (ii) a carbamoyl group,
    (iii) a $C_{1-6}$ alkyl group, and
    (iv) an oxo group,
(8) a formyl group,
(9) a carboxy group,
(10) a $C_{1-6}$ alkyl-carbonyl group (e.g., isobutylcarbonyl) optionally substituted by 1 to 3 substituents selected from
  (a) a halogen atom,
  (b) a $C_{1-6}$ alkoxy-carbonyl group,
  (c) a $C_{6-14}$ aryl group, and
  (d) a $C_{1-6}$ alkoxy group,
(11) a $C_{1-6}$ alkoxy-carbonyl group (e.g., ethoxycarbonyl) optionally substituted by 1 to 3 substituents selected from
  (a) a halogen atom,
  (b) a $C_{6-14}$ aryl group, and
  (c) a $C_{1-6}$ alkoxy group,
(12) a $C_{3-10}$ cycloalkyl-carbonyl group (e.g., cyclopropylcarbonyl, cyclopentylcarbonyl, cyclohexylcarbonyl),
(13) a $C_{6-14}$ aryl-carbonyl group (e.g., benzoyl) optionally substituted by 1 to 3 halogen atoms,
(14) a carbamoyl group optionally mono- or di-substituted by substituent(s) selected from
  (a) a $C_{1-6}$ alkyl group (e.g., methyl, ethyl, isopropyl isobutyl, tert-butyl) optionally substituted by 1 to 3 substituents selected from
    (i) a halogen atom,
    (ii) a $C_{1-6}$ alkoxy-carbonyl group (e.g., methoxycarbonyl) optionally substituted by 1 to 3 $C_{6-14}$ aryl groups (e.g., phenyl),
    (iii) a $C_{6-14}$ aryl group (e.g., phenyl) optionally substituted by 1 to 3 substituents selected from
      (A) a $C_{1-6}$ alkoxy-carbonyl group (e.g., methoxycarbonyl) and
      (B) a carboxy group,
    (iv) a $C_{1-6}$ alkoxy group,
    (v) a hydroxy group,
    (vi) a 4- to 7-membered aromatic heterocyclic group,
    (vii) a carboxy group,
    (viii) a $C_{3-10}$ cycloalkyl group (e.g., cyclopropyl), and
    (ix) a $C_{1-6}$ alkylsulfonyl group (e.g., methylsulfonyl),
  (b) a $C_{3-10}$ cycloalkyl group,
  (c) a $C_{6-14}$ aryl group (e.g., phenyl) optionally substituted by 1 to 3 substituents selected from
    (i) a halogen atom,
    (ii) a $C_{1-6}$ alkyl group (e.g., ethyl) optionally substituted by 1 to 3 substituents selected from
      (A) a halogen atom,
      (B) a carboxy group, and
      (C) a $C_{1-6}$ alkoxy-carbonyl group (e.g., methoxycarbonyl),
    (iii) a $C_{1-6}$ alkoxy group (e.g., methoxy) optionally substituted by 1 to 3 substituents selected from
      (A) a carboxy group,
      (B) a $C_{1-6}$ alkoxy-carbonyl group (e.g., methoxycarbonyl), and
      (C) a $C_{6-14}$ aryl group (e.g., phenyl), and
    (iv) a hydroxy group,
  (d) a 4- to 7-membered aromatic heterocyclic group (e.g., pyridyl (e.g., 2-pyridyl), thiazolyl) optionally substituted by 1 to 3 substituents selected from
    (i) a carboxy group, and
    (ii) a $C_{1-6}$ alkyl group optionally substituted by a carboxy group,
  (e) a sulfamoyl group optionally mono- or di-substituted by a $C_{1-6}$ alkyl group (e.g., methyl) optionally substituted by a $C_{3-10}$ cycloalkyl group (e.g., cyclopropyl),
  (f) a sulfonyl group optionally mono- or di-substituted by a $C_{1-6}$ alkyl group (e.g., pentyl),
  (g) a $C_{1-6}$ alkoxy group, and
  (h) a 4- to 7-membered nonaromatic heterocyclic group (e.g., pyrrolidinyl, piperidinyl, tetrahydrothiopyranyl) optionally substituted by 1 to 3 substituents selected from
    (i) a carboxy group,
    (ii) a $C_{1-6}$ alkyl-carbonyl group (e.g., acetyl), (iii) a $C_{1-6}$ alkoxy-carbonyl group (e.g., tert-butoxycarbonyl, ethoxycarbonyl),
(iv) a $C_{1-6}$ alkoxy-carbonyl-carbonyl group,
(v) a carboxy-carbonyl group,
(vi) a carbamoyl group optionally mono- or di-substituted by $C_{1-6}$ alkyl groups (e.g., ethyl),
(vii) a $C_{1-6}$ alkyl-sulfonyl group (e.g., methylsulfonyl), and
(viii) an oxo group;
(15) a $C_{1-6}$ alkylsulfonyl group optionally substituted by 1 to 3 substituents selected from
  (a) a halogen atom, and
  (b) a $C_{6-14}$ aryl group,
(16) a $C_{6-14}$ arylsulfonyl group optionally substituted by 1 to 3 halogen atoms,
(17) a sulfamoyl group optionally mono- or di-substituted by substituent(s) selected from $C_{1-6}$ alkyl groups optionally substituted by 1 to 3 substituents selected from
  (a) a halogen atom, and
  (b) a 4- to 7-membered nonaromatic heterocyclic group optionally substituted by an oxo group,
(18) a thiocarbamoyl group optionally mono- or di-substituted by substituent(s) selected from a $C_{1-6}$ alkyl group optionally substituted by 1 to 3 halogen atoms,
(19) a 4- to 7-membered aromatic heterocyclylcarbonyl group optionally substituted by 1 to 3 substituents selected from $C_{1-6}$ alkyl groups optionally substituted by 1 to 3 halogen atoms,
(20) a 4- to 7-membered nonaromatic heterocyclylcarbonyl group (e.g., piperidinylcarbonyl, pyrrolidinylcarbonyl) optionally substituted by 1 to 3 substituents selected from
  (a) a carboxy group,
  (b) a $C_{1-6}$ alkoxy group optionally substituted by a carboxy group,
  (c) a $C_{1-6}$ alkyl group optionally substituted by 1 to 3 halogen atoms, and
  (d) a $C_{1-6}$ alkoxy-carbonyl group (e.g., methoxycarbonyl),
(21) a hydroxy group optionally substituted by 1 to 3 substituents selected from
  (a) a $C_{1-6}$ alkyl group (e.g., ethyl, isopropyl, tert-butyl) optionally substituted by 1 to 3 halogen atoms (e.g., chlorine atom), and
  (b) a $C_{6-14}$ aryl group (e.g., phenyl), or
(22) a fused ring group (e.g., indanyl, tetrahydronaphthyl, quinolyl, indolyl, benzimidazolyl) optionally substituted by 1 to 3 substituents selected from
  (a) a carboxy group,
  (b) a $C_{1-6}$ alkoxy group optionally substituted by a carboxy group, and
  (c) a $C_{1-6}$ alkyl group (e.g., methyl) optionally substituted by a carboxy group.

R is more preferably
(1) a $C_{1-10}$ alkyl group (e.g., methyl, ethyl, propyl, isopropyl, tert-butyl, isobutyl, pentyl) optionally substituted by 1 to 3 substituents selected from
  (a) a carbamoyl group optionally mono- or di-substituted by substituent(s) selected from
    (i) a carboxy group,
    (ii) a $C_{1-6}$ alkyl group (e.g., methyl) optionally substituted by 1 to 3 substituents selected from
      (A) a carboxy group, and
      (B) a $C_{6-14}$ aryl group (e.g., phenyl) optionally substituted by a carboxy group,
    (iii) a $C_{1-6}$ alkylsulfonyl group (e.g., methylsulfonyl),
    (iv) a $C_{6-14}$ aryl group,
    (v) a 4- to 7-membered aromatic heterocyclic group, and
    (vi) a sulfamoyl group optionally substituted by a $C_{1-6}$ alkyl group (e.g., methyl) optionally substituted by a $C_{3-10}$ cycloalkyl (e.g., cyclopropyl),
  (b) a 4- to 7-membered aromatic heterocyclylthio group (e.g., pyrazolylthio (e.g., pyrazol-5-ylthio), tetrazolylthio (e.g., tetrazol-5-ylthio)) optionally substituted by 1 to 3 substituents selected from
    (i) a carboxy group,
    (ii) a $C_{1-6}$ alkyl group (e.g., methyl) optionally substituted by a carboxy group, and
    (iii) a $C_{6-14}$ aryl group,
  (c) a 4- to 7-membered aromatic heterocyclic group (e.g., tetrazolyl (e.g., tetrazol-5-yl, tetrazol-1-yl), imidazolyl) optionally substituted by 1 to 3 substituents selected from
    (i) a carboxy group, and
    (ii) a $C_{1-6}$ alkyl group,
  (d) a 4- to 7-membered nonaromatic heterocyclic group (e.g., imidazolidinyl (e.g., imidazolidin-5-yl), piperidinyl (e.g., piperidin-4-yl)) optionally substituted by 1 to 3 substituents selected from
    (i) a carboxy group,
    (ii) a $C_{1-6}$ alkyl group (e.g., methyl) optionally substituted by 1 to 3 substituents selected from
      (A) a carboxy group,
      (B) a $C_{1-6}$ alkoxy-carbonyl group (e.g., methoxycarbonyl) optionally substituted by a $C_{6-14}$ aryl group (e.g., phenyl), and
      (C) a $C_{6-14}$ aryl group (e.g., phenyl) optionally substituted by a $C_{1-6}$ alkoxy-carbonyl group (e.g., methoxycarbonyl), and
    (iii) an oxo group,
  (e) a halogen atom,
  (f) a cyano group,
  (g) a hydroxy group,
  (h) a carboxy group,
  (i) a $C_{1-6}$ alkoxy group (e.g., methoxy, ethoxy) optionally substituted by 1 to 3 substituents selected from
    (i) a halogen atom,
    (ii) a carboxy group,
    (iii) a $C_{1-6}$ alkoxy group, and
    (iv) a $C_{1-6}$ alkoxy-carbonyl group, and
    (v) a $C_{6-14}$ aryl group (e.g., phenyl),
  (j) an amino group optionally mono- or di-substituted by substituent(s) selected from
    (i) a $C_{1-6}$ alkyl group,
    (ii) a $C_{1-6}$ alkyl-carbonyl group (e.g., acetyl),
    (iii) $C_{6-14}$ aryl-carbonyl group (e.g., benzoyl),
    (iv) a $C_{1-6}$ alkoxy-carbonyl group (e.g., tert-butoxycarbonyl),
    (v) a $C_{1-6}$ alkylsulfonyl group,
    (vi) a carbamoyl group optionally mono- or di-substituted by a $C_{1-6}$ alkyl group, and
    (vii) a 4- to 7-membered aromatic heterocyclic group,
  (k) a $C_{1-6}$ alkyl-carbonyl group (e.g., acetyl) optionally substituted by 1 to 3 substituents selected from
    (i) a halogen atom,
    (ii) a $C_{1-6}$ alkoxy group, and
    (iii) a $C_{6-14}$ aryl group,
  (l) a $C_{1-6}$ alkoxy-carbonyl group (e.g., ethoxycarbonyl) optionally substituted by 1 to 3 substituents selected from
    (i) a halogen atom,
    (ii) a $C_{1-6}$ alkoxy group, and
    (iii) a $C_{6-14}$ aryl group,
  (m) a $C_{6-14}$ aryloxy group (e.g., phenyloxy),
  (n) a $C_{6-14}$ aryl group (e.g., phenyl) optionally substituted by 1 to 3 substituents selected from (i) a $C_{1-6}$ alkyl group,
(ii) a hydroxy group,
(iii) a $C_{1-6}$ alkoxy group (e.g., methoxy), and
(iv) a halogen atom (e.g., chlorine atom), and
(o) a $C_{3-10}$ cycloalkyl group (e.g., cyclobutyl, cyclopentyl) optionally substituted by 1 to 3 substituents selected from
(i) a $C_{1-6}$ alkyl group (e.g., methyl),
(ii) a $C_{1-6}$ alkyl-carbonyl group (e.g., acetyl), and
(iii) an oxo group
(the $C_{3-10}$ cycloalkyl group may form a fused ring group with a benzene ring optionally substituted by a $C_{1-6}$ alkoxy group (e.g., methoxy)),
(2) a $C_{3-10}$ cycloalkyl group (e.g., cyclopropyl, cyclobutyl, adamantyl) optionally substituted by 1 to 3 substituents selected from
(a) a carboxy group,
(b) a $C_{1-6}$ alkyl group (e.g., methyl),
(c) a hydroxy group, and
(d) a $C_{1-6}$ alkoxy-carbonyl group (e.g., methoxycarbonyl),
(3) a $C_{2-10}$ alkenyl group (e.g., ethenyl) optionally substituted by 1 to 3 substituents selected from
(a) a carbamoyl group optionally mono- or di-substituted by substituent(s) selected from
(i) a $C_{1-6}$ alkyl group (e.g., methyl),
(ii) a $C_{6-14}$ aryl group, and
(iii) a 4- to 7-membered aromatic heterocyclic group,
(b) a carboxy group, and
(c) a hydroxy group,
(4) a $C_{6-14}$ aryl group (e.g., phenyl) optionally substituted by 1 to 3 substituents selected from
(a) a carboxy group,
(b) a $C_{1-6}$ alkyl group (e.g., methyl) optionally substituted by 1 to 3 substituents selected from
(i) a halogen atoms (e.g., chlorine atom), and
(ii) an amino group optionally mono- or di-substituted by 4- to 7-membered nonaromatic heterocyclic groups (e.g., tetrahydrothiopyranyl) optionally substituted by an oxo group,
(c) a $C_{1-6}$ alkoxy group (e.g., methoxy) optionally substituted by 1 to 3 substituents selected from
(i) a carboxy group,
(ii) a hydroxy group,
(iii) a $C_{6-14}$ aryl group (e.g., phenyl),
(iv) a 4- to 7-membered nonaromatic heterocyclic group (e.g., piperidinyl) optionally substituted by 1 to 3 $C_{1-6}$ alkoxy-carbonyl groups (e.g., tert-butoxycarbonyl), and
(v) a $C_{1-6}$ alkoxy-carbonyl group (e.g., methoxycarbonyl),
(d) a halogen atom (e.g., fluorine atom),
(e) a 4- to 7-membered nonaromatic heterocyclic group (e.g., dihydrooxadiazolyl, imidazolidinyl) optionally substituted by 1 to 3 substituents selected from
(i) a carboxy group,
(ii) a $C_{1-6}$ alkyl group,
(iii) an oxo group, and
(iv) a $C_{1-6}$ alkyl group (e.g., methyl) optionally substituted by 1 to 3 substituents selected from
(A) a carboxy group, and
(B) a $C_{1-6}$ alkoxy-carbonyl group (e.g., tert-butoxycarbonyl),
(f) a cyano group,
(g) a hydroxy group,
(h) a $C_{1-6}$ alkoxy-carbonyl group (e.g., methoxycarbonyl), and
(i) a $C_{6-14}$ aryl group (e.g., phenyl) optionally substituted by a $C_{1-6}$ alkyl group (e.g., methyl) optionally substituted by a carboxy group,
(5) a 4- to 7-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
(a) a halogen atom (e.g., chlorine atom),
(b) a hydroxy group,
(c) a $C_{1-6}$ alkyl group (e.g., methyl) optionally substituted by 1 to 3 substituents selected from
(i) a carboxy group,
(ii) a $C_{1-6}$ alkoxy-carbonyl group (e.g., methoxycarbonyl, tert-butoxycarbonyl), and
(iii) a halogen atom (e.g., chlorine atom, fluorine atom),
(d) a $C_{3-10}$ cycloalkyl group (e.g., cyclohexyl),
(e) a $C_{6-14}$ aryl group (e.g., phenyl) optionally substituted by 1 to 3 substituents selected from
(i) a $C_{1-6}$ alkyl group,
(ii) a hydroxy group,
(iii) a $C_{1-6}$ alkoxy group, and
(iv) a halogen atom,
(f) a $C_{1-6}$ alkylthio group (e.g., methylthio) optionally substituted by 1 to 3 substituents selected from
(i) a carboxy group,
(ii) a hydroxy group,
(iii) a $C_{1-6}$ alkoxy group (e.g., methoxy), and
(iv) a $C_{1-6}$ alkoxy-carbonyl group (e.g., methoxycarbonyl, ethoxycarbonyl, tert-butoxycarbonyl),
(g) a $C_{7-13}$ aralkyloxy group (e.g., benzyloxy),
(h) a mercapto group,
(i) a $C_{1-6}$ alkoxy group (e.g., methoxy) optionally substituted by 1 to 3 substituents selected from
(i) a halogen atom,
(ii) a carboxy group,
(iii) a $C_{1-6}$ alkoxy group,
(iv) a $C_{1-6}$ alkoxy-carbonyl group (e.g., methoxycarbonyl, tert-butoxycarbonyl), and
(v) a $C_{6-14}$ aryl group (e.g., phenyl),
(j) a $C_{1-6}$ alkyl-carbonyl group (e.g., acetyl) optionally substituted by 1 to 3 substituents selected from
(i) a halogen atom,
(ii) a $C_{1-6}$ alkoxy group, and
(iii) a $C_{6-14}$ aryl group,
(k) a $C_{1-6}$ alkoxy-carbonyl group (e.g., tert-butoxycarbonyl) optionally substituted by 1 to 3 substituents selected from
(i) a halogen atom,
(ii) a $C_{1-6}$ alkoxy group, and
(iii) a $C_{6-14}$ aryl group,
(l) a hydroxy group,
(m) a $C_{3-10}$ cycloalkyl group, and
(n) a 4- to 7-membered nonaromatic heterocyclic group (e.g., imidazolidinyl, piperidinyl) optionally substituted by 1 to 3 $C_{1-6}$ alkoxycarbonyl groups (e.g., tert-butoxycarbonyl),
(6) a 4- to 7-membered nonaromatic heterocyclic group (e.g., pyrrolidinyl (e.g., 2-pyrrolidinyl), tetrahydrofuranyl (e.g., tetrahydrofuran-3-yl, tetrahydrofuran-2-yl), thiazolidinyl (e.g., thiazolidin-4-yl), piperidinyl (e.g., 1-piperidinyl, 2-piperidinyl, 4-piperidinyl), pyranyl (e.g., 2-pyranyl), tetrahydropyrimidinyl (e.g., tetrahydropyrimidin-4-yl, tetrahydropyrimidin-5-yl), hexahydropyrimidinyl (e.g., hexahydropyrimidin-4-yl), 5H-[1,3]thiazolo[3,2-a]pyrimidinyl (e.g., 5H-[1,3]thiazolo[3,2-a]pyrimidin-6-yl, 2-oxabicyclo[2,2,1]heptan-1-yl, morpholinyl) optionally substituted by 1 to 3 substituents selected from
(a) a halogen atom (e.g., chlorine atom),
(b) a hydroxy group, (c) a $C_{1-6}$ alkyl group (e.g., methyl) optionally substituted by 1 to 3 substituents selected from
  (i) a carboxy group,
  (ii) a halogen atom (e.g., chlorine atom),
  (iii) a $C_{6-14}$ aryl group (e.g., phenyl), and
  (iv) a $C_{1-6}$ alkoxy-carbonyl group (e.g., methoxycarbonyl),
(d) a $C_{6-14}$ aryl group (e.g., phenyl) optionally substituted by 1 to 3 substituents selected from
  (i) a $C_{1-6}$ alkyl group,
  (ii) a hydroxy group,
  (iii) a $C_{1-6}$ alkoxy group, and
  (iv) a halogen atom,
(e) a $C_{1-6}$ alkylthio group (e.g., methylthio) optionally substituted by 1 to 3 substituents selected from
  (i) a carboxy group,
  (ii) a hydroxy group,
  (iii) a $C_{1-6}$ alkoxy group (e.g., methoxy), and
  (iv) a $C_{1-6}$ alkoxy-carbonyl group (e.g., methoxycarbonyl, tert-butoxycarbonyl),
(f) a $C_{7-13}$ aralkyloxy group (e.g., benzyloxy),
(g) a mercapto group,
(h) a $C_{1-6}$ alkoxy group (e.g., methoxy) optionally substituted by 1 to 3 substituents selected from
  (i) a halogen atom,
  (ii) a carboxy group,
  (iii) a $C_{1-6}$ alkoxy group, and
  (iv) a $C_{1-6}$ alkoxy-carbonyl group (e.g., methoxycarbonyl, tert-butoxycarbonyl);
(i) a $C_{1-6}$ alkyl-carbonyl group (e.g., acetyl) optionally substituted by 1 to 3 substituents selected from
  (i) a halogen atom,
  (ii) a $C_{1-6}$ alkoxy group, and
  (iii) a $C_{6-14}$ aryl group,
(j) a $C_{1-6}$ alkoxy-carbonyl group (e.g., tert-butoxycarbonyl) optionally substituted by 1 to 3 substituents selected from
  (i) a halogen atom,
  (ii) a $C_{1-6}$ alkoxy group, and
  (iii) a $C_{6-14}$ aryl group, and
(k) an oxo group,
(7) an amino group optionally mono- or di-substituted by substituent(s) selected from
  (a) $C_{3-10}$ cycloalkyl group,
  (b) a $C_{6-14}$ aryl group (e.g., phenyl) optionally substituted by 1 to 3 substituents selected from
    (i) a hydroxy group,
    (ii) a carbamoyl group,
    (iii) a $C_{1-6}$ alkyl group, and
    (iv) a $C_{1-6}$ alkoxy group (e.g., methoxy) optionally substituted by 1 to 3 substituents selected from
      (A) a carboxy group,
      (B) a $C_{6-14}$ aryl group (e.g., phenyl), and
      (C) a $C_{1-6}$ alkoxy-carbonyl group (e.g., methoxycarbonyl),
  (c) a $C_{1-6}$ alkyl group (e.g., methyl, ethyl) optionally substituted by 1 to 3 substituents selected from
    (i) a carboxy group,
    (ii) a $C_{1-6}$ alkoxy group, and
    (iii) a $C_{1-6}$ alkoxy-carbonyl group (e.g., ethoxycarbonyl),
  (d) a $C_{7-13}$ aralkyl group,
  (e) a 4- to 7-membered aromatic heterocyclic group (e.g., triazolyl, tetrazolyl, pyridyl) optionally substituted by 1 to 3 substituents selected from
    (i) a hydroxy group,
    (ii) a carbamoyl group, and
    (iii) a $C_{1-6}$ alkyl group, and
  (f) a 4- to 7-membered nonaromatic heterocyclic group (e.g., piperidinyl, morpholinyl) optionally substituted by 1 to 3 substituents selected from
    (i) a hydroxy group,
    (ii) a carbamoyl group,
    (iii) a $C_{1-6}$ alkyl group, and
    (iv) an oxo group,
(8) a formyl group,
(9) a carboxy group,
(10) a $C_{1-6}$ alkyl-carbonyl group (e.g., isobutylcarbonyl) optionally substituted by 1 to 3 substituents selected from
  (a) a halogen atom,
  (b) a $C_{1-6}$ alkoxy-carbonyl group,
  (c) a $C_{6-14}$ aryl group, and
  (d) a $C_{1-6}$ alkoxy group,
(11) a $C_{1-6}$ alkoxy-carbonyl group (e.g., ethoxycarbonyl) optionally substituted by 1 to 3 substituents selected from
  (a) a halogen atom,
  (b) a $C_{6-14}$ aryl group, and
  (c) a $C_{1-6}$ alkoxy group,
(12) a $C_{3-10}$ cycloalkyl-carbonyl group (e.g., cyclopropylcarbonyl, cyclopentylcarbonyl, cyclohexylcarbonyl),
(13) a $C_{6-14}$ aryl-carbonyl group (e.g., benzoyl) optionally substituted by 1 to 3 halogen atoms,
(14) a carbamoyl group optionally mono- or di-substituted by substituent(s) selected from
  (a) a $C_{1-6}$ alkyl group (e.g., methyl, ethyl, isopropyl isobutyl, tert-butyl) optionally substituted by 1 to 3 substituents selected from
    (i) a halogen atom,
    (ii) a $C_{1-6}$ alkoxy-carbonyl group (e.g., methoxycarbonyl) optionally substituted by 1 to 3 $C_{6-14}$ aryl groups (e.g., phenyl),
    (iii) a $C_{6-14}$ aryl group (e.g., phenyl) optionally substituted by 1 to 3 substituents selected from
      (A) a $C_{1-6}$ alkoxy-carbonyl group (e.g., methoxycarbonyl), and
      (B) a carboxy group,
    (iv) a $C_{1-6}$ alkoxy group,
    (v) a hydroxy group,
    (vi) a 4- to 7-membered aromatic heterocyclic group,
    (vii) a carboxy group,
    (viii) a $C_{3-10}$ cycloalkyl group (e.g., cyclopropyl), and
    (ix) a $C_{1-6}$ alkylsulfonyl group (e.g., methylsulfonyl),
  (b) a $C_{3-10}$ cycloalkyl group,
  (c) a $C_{6-14}$ aryl group (e.g., phenyl) optionally substituted by 1 to 3 substituents selected from
    (i) a halogen atom,
    (ii) a $C_{1-6}$ alkyl group (e.g., ethyl) optionally substituted by 1 to 3 substituents selected from
      (A) a halogen atom,
      (B) a carboxy group, and
      (C) a $C_{1-6}$ alkoxy-carbonyl group (e.g., methoxycarbonyl),
    (iii) a $C_{1-6}$ alkoxy group (e.g., methoxy) optionally substituted by 1 to 3 substituents selected from
      (A) a carboxy group,
      (B) a $C_{1-6}$ alkoxy-carbonyl group (e.g., methoxycarbonyl), and
      (C) a $C_{6-14}$ aryl group (e.g., phenyl), and
    (iv) a hydroxy group,
  (d) a 4- to 7-membered aromatic heterocyclic group (e.g., pyridyl (e.g., 2-pyridyl)) optionally substituted by 1 to 3 substituents selected from
    (i) a carboxy group, and
    (ii) a $C_{1-6}$ alkyl group optionally substituted by a carboxy group, (e) a sulfamoyl group optionally mono- or di-substituted by a $C_{1-6}$ alkyl group (e.g., methyl) optionally substituted by a $C_{3-10}$ cycloalkyl group (e.g., cyclopropyl),
(f) a sulfonyl group optionally mono- or di-substituted by a $C_{1-6}$ alkyl group (e.g., pentyl),
(h) a 4- to 7-membered nonaromatic heterocyclic group (e.g., pyrrolidinyl, piperidinyl, tetrahydrothiopyranyl) optionally substituted by 1 to 3 substituents selected from
  (i) a carboxy group,
  (ii) a $C_{1-6}$ alkyl-carbonyl group (e.g., acetyl),
  (iii) a $C_{1-6}$ alkoxy-carbonyl group (e.g., tert-butoxycarbonyl, ethoxycarbonyl),
  (iv) a $C_{1-6}$ alkoxy-carbonyl-carbonyl group,
  (v) a carboxy-carbonyl group,
  (vi) a carbamoyl group optionally mono- or di-substituted by $C_{1-6}$ alkyl groups (e.g., ethyl),
  (vii) a $C_{1-6}$ alkyl-sulfonyl group (e.g., methylsulfonyl), and
  (viii) an oxo group,
(f) a sulfamoyl group optionally mono- or di-substituted by a $C_{1-6}$ alkyl group (e.g., methyl) optionally substituted by a $C_{3-10}$ cycloalkyl group (e.g., cyclopropyl),
(g) a sulfonyl group optionally mono- or di-substituted by a $C_{1-6}$ alkyl group (e.g., pentyl), and
(h) a $C_{1-6}$ alkoxy group,
(15) a $C_{1-6}$ alkylsulfonyl group optionally substituted by 1 to 3 substituents selected from
  (a) a halogen atom, and
  (b) a $C_{6-14}$ aryl group,
(16) a $C_{6-14}$ arylsulfonyl group optionally substituted by 1 to 3 halogen atoms,
(17) a sulfamoyl group optionally mono- or di-substituted by substituent(s) selected from $C_{1-6}$ alkyl groups optionally substituted by 1 to 3 substituents selected from
  (a) a halogen atom, and
  (b) a 4- to 7-membered nonaromatic heterocyclic group optionally substituted by an oxo group,
(18) a thiocarbamoyl group optionally mono- or di-substituted by substituent(s) selected from a $C_{1-6}$ alkyl group optionally substituted by 1 to 3 halogen atoms,
(19) a 4- to 7-membered aromatic heterocyclylcarbonyl group optionally substituted by 1 to 3 substituents selected from $C_{1-6}$ alkyl groups optionally substituted by 1 to 3 halogen atoms,
(20) a 4- to 7-membered nonaromatic heterocyclylcarbonyl group (e.g., piperidinylcarbonyl, pyrrolidinylcarbonyl) optionally substituted by 1 to 3 substituents selected from
  (a) a carboxy group,
  (b) $C_{1-6}$ alkyl groups optionally substituted by 1 to 3 halogen atoms, and
  (c) a $C_{1-6}$ alkoxy-carbonyl group (e.g., methoxycarbonyl), or
(21) a hydroxy group optionally substituted by 1 to 3 substituents selected from
  (a) a $C_{1-6}$ alkyl group (e.g., ethyl, isopropyl, tert-butyl) optionally substituted by 1 to 3 halogen atoms (e.g., chlorine atom), and
  (b) a $C_{6-14}$ aryl group (e.g., phenyl).
R is more preferably
(1) a $C_{1-10}$ alkyl group (e.g., methyl, ethyl, propyl, isopropyl, tert-butyl, isobutyl, pentyl) optionally substituted by 1 to 3 substituents selected from
  (a) a carbamoyl group optionally mono- or di-substituted by substituent(s) selected from
    (i) a carboxy group,
    (ii) a $C_{1-6}$ alkyl group (e.g., methyl) optionally substituted by 1 to 3 substituents selected from
      (A) a carboxy group, and
      (B) a $C_{6-14}$ aryl group (e.g., phenyl) optionally substituted by a carboxy group,
    (iii) a $C_{1-6}$ alkylsulfonyl group (e.g., methylsulfonyl),
    (iv) a $C_{6-14}$ aryl group, and
    (v) a 5- or 6-membered aromatic heterocyclic group,
    (vi) a sulfamoyl group optionally substituted by a $C_{1-6}$ alkyl group (e.g., methyl) optionally substituted by a $C_{3-10}$ cycloalkyl (e.g., cyclopropyl),
  (b) a 5- or 6-membered aromatic heterocyclylthio group (e.g., pyrazol-5-ylthio (e.g., pyrazol-5-ylthio), tetrazolylthio (e.g., tetrazol-5-ylthio)) optionally substituted by 1 to 3 substituents selected from
    (i) a carboxy group,
    (ii) a $C_{1-6}$ alkyl group (e.g., methyl) optionally substituted by a carboxy group, and
    (iii) a $C_{6-14}$ aryl group,
  (c) a 5- or 6-membered aromatic heterocyclic group (e.g., tetrazolyl (e.g., tetrazol-5-yl, tetrazol-1-yl)) optionally substituted by 1 to 3 substituents selected from
    (i) a carboxy group, and
    (ii) a $C_{1-6}$ alkyl group,
  (d) a 5- or 6-membered nonaromatic heterocyclic group (e.g., imidazolidinyl (e.g., imidazolidin-5-yl), piperidinyl (e.g., piperidin-4-yl)) optionally substituted by 1 to 3 substituents selected from
    (i) a carboxy group,
    (ii) a $C_{1-6}$ alkyl group (e.g., methyl) optionally substituted by 1 to 3 substituents selected from
      (A) a carboxy group,
      (B) a $C_{1-6}$ alkoxy-carbonyl group (e.g., methoxycarbonyl) optionally substituted by a $C_{6-14}$ aryl group (e.g., phenyl), and
      (C) a $C_{6-14}$ aryl group (e.g., phenyl) optionally substituted by a $C_{1-6}$ alkoxy-carbonyl group (e.g., methoxycarbonyl), and
    (iii) an oxo group,
  (e) a cyano group,
  (f) a hydroxy group,
  (g) a carboxy group,
  (h) a $C_{1-6}$ alkoxy group (e.g., methoxy, ethoxy) optionally substituted by 1 to 3 $C_{6-14}$ aryl groups (e.g., phenyl),
  (i) an amino group optionally mono- or di-substituted by substituent(s) selected from
    (i) a $C_{1-6}$ alkyl group,
    (ii) a $C_{1-6}$ alkyl-carbonyl group (e.g., acetyl),
    (iii) $C_{6-14}$ aryl-carbonyl group (e.g., benzoyl), and
    (iv) a $C_{1-6}$ alkoxy-carbonyl group (e.g., tert-butoxycarbonyl),
  (j) a $C_{1-6}$ alkyl-carbonyl group (e.g., acetyl),
  (k) a $C_{1-6}$ alkoxy-carbonyl group (e.g., ethoxycarbonyl),
  (l) a $C_{6-14}$ aryloxy group (e.g., phenyloxy),
  (m) a $C_{6-14}$ aryl group (e.g., phenyl) optionally substituted by 1 to 3 substituents selected from
    (i) a hydroxy group,
    (ii) a $C_{1-6}$ alkoxy group (e.g., methoxy), and
    (iii) a halogen atom (e.g., chlorine atom),
  (n) a $C_{3-10}$ cycloalkyl group (e.g., cyclobutyl, cyclopentyl) optionally substituted by 1 to 3 substituents selected from
    (i) a $C_{1-6}$ alkyl group (e.g., methyl),
    (ii) a $C_{1-6}$ alkyl-carbonyl group (e.g., acetyl), and
    (iii) an oxo group
  (the $C_{3-10}$ cycloalkyl group may form a fused ring group with a benzene ring optionally substituted by a $C_{1-6}$ alkoxy group (e.g., methoxy)), and
  (o) a hydroxy group;

(2) a $C_{3-10}$ cycloalkyl group (e.g., cyclopropyl, adamantyl) optionally substituted by 1 to 3 substituents selected from
    (a) a carboxy group,
    (b) a $C_{1-6}$ alkyl group,
    (c) a hydroxy group, and
    (d) a $C_{1-6}$ alkoxy-carbonyl group (e.g., methoxycarbonyl),
(3) a $C_{2-10}$ alkenyl group (e.g., ethenyl) optionally substituted by 1 to 3 carbamoyl groups optionally mono- or di-substituted by $C_{1-6}$ alkyl groups (e.g., methyl),
(4) a $C_{6-14}$ aryl group (e.g., phenyl) optionally substituted by 1 to 3 substituents selected from
    (a) a carboxy group,
    (b) a $C_{1-6}$ alkyl group (e.g., methyl) optionally substituted by 1 to 3 substituents selected from
        (i) a halogen atom (e.g., chlorine atom), and
        (ii) an amino groups optionally mono- or di-substituted by substituent(s) selected from
            (A) a $C_{1-6}$ alkyl group, and
            (B) a 5- or 6-membered nonaromatic heterocyclic group (e.g., tetrahydrothiopyranyl) optionally substituted by an oxo group,
    (c) a $C_{1-6}$ alkoxy group (e.g., methoxy) optionally substituted by 1 to 3 substituents selected from
        (i) a carboxy group,
        (ii) a $C_{6-14}$ aryl group (e.g., phenyl),
        (iii) a 5- or 6-membered nonaromatic heterocyclic group (e.g., piperidinyl) optionally substituted by 1 to 3 substituents selected from
            (A) a carboxy-carbonyl group,
            (B) a $C_{1-6}$ alkoxy-carbonyl group (e.g., tert-butoxycarbonyl), and
            (C) a $C_{1-6}$ alkoxy-carbonyl-carbonyl group, and
        (iv) a hydroxy group,
    (d) a halogen atom (e.g., fluorine atom),
    (e) a 5- or 6-membered nonaromatic heterocyclic group (e.g., dihydrooxadiazolyl, imidazolidinyl) optionally substituted by 1 to 3 substituents selected from
        (i) a carboxy group,
        (ii) an oxo group, and
        (iii) a $C_{1-6}$ alkyl group (e.g., methyl) optionally substituted by 1 to 3 substituents selected from
            (A) a carboxy group,
            (B) a $C_{1-6}$ alkoxy-carbonyl group (e.g., tert-butoxycarbonyl), and
            (C) a $C_{1-6}$ alkoxy-carbonyl group (e.g., tert-butoxycarbonyl),
    (f) a cyano group,
    (g) a hydroxy group,
    (h) a $C_{1-6}$ alkoxy-carbonyl group (e.g., methoxycarbonyl),
    (i) a $C_{6-14}$ aryl group (e.g., phenyl) optionally substituted by a $C_{1-6}$ alkyl group (e.g., methyl) optionally substituted by a carboxy group,
(5) a 5- or 6-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
    (a) a halogen atom (e.g., chlorine atom),
    (b) a hydroxy group,
    (c) a $C_{1-6}$ alkyl group (e.g., methyl, ethyl) optionally substituted by 1 to 3 substituents selected from
        (i) a carboxy group,
        (ii) a halogen atom (e.g., chlorine atom, fluorine atom), and
        (iii) a $C_{1-6}$ alkoxy-carbonyl group (e.g., methoxycarbonyl, tert-butoxycarbonyl),
    (d) a $C_{3-10}$ cycloalkyl group (e.g., cyclohexyl),
    (e) a $C_{6-14}$ aryl group (e.g., phenyl),
    (f) a $C_{1-6}$ alkylthio group (e.g., methylthio) optionally substituted by 1 to 3 substituents selected from
        (i) a carboxy group, and
        (ii) a $C_{1-6}$ alkoxy-carbonyl group (e.g., methoxycarbonyl, ethoxycarbonyl, tert-butoxycarbonyl),
    (g) a mercapto group,
    (h) a $C_{1-6}$ alkoxy group (e.g., methoxy) optionally substituted by 1 to 3 substituents selected from
        (i) a halogen atom,
        (ii) a carboxy group,
        (iii) a $C_{1-6}$ alkoxy-carbonyl group (e.g., methoxycarbonyl, tert-butoxycarbonyl), and
        (iv) a $C_{6-14}$ aryl group (e.g., phenyl),
    (i) a 5- or 6-membered nonaromatic heterocyclic group (e.g., imidazolidinyl, piperidinyl) optionally substituted by 1 to 3 alkoxy-carbonyl groups (e.g., tert-butoxycarbonyl), and
    (j) a $C_{1-6}$ alkylthio group optionally substituted by 1 to 3 carboxy groups,
(6) a 5- or 6-membered nonaromatic heterocyclic group (e.g., pyrrolidinyl (e.g., 2-pyrrolidinyl), tetrahydrofuranyl (e.g., tetrahydrofuran-3-yl, tetrahydrofuran-2-yl), thiazolidinyl (e.g., thiazolidin-4-yl), piperidinyl (e.g., 1-piperidinyl, 2-piperidinyl, 4-piperidinyl), pyranyl (e.g., 2-pyranyl), tetrahydropyrimidinyl (e.g., tetrahydropyrimidin-4-yl, tetrahydropyrimidin-5-yl), hexahydropyrimidinyl (e.g., hexahydropyrimidin-4-yl), 5H-[1,3]thiazolo[3,2-a]pyrimidinyl (e.g., 5H-[1,3]thiazolo[3,2-a]pyrimidin-6-yl), 2-oxabicyclo[2,2,1]heptan-1-yl, morpholinyl) optionally substituted by 1 to 3 substituents selected from
    (a) a hydroxy group,
    (b) a $C_{1-6}$ alkyl group (e.g., methyl) optionally substituted by 1 to 3 substituents selected from
        (i) a carboxy group,
        (ii) a $C_{6-14}$ aryl group (e.g., phenyl), and
        (iii) a $C_{1-6}$ alkoxy-carbonyl group (e.g., methoxycarbonyl),
    (c) a $C_{6-14}$ aryl group (e.g., phenyl)
    (d) a $C_{1-6}$ alkyl-carbonyl group (e.g., acetyl),
    (e) a $C_{1-6}$ alkoxy-carbonyl group (e.g., tert-butoxycarbonyl), and
    (f) an oxo group,
(7) an amino group optionally mono- or di-substituted by substituent(s) selected from
    (a) a $C_{6-14}$ aryl group (e.g., phenyl) optionally substituted by 1 to 3 substituents selected from
        (i) a hydroxy group, and
        (ii) a $C_{1-6}$ alkoxy group (e.g., methoxy) optionally substituted by 1 to 3 substituents selected from
            (A) a carboxy group,
            (B) a $C_{6-14}$ aryl group (e.g., phenyl), and
            (C) a $C_{1-6}$ alkoxy-carbonyl group (e.g., methoxycarbonyl),
    (b) a $C_{1-6}$ alkyl group (e.g., methyl, ethyl) optionally substituted by 1 to 3 substituents selected from
        (i) a carboxy group, and
        (ii) a $C_{1-6}$ alkoxy-carbonyl group (e.g., ethoxycarbonyl),
    (c) a 5- or 6-membered aromatic heterocyclic group (e.g., triazolyl, tetrazolyl, pyridyl) optionally substituted by 1 to 3 substituents selected from
        (i) a hydroxy group, and
        (ii) a carbamoyl group, and
    (d) a 5- or 6-membered nonaromatic heterocyclic group (e.g., piperidinyl) optionally substituted by 1 to 3 substituents selected from
        (i) a hydroxy group, and
        (ii) a carbamoyl group, (8) a carboxy group,
(9) a $C_{1-6}$ alkyl-carbonyl group (e.g., isobutylcarbonyl),
(10) a $C_{1-6}$ alkoxy-carbonyl group (e.g., ethoxycarbonyl),
(11) a $C_{6-14}$ aryl-carbonyl group (e.g., benzoyl) optionally substituted by 1 to 3 halogen atoms,
(12) a carbamoyl group optionally mono- or di-substituted by substituent(s) selected from
    (a) a $C_{1-6}$ alkyl group (e.g., methyl, ethyl, isopropyl, isobutyl, tert-butyl) optionally substituted by 1 to 3 substituents selected from
        (i) a halogen atom,
        (ii) a $C_{1-6}$ alkoxy-carbonyl group (e.g., methoxycarbonyl) optionally substituted by 1 to 3 $C_{6-14}$ aryl groups (e.g., phenyl),
        (iii) a $C_{6-14}$ aryl group (e.g., phenyl) optionally substituted by 1 to 3 substituents selected from
            (A) a $C_{1-6}$ alkoxy-carbonyl group (e.g., methoxycarbonyl), and
            (B) a carboxy group,
        (iv) a hydroxy group,
        (v) a carboxy group,
        (vi) a $C_{3-10}$ cycloalkyl group (e.g., cyclopropyl), and
        (vii) a $C_{1-6}$ alkylsulfonyl group (e.g., methylsulfonyl),
    (b) a $C_{6-14}$ aryl group (e.g., phenyl) optionally substituted by 1 to 3 substituents selected from
        (i) a halogen atom,
        (ii) a $C_{1-6}$ alkyl group (e.g., ethyl) optionally substituted by 1 to 3 substituents selected from
            (A) a halogen atom,
            (B) a carboxy group, and
            (C) a $C_{1-6}$ alkoxy-carbonyl group (e.g., methoxycarbonyl),
        (iii) a $C_{1-6}$ alkoxy group (e.g., methoxy) optionally substituted by 1 to 3 substituents selected from
            (A) a carboxy group,
            (B) a $C_{1-6}$ alkoxy-carbonyl group (e.g., methoxycarbonyl), and
            (C) a $C_{6-14}$ aryl group (e.g., phenyl), and
        (iv) a hydroxy group,
    (c) a 5- or 6-membered aromatic heterocyclic group (e.g., pyridyl (e.g., 2-pyridyl)),
    (d) a sulfamoyl group optionally mono- or di-substituted by a $C_{1-6}$ alkyl group (e.g., methyl) optionally substituted by a $C_{3-10}$ cycloalkyl group (e.g., cyclopropyl),
    (e) a sulfonyl group optionally mono- or di-substituted by a $C_{1-6}$ alkyl group (e.g., pentyl),
    (f) a 5- or 6-membered nonaromatic heterocyclic group (e.g., pyrrolidinyl, piperidinyl, tetrahydrothiopyranyl) optionally substituted by 1 to 3 substituents selected from
        (i) a carboxy group,
        (ii) a $C_{1-6}$ alkyl-carbonyl group (e.g., acetyl),
        (iii) a $C_{1-6}$ alkoxy-carbonyl group (e.g., tert-butoxycarbonyl, ethoxycarbonyl),
        (iv) a $C_{1-6}$ alkoxy-carbonyl-carbonyl group,
        (v) a carboxy-carbonyl group,
        (vi) a carbamoyl group optionally mono- or di-substituted by $C_{1-6}$ alkyl groups (e.g., ethyl),
        (vii) a $C_{1-6}$ alkyl-sulfonyl group (e.g., methylsulfonyl), and
        (viii) an oxo group,
(13) a 5- or 6-membered nonaromatic heterocyclylcarbonyl group (e.g., piperidinylcarbonyl, pyrrolidinylcarbonyl) optionally substituted by 1 to 3 substituents selected from
    (a) a carboxy group,
    (b) a $C_{1-6}$ alkoxy group optionally substituted by a carboxy group,
    (c) a $C_{1-6}$ alkyl group optionally substituted by 1 to 3 halogen atoms, and
    (d) a $C_{1-6}$ alkoxy-carbonyl group (e.g., methoxycarbonyl), or
(14) a hydroxy group optionally substituted by a substituent selected from
    (a) a $C_{1-6}$ alkyl group (e.g., ethyl, isopropyl, tert-butyl) optionally substituted by 1 to 3 halogen atoms (e.g., chlorine atom), and
    (b) a $C_{6-14}$ aryl group (e.g., phenyl).
R is more preferably
(1) a $C_{1-10}$ alkyl group (e.g., methyl, ethyl, propyl, isopropyl, tert-butyl, isobutyl, pentyl) optionally substituted by 1 to 3 substituents selected from
    (a) a carbamoyl group optionally mono- or di-substituted by
        (i) a $C_{1-6}$ alkylsulfonyl group (e.g., methylsulfonyl), and
        (ii) a sulfamoyl group optionally substituted by a $C_{1-6}$ alkyl group (e.g., methyl) optionally substituted by $C_{3-10}$ cycloalkyl (e.g., cyclopropyl),
    (b) a 5- or 6-membered aromatic heterocyclic group (e.g., tetrazolyl (e.g., tetrazol-5-yl, tetrazol-1-yl)) optionally substituted by 1 to 3 substituents selected from
        (i) a carboxy group, and
        (ii) a $C_{1-6}$ alkyl group (e.g., methyl),
    (c) a 5- or 6-membered nonaromatic heterocyclic group (e.g., imidazolidinyl (e.g., imidazolidin-5-yl), piperidinyl (e.g., piperidin-4-yl)) optionally substituted by 1 to 3 substituents selected from
        (i) a carboxy group, and
        (ii) an oxo group,
    (d) a carboxy group,
    (e) a $C_{1-6}$ alkoxy-carbonyl group (e.g., ethoxycarbonyl),
    (f) a $C_{3-10}$ cycloalkyl group (e.g., cyclobutyl, cyclopentyl), and
    (g) a hydroxy group;
(2) a $C_{3-10}$ cycloalkyl group (e.g., cyclopropyl, adamantyl) optionally substituted by 1 to 3 carboxy groups,
(3) a $C_{6-14}$ aryl group (e.g., phenyl) optionally substituted by 1 to 3 substituents selected from
    (a) a carboxy group,
    (b) a $C_{1-6}$ alkyl group (e.g., methyl) optionally substituted by 1 to 3 amino groups optionally mono- or di-substituted by substituent(s) selected from
        (i) a $C_{1-6}$ alkyl group, and
        (ii) a 5- or 6-membered nonaromatic heterocyclic group (e.g., tetrahydrothiopyranyl) optionally substituted by an oxo group,
    (c) a $C_{1-6}$ alkoxy group optionally substituted by 1 to 3 substituents selected from
        (i) a carboxy group, and
        (ii) a 5- or 6-membered nonaromatic heterocyclic group (e.g., piperidinyl) optionally substituted by a carboxy-carbonyl group or a $C_{1-6}$ alkoxy-carbonyl-carbonyl group,
    (d) a 5- or 6-membered nonaromatic heterocyclic group (e.g., dihydrooxadiazolyl, imidazolidinyl) optionally substituted by 1 to 3 substituents selected from
        (i) a carboxy group,
        (ii) an oxo group, and
        (iv) a $C_{1-6}$ alkyl group (e.g., methyl) optionally substituted by 1 to 3 substituents selected from
            (A) a carboxy group, and
            (B) a $C_{1-6}$ alkoxy-carbonyl group (e.g., tert-butoxycarbonyl), and
    (e) a $C_{6-14}$ aryl group (e.g., phenyl) optionally substituted by a carboxy-$C_{1-6}$ alkyl group (e.g., carboxy-methyl);
(4) a 5- or 6-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
    (a) a $C_{1-6}$ alkyl group (e.g., methyl, ethyl) optionally substituted by 1 to 3 carboxy groups,
    (b) a $C_{1-6}$ alkoxy group (e.g., methoxy) optionally substituted by 1 to 3 carboxy groups, and
    (c) a $C_{1-6}$ alkylthio group (e.g., methylthio) optionally substituted by 1 to 3 carboxy groups;
(5) an amino group optionally mono- or di-substituted by substituents selected from
    (a) a $C_{6-14}$ aryl group (e.g., phenyl) optionally substituted by 1 to 3 carboxy-$C_{1-6}$ alkoxy groups,
    (b) a $C_{1-6}$ alkyl group (e.g., methyl, ethyl) optionally substituted by 1 to 3 carboxy groups, and
    (c) a 5- or 6-membered aromatic heterocyclic group optionally substituted by 1 to 3 substituents selected from
        (i) a hydroxy group, and
        (ii) a carbamoyl group;
(6) a carboxy group; or
(7) a carbamoyl group optionally mono- or di-substituted by substituents selected from
    (a) a $C_{1-6}$ alkyl group (e.g., methyl, ethyl, isopropyl isobutyl, tert-butyl) optionally substituted by 1 to 3 substituents selected from
        (i) a $C_{6-14}$ aryl group (e.g., phenyl) optionally substituted by 1 to 3 substituents selected from
            (A) a carboxy group, and
            (B) a carboxy-$C_{1-6}$ alkyl group,
        (ii) a carboxy group, and
        (iii) a $C_{1-6}$ alkyl-sulfonyl group (e.g., methylsulfonyl),
    (b) a $C_{6-14}$ aryl group (e.g., phenyl) optionally substituted by 1 to 3 carboxy-$C_{1-6}$ alkyl groups (e.g., carboxy-ethyl) or carboxy-$C_{1-6}$ alkoxy groups (e.g., carboxy-methoxy),
    (c) a 5- or 6-membered nonaromatic heterocyclic group (e.g., piperidinyl, tetrahydrothiopyranyl) optionally substituted by 1 to 3 substituents selected from
        (i) a carboxy group,
        (ii) a carboxy-carbonyl group, and
        (iii) a carboxy-$C_{1-6}$ alkoxy group (e.g., carboxy-methoxy), and
    (d) a $C_{1-6}$ alkyl-sulfamoyl group (e.g., methyl-sulfamoyl) optionally substituted by 1 to 3 $C_{3-10}$ cycloalkyl groups (e.g., cyclopropyl), or
(8) a 5- or 6-membered nonaromatic heterocyclylcarbonyl group (e.g., piperidinylcarbonyl, pyrrolidinylcarbonyl) optionally substituted by 1 to 3 substituents selected from
    (a) a carboxy group,
    (b) a $C_{1-6}$ alkoxy group optionally substituted by a carboxy group,
    (c) a $C_{1-6}$ alkyl group optionally substituted by 1 to 3 halogen atoms, and
    (d) a $C_{1-6}$ alkoxy-carbonyl group (e.g., methoxycarbonyl).
R is more preferably,
(1) a $C_{1-10}$ alkyl group (e.g., methyl, ethyl, propyl, isopropyl, tert-butyl, isobutyl, pentyl) optionally substituted by 1 to 3 substituents selected from
    (a) a carbamoyl group optionally mono- or di-substituted by
        (i) a $C_{1-6}$ alkylsulfonyl group (e.g., methylsulfonyl), and
        (ii) a sulfamoyl group optionally substituted by a $C_{1-6}$ alkyl group (e.g., methyl) optionally substituted by $C_{3-10}$ cycloalkyl (e.g., cyclopropyl),
    (b) a 5- or 6-membered aromatic heterocyclic group (e.g., tetrazolyl (e.g., tetrazol-5-yl, tetrazol-1-yl), indolyl (e.g., indol-3-yl)) optionally substituted by 1 to 3 substituents selected from
        (i) a carboxy group, and
        (ii) a $C_{1-6}$ alkyl group (e.g., methyl),
    (c) a 5- or 6-membered nonaromatic heterocyclic group (e.g., imidazolidinyl (e.g., imidazolidin-5-yl), piperidinyl (e.g., piperidin-4-yl)) optionally substituted by 1 to 3 carboxy groups, and
    (d) a carboxy group;
(2) a $C_{6-14}$ aryl group (e.g., phenyl) optionally substituted by 1 to 3 substituents selected from
    (a) a carboxy group,
    (b) a $C_{1-6}$ alkoxy group optionally substituted by 1 to 3 carboxy groups, and
    (c) a 5- or 6-membered nonaromatic heterocyclic group (e.g., piperidinyl) optionally substituted by 1 to 3 carboxy groups, and
    (d) a $C_{6-14}$ aryl group (e.g., phenyl) optionally substituted by a carboxy-$C_{1-6}$ alkyl group (e.g., carboxy-methyl);
(3) a 5- or 6-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
    (a) a $C_{1-6}$ alkyl group (e.g., methyl, ethyl) optionally substituted by 1 to 3 carboxy groups, and
    (b) a $C_{1-6}$ alkoxy group (e.g., methoxy) optionally substituted by 1 to 3 carboxy groups;
(4) an amino group optionally mono- or di-substituted by substituents selected from
    (a) a $C_{6-14}$ aryl group (e.g., phenyl) optionally substituted by 1 to 3 carboxy-$C_{1-6}$ alkoxy groups,
    (b) a $C_{1-6}$ alkyl group (e.g., methyl, ethyl) optionally substituted by 1 to 3 carboxy groups, and
    (c) a 5- or 6-membered aromatic heterocyclic group optionally substituted by 1 to 3 substituents selected from
        (i) a hydroxy group, and
        (ii) a carbamoyl group;
(5) a carboxy group; or
(6) a carbamoyl group optionally mono- or di-substituted by substituents selected from
    (a) a $C_{1-6}$ alkyl group (e.g., methyl, ethyl, isopropyl isobutyl, tert-butyl) optionally substituted by 1 to 3 substituents selected from
        (i) a $C_{6-14}$ aryl group (e.g., phenyl) optionally substituted by 1 to 3 substituents selected from
            (A) a carboxy group, and
            (B) a carboxy-$C_{1-6}$ alkyl group,
        (ii) a carboxy group, and
        (iii) a $C_{1-6}$ alkyl-sulfonyl group (e.g., methylsulfonyl), and
    (b) a 5- or 6-membered nonaromatic heterocyclic group (e.g., piperidinyl, tetrahydrothiopyranyl) optionally substituted by 1 to 3 substituents selected from
        (i) a carboxy group,
        (ii) a carboxy-carbonyl group, and
        (iii) a carboxy-$C_{1-6}$ alkoxy group (e.g., carboxy-methoxy).
Preferable examples of compound (I) include the following compounds.
[Compound A1]
Compound (I) represented by the formula (I), wherein ring A is a benzene ring optionally further substituted by 1 to 3 substituents selected from (1) a halogen atom,
(2) an optionally substituted $C_{1-6}$ alkyl group,
(3) an optionally substituted $C_{2-10}$ alkenyl group,
(4) an optionally substituted $C_{1-6}$ alkoxy group,
(5) a cyano group,
(6) an optionally substituted $C_{6-14}$ aryl group,
(7) an optionally substituted aromatic heterocyclic group, and
(8) an optionally substituted nonaromatic heterocyclic group; ring B is a piperazine ring optionally further substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms; and
R is
(1) an optionally substituted hydrocarbon group,
(2) an optionally substituted heterocyclic group,
(3) an optionally substituted amino group, or
(4) an acyl group.

[Compound A2]

Compound (I) represented by the formula (I), wherein ring A is a benzene ring optionally further substituted by 1 to 3 substituents selected from
(1) a halogen atom (e.g., chlorine atom, bromine atom),
(2) an optionally substituted $C_{1-6}$ alkyl group (e.g., methyl, isopropyl, 1-hydroxy-1-methylethyl),
(3) an optionally substituted $C_{2-10}$ alkenyl group (e.g., ethenyl, 1-propenyl, isopropenyl),
(4) an optionally substituted $C_{1-6}$ alkoxy group,
(5) a cyano group,
(6) an optionally substituted $C_{6-14}$ aryl group,
(7) an optionally substituted 4- to 7-membered aromatic heterocyclic group, and
(8) an optionally substituted 4- to 7-membered nonaromatic heterocyclic group; ring B is a piperazine ring optionally further substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms; and
R is
(1) a $C_{1-10}$ alkyl group (e.g., methyl, ethyl, propyl, isopropyl, tert-butyl, isobutyl, pentyl) optionally substituted by 1 to 3 substituents selected from
  (a) a carbamoyl group optionally mono- or di-substituted by substituent(s) selected from
    (i) a carboxy group,
    (ii) a $C_{1-6}$ alkyl group (e.g., methyl) optionally substituted by 1 to 3 substituents selected from
      (A) a carboxy group, and
      (B) a $C_{6-14}$ aryl group (e.g., phenyl) optionally substituted by a carboxy group,
    (iii) a $C_{1-6}$ alkylsulfonyl group (e.g., methylsulfonyl),
    (iv) a $C_{6-14}$ aryl group,
    (v) a 4- to 7-membered aromatic heterocyclic group, and
    (vi) a sulfamoyl group optionally substituted by a $C_{1-6}$ alkyl group (e.g., methyl) optionally substituted by a $C_{3-10}$ cycloalkyl (e.g., cyclopropyl),
  (b) a 4- to 7-membered aromatic heterocyclylthio group (e.g., pyrazolylthio (e.g., pyrazol-5-ylthio), tetrazolylthio (e.g., tetrazol-5-ylthio), benzimidazolylthio (e.g., benzimidazol-2-ylthio)) optionally substituted by 1 to 3 substituents selected from
    (i) a carboxy group,
    (ii) a $C_{1-6}$ alkyl group (e.g., methyl) optionally substituted by a carboxy group, and
    (iii) a $C_{6-14}$ aryl group,
  (c) a 4- to 7-membered aromatic heterocyclic group (e.g., tetrazolyl (e.g., tetrazol-5-yl, tetrazol-1-yl), imidazolyl) optionally substituted by 1 to 3 substituents selected from
    (i) a carboxy group,
    (ii) a $C_{1-6}$ alkyl group, and
    (iii) a $C_{1-6}$ alkylthio group (e.g., methylthio) optionally substituted by a carboxy group,
  (d) a 4- to 7-membered nonaromatic heterocyclic group (e.g., imidazolidinyl (e.g., imidazolidin-5-yl), piperidinyl (e.g., piperidin-4-yl)) optionally substituted by 1 to 3 substituents selected from
    (i) a carboxy group,
    (ii) a $C_{1-6}$ alkyl group (e.g., methyl) optionally substituted by 1 to 3 substituents selected from
      (A) a carboxy group,
      (B) a $C_{1-6}$ alkoxy-carbonyl group (e.g., methoxycarbonyl) optionally substituted by a $C_{6-14}$ aryl group (e.g., phenyl), and
      (C) a $C_{6-14}$ aryl group (e.g., phenyl) optionally substituted by a $C_{1-6}$ alkoxy-carbonyl group (e.g., methoxycarbonyl),
    (iii) an oxo group, and
    (iv) a $C_{7-13}$ aralkyl group (e.g., benzyl) optionally substituted by a carboxy group,
  (e) a halogen atom,
  (f) a cyano group,
  (g) a hydroxy group,
  (h) a carboxy group,
  (i) a $C_{1-6}$ alkoxy group (e.g., methoxy, ethoxy) optionally substituted by 1 to 3 substituents selected from
    (i) a halogen atom,
    (ii) a carboxy group,
    (iii) a $C_{1-6}$ alkoxy group,
    (iv) a $C_{1-6}$ alkoxy-carbonyl group, and
    (v) a $C_{6-14}$ aryl group (e.g., phenyl)
  (j) an amino group optionally mono- or di-substituted by substituent(s) selected from
    (i) a $C_{1-6}$ alkyl group,
    (ii) a $C_{1-6}$ alkyl-carbonyl group (e.g., acetyl),
    (iii) $C_{6-14}$ aryl-carbonyl group (e.g., benzoyl),
    (iv) a $C_{1-6}$ alkoxy-carbonyl group (e.g., tert-butoxycarbonyl),
    (v) a $C_{1-6}$ alkylsulfonyl group,
    (vi) a carbamoyl group optionally mono- or di-substituted by a $C_{1-6}$ alkyl group, and
    (vii) a 4- to 7-membered aromatic heterocyclic group,
  (k) a $C_{1-6}$ alkyl-carbonyl group (e.g., acetyl) optionally substituted by 1 to 3 substituents selected from
    (i) a halogen atom,
    (ii) a $C_{1-6}$ alkoxy group, and
    (iii) a $C_{6-14}$ aryl group,
  (l) a $C_{1-6}$ alkoxy-carbonyl group (e.g., ethoxycarbonyl) optionally substituted by 1 to 3 substituents selected from
    (i) a halogen atom,
    (ii) a $C_{1-6}$ alkoxy group, and
    (iii) a $C_{6-14}$ aryl group,
  (m) a $C_{6-14}$ aryloxy group (e.g., phenyloxy),
  (n) a $C_{6-14}$ aryl group (e.g., phenyl) optionally substituted by 1 to 3 substituents selected from
    (i) a $C_{1-6}$ alkyl group,
    (ii) a hydroxy group,
    (iii) a $C_{1-6}$ alkoxy group (e.g., methoxy), and
    (iv) a halogen atom (e.g., chlorine atom), and (o) a $C_{3-10}$ cycloalkyl group (e.g., cyclobutyl, cyclopentyl) optionally substituted by 1 to 3 substituents selected from
    (i) a $C_{1-6}$ alkyl group (e.g., methyl),
    (ii) a $C_{1-6}$ alkyl-carbonyl group (e.g., acetyl), and
    (iii) an oxo group
(the $C_{3-10}$ cycloalkyl group may form a fused ring group with a benzene ring optionally substituted by a $C_{1-6}$ alkoxy group (e.g., methoxy));
(2) a $C_{3-10}$ cycloalkyl group (e.g., cyclopropyl, cyclobutyl, adamantyl) optionally substituted by 1 to 3 substituents selected from
    (a) a carboxy group,
    (b) a $C_{1-6}$ alkyl group (e.g., methyl),
    (c) a hydroxy group, and
    (d) a $C_{1-6}$ alkoxy-carbonyl group (e.g., methoxycarbonyl),
(3) a $C_{2-10}$ alkenyl group (e.g., ethenyl) optionally substituted by 1 to 3 substituents selected from
    (a) a carbamoyl group optionally mono- or di-substituted by substituent(s) selected from
        (i) a $C_{1-6}$ alkyl group (e.g., methyl),
        (ii) a $C_{6-14}$ aryl group, and
        (iii) a 4- to 7-membered aromatic heterocyclic group,
    (b) a carboxy group, and
    (c) a hydroxy group,
(4) a $C_{6-14}$ aryl group (e.g., phenyl) optionally substituted by 1 to 3 substituents selected from
    (a) a carboxy group,
    (b) a $C_{1-6}$ alkyl group (e.g., methyl) optionally substituted by 1 to 3 substituents selected from
        (i) a halogen atom (e.g., chlorine atom),
        (ii) a 4- to 7-membered nonaromatic heterocyclic group (e.g., pyrrolidinyl) optionally substituted by 1 to 3 substituents selected from
            (A) a hydroxy group, and
            (B) an oxo group, and
        (iii) an amino group optionally mono- or di-substituted by substituent(s) selected from
            (A) a $C_{1-6}$ alkyl group, and
            (B) a 4- to 7-membered nonaromatic heterocyclic group (e.g., tetrahydrothiopyranyl) optionally substituted by an oxo group,
    (c) a $C_{1-6}$ alkoxy group (e.g., methoxy, ethoxy) optionally substituted by 1 to 3 substituents selected from
        (i) a carboxy group,
        (ii) a hydroxy group,
        (iii) a $C_{6-14}$ aryl group (e.g., phenyl),
        (iv) a 4- to 7-membered nonaromatic heterocyclic group (e.g., piperidinyl, dihydrooxadiazolyl) optionally substituted by 1 to 3 substituents selected from
            (A) an oxo group,
            (B) a carboxy-carbonyl group optionally substituted by $C_{1-6}$ alkyl (e.g., methyl),
            (C) $C_{1-6}$ alkyl (e.g., methyl), and
            (D) a $C_{1-6}$ alkoxy-carbonyl group (e.g., tert-butoxycarbonyl),
        (v) a $C_{1-6}$ alkoxy-carbonyl group (e.g., methoxycarbonyl),
        (vi) an amino group optionally mono- or di-substituted by substituent(s) selected from
            (A) a $C_{1-6}$ alkyl group (e.g., methyl),
            (B) a carboxy-carbonyl group, and
            (C) a $C_{1-6}$ alkylsulfonyl group (e.g., methylsulfonyl),
        (vii) a 4- to 7-membered aromatic heterocyclic group (e.g., tetrazolyl), and
        (viii) a carbamoyl group optionally mono- or di-substituted by substituent(s) selected from
            (A) a $C_{1-6}$ alkylsulfonyl group (e.g., pentylsulfonyl),
            (B) a $C_{3-10}$ cycloalkyl group, and
            (C) a methylaminosulfonyl group optionally substituted by $C_{3-10}$ cycloalkyl (e.g., cyclopropyl),
    (d) a halogen atom (e.g., fluorine atom),
    (e) a 4- to 7-membered nonaromatic heterocyclic group (e.g., dihydrooxadiazolyl, imidazolidinyl) optionally substituted by 1 to 3 substituents selected from
        (i) a carboxy group,
        (ii) a $C_{1-6}$ alkyl group,
        (iii) an oxo group, and
        (iv) a $C_{1-6}$ alkyl group (e.g., methyl) optionally substituted by 1 to 3 substituents selected from
            (A) a carboxy group, and
            (B) a $C_{1-6}$ alkoxy-carbonyl group (e.g., tert-butoxycarbonyl),
    (f) a cyano group,
    (g) a hydroxy group,
    (h) a $C_{1-6}$ alkoxy-carbonyl group (e.g., methoxycarbonyl),
    (i) a 4- to 7-membered nonaromatic heterocycleoxy group (e.g., piperazinyloxy) optionally substituted by 1 to 3 substituents selected from
        (i) a carboxy-carbonyl group, and
        (ii) a $C_{1-6}$ alkyl group (e.g., methyl), and
    (j) a $C_{6-14}$ aryl group (e.g., phenyl) optionally substituted by a $C_{1-6}$ alkyl group (e.g., methyl) optionally substituted by a carboxy group,
(5) a 4- to 7-membered aromatic heterocyclic group (e.g., pyrazolyl, tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
    (a) a halogen atom (e.g., chlorine atom),
    (b) a hydroxy group,
    (c) a $C_{1-6}$ alkyl group (e.g., methyl, ethyl) optionally substituted by 1 to 3 substituents selected from
        (i) a carboxy group,
        (ii) a halogen atom (e.g., chlorine atom, fluorine atom),
        (iii) a 4- to 7-membered nonaromatic heterocyclic group (e.g., pyrrolidinyl) optionally substituted by a hydroxy group,
        (iv) an amino group optionally mono- or di-substituted by substituent(s) selected from
            (A) a $C_{1-6}$ alkyl group, and
            (B) a 4- to 7-membered nonaromatic heterocyclic group (e.g., tetrahydrothiopyranyl) optionally substituted by an oxo group, and
        (v) a $C_{1-6}$ alkoxy-carbonyl group (e.g., methoxycarbonyl, tert-butoxycarbonyl),
    (d) a $C_{3-10}$ cycloalkyl group (e.g., cyclohexyl),
    (e) a $C_{6-14}$ aryl group (e.g., phenyl) optionally substituted by 1 to 3 substituents selected from
        (i) a $C_{1-6}$ alkyl group,
        (ii) a hydroxy group,
        (iii) a $C_{1-6}$ alkoxy group, and
        (iv) a halogen atom,
    (f) a $C_{1-6}$ alkylthio group (e.g., methylthio) optionally substituted by 1 to 3 substituents selected from
        (i) a carboxy group,
        (ii) a hydroxy group,
        (iii) a $C_{1-6}$ alkoxy group (e.g., methoxy), and
        (iv) a $C_{1-6}$ alkoxy-carbonyl group (e.g., methoxycarbonyl, ethoxycarbonyl, tert-butoxycarbonyl),
    (g) a $C_{7-13}$ aralkyloxy group (e.g., benzyloxy),
    (h) a mercapto group,
    (i) a $C_{1-6}$ alkoxy group (e.g., methoxy, ethoxy) optionally substituted by 1 to 3 substituents selected from (i) a halogen atom,
(ii) a carboxy group,
(iii) a $C_{1-6}$ alkoxy group,
(iv) a $C_{1-6}$ alkoxy-carbonyl group (e.g., methoxycarbonyl, tert-butoxycarbonyl),
(v) a 4- to 7-membered nonaromatic heterocyclic group (e.g., piperidinyl, dihydrooxadiazolyl) optionally substituted by 1 to 3 substituents selected from
(A) an oxo group,
(B) a carboxy-carbonyl group, and
(C) a $C_{1-6}$ alkyl group (e.g., methyl),
(vi) an amino group optionally mono- or di-substituted by substituent(s) selected from
(A) a $C_{1-6}$ alkyl group (e.g., methyl),
(B) a carboxy-carbonyl group, and
(C) a $C_{1-6}$ alkylsulfonyl group (e.g., methylsulfonyl),
(vii) a 4- to 7-membered aromatic heterocyclic group (e.g., tetrazolyl),
(viii) a carbamoyl group optionally mono- or di-substituted by substituent(s) selected from
(A) a $C_{1-6}$ alkylsulfonyl group (e.g., pentylsulfonyl),
(B) a $C_{3-10}$ cycloalkyl group, and
(C) a methylaminosulfonyl group optionally substituted by $C_{3-10}$ cycloalkyl (e.g., cyclopropyl), and
(ix) a $C_{6-14}$ aryl group (e.g., phenyl),
(j) a $C_{1-6}$ alkyl-carbonyl group (e.g., acetyl) optionally substituted by 1 to 3 substituents selected from
(i) a halogen atom,
(ii) a $C_{1-6}$ alkoxy group, and
(iii) a $C_{6-14}$ aryl group,
(k) a $C_{1-6}$ alkoxy-carbonyl group (e.g., tert-butoxycarbonyl) optionally substituted by 1 to 3 substituents selected from
(i) a halogen atom,
(ii) a $C_{1-6}$ alkoxy group, and
(iii) a $C_{6-14}$ aryl group,
(l) a 4- to 7-membered nonaromatic heterocycleoxy group (e.g., piperazinyloxy) optionally substituted by 1 to 3 substituents selected from
(i) a carboxy-carbonyl group,
(ii) a $C_{1-6}$ alkyl group (e.g., methyl), and
(iii) a $C_{1-6}$ alkoxy-carbonyl group (tert-butoxycarbonyl),
(m) a 4- to 7-membered nonaromatic heterocyclic group (e.g., imidazolidinyl, piperidinyl) optionally substituted by 1 to 3 substituents selected from
(i) a $C_{1-6}$ alkyl group (e.g., methyl) optionally substituted by a carboxy group,
(ii) a $C_{1-6}$ alkoxy-carbonyl group (e.g., tert-butoxycarbonyl) and
(iii) an oxo group, and
(n) an amino group optionally mono- or di-substituted by substituent(s) selected from
(i) a carboxy-carbonyl group, and
(ii) a $C_{1-6}$ alkyl group,
(6) a 4- to 7-membered nonaromatic heterocyclic group (e.g., pyrrolidinyl (e.g., 2-pyrrolidinyl), tetrahydrofuranyl (e.g., tetrahydrofuran-3-yl, tetrahydrofuran-2-yl), thiazolidinyl (e.g., thiazolidin-4-yl), piperidinyl (e.g., 1-piperidinyl, 2-piperidinyl, 4-piperidinyl), pyranyl (e.g., 2-pyranyl), tetrahydropyrimidinyl (e.g., tetrahydropyrimidin-4-yl, tetrahydropyrimidin-5-yl), hexahydropyrimidinyl (e.g., hexahydropyrimidin-4-yl), 5H-[1,3]thiazolo[3,2-a]pyrimidinyl (e.g., 5H-[1,3]thiazolo[3,2-a]pyrimidin-6-yl), 2-oxabicyclo[2,2,1]heptan-1-yl, dihydrobenzofuran, indolinyl, morpholinyl) optionally substituted by 1 to 3 substituents selected from (a) a halogen atom (e.g., chlorine atom),
(b) a hydroxy group,
(c) a $C_{1-6}$ alkyl group (e.g., methyl) optionally substituted by 1 to 3 substituents selected from
(i) a carboxy group,
(ii) a halogen atom (e.g., chlorine atom),
(iii) a $C_{6-14}$ aryl group (e.g., phenyl), and
(iv) a $C_{1-6}$ alkoxy-carbonyl group (e.g., methoxycarbonyl),
(d) a $C_{6-14}$ aryl group (e.g., phenyl) optionally substituted by 1 to 3 substituents selected from
(i) a $C_{1-6}$ alkyl group,
(ii) a hydroxy group,
(iii) a $C_{1-6}$ alkoxy group, and
(iv) a halogen atom,
(e) a $C_{1-6}$ alkylthio group (e.g., methylthio) optionally substituted by 1 to 3 substituents selected from
(i) a carboxy group,
(ii) a hydroxy group,
(iii) a $C_{1-6}$ alkoxy group (e.g., methoxy), and
(iv) a $C_{1-6}$ alkoxy-carbonyl group (e.g., methoxycarbonyl, tert-butoxycarbonyl),
(f) a $C_{7-13}$ aralkyloxy group (e.g., benzyloxy),
(g) a mercapto group,
(h) a $C_{1-6}$ alkoxy group (e.g., methoxy) optionally substituted by 1 to 3 substituents selected from
(i) a halogen atom,
(ii) a carboxy group,
(iii) a $C_{1-6}$ alkoxy group, and
(iv) a $C_{1-6}$ alkoxy-carbonyl group (e.g., methoxycarbonyl, tert-butoxycarbonyl);
(i) a $C_{1-6}$ alkyl-carbonyl group (e.g., acetyl) optionally substituted by 1 to 3 substituents selected from
(i) a halogen atom,
(ii) a $C_{1-6}$ alkoxy group,
(iii) a $C_{6-14}$ aryl group, and
(iv) a carboxy group,
(j) a $C_{1-6}$ alkoxy-carbonyl group (e.g., tert-butoxycarbonyl) optionally substituted by 1 to 3 substituents selected from
(i) a halogen atom,
(ii) a $C_{1-6}$ alkoxy group, and
(iii) a $C_{6-14}$ aryl group,
(k) an oxo group, and
(l) a carboxy group,
(7) an amino group optionally mono- or di-substituted by substituent(s) selected from
(a) $C_{3-10}$ cycloalkyl group,
(b) a $C_{6-14}$ aryl group (e.g., phenyl) optionally substituted by 1 to 3 substituents selected from
(i) a hydroxy group,
(ii) a carbamoyl group,
(iii) a $C_{1-6}$ alkyl group, and
(iv) a $C_{1-6}$ alkoxy group (e.g., methoxy) optionally substituted by 1 to 3 substituents selected from
(A) a carboxy group,
(B) a $C_{6-14}$ aryl group (e.g., phenyl), and
(C) a $C_{1-6}$ alkoxy-carbonyl group (e.g., methoxycarbonyl);
(c) a $C_{1-6}$ alkyl group (e.g., methyl, ethyl) optionally substituted by 1 to 3 substituents selected from
(i) a carboxy group,
(ii) a $C_{1-6}$ alkoxy group, and
(iii) a $C_{1-6}$ alkoxy-carbonyl group (e.g., ethoxycarbonyl),
(d) a $C_{7-13}$ aralkyl group,
(e) a 4- to 7-membered aromatic heterocyclic group (e.g., triazolyl, tetrazolyl, thiazolyl, pyridyl) optionally substituted by 1 to 3 substituents selected from (i) a hydroxy group,
(ii) a carbamoyl group, and
(iii) a $C_{1-6}$ alkyl group (e.g., methyl) optionally substituted by a carboxy group, and
(f) a 4- to 7-membered nonaromatic heterocyclic group (e.g., piperidinyl, morpholinyl) optionally substituted by 1 to 3 substituents selected from
(i) a hydroxy group,
(ii) a carbamoyl group,
(iii) a $C_{1-6}$ alkyl group, and
(iv) an oxo group,
(8) a formyl group,
(9) a carboxy group,
(10) a $C_{1-6}$ alkyl-carbonyl group (e.g., isobutylcarbonyl) optionally substituted by 1 to 3 substituents selected from
(a) a halogen atom,
(b) a $C_{1-6}$ alkoxy-carbonyl group,
(c) a $C_{6-14}$ aryl group, and
(d) a $C_{1-6}$ alkoxy group,
(11) a $C_{1-6}$ alkoxy-carbonyl group (e.g., ethoxycarbonyl) optionally substituted by 1 to 3 substituents selected from
(a) a halogen atom,
(b) a $C_{6-14}$ aryl group, and
(c) a $C_{1-6}$ alkoxy group,
(12) a $C_{3-10}$ cycloalkyl-carbonyl group (e.g., cyclopropylcarbonyl, cyclopentylcarbonyl, cyclohexylcarbonyl),
(13) a $C_{6-14}$ aryl-carbonyl group (e.g., benzoyl) optionally substituted by 1 to 3 halogen atoms,
(14) a carbamoyl group optionally mono- or di-substituted by substituent(s) selected from
(a) a $C_{1-6}$ alkyl group (e.g., methyl, ethyl, isopropyl isobutyl, tert-butyl) optionally substituted by 1 to 3 substituents selected from
(i) a halogen atom,
(ii) a $C_{1-6}$ alkoxy-carbonyl group (e.g., methoxycarbonyl) optionally substituted by 1 to 3 $C_{6-14}$ aryl groups (e.g., phenyl),
(iii) a $C_{6-14}$ aryl group (e.g., phenyl) optionally substituted by 1 to 3 substituents selected from
(A) a $C_{1-6}$ alkoxy-carbonyl group (e.g., methoxycarbonyl) and
(B) a carboxy group,
(iv) a $C_{1-6}$ alkoxy group,
(v) a hydroxy group,
(vi) a 4- to 7-membered aromatic heterocyclic group,
(vii) a carboxy group,
(viii) a $C_{3-10}$ cycloalkyl group (e.g., cyclopropyl), and
(ix) a $C_{1-6}$ alkylsulfonyl group (e.g., methylsulfonyl),
(b) a $C_{3-10}$ cycloalkyl group,
(c) a $C_{6-14}$ aryl group (e.g., phenyl) optionally substituted by 1 to 3 substituents selected from
(i) a halogen atom,
(ii) a $C_{1-6}$ alkyl group (e.g., ethyl) optionally substituted by 1 to 3 substituents selected from
(A) a halogen atom,
(B) a carboxy group, and
(C) a $C_{1-6}$ alkoxy-carbonyl group (e.g., methoxycarbonyl),
(iii) a $C_{1-6}$ alkoxy group (e.g., methoxy) optionally substituted by 1 to 3 substituents selected from
(A) a carboxy group,
(B) a $C_{1-6}$ alkoxy-carbonyl group (e.g., methoxycarbonyl), and
(C) a $C_{6-14}$ aryl group (e.g., phenyl), and
(iv) a hydroxy group,
(d) a 4- to 7-membered aromatic heterocyclic group (e.g., pyridyl (e.g., 2-pyridyl), thiazolyl) optionally substituted by 1 to 3 substituents selected from
(i) a carboxy group, and
(ii) a $C_{1-6}$ alkyl group optionally substituted by a carboxy group,
(e) a sulfamoyl group optionally mono- or di-substituted by a $C_{1-6}$ alkyl group (e.g., methyl) optionally substituted by a $C_{3-10}$ cycloalkyl group (e.g., cyclopropyl),
(f) a sulfonyl group optionally mono- or di-substituted by a $C_{1-6}$ alkyl group (e.g., pentyl),
(g) a $C_{1-6}$ alkoxy group, and
(h) a 4- to 7-membered nonaromatic heterocyclic group (e.g., pyrrolidinyl, piperidinyl, tetrahydrothiopyranyl) optionally substituted by 1 to 3 substituents selected from
(i) a carboxy group,
(ii) a $C_{1-6}$ alkyl-carbonyl group (e.g., acetyl),
(iii) a $C_{1-6}$ alkoxy-carbonyl group (e.g., tert-butoxycarbonyl, ethoxycarbonyl),
(iv) a $C_{1-6}$ alkoxy-carbonyl-carbonyl group,
(v) a carboxy-carbonyl group,
(vi) a carbamoyl group optionally mono- or di-substituted by $C_{1-6}$ alkyl groups (e.g., ethyl),
(vii) a $C_{1-6}$ alkyl-sulfonyl group (e.g., methylsulfonyl), and
(viii) an oxo group;
(15) a $C_{1-6}$ alkylsulfonyl group optionally substituted by 1 to 3 substituents selected from
(a) a halogen atom, and
(b) a $C_{6-14}$ aryl group,
(16) a $C_{6-14}$ arylsulfonyl group optionally substituted by 1 to 3 halogen atoms,
(17) a sulfamoyl group optionally mono- or di-substituted by substituent(s) selected from $C_{1-6}$ alkyl groups optionally substituted by 1 to 3 substituents selected from
(a) a halogen atom, and
(b) a 4- to 7-membered nonaromatic heterocyclic group optionally substituted by an oxo group,
(18) a thiocarbamoyl group optionally mono- or di-substituted by substituent(s) selected from a $C_{1-6}$ alkyl group optionally substituted by 1 to 3 halogen atoms,
(19) a 4- to 7-membered aromatic heterocyclylcarbonyl group optionally substituted by 1 to 3 substituents selected from $C_{1-6}$ alkyl groups optionally substituted by 1 to 3 halogen atoms,
(20) a 4- to 7-membered nonaromatic heterocyclylcarbonyl group (e.g., piperidinylcarbonyl, pyrrolidinylcarbonyl) optionally substituted by 1 to 3 substituents selected from
(a) a carboxy group,
(b) a $C_{1-6}$ alkoxy group optionally substituted by a carboxy group,
(c) a $C_{1-6}$ alkyl group optionally substituted by 1 to 3 halogen atoms, and
(d) a $C_{1-6}$ alkoxy-carbonyl group (e.g., methoxycarbonyl),
(21) a hydroxy group optionally substituted by 1 to 3 substituents selected from
(a) a $C_{1-6}$ alkyl group (e.g., ethyl, isopropyl, tert-butyl) optionally substituted by 1 to 3 halogen atoms (e.g., chlorine atom), and
(b) a $C_{6-14}$ aryl group (e.g., phenyl),
or
(22) a fused ring group (e.g., indanyl, tetrahydronaphthyl, quinolyl, indolyl, benzimidazolyl) optionally substituted by 1 to 3 substituents selected from
(a) a carboxy group,
(b) a $C_{1-6}$ alkoxy group optionally substituted by a carboxy group, and (c) a $C_{1-6}$ alkyl group (e.g., methyl) optionally substituted by a carboxy group.

[Compound A3]

Compound (I) represented by the formula (I), wherein ring A is a benzene ring optionally substituted by 1 to 3 substituents selected from
(1) a halogen atom (e.g., chlorine atom, bromine atom),
(2) a $C_{1-6}$ alkyl group (e.g., methyl, isopropyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by a $C_{1-6}$ alkyl group,
(3) a $C_{2-10}$ alkenyl group (e.g., ethenyl, 1-propenyl, isopropenyl),
(4) a $C_{1-6}$ alkoxy group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by a $C_{1-6}$ alkyl group,
(5) a cyano group,
(6) a $C_{6-14}$ aryl group optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom,
(7) a 4- to 7-membered aromatic heterocyclic group optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom, and
(8) a 4- to 7-membered nonaromatic heterocyclic group optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;

ring B is a piperazine ring; and

R is
(1) a $C_{1-10}$ alkyl group (e.g., methyl, ethyl, propyl, isopropyl, tert-butyl, isobutyl, pentyl) optionally substituted by 1 to 3 substituents selected from
    (a) a carbamoyl group optionally mono- or di-substituted by substituent(s) selected from
        (i) a carboxy group,
        (ii) a $C_{1-6}$ alkyl group (e.g., methyl) optionally substituted by 1 to 3 substituents selected from
            (A) a carboxy group, and
            (B) a $C_{6-14}$ aryl group (e.g., phenyl) optionally substituted by a carboxy group,
        (iii) a $C_{1-6}$ alkylsulfonyl group (e.g., methylsulfonyl),
        (iv) a $C_{6-14}$ aryl group,
        (v) a 4- to 7-membered aromatic heterocyclic group, and
        (vi) a sulfamoyl group optionally substituted by a $C_{1-6}$ alkyl group (e.g., methyl) optionally substituted by a $C_{3-10}$ cycloalkyl (e.g., cyclopropyl),
    (b) a 4- to 7-membered aromatic heterocyclylthio group (e.g., pyrazolylthio (e.g., pyrazol-5-ylthio), tetrazolylthio (e.g., tetrazol-5-ylthio)) optionally substituted by 1 to 3 substituents selected from
        (i) a carboxy group,
        (ii) a $C_{1-6}$ alkyl group (e.g., methyl) optionally substituted by a carboxy group, and
        (iii) a $C_{6-14}$ aryl group,
    (c) a 4- to 7-membered aromatic heterocyclic group (e.g., tetrazolyl (e.g., tetrazol-5-yl, tetrazol-1-yl), imidazolyl) optionally substituted by 1 to 3 substituents selected from
        (i) a carboxy group, and
        (ii) a $C_{1-6}$ alkyl group,
    (d) a 4- to 7-membered nonaromatic heterocyclic group (e.g., imidazolidinyl (e.g., imidazolidin-5-yl), piperidinyl (e.g., piperidin-4-yl)) optionally substituted by 1 to 3 substituents selected from
        (i) a carboxy group,
        (ii) a $C_{1-6}$ alkyl group (e.g., methyl) optionally substituted by 1 to 3 substituents selected from
            (A) a carboxy group,
            (B) a $C_{1-6}$ alkoxy-carbonyl group (e.g., methoxycarbonyl) optionally substituted by a $C_{6-14}$ aryl group (e.g., phenyl), and
            (C) a $C_{6-14}$ aryl group (e.g., phenyl) optionally substituted by a $C_{1-6}$ alkoxy-carbonyl group (e.g., methoxycarbonyl), and
        (iii) an oxo group,
    (e) a halogen atom,
    (f) a cyano group,
    (g) a hydroxy group,
    (h) a carboxy group,
    (i) a $C_{1-6}$ alkoxy group (e.g., methoxy, ethoxy) optionally substituted by 1 to 3 substituents selected from
        (i) a halogen atom,
        (ii) a carboxy group,
        (iii) a $C_{1-6}$ alkoxy group, and
        (iv) a $C_{1-6}$ alkoxy-carbonyl group, and
        (v) a $C_{6-14}$ aryl group (e.g., phenyl),
    (j) an amino group optionally mono- or di-substituted by substituent(s) selected from
        (i) a $C_{1-6}$ alkyl group,
        (ii) a $C_{1-6}$ alkyl-carbonyl group (e.g., acetyl),
        (iii) $C_{6-14}$ aryl-carbonyl group (e.g., benzoyl),
        (iv) a $C_{1-6}$ alkoxy-carbonyl group (e.g., tert-butoxycarbonyl),
        (v) a $C_{1-6}$ alkylsulfonyl group,
        (vi) a carbamoyl group optionally mono- or di-substituted by a $C_{1-6}$ alkyl group, and
        (vii) a 4- to 7-membered aromatic heterocyclic group,
    (k) a $C_{1-6}$ alkyl-carbonyl group (e.g., acetyl) optionally substituted by 1 to 3 substituents selected from
        (i) a halogen atom,
        (ii) a $C_{1-6}$ alkoxy group, and
        (iii) a $C_{6-14}$ aryl group,
    (l) a $C_{1-6}$ alkoxy-carbonyl group (e.g., ethoxycarbonyl) optionally substituted by 1 to 3 substituents selected from
        (i) a halogen atom,
        (ii) a $C_{1-6}$ alkoxy group, and
        (iii) a $C_{6-14}$ aryl group, (m) a $C_{6-14}$ aryloxy group (e.g., phenyloxy),
(n) a $C_{6-14}$ aryl group (e.g., phenyl) optionally substituted by 1 to 3 substituents selected from
  (i) a $C_{1-6}$ alkyl group,
  (ii) a hydroxy group,
  (iii) a $C_{1-6}$ alkoxy group (e.g., methoxy), and
  (iv) a halogen atom (e.g., chlorine atom), and
(o) a $C_{3-10}$ cycloalkyl group (e.g., cyclobutyl, cyclopentyl) optionally substituted by 1 to 3 substituents selected from
  (i) a $C_{1-6}$ alkyl group (e.g., methyl),
  (ii) a $C_{1-6}$ alkyl-carbonyl group (e.g., acetyl), and
  (iii) an oxo group
(the $C_{3-10}$ cycloalkyl group may form a fused ring group with a benzene ring optionally substituted by a $C_{1-6}$ alkoxy group (e.g., methoxy)),
(2) a $C_{3-10}$ cycloalkyl group (e.g., cyclopropyl, cyclobutyl, adamantyl) optionally substituted by 1 to 3 substituents selected from
  (a) a carboxy group,
  (b) a $C_{1-6}$ alkyl group (e.g., methyl),
  (c) a hydroxy group, and
  (d) a $C_{1-6}$ alkoxy-carbonyl group (e.g., methoxycarbonyl),
(3) a $C_{2-10}$ alkenyl group (e.g., ethenyl) optionally substituted by 1 to 3 substituents selected from
  (a) a carbamoyl group optionally mono- or di-substituted by substituent(s) selected from
    (i) a $C_{1-6}$ alkyl group (e.g., methyl),
    (ii) a $C_{6-14}$ aryl group, and
    (iii) a 4- to 7-membered aromatic heterocyclic group,
  (b) a carboxy group, and
  (c) a hydroxy group,
(4) a $C_{6-14}$ aryl group (e.g., phenyl) optionally substituted by 1 to 3 substituents selected from
  (a) a carboxy group,
  (b) a $C_{1-6}$ alkyl group (e.g., methyl) optionally substituted by 1 to 3 substituents selected from
    (i) a halogen atoms (e.g., chlorine atom), and
    (ii) an amino group optionally mono- or di-substituted by 4- to 7-membered nonaromatic heterocyclic groups (e.g., tetrahydrothiopyranyl) optionally substituted by an oxo group,
  (c) a $C_{1-6}$ alkoxy group (e.g., methoxy) optionally substituted by 1 to 3 substituents selected from
    (i) a carboxy group,
    (ii) a hydroxy group,
    (iii) a $C_{6-14}$ aryl group (e.g., phenyl),
    (iv) a 4- to 7-membered nonaromatic heterocyclic group (e.g., piperidinyl) optionally substituted by 1 to 3 $C_{1-6}$ alkoxy-carbonyl groups (e.g., tert-butoxycarbonyl), and
    (v) a $C_{1-6}$ alkoxy-carbonyl group (e.g., methoxycarbonyl),
  (d) a halogen atom (e.g., fluorine atom),
  (e) a 4- to 7-membered nonaromatic heterocyclic group (e.g., dihydrooxadiazolyl, imidazolidinyl) optionally substituted by 1 to 3 substituents selected from
    (i) a carboxy group,
    (ii) a $C_{1-6}$ alkyl group,
    (iii) an oxo group, and
    (iv) a $C_{1-6}$ alkyl group (e.g., methyl) optionally substituted by 1 to 3 substituents selected from
      (A) a carboxy group, and
      (B) a $C_{1-6}$ alkoxy-carbonyl group (e.g., tert-butoxycarbonyl),
  (f) a cyano group,
  (g) a hydroxy group,
  (h) a $C_{1-6}$ alkoxy-carbonyl group (e.g., methoxycarbonyl), and
  (i) a $C_{6-14}$ aryl group (e.g., phenyl) optionally substituted by a $C_{1-6}$ alkyl group (e.g., methyl) optionally substituted by a carboxy group,
(5) a 4- to 7-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
  (a) a halogen atom (e.g., chlorine atom),
  (b) a hydroxy group,
  (c) a $C_{1-6}$ alkyl group (e.g., methyl) optionally substituted by 1 to 3 substituents selected from
    (i) a carboxy group,
    (ii) a $C_{1-6}$ alkoxy-carbonyl group (e.g., methoxycarbonyl, tert-butoxycarbonyl), and
    (iii) a halogen atom (e.g., chlorine atom, fluorine atom),
  (d) a $C_{3-10}$ cycloalkyl group (e.g., cyclohexyl),
  (e) a $C_{6-14}$ aryl group (e.g., phenyl) optionally substituted by 1 to 3 substituents selected from
    (i) a $C_{1-6}$ alkyl group,
    (ii) a hydroxy group,
    (iii) a $C_{1-6}$ alkoxy group, and
    (iv) a halogen atom,
  (f) a $C_{1-6}$ alkylthio group (e.g., methylthio) optionally substituted by 1 to 3 substituents selected from
    (i) a carboxy group,
    (ii) a hydroxy group,
    (iii) a $C_{1-6}$ alkoxy group (e.g., methoxy), and
    (iv) a $C_{1-6}$ alkoxy-carbonyl group (e.g., methoxycarbonyl, ethoxycarbonyl, tert-butoxycarbonyl),
  (g) a $C_{7-13}$ aralkyloxy group (e.g., benzyloxy),
  (h) a mercapto group,
  (i) a $C_{1-6}$ alkoxy group (e.g., methoxy) optionally substituted by 1 to 3 substituents selected from
    (i) a halogen atom,
    (ii) a carboxy group,
    (iii) a $C_{1-6}$ alkoxy group,
    (iv) a $C_{1-6}$ alkoxy-carbonyl group (e.g., methoxycarbonyl, tert-butoxycarbonyl), and
    (v) a $C_{6-14}$ aryl group (e.g., phenyl),
  (j) a $C_{1-6}$ alkyl-carbonyl group (e.g., acetyl) optionally substituted by 1 to 3 substituents selected from
    (i) a halogen atom,
    (ii) a $C_{1-6}$ alkoxy group, and
    (iii) a $C_{6-14}$ aryl group,
  (k) a $C_{1-6}$ alkoxy-carbonyl group (e.g., tert-butoxycarbonyl) optionally substituted by 1 to 3 substituents selected from
    (i) a halogen atom,
    (ii) a $C_{1-6}$ alkoxy group, and
    (iii) a $C_{6-14}$ aryl group,
  (l) a hydroxy group,
  (m) a $C_{3-10}$ cycloalkyl group, and
  (n) a 4- to 7-membered nonaromatic heterocyclic group (e.g., imidazolidinyl, piperidinyl) optionally substituted by 1 to 3 $C_{1-6}$ alkoxycarbonyl groups (e.g., tert-butoxycarbonyl),
(6) a 4- to 7-membered nonaromatic heterocyclic group (e.g., pyrrolidinyl (e.g., 2-pyrrolidinyl), tetrahydrofuranyl (e.g., tetrahydrofuran-3-yl, tetrahydrofuran-2-yl), thiazolidinyl (e.g., thiazolidin-4-yl), piperidinyl (e.g., 1-piperidinyl, 2-piperidinyl, 4-piperidinyl), pyranyl (e.g., 2-pyranyl), tetrahydropyrimidinyl (e.g., tetrahydropyrimidin-4-yl, tetrahydropyrimidin-5-yl), hexahydropyrimidinyl (e.g., hexahydropyrimidin-4-yl), 5H-[1,3]thiazolo[3,2-a]pyrimidinyl (e.g., 5H-[1,3]thiazolo[3,2-a]pyrimidin-6-yl, 2-oxabicyclo[2,2,1]heptan-1-yl, morpholinyl) optionally substituted by 1 to 3 substituents selected from
- (a) a halogen atom (e.g., chlorine atom),
- (b) a hydroxy group,
- (c) a $C_{1-6}$ alkyl group (e.g., methyl) optionally substituted by 1 to 3 substituents selected from
  - (i) a carboxy group,
  - (ii) a halogen atom (e.g., chlorine atom),
  - (iii) a $C_{6-14}$ aryl group (e.g., phenyl), and
  - (iv) a $C_{1-6}$ alkoxy-carbonyl group (e.g., methoxycarbonyl),
- (d) a $C_{6-14}$ aryl group (e.g., phenyl) optionally substituted by 1 to 3 substituents selected from
  - (i) a $C_{1-6}$ alkyl group,
  - (ii) a hydroxy group,
  - (iii) a $C_{1-6}$ alkoxy group, and
  - (iv) a halogen atom,
- (e) a $C_{1-6}$ alkylthio group (e.g., methylthio) optionally substituted by 1 to 3 substituents selected from
  - (i) a carboxy group,
  - (ii) a hydroxy group,
  - (iii) a $C_{1-6}$ alkoxy group (e.g., methoxy), and
  - (iv) a $C_{1-6}$ alkoxy-carbonyl group (e.g., methoxycarbonyl, tert-butoxycarbonyl),
- (f) a $C_{7-13}$ aralkyloxy group (e.g., benzyloxy),
- (g) a mercapto group,
- (h) a $C_{1-6}$ alkyl group (e.g., methoxy) optionally substituted by 1 to 3 substituents selected from
  - (i) a halogen atom,
  - (ii) a carboxy group,
  - (iii) a $C_{1-6}$ alkoxy group, and
  - (iv) a $C_{1-6}$ alkoxy-carbonyl group (e.g., methoxycarbonyl, tert-butoxycarbonyl);
- (i) a $C_{1-6}$ alkyl-carbonyl group (e.g., acetyl) optionally substituted by 1 to 3 substituents selected from
  - (i) a halogen atom,
  - (ii) a $C_{1-6}$ alkoxy group, and
  - (iii) a $C_{6-14}$ aryl group,
- (j) a $C_{1-6}$ alkoxy-carbonyl group (e.g., tert-butoxycarbonyl) optionally substituted by 1 to 3 substituents selected from
  - (i) a halogen atom,
  - (ii) a $C_{1-6}$ alkoxy group, and
  - (iii) a $C_{6-14}$ aryl group, and
- (k) an oxo group, (7) an amino group optionally mono- or di-substituted by substituent(s) selected from
- (a) $C_{3-10}$ cycloalkyl group,
- (b) a $C_{6-14}$ aryl group (e.g., phenyl) optionally substituted by 1 to 3 substituents selected from
  - (i) a hydroxy group,
  - (ii) a carbamoyl group,
  - (iii) a $C_{1-6}$ alkyl group, and
  - (iv) a $C_{1-6}$ alkoxy group (e.g., methoxy) optionally substituted by 1 to 3 substituents selected from
    - (A) a carboxy group,
    - (B) a $C_{6-14}$ aryl group (e.g., phenyl), and
    - (C) a $C_{1-6}$ alkoxy-carbonyl group (e.g., methoxycarbonyl),
- (c) a $C_{1-6}$ alkyl group (e.g., methyl, ethyl) optionally substituted by 1 to 3 substituents selected from
  - (i) a carboxy group,
  - (ii) a $C_{1-6}$ alkoxy group, and
  - (iii) a $C_{1-6}$ alkoxy-carbonyl group (e.g., ethoxycarbonyl),
- (d) a $C_{7-13}$ aralkyl group,
- (e) a 4- to 7-membered aromatic heterocyclic group (e.g., triazolyl, tetrazolyl, pyridyl) optionally substituted by 1 to 3 substituents selected from
  - (i) a hydroxy group,
  - (ii) a carbamoyl group, and
  - (iii) a $C_{1-6}$ alkyl group, and
- (f) a 4- to 7-membered nonaromatic heterocyclic group (e.g., piperidinyl, morpholinyl) optionally substituted by 1 to 3 substituents selected from
  - (i) a hydroxy group,
  - (ii) a carbamoyl group,
  - (iii) a $C_{1-6}$ alkyl group, and
  - (iv) an oxo group, (8) a formyl group,
(9) a carboxy group,
(10) a $C_{1-6}$ alkyl-carbonyl group (e.g., isobutylcarbonyl) optionally substituted by 1 to 3 substituents selected from
- (a) a halogen atom,
- (b) a $C_{1-6}$ alkoxy-carbonyl group,
- (c) a $C_{6-14}$ aryl group, and
- (d) a $C_{1-6}$ alkoxy group,

(11) a $C_{1-6}$ alkoxy-carbonyl group (e.g., ethoxycarbonyl) optionally substituted by 1 to 3 substituents selected from
- (a) a halogen atom,
- (b) a $C_{6-14}$ aryl group, and
- (c) a $C_{1-6}$ alkoxy group,

(12) a $C_{3-10}$ cycloalkyl-carbonyl group (e.g., cyclopropylcarbonyl, cyclopentylcarbonyl, cyclohexylcarbonyl),
(13) a $C_{6-14}$ aryl-carbonyl group (e.g., benzoyl) optionally substituted by 1 to 3 halogen atoms,
(14) a carbamoyl group optionally mono- or di-substituted by substituent(s) selected from
- (a) a $C_{1-6}$ alkyl group (e.g., methyl, ethyl, isopropyl isobutyl, tert-butyl) optionally substituted by 1 to 3 substituents selected from
  - (i) a halogen atom,
  - (ii) a $C_{1-6}$ alkoxy-carbonyl group (e.g., methoxycarbonyl) optionally substituted by 1 to 3 $C_{6-14}$ aryl groups (e.g., phenyl),
  - (iii) a $C_{6-14}$ aryl group (e.g., phenyl) optionally substituted by 1 to 3 substituents selected from
    - (A) a $C_{1-6}$ alkoxy-carbonyl group (e.g., methoxycarbonyl), and
    - (B) a carboxy group,
  - (iv) a $C_{1-6}$ alkoxy group,
  - (v) a hydroxy group,
  - (vi) a 4- to 7-membered aromatic heterocyclic group,
  - (vii) a carboxy group,
  - (viii) a $C_{3-10}$ cycloalkyl group (e.g., cyclopropyl), and
  - (ix) a $C_{1-6}$ alkylsulfonyl group (e.g., methylsulfonyl),
- (b) a $C_{3-10}$ cycloalkyl group,
- (c) a $C_{6-14}$ aryl group (e.g., phenyl) optionally substituted by 1 to 3 substituents selected from
  - (i) a halogen atom,
  - (ii) a $C_{1-6}$ alkyl group (e.g., ethyl) optionally substituted by 1 to 3 substituents selected from
    - (A) a halogen atom,
    - (B) a carboxy group, and
    - (C) a $C_{1-6}$ alkoxy-carbonyl group (e.g., methoxycarbonyl),
  - (iii) a $C_{1-6}$ alkoxy group (e.g., methoxy) optionally substituted by 1 to 3 substituents selected from
    - (A) a carboxy group,
    - (B) a $C_{1-6}$ alkoxy-carbonyl group (e.g., methoxycarbonyl), and
    - (C) a $C_{6-14}$ aryl group (e.g., phenyl), and
  - (iv) a hydroxy group,
- (d) a 4- to 7-membered aromatic heterocyclic group (e.g., pyridyl (e.g., 2-pyridyl)) optionally substituted by 1 to 3 substituents selected from (i) a carboxy group, and
(ii) a $C_{1-6}$ alkyl group optionally substituted by a carboxy group,
(e) a sulfamoyl group optionally mono- or di-substituted by a $C_{1-6}$ alkyl group (e.g., methyl) optionally substituted by a $C_{3-10}$ cycloalkyl group (e.g., cyclopropyl),
(f) a sulfonyl group optionally mono- or di-substituted by a $C_{1-6}$ alkyl group (e.g., pentyl),
(h) a 4- to 7-membered nonaromatic heterocyclic group (e.g., pyrrolidinyl, piperidinyl, tetrahydrothiopyranyl) optionally substituted by 1 to 3 substituents selected from
(i) a carboxy group,
(ii) a $C_{1-6}$ alkyl-carbonyl group (e.g., acetyl),
(iii) a $C_{1-6}$ alkoxy-carbonyl group (e.g., tert-butoxycarbonyl, ethoxycarbonyl),
(iv) a $C_{1-6}$ alkoxy-carbonyl-carbonyl group,
(v) a carboxy-carbonyl group,
(vi) a carbamoyl group optionally mono- or di-substituted by $C_{1-6}$ alkyl groups (e.g., ethyl),
(vii) a $C_{1-6}$ alkyl-sulfonyl group (e.g., methylsulfonyl), and
(viii) an oxo group,
(f) a sulfamoyl group optionally mono- or di-substituted by a $C_{1-6}$ alkyl group (e.g., methyl) optionally substituted by a $C_{3-10}$ cycloalkyl group (e.g., cyclopropyl),
(g) a sulfonyl group optionally mono- or di-substituted by a $C_{1-6}$ alkyl group (e.g., pentyl), and
(h) a $C_{1-6}$ alkoxy group,
(15) a $C_{1-6}$ alkylsulfonyl group optionally substituted by 1 to 3 substituents selected from
(a) a halogen atom, and
(b) a $C_{6-14}$ aryl group,
(16) a $C_{6-14}$ arylsulfonyl group optionally substituted by 1 to 3 halogen atoms,
(17) a sulfamoyl group optionally mono- or di-substituted by substituent(s) selected from $C_{1-6}$ alkyl groups optionally substituted by 1 to 3 substituents selected from
(a) a halogen atom, and
(b) a 4- to 7-membered nonaromatic heterocyclic group optionally substituted by an oxo group,
(18) a thiocarbamoyl group optionally mono- or di-substituted by substituent(s) selected from a $C_{1-6}$ alkyl group optionally substituted by 1 to 3 halogen atoms,
(19) a 4- to 7-membered aromatic heterocyclylcarbonyl group optionally substituted by 1 to 3 substituents selected from $C_{1-6}$ alkyl groups optionally substituted by 1 to 3 halogen atoms,
(20) a 4- to 7-membered nonaromatic heterocyclylcarbonyl group (e.g., piperidinylcarbonyl, pyrrolidinylcarbonyl) optionally substituted by 1 to 3 substituents selected from
(a) a carboxy group,
(b) $C_{1-6}$ alkyl groups optionally substituted by 1 to 3 halogen atoms, and
(c) a $C_{1-6}$ alkoxy-carbonyl group (e.g., methoxycarbonyl), or
(21) a hydroxy group optionally substituted by 1 to 3 substituents selected from
(a) a $C_{1-6}$ alkyl group (e.g., ethyl, isopropyl, tert-butyl) optionally substituted by 1 to 3 halogen atoms (e.g., chlorine atom), and
(b) a $C_{6-14}$ aryl group (e.g., phenyl).

[Compound A4]

Compound (I) represented by the formula (I), wherein ring A is a benzene ring optionally substituted by 1 to 3 substituents selected from
(a) a halogen atom (e.g., chlorine atom, bromine atom),
(b) a $C_{2-10}$ alkenyl group (e.g., ethenyl, 1-propenyl, 1-methylethenyl) or (c) a $C_{1-6}$ alkyl group (e.g., methyl, isopropyl) optionally substituted by 1 to 3 hydroxy groups;
ring B is a piperazine ring; and
R is
(1) a $C_{1-10}$ alkyl group (e.g., methyl, ethyl, propyl, isopropyl, tert-butyl, isobutyl, pentyl) optionally substituted by 1 to 3 substituents selected from
(a) a carbamoyl group optionally mono- or di-substituted by substituent(s) selected from
(i) a carboxy group,
(ii) a $C_{1-6}$ alkyl group (e.g., methyl) optionally substituted by 1 to 3 substituents selected from
(A) a carboxy group, and
(B) a $C_{6-14}$ aryl group (e.g., phenyl) optionally substituted by a carboxy group,
(iii) a $C_{1-6}$ alkylsulfonyl group (e.g., methylsulfonyl),
(iv) a $C_{6-14}$ aryl group, and
(v) a 5- or 6-membered aromatic heterocyclic group,
(vi) a sulfamoyl group optionally substituted by a $C_{1-6}$ alkyl group (e.g., methyl) optionally substituted by a $C_{3-10}$ cycloalkyl (e.g., cyclopropyl),
(b) a 5- or 6-membered aromatic heterocyclylthio group (e.g., pyrazol-5-ylthio (e.g., pyrazol-5-ylthio), tetrazolylthio (e.g., tetrazol-5-ylthio)) optionally substituted by 1 to 3 substituents selected from
(i) a carboxy group,
(ii) a $C_{1-6}$ alkyl group (e.g., methyl) optionally substituted by a carboxy group, and
(iii) a $C_{6-14}$ aryl group,
(c) a 5- or 6-membered aromatic heterocyclic group (e.g., tetrazolyl (e.g., tetrazol-5-yl, tetrazol-1-yl)) optionally substituted by 1 to 3 substituents selected from
(i) a carboxy group, and
(ii) a $C_{1-6}$ alkyl group,
(d) a 5- or 6-membered nonaromatic heterocyclic group (e.g., imidazolidinyl (e.g., imidazolidin-5-yl), piperidinyl (e.g., piperidin-4-yl)) optionally substituted by 1 to 3 substituents selected from
(i) a carboxy group,
(ii) a $C_{1-6}$ alkyl group (e.g., methyl) optionally substituted by 1 to 3 substituents selected from
(A) a carboxy group,
(B) a $C_{1-6}$ alkoxy-carbonyl group (e.g., methoxycarbonyl) optionally substituted by a $C_{6-14}$ aryl group (e.g., phenyl), and
(C) a $C_{6-14}$ aryl group (e.g., phenyl) optionally substituted by a $C_{1-6}$ alkoxy-carbonyl group (e.g., methoxycarbonyl), and
(iii) an oxo group,
(e) a cyano group,
(f) a hydroxy group,
(g) a carboxy group,
(h) a $C_{1-6}$ alkoxy group (e.g., methoxy, ethoxy) optionally substituted by 1 to 3 $C_{6-14}$ aryl groups (e.g., phenyl),
(i) an amino group optionally mono- or di-substituted by substituent(s) selected from
(i) a $C_{1-6}$ alkyl group,
(ii) a $C_{1-6}$ alkyl-carbonyl group (e.g., acetyl),
(iii) $C_{6-14}$ aryl-carbonyl group (e.g., benzoyl), and
(iv) a $C_{1-6}$ alkoxy-carbonyl group (e.g., tert-butoxycarbonyl),
(j) a $C_{1-6}$ alkyl-carbonyl group (e.g., acetyl),
(k) a $C_{1-6}$ alkoxy-carbonyl group (e.g., ethoxycarbonyl),
(l) a $C_{6-14}$ aryloxy group (e.g., phenyloxy),
(m) a $C_{6-14}$ aryl group (e.g., phenyl) optionally substituted by 1 to 3 substituents selected from (i) a hydroxy group,
(ii) a $C_{1-6}$ alkoxy group (e.g., methoxy), and
(iii) a halogen atom (e.g., chlorine atom),
(n) a $C_{3-10}$ cycloalkyl group (e.g., cyclobutyl, cyclopentyl) optionally substituted by 1 to 3 substituents selected from
(i) a $C_{1-6}$ alkyl group (e.g., methyl),
(ii) a $C_{1-6}$ alkyl-carbonyl group (e.g., acetyl), and
(iii) an oxo group
(the $C_{3-10}$ cycloalkyl group may form a fused ring group with a benzene ring optionally substituted by a $C_{1-6}$ alkoxy group (e.g., methoxy)), and
(o) a hydroxy group;
(2) a $C_{3-10}$ cycloalkyl group (e.g., cyclopropyl, adamantyl) optionally substituted by 1 to 3 substituents selected from
(a) a carboxy group,
(b) a $C_{1-6}$ alkyl group,
(c) a hydroxy group, and
(d) a $C_{1-6}$ alkoxy-carbonyl group (e.g., methoxycarbonyl),
(3) a $C_{2-10}$ alkenyl group (e.g., ethenyl) optionally substituted by 1 to 3 carbamoyl groups optionally mono- or di-substituted by $C_{1-6}$ alkyl groups (e.g., methyl),
(4) a $C_{6-14}$ aryl group (e.g., phenyl) optionally substituted by 1 to 3 substituents selected from
(a) a carboxy group,
(b) a $C_{1-6}$ alkyl group (e.g., methyl) optionally substituted by 1 to 3 substituents selected from
(i) a halogen atom (e.g., chlorine atom), and
(ii) an amino group optionally mono- or di-substituted by substituent(s) selected from
(A) a $C_{1-6}$ alkyl group, and
(B) a 5- or 6-membered nonaromatic heterocyclic group (e.g., tetrahydrothiopyranyl) optionally substituted by an oxo group,
(c) a $C_{1-6}$ alkoxy group (e.g., methoxy) optionally substituted by 1 to 3 substituents selected from
(i) a carboxy group,
(ii) a $C_{6-14}$ aryl group (e.g., phenyl),
(iii) a 5- or 6-membered nonaromatic heterocyclic group (e.g., piperidinyl) optionally substituted by 1 to 3 substituents selected from
(A) a carboxy-carbonyl group,
(B) a $C_{1-6}$ alkoxy-carbonyl group (e.g., tert-butoxycarbonyl), and
(C) a $C_{1-6}$ alkoxy-carbonyl-carbonyl group, and
(iv) a hydroxy group,
(d) a halogen atom (e.g., fluorine atom),
(e) a 5- or 6-membered nonaromatic heterocyclic group (e.g., dihydrooxadiazolyl, imidazolidinyl) optionally substituted by 1 to 3 substituents selected from
(i) a carboxy group,
(ii) an oxo group, and
(iii) a $C_{1-6}$ alkyl group (e.g., methyl) optionally substituted by 1 to 3 substituents selected from
(A) a carboxy group and a $C_{1-6}$ alkoxy-carbonyl group (e.g., tert-butoxycarbonyl), and
(B) a $C_{1-6}$ alkoxy-carbonyl group (e.g., tert-butoxycarbonyl),
(f) a cyano group,
(g) a hydroxy group,
(h) a $C_{1-6}$ alkoxy-carbonyl group (e.g., methoxycarbonyl),
(i) a $C_{6-14}$ aryl group (e.g., phenyl) optionally substituted by a $C_{1-6}$ alkyl group (e.g., methyl) optionally substituted by a carboxy group,
(5) a 5- or 6-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
(a) a halogen atom (e.g., chlorine atom),
(b) a hydroxy group,
(c) a $C_{1-6}$ alkyl group (e.g., methyl, ethyl) optionally substituted by 1 to 3 substituents selected from
(i) a carboxy group,
(ii) a halogen atom (e.g., chlorine atom, fluorine atom), and
(iii) a $C_{1-6}$ alkoxy-carbonyl group (e.g., methoxycarbonyl, tert-butoxycarbonyl),
(d) a $C_{3-10}$ cycloalkyl group (e.g., cyclohexyl),
(e) a $C_{6-14}$ aryl group (e.g., phenyl),
(f) a $C_{1-6}$ alkylthio group (e.g., methylthio) optionally substituted by 1 to 3 substituents selected from
(i) a carboxy group, and
(ii) a $C_{1-6}$ alkoxy-carbonyl group (e.g., methoxycarbonyl, ethoxycarbonyl, tert-butoxycarbonyl),
(g) a mercapto group,
(h) a $C_{1-6}$ alkoxy group (e.g., methoxy) optionally substituted by 1 to 3 substituents selected from
(i) a halogen atom,
(ii) a carboxy group,
(iii) a $C_{1-6}$ alkoxy-carbonyl group (e.g., methoxycarbonyl, tert-butoxycarbonyl), and
(iv) a $C_{6-14}$ aryl group (e.g., phenyl),
(h) a 5- or 6-membered nonaromatic heterocyclic group (e.g., imidazolidinyl, piperidinyl) optionally substituted by 1 to 3 alkoxy-carbonyl groups (e.g., tert-butoxycarbonyl), and
(i) a $C_{1-6}$ alkylthio group optionally substituted by 1 to 3 carboxy groups,
(6) a 5- or 6-membered nonaromatic heterocyclic group (e.g., pyrrolidinyl (e.g., 2-pyrrolidinyl), tetrahydrofuranyl (e.g., tetrahydrofuran-3-yl, tetrahydrofuran-2-yl), thiazolidinyl (e.g., thiazolidin-4-yl), piperidinyl (e.g., 1-piperidinyl, 2-piperidinyl, 4-piperidinyl), pyranyl (e.g., 2-pyranyl), tetrahydropyrimidinyl (e.g., tetrahydropyrimidin-4-yl, tetrahydropyrimidin-5-yl), hexahydropyrimidinyl (e.g., hexahydropyrimidin-4-yl), 5H-[1,3]thiazolo[3,2-a]pyrimidinyl (e.g., 5H-[1,3]thiazolo[3,2-a]pyrimidin-6-yl), 2-oxabicyclo[2,2,1]heptan-1-yl, morpholinyl) optionally substituted by 1 to 3 substituents selected from
(a) a hydroxy group,
(b) a $C_{1-6}$ alkyl group (e.g., methyl) optionally substituted by 1 to 3 substituents selected from
(i) a carboxy group,
(ii) a $C_{6-14}$ aryl group (e.g., phenyl), and
(iii) a $C_{1-6}$ alkoxy-carbonyl group (e.g., methoxycarbonyl),
(c) a $C_{6-14}$ aryl group (e.g., phenyl)
(d) a $C_{1-6}$ alkyl-carbonyl group (e.g., acetyl),
(e) a $C_{1-6}$ alkoxy-carbonyl group (e.g., tert-butoxycarbonyl), and
(f) an oxo group,
(7) an amino group optionally mono- or di-substituted by substituent(s) selected from
(a) a $C_{6-14}$ aryl group (e.g., phenyl) optionally substituted by 1 to 3 substituents selected from
(i) a hydroxy group, and
(ii) a $C_{1-6}$ alkoxy group (e.g., methoxy) optionally substituted by 1 to 3 substituents selected from
(A) a carboxy group,
(B) a $C_{6-14}$ aryl group (e.g., phenyl), and
(C) a $C_{1-6}$ alkoxy-carbonyl group (e.g., methoxycarbonyl),
(b) a $C_{1-6}$ alkyl group (e.g., methyl, ethyl) optionally substituted by 1 to 3 substituents selected from (i) a carboxy group, and
(ii) a $C_{1-6}$ alkoxy-carbonyl group (e.g., ethoxycarbonyl),
(c) a 5- or 6-membered aromatic heterocyclic group (e.g., triazolyl, tetrazolyl, pyridyl) optionally substituted by 1 to 3 substituents selected from
(i) a hydroxy group, and
(ii) a carbamoyl group, and
(d) a 5- or 6-membered nonaromatic heterocyclic group (e.g., piperidinyl) optionally substituted by 1 to 3 substituents selected from
(i) a hydroxy group, and
(ii) a carbamoyl group,
(8) a carboxy group,
(9) a $C_{1-6}$ alkyl-carbonyl group (e.g., isobutylcarbonyl),
(10) a $C_{1-6}$ alkoxy-carbonyl group (e.g., ethoxycarbonyl),
(11) a $C_{6-14}$ aryl-carbonyl group (e.g., benzoyl) optionally substituted by 1 to 3 halogen atoms,
(12) a carbamoyl group optionally mono- or di-substituted by substituent(s) selected from
(a) a $C_{1-6}$ alkyl group (e.g., methyl, ethyl, isopropyl, isobutyl, tert-butyl) optionally substituted by 1 to 3 substituents selected from
(i) a halogen atom,
(ii) a $C_{1-6}$ alkoxy-carbonyl group (e.g., methoxycarbonyl) optionally substituted by 1 to 3 $C_{6-14}$ aryl groups (e.g., phenyl),
(iii) a $C_{6-14}$ aryl group (e.g., phenyl) optionally substituted by 1 to 3 substituents selected from
(A) a $C_{1-6}$ alkoxy-carbonyl group (e.g., methoxycarbonyl), and
(B) a carboxy group,
(iv) a hydroxy group,
(v) a carboxy group,
(vi) a $C_{3-10}$ cycloalkyl group (e.g., cyclopropyl), and
(vii) a $C_{1-6}$ alkylsulfonyl group (e.g., methylsulfonyl),
(b) a $C_{6-14}$ aryl group (e.g., phenyl) optionally substituted by 1 to 3 substituents selected from
(i) a halogen atom,
(ii) a $C_{1-6}$ alkyl group (e.g., ethyl) optionally substituted by 1 to 3 substituents selected from
(A) a halogen atom,
(B) a carboxy group, and
(C) a $C_{1-6}$ alkoxy-carbonyl group (e.g., methoxycarbonyl),
(iii) a $C_{1-6}$ alkoxy group (e.g., methoxy) optionally substituted by 1 to 3 substituents selected from
(A) a carboxy group,
(B) a $C_{1-6}$ alkoxy-carbonyl group (e.g., methoxycarbonyl), and
(C) a $C_{6-14}$ aryl group (e.g., phenyl), and
(iv) a hydroxy group,
(c) a 5- or 6-membered aromatic heterocyclic group (e.g., pyridyl (e.g., 2-pyridyl)),
(d) a sulfamoyl group optionally mono- or di-substituted by a $C_{1-6}$ alkyl group (e.g., methyl) optionally substituted by a $C_{3-10}$ cycloalkyl group (e.g., cyclopropyl),
(e) a sulfonyl group optionally mono- or di-substituted by a $C_{1-6}$ alkyl group (e.g., pentyl), and
(f) a 5- or 6-membered nonaromatic heterocyclic group (e.g., pyrrolidinyl, piperidinyl, tetrahydrothiopyranyl) optionally substituted by 1 to 3 substituents selected from
(i) a carboxy group,
(ii) a $C_{1-6}$ alkyl-carbonyl group (e.g., acetyl),
(iii) a $C_{1-6}$ alkoxy-carbonyl group (e.g., tert-butoxycarbonyl, ethoxycarbonyl),
(iv) a $C_{1-6}$ alkoxy-carbonyl-carbonyl group,
(v) a carboxy-carbonyl group, (vi) a carbamoyl group optionally mono- or di-substituted by $C_{1-6}$ alkyl groups (e.g., ethyl),
(vii) a $C_{1-6}$ alkyl-sulfonyl group (e.g., methylsulfonyl), and
(viii) an oxo group,
(13) a 5- or 6-membered nonaromatic heterocyclylcarbonyl group (e.g., piperidinylcarbonyl, pyrrolidinylcarbonyl) optionally substituted by 1 to 3 substituents selected from
(a) a carboxy group,
(b) a $C_{1-6}$ alkoxy group optionally substituted by a carboxy group,
(c) a $C_{1-6}$ alkyl group optionally substituted by 1 to 3 halogen atoms, and
(d) a $C_{1-6}$ alkoxy-carbonyl group (e.g., methoxycarbonyl), or
(14) a hydroxy group optionally substituted by a substituent selected from
(a) a $C_{1-6}$ alkyl group (e.g., ethyl, isopropyl, tert-butyl) optionally substituted by 1 to 3 halogen atoms (e.g., chlorine atom), and
(b) a $C_{6-14}$ aryl group (e.g., phenyl).
[Compound A5]
Compound (I) represented by the formula (I), wherein ring A is a benzene ring optionally substituted by 1 to 3 substituents selected from
(a) a halogen atom (e.g., chlorine atom, bromine atom), and
(b) a $C_{1-6}$ alkyl group (e.g., methyl, isopropyl); ring B is a piperazine ring; and
R is
(1) a $C_{1-10}$ alkyl group (e.g., methyl, ethyl, propyl, isopropyl, tert-butyl, isobutyl, pentyl) optionally substituted by 1 to 3 substituents selected from
(a) a carbamoyl group optionally mono- or di-substituted by
(i) a $C_{1-6}$ alkylsulfonyl group (e.g., methylsulfonyl), and
(ii) a sulfamoyl group optionally, substituted by a $C_{1-6}$ alkyl group (e.g., methyl) optionally substituted by $C_{3-10}$ cycloalkyl (e.g., cyclopropyl),
(b) a 5- or 6-membered aromatic heterocyclic group (e.g., tetrazolyl (e.g., tetrazol-5-yl, tetrazol-1-yl)) optionally substituted by 1 to 3 substituents selected from
(i) a carboxy group, and
(ii) a $C_{1-6}$ alkyl group (e.g., methyl),
(c) a 5- or 6-membered nonaromatic heterocyclic group (e.g., imidazolidinyl (e.g., imidazolidin-5-yl), piperidinyl (e.g., piperidin-4-yl)) optionally substituted by 1 to 3 carboxy groups, and
(d) a carboxy group;
(2) a $C_{6-14}$ aryl group (e.g., phenyl) optionally substituted by 1 to 3 substituents selected from
(a) a carboxy group,
(b) a $C_{1-6}$ alkoxy group optionally substituted by 1 to 3 carboxy groups, and
(c) a 5- or 6-membered nonaromatic heterocyclic group (e.g., dihydrooxadiazolyl, imidazolidinyl) optionally substituted by 1 to 3 carboxy groups, and
(d) a $C_{6-14}$ aryl group (e.g., phenyl) optionally substituted by a carboxy-$C_{1-6}$ alkyl group;
(3) a 5- or 6-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
(a) a $C_{1-6}$ alkyl group (e.g., methyl, ethyl) optionally substituted by 1 to 3 carboxy groups, and (b) a $C_{1-6}$ alkoxy group (e.g., methoxy) optionally substituted by 1 to 3 carboxy groups;
(4) an amino group optionally mono- or di-substituted by substituents selected from
  (a) a $C_{6-14}$ aryl group (e.g., phenyl) optionally substituted by 1 to 3 carboxy-$C_{1-6}$ alkoxy groups,
  (b) a $C_{1-6}$ alkyl group (e.g., methyl, ethyl) optionally substituted by 1 to 3 carboxy groups, and
  (c) a 5- or 6-membered aromatic heterocyclic group optionally substituted by 1 to 3 substituents selected from
    (i) a hydroxy group, and
    (ii) a carbamoyl group;
(5) a carboxy group; or
(6) a carbamoyl group optionally mono- or di-substituted by substituents selected from
  (a) a $C_{1-6}$ alkyl group (e.g., methyl, ethyl, isopropyl isobutyl, tert-butyl) optionally substituted by 1 to 3 substituents selected from
    (i) a $C_{6-14}$ aryl group (e.g., phenyl) optionally substituted by 1 to 3 substituents selected from
      (A) a carboxy group, and
      (B) a carboxy-$C_{1-6}$ alkyl group,
    (ii) a carboxy group, and
    (iii) a $C_{1-6}$ alkyl-sulfonyl group (e.g., methylsulfonyl), and
  (b) a 5- or 6-membered nonaromatic heterocyclic group (e.g., piperidinyl, tetrahydrothiopyranyl) optionally substituted by 1 to 3 substituents selected from
    (i) a carboxy group,
    (ii) a carboxy-carbonyl group, and
    (iii) a carboxy-$C_{1-6}$ alkoxy group (e.g., carboxy-methoxy).

[Compound B]

Compound (I) represented by the formula (I), wherein ring A is a benzene ring optionally substituted by 1 to 3 substituents selected from
  (a) a halogen atom (e.g., chlorine atom, bromine atom), and
  (b) a $C_{1-6}$ alkyl group (e.g., methyl, isopropyl);
ring B is a piperazine ring; and
R is
(1) a $C_{1-10}$ alkyl group (e.g., methyl, ethyl, propyl, isopropyl, tert-butyl, isobutyl, pentyl) optionally substituted by 1 to 3 substituents selected from
  (a) a carbamoyl group optionally mono- or di-substituted by
    (i) a $C_{1-6}$ alkylsulfonyl group (e.g., methylsulfonyl), and
    (ii) a sulfamoyl group optionally substituted by a $C_{1-6}$ alkyl group (e.g., methyl) optionally substituted by $C_{3-10}$ cycloalkyl (e.g., cyclopropyl),
  (b) a 5- or 6-membered aromatic heterocyclic group (e.g., tetrazolyl (e.g., tetrazol-5-yl, tetrazol-1-yl),
  (c) a 5- or 6-membered nonaromatic heterocyclic group (e.g., imidazolidinyl (e.g., imidazolidin-5-yl), piperidinyl (e.g., piperidin-4-yl)) optionally substituted by 1 to 3 oxo groups, and
  (d) a hydroxy group,
  (e) a carboxy group, and
  (f) a $C_{3-10}$ cycloalkyl group;
(2) a $C_{6-14}$ aryl group (e.g., phenyl) optionally substituted by 1 to 3 substituents selected from
  (a) a carboxy group,
  (b) a $C_{1-6}$ alkoxy group optionally substituted by 1 to 3 substituents selected from
    (i) a carboxy group, and
    (ii) a 5- or 6-membered nonaromatic heterocyclic group,
  (c) a 5- or 6-membered nonaromatic heterocyclic group (e.g., dihydrooxadiazolyl, imidazolidinyl) optionally substituted by 1 to 3 oxo groups, and
  (d) a $C_{6-14}$ aryl group (e.g., phenyl) optionally substituted by a carboxy-$C_{1-6}$ alkyl group;
(3) a $C_{3-10}$ cycloalkyl group optionally substituted by 1 to 3 carboxy groups;
(4) a 5- or 6-membered aromatic heterocyclic group (e.g., tetrazolyl, imidazolyl (e.g., 4-imidazolyl), oxazolyl (e.g., 4-oxazolyl), pyridyl (e.g., 2-pyridyl, 3-pyridyl), triazolyl (e.g., 1,2,4-triazol-3-yl), furyl (e.g., 3-furyl), isoxazolyl (e.g., 5-isoxazolyl), pyrrolyl (e.g., 2-pyrrolyl), pyrazolyl (e.g., 5-pyrazolyl)) optionally substituted by 1 to 3 substituents selected from
  (a) a $C_{1-6}$ alkyl group (e.g., methyl, ethyl) optionally substituted by 1 to 3 carboxy groups,
  (b) a $C_{1-6}$ alkylthio group optionally substituted by 1 to 3 carboxy groups, and
  (c) a $C_{1-6}$ alkoxy group (e.g., methoxy) optionally substituted by 1 to 3 carboxy groups;
(5) an amino group optionally mono- or di-substituted by substituents selected from
  (a) a $C_{1-6}$ alkyl group (e.g., methyl, ethyl) optionally substituted by 1 to 3 carboxy groups, and
  (b) a $C_{6-14}$ aryl group (e.g., phenyl);
(6) a carboxy group;
(7) a carbamoyl group optionally mono- or di-substituted by substituents selected from
  (a) a $C_{1-6}$ alkyl group (e.g., methyl, ethyl, isopropyl isobutyl, tert-butyl) optionally substituted by 1 to 3 substituents selected from
    (i) a $C_{6-14}$ aryl group (e.g., phenyl) optionally substituted by 1 to 3 carboxy groups, and
    (ii) a carboxy group,
  (b) a $C_{6-14}$ aryl group optionally substituted by 1 to 3 substituents selected from
    (i) a $C_{1-6}$ alkyl group optionally substituted by 1 to 3 carboxy groups, and
    (ii) a $C_{1-6}$ alkoxy group optionally substituted by 1 to 3 carboxy groups, and
  (c) a sulfamoyl group optionally mono- or di-substituted by a $C_{1-6}$ alkyl group optionally substituted by a $C_{3-10}$ cycloalkyl group; or
(8) a 5- or 6-membered nonaromatic heterocyclylcarbonyl group optionally substituted by 1 to 3 carboxy groups.

[Compound C]

N-{[4-(2-tert-Butylphenyl)piperazin-1-yl]carbonyl}glycine or a salt thereof,

3-[4-(2-tert-Butylphenyl)piperazin-1-yl]-3-oxopropanoic acid or a salt thereof,

[4-(2-tert-Butyl-4-chlorophenyl)piperazin-1-yl](oxo)acetic acid or a salt thereof, 2-[4-(2-tert-Butylphenyl)piperazin-1-yl]-2-oxoacetic acid or a salt thereof, or

[(5-{[4-(2-tert-Butylphenyl)piperazin-1-yl]carbonyl}isoxazol-3-yl)oxy]acetic acid or a salt thereof.

When compound (I) is in the form of a salt, the salt is preferably a pharmacologically acceptable salt. Examples thereof include salt with inorganic base, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (I) may be labeled with an isotope (e.g., $^3$H, $^{14}$C, $^{35}$S, $^{125}$I) and the like.

In addition, compound (I) may be a non-solvate (e.g., anhydride) or a solvate (e.g., hydrate).

Furthermore, a deuterium converter wherein $^1$H is converted to $^2$H (D) is also encompassed in compound (I).

Compound (I) may be a crystal.

The crystal of compound (I) can be produced by crystallization of compound (I) by applying a crystallization method known per se.

Compound (I) may also be a pharmaceutically acceptable cocrystal or cocrystallized salt. Here, each of cocrystals or cocrystallized salts has different physical properties (e.g., structure, melting point, melting heat, hygroscopicity, solubility, stability, etc.), and refers to a crystalline substance that is comprised of two or more types of distinctive solids at room temperature. A cocrystal or cocrystallized salt may be produced according to a cocrystallization technique known per se.

In the present specification, the melting point means a melting point measured using, for example, Micro Melting Point Determination Apparatus (Yanaco, MP-500D type or Buchi, B-545% type) or DSC (differential scanning calorimetry analysis) apparatus (SEIKO, EXSTAR6000) and the like.

In general, the melting point sometimes varies depending on the measurement device, measurement conditions and the like. The crystal in the present specification may show a value different from the melting point indicated in the present specification, as long as it is within a general error range.

The crystal of compound (I) is superior in the physicochemical properties (e.g., melting point, solubility, stability) and biological properties (e.g., pharmacokinetic profiles (absorbability, distribution, metabolism and excretion), efficacy expression) and is extremely useful as a pharmaceutical agent.

The pharmaceutical composition can be produced according to a method conventionally used in the field of pharmaceutical preparation, such as the method described in Japan Pharmacopoeia and the like.

The compound (I) may be used as a prodrug. A prodrug of the compound (I) means a compound which is converted to the compound (I) with a reaction due to an enzyme, an gastric acid, and the like under the physiological condition in, the living body, that is, a compound which is converted to the compound (I) with oxidation, reduction, hydrolysis, and the like according to an enzyme; a compound which is converted to the compound (I) by hydrolysis and the like due to gastric acid and the like.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation); a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation) and the like. Any of these compounds can be produced from compound (I) by a method known per se.

A prodrug for compound (I) may also be one which is converted into compound (I) under a physiological condition, such as those described in Development of Pharmaceutical Products, Vol. 7, Design of Molecules, p. 163-198 (1990), Hirokawa Shoten.

The production methods of compound (I) are explained in the following.

Compound (I) can be produced according to a method known per se, for example, the methods described in detail in the following or a method analogous thereto.

Unless otherwise specified, each symbol in the following reaction is as defined above. In addition, $R^1$, $R^2$, $R^3$, $R^4$, X, Y, $Z^1$, $Z^2$ and $Z^3$ mean the following.

$R^1$ is an optionally substituted $C_{1-6}$ alkyl group, an optionally substituted $C_{6-14}$ aryl group (e.g., phenyl etc.) or an optionally substituted 4- to 7-membered aromatic heterocyclic group.

$R^2$ is an optionally substituted $C_{1-6}$ alkyl group (e.g., methyl, ethoxycarbonylmethyl etc.) or an optionally substituted $C_{7-13}$ aralkyl group (e.g., benzyl etc.).

$R^3$ and $R^4$ are each independently a hydrogen atom, or a substituent according to the definition of R, or $R^3$ and $R^4$ may form an optionally substituted nitrogen-containing heterocycle.

X is a leaving group. Specific examples of X include a halogen atom (preferably chlorine, bromine, iodine), an optionally halogenated $C_{1-6}$ alkylsulfonyloxy group (e.g., methanesulfonyloxy, ethanesulfonyloxy, trifluoromethanesulfonyloxy), a $C_{6-14}$ arylsulfonyloxy group optionally having substituent(s) (e.g., benzenesulfonyloxy, p-toluenesulfonyloxy) and the like.

Y is a hydrogen atom or an amino-protecting group.

$Z^1$ is a leaving group. Specific examples of $Z^1$ include a halogen atom (preferably chlorine, bromine, fluorine), a hydroxy group and the like.

$Z^2$ and $Z^3$ are each independently a leaving group. Specific examples of $Z^2$ and $Z^3$ include a halogen atom (preferably chlorine), an N-succinimidyl group, an N-imidazolyl group, a 2,2,2-trichloroethoxy group and the like.

In the following production methods, the "ether solvents", "halogenated hydrocarbon solvents", "aromatic solvents", "nitrile solvents", "ester solvents", "amide solvents", "ketone solvents", "sulfoxide solvents", "alcohol solvents" and "organic acid solvents" each mean the following.

Examples of the "ether solvents" include diethyl ether, tetrahydrofuran (THF), 1,4-dioxane, 1,2-dimethoxyethane, diethylene glycol dimethyl ether and the like.

Examples of the "halogenated hydrocarbon solvents" include dichloromethane, chloroform, 1,2-dichloroethane, carbon tetrachloride, 1,1,2,2-tetrachloroethane and the like.

Examples of the "aromatic solvents" include benzene, toluene, xylene, pyridine, mesitylene and the like.

Examples of the "nitrile solvents" include acetonitrile, propionitrile and the like.

Examples of the "ester solvents" include ethyl acetate, methyl acetate and the like.

Examples of the "amide solvents" include N,N-dimethylformamide (DMF), N,N-dimethylacetamide, N-methylpyrrolidone and the like.

Examples of the "ketone solvents" include acetone, methylethyl ketone and the like.

Examples of the "sulfoxide solvents" include dimethyl sulfoxide (DMSO) and the like.

Examples of the "alcohol solvents" include methanol, ethanol, isopropanol, tert-butanol and the like.

Examples of the "organic acid solvents" include formic acid, acetic acid, trifluoroacetic acid, methanesulfonic acid and the like.

When a specific production method is not indicated, the starting material compounds in the following production methods may be commercially easily available, or can be produced according to a method known per se or a method analogous thereto.

In addition, the compound used as a starting material compound may be used in the form of a salt. Examples of the salt include those similar to the salts used for compound (I).

(Production Method A)

Compound (I) can be produced, for example, according to the following Reaction scheme 1.

(Reaction scheme 1)

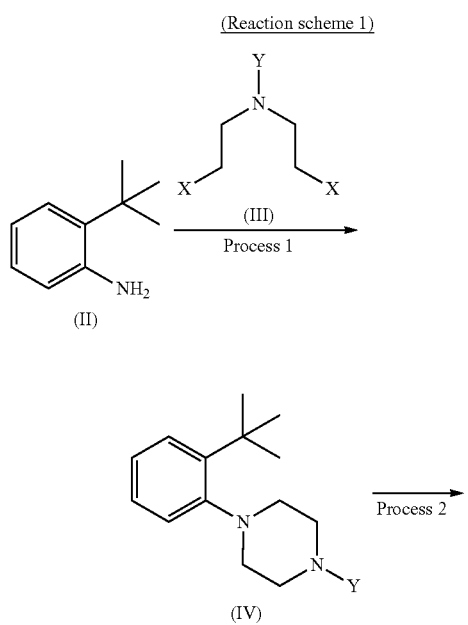

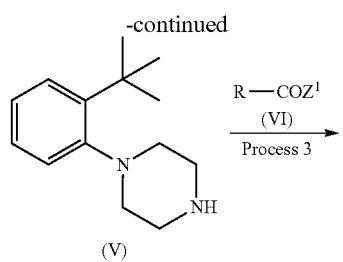

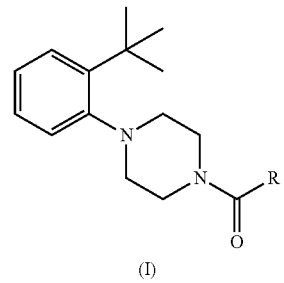

In this production method, compound (I) can be produced from compound (II) as a starting material compound by the following processes.

Process 1: Cyclization by alkylation
Process 2: Deprotection
Process 3: Acylation Each process is specifically explained in the following.

(Process 1)

Compound (IV) can be produced by subjecting compound (II) and compound (III) to cyclization by alkylation.

Where necessary, a base may be used for this reaction.

Examples of the base include amines (e.g., triethylamine, N,N-diisopropylethylamine, pyridine, 4-dimethylaminopyridine, 1,8-diazabicyclo[5.4.0]-7-undecene); alkali metal carbonates (e.g., potassium carbonate, sodium carbonate, cesium carbonate, sodium hydrogen carbonate, potassium hydrogen carbonate); alkali metal phosphates (e.g., tripotassium phosphate, trisodium phosphate); alkali metal acetates (sodium acetate, potassium acetate); alkali metal hydrides (e.g., sodium hydride, potassium hydride); alkali metal hydroxides (e.g., sodium hydroxide, potassium hydroxide); alkali metal $C_{1-6}$ alkoxides (e.g., sodium methoxide, sodium tert-butoxide, potassium tert-butoxide) and the like. Among these, potassium carbonate, sodium carbonate, sodium hydrogen carbonate and the like are preferable.

The amount of the base to be used is generally 0.1 to 100 equivalents, preferably 1 to 10 equivalents, relative to 1 equivalent of compound (II).

In addition, an additive (e.g., sodium iodide, potassium iodide etc.) may be used as necessary in this reaction.

The amount of the additive to be used is generally 0.1 to equivalents, preferably, 0.5 equivalent to 5 equivalents, relative to 1 equivalent of compound (II).

Specific examples of compound (III) include bis-(2-chloroethyl)amine and the like.

Compound (III) may be a commercially available product, or can be produced by a method known per se or a method analogous thereto.

The amount of compound (III) to be used is generally 1 to 100 equivalents, preferably, 1 to 5 equivalents, relative to 1 equivalent of compound (II).

This reaction is performed without solvent or in an inert solvent. Examples of the inert solvent include ether solvents, halogenated hydrocarbon solvents, nitrile solvents, aromatic solvents, ester solvents, amide solvents, water and the like.

Two or more kinds of these solvents may be used in a mixture at an appropriate ratio. Among these, diethylene glycol dimethylether, tetrahydrofuran, acetonitrile, N,N-dimethylformamide, N,N-dimethylacetamide, dimethyl sulfoxide and the like are preferable.

Where necessary, a phase transfer catalyst (e.g., tetrabutylammonium bromide, tetrabutylammonium hydrogen sulfate etc.) may be used for this reaction.

The amount of the phase transfer catalyst to be used is generally 0.01 to 0.5 equivalent, preferably 0.01 equivalent to 0.1 equivalent, relative to 1 equivalent of compound (II).

The reaction temperature of this reaction is generally about 30° C. to 200° C., preferably 60° C. to 180° C.

The reaction time of this reaction is generally 0.5 hr to 24 hr.

Compound (II) may be a commercially available product, or can be produced by a method known per se (e.g., methods described in WO2006/66978 and US2003/225106), or a method analogous thereto.

(Process 2)

Compound (V) can be produced by removing Y, which is an amino-protecting group, of compound (IV). The protecting group Y of compound (IV) can be removed by a method known per se, for example, the method described in Protective Groups in Organic Synthesis), John Wiley and Sons (1980) or methods analogous thereto. The protecting group Y can be removed by, for example, a method using acid, base and the like, and the like.

(Process 3)

Compound (I) can be produced by subjecting compound (V) and compound (VI) to acylation.

As compound (VI), for example, a commercially available product such as carboxylic acid, halogenated acyl and the like can be used. In addition, compound (VI) can also be produced by a method known per se (the method described in Experimental Chemistry Course (Jikken Kagaku Koza), 5th Edition, vol. 16, 1 page, 117 page (2005) Maruzen Co., Ltd.; and the like), such as activation of carboxylic acid and the like.

The amount of compound (VI) to be used in the following reactions is generally 1 to 100 equivalents, preferably 1 to 40 equivalents, per 1 equivalent of compound (V).

When $Z^1$ of compound (VI) is a halogen atom, the reaction can be performed in the presence of a base. Examples of the base include amines (e.g., triethylamine, N,N-diisopropylethylamine, pyridine, 4-dimethylaminopyridine), alkali metal carbonates (e.g., potassium carbonate, sodium carbonate, cesium carbonate), hydroxide alkali metals (e.g., lithium hydroxide, sodium hydroxide, potassium hydroxide) and the like. Among these, triethylamine, N,N-diisopropylethylamine, pyridine, 4-dimethylaminopyridine, potassium carbonate, sodium carbonate and the like are preferable.

The amount of the base to be used is generally 0.1 to 100 equivalents, preferably 1 to 10 equivalents, per 1 equivalent of compound (VI).

This reaction is performed, for example, in a solvent such as ether solvents, halogenated hydrocarbon solvents, nitrile solvents, aromatic solvents, ester solvents, amide solvents, water and the like. Two or more kinds of these solvents may be used in a mixture at an appropriate ratio. Among these, tetrahydrofuran, dichloromethane, pyridine, ethyl acetate-water and the like are preferable.

The reaction temperature of this reaction is generally about 0° C. to 100° C., preferably 0 to 80° C.

The reaction time of this reaction is, for example, 0.5 hr to 1 day.

When $Z^1$ of compound (VI) is a hydroxy group, the reaction can be performed using a condensation agent (e.g., 1-ethyl-3-(3'-dimethylaminopropyl)carbodiimide (EDCI), O-benzotriazole-N,N,N',N'-tetramethyluronium hexafluorophosphate (HBTU), O-(7-azabenzotriazol-1-yl)-N,N,N',N'-tetramethyluronium hexafluorophosphate (HATU), 1,3-dicyclohexylcarbodiimide (DCC), bis(2-oxo-3-oxazolidinyl)phosphine chloride (BOP—Cl) and (benzotriazol-1-yloxy)tripyrrolidinophosphonium hexafluoro phosphate (PyBOP)). Among these, EDCI, HBTU and the like are preferable.

The amount of the condensation agent to be used is generally 1 to 10 equivalents, preferably 1 to 3 equivalents, per 1 equivalent of compound (VI).

To promote this reaction, an additive such as N-hydroxysuccinimide (HOSu), N-hydroxybenzotriazole (HOBt), amines (e.g., triethylamine, N,N-diisopropylethylamine, pyridine, 4-dimethylaminopyridine) and the like may be used in combination with a condensation agent.

The amount of the additive to be used is generally 0.1 to 100 equivalents, preferably 0.1 to 10 equivalents, per 1 equivalent of compound (VI).

This reaction is generally performed in an inert solvent (e.g., ether solvents, halogenated hydrocarbon solvents, nitrile solvents, amide solvents). Two or more kinds of these solvents may be used in a mixture at an appropriate ratio. Among these, tetrahydrofuran, dichloromethane, acetonitrile and the like are preferable.

The reaction temperature of this reaction is generally about 0° C. to 100° C., preferably 0° C. to 80° C.

The reaction time of this reaction is, for example, 0.5 hr to 3 days.

When $Z^1$ of compound (VI) is a hydroxy group, the reaction can be performed according to a method known per se (e.g., the method described in Experimental Chemistry Course (Jikken Kagaku Koza), 5th Edition, vol. 16, 99 page (2005) Maruzen Co., Ltd.; and the like) and using a halogenating reagent (e.g., thionyl chloride, oxalyl chloride, dichlorotriphenylphosphorane, diethylaminosulfur trifluoride (DAST), cyanuryl fluoride), wherein the hydroxy group is converted to a halogen atom (preferably, chlorine, bromine, fluorine), and compound (I) can also be produced according to the aforementioned method.

The amount of the halogenating reagent to be used is generally 1 to 100 equivalents, preferably 1 to 10 equivalents, per 1 equivalent of compound (I).

To promote the reaction, an additive such as N,N-dimethylformamide, amines (e.g., triethylamine, N,N-diisopropylethylamine, pyridine, 4-dimethylaminopyridine) and the like may be used in this reaction.

The amount of the additive to be used is generally 0.1 to 100 equivalents, preferably 0.1 to 10 equivalents, per 1 equivalent of compound (VI).

This reaction is generally performed in an inert solvent (e.g., ether solvents, halogenated hydrocarbon solvents, nitrile solvents, amide solvents) or without solvent. Two or more kinds of these solvents may be used in a mixture at an appropriate ratio. Among these, tetrahydrofuran, dichloromethane, acetonitrile, N,N-dimethylformamide and the like are preferable.

The reaction temperature of this reaction is generally about −20° C. to 150° C., preferably 0° C. to 90° C.

The reaction time of this reaction is, for example, 0.5 hr to 3 days.

When $Z^1$ of compound (VI) is a group that forms an active ester group such as phenyloxy group, (succinimide-1-yl)oxy group, (benzothiazol-2-yl)thio group and the like, the reaction can be performed in the presence of a base.

Examples of the base include amines (e.g., triethylamine, N,N-diisopropylethylamine, pyridine, 4-dimethylaminopyridine), alkali metal carbonate (e.g., potassium carbonate, sodium carbonate, cesium carbonate) and the like. Among these, triethylamine, N,N-diisopropylethylamine, pyridine, 4-dimethylaminopyridine and the like are preferable.

The amount of the base to be used is generally 0.1 to 100 equivalents, preferably 1 to 10 equivalents, per 1 equivalent of compound (VI).

This reaction is performed in a solvent such as ether solvents, halogenated hydrocarbon solvents, nitrile solvents, aromatic solvents, ester solvents, amide solvents and the like. Two or more kinds of these solvents may be used in a mixture at an appropriate ratio. Among these, tetrahydrofuran, dichloromethane, pyridine and the like are preferable.

The reaction temperature of this reaction is generally about 0° C. to 100° C., preferably 0 to 80° C.

The reaction time of this reaction is, for example, 0.5 hr to 1 day.

(Production Method B)

Of compound (I), the compound represented by the following formula (Ia), (Ib) or (Ic) (compound (Ia), compound (Ib) or compound (Ic)) can be produced, for example, according to the following Reaction scheme 2.

This reaction is performed, for example, in a solvent such as ether solvents, halogenated hydrocarbon solvents, nitrile solvents, aromatic solvents, ester solvents, amide solvents, water and the like. Two or more kinds of these solvents may be used in a mixture at an appropriate ratio. Among these, tetrahydrofuran, dichloromethane, pyridine, ethyl acetate-water and the like are preferable.

The reaction temperature of this reaction is generally about 0° C. to 100° C., preferably 0 to 80° C.

The reaction time of this reaction is, for example, 0.5 hr to 1 day.

(Process 5)

Compound (1b) can be produced by subjecting compound (1a) and compound (VIII) to alkylation in the presence of a base.

Examples of the base include amines (e.g., triethylamine, N,N-diisopropylethylamine, pyridine, 4-dimethylaminopyridine, 1,8-diazabicyclo[5.4.0]-7-undecene); alkali metal carbonates (e.g., potassium carbonate, sodium carbonate, cesium carbonate, sodium hydrogen carbonate, potassium hydrogen carbonate); alkali metal phosphates (e.g., tripotassium phosphate, trisodium phosphate); alkali metal acetates

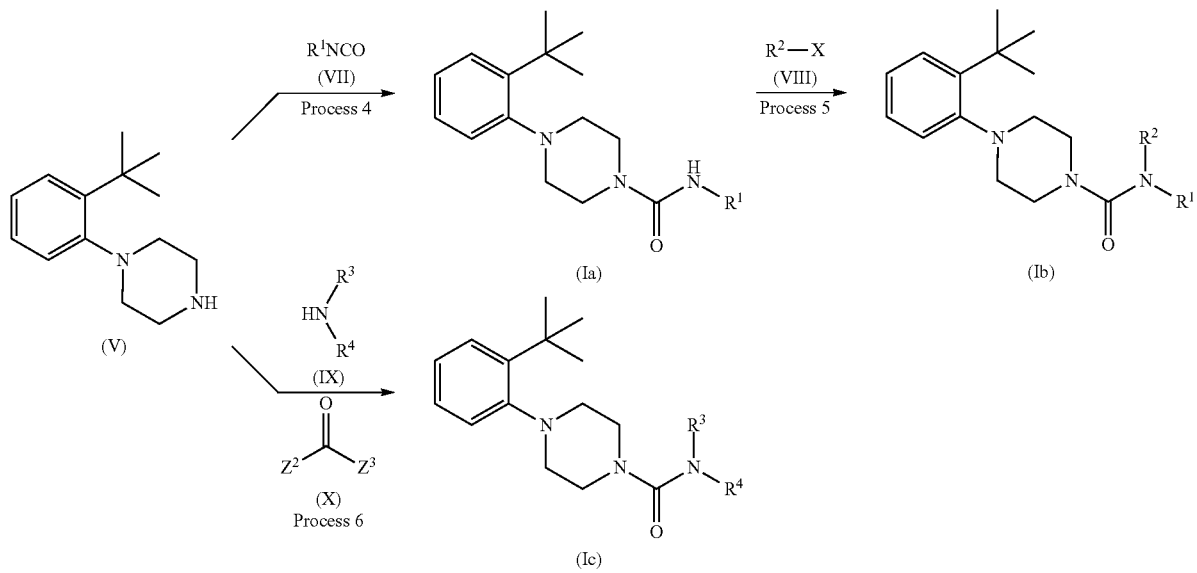

(Reaction scheme 2)

In this production method, compound (1a), compound (1b) and compound (1c) can be produced from compound (V) as a starting material compound by the following processes.

Process 4: Ureation
Process 5: Alkylation
Process 6: Acylation

Each process is specifically explained below.
(Process 4)

Compound (Ia) can be produced by subjecting compound (V) and compound (VII) to ureation reaction.

As compound (VII), a commercially available product can be used. In addition, compound (VII) can also be produced according to a method known per se (e.g., the method described in Experimental Chemistry Course (Jikken Kagaku Koza), 4th Edition, vol. 20, 473-483 pages (1992) Maruzen Co., Ltd.; and the like).

The amount of compound (VII) to be used is generally 1 to equivalents, preferably 1 to 3 equivalents, per 1 equivalent of compound (V).

(e.g., sodium acetate, potassium acetate); alkali metal hydrides (e.g., sodium hydride, potassium hydride); alkali metal hydroxides (e.g., sodium hydroxide, potassium hydroxide); alkali metal $C_{1-6}$ alkoxides (e.g., sodium methoxide, sodium tert-butoxide, potassium tert-butoxide) and the like. Among these, sodium hydride, sodium carbonate, potassium tert-butoxide and the like are preferable.

The amount of the base to be used is generally 0.1 to 100 equivalents, preferably 1 to 10 equivalents, per 1 equivalent of compound (VIII).

In addition, an additive (e.g., sodium iodide, potassium iodide etc.) may be used as necessary for this reaction.

The amount of the additive to be used is generally 0.1 to equivalents, preferably 0.5 equivalent to 5 equivalents, per 1 equivalent of compound (VIII).

Specific examples of compound (VIII) include methyl iodide, ethyl bromoacetate, benzyl bromide and the like.

Compound (VIII) may be a commercially available product, to or can be produced by a method known per se or a method analogous thereto.

The amount of compound (VIII) to be used is generally 1 to 100 equivalents, preferably 1 to 5 equivalents, per 1 equivalent of compound (1a).

This reaction is performed without solvent or in an inert solvent. Examples of the inert solvent include ether solvents, halogenated hydrocarbon solvents, nitrile solvents, aromatic solvents, ester solvents, amide solvents, water and the like can be mentioned. Two or more kinds of these solvents may be used in a mixture at an appropriate ratio. Among these, tetrahydrofuran, acetonitrile, N,N-dimethylformamide, N,N-dimethylacetamide, dimethyl sulfoxide and the like are preferable.

Where necessary, a phase transfer catalyst (e.g., tetrabutylammonium bromide, tetrabutylammonium hydrogen sulfate etc.) may be used for this reaction.

The amount of the phase transfer catalyst to be used is generally 0.01 to 0.5 equivalents, preferably 0.01 equivalent to 0.1 equivalent, per 1 equivalent of compound (1a).

The reaction temperature of this reaction is generally about −10° C. to 150° C., preferably 0° C. to 80° C.

The reaction time of this reaction is generally 0.5 hr to 24 hr.

(Process 6)

Compound (Ic) can be produced by subjecting compound (V), compound (IX) and compound (X) to acylation reaction.

A base may be used as necessary for this reaction.

Examples of the base include amines (e.g., triethylamine, N,N-diisopropylethylamine, pyridine, 4-dimethylaminopyridine, 1,8-diazabicyclo[5.4.0]-7-undecene); alkali metal carbonates (e.g., potassium carbonate, sodium carbonate, cesium carbonate, sodium hydrogen carbonate, potassium hydrogen carbonate); alkali metal phosphates (e.g., tripotassium phosphate, trisodium phosphate); alkali metal acetates (e.g., sodium acetate, potassium acetate); alkali metal hydrides (e.g., sodium hydride, potassium hydride); alkali metal hydroxides (e.g., sodium hydroxide, potassium hydroxide); alkali metal $C_{1-6}$ alkoxides (e.g., sodium methoxide, sodium tert-butoxide, potassium tert-butoxide) and the like. Among these, triethylamine, N,N-diisopropylethylamine, pyridine and the like are preferable.

The amount of the base to be used is generally 0.1 to 100 equivalents, preferably 1 to 10 equivalents, per 1 equivalent of compound (V).

Specific examples of compound (X) include N,N'-disuccinimidyl carbonate, 1,1'-carbonyldiimidazole, 2,2,2-trichloroethyl chloroformate and the like.

Compound (X) may be a commercially available product.

The amount of compound (X) to be used is generally 0.1 to equivalents, preferably 0.5 to 2 equivalents, per 1 equivalent of compound (V).

This reaction is generally performed in an inert solvent. Examples of the inert solvent include ether solvents, halogenated hydrocarbon solvents, nitrile solvents, aromatic solvents, ester solvents, amide solvents, water and the like. Two or more kinds of these solvents may be used in a mixture at an appropriate ratio. Among these, tetrahydrofuran, dichloromethane, acetonitrile, N,N-dimethylformamide, and the like are preferable.

The reaction temperature of this reaction is generally about −10° C. to 120° C., preferably 0° C. to 100° C.

The reaction time of this reaction is generally 0.5 hr to 24 hr.

Compound (IX) may be a commercially available product, or can be produced by a method known per se or a method analogous thereto.

In the above-mentioned production methods, when the starting material compound has amino group, carboxyl group, hydroxy group or carbonyl group as a substituent, a protecting group generally used in peptide chemistry and the like may be introduced into these groups. The object compound can be obtained by removing the protecting group as necessary after the reaction.

Examples of the amino-protecting group include a formyl group, a $C_{1-6}$ alkyl-carbonyl group (e.g., acetyl, propanoyl), a $C_{1-6}$ alkoxy-carbonyl group (e.g., methoxycarbonyl, ethoxycarbonyl), a benzoyl group, a $C_{7-13}$ aralkyl-carbonyl group (e.g., benzylcarbonyl), a $C_{7-13}$ aralkyloxy-carbonyl group (e.g., benzyloxycarbonyl, 9-fluorenylmethoxycarbonyl), a $C_{7-13}$ aralkyl group (e.g., benzyl, benzhydryl), a trityl group, a phthaloyl group, an N,N-dimethylaminomethylene group, a trisubstituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group, a nitro group and the like.

Examples of the carboxyl-protecting group include a $C_{1-6}$ alkyl group, a $C_{7-20}$ aralkyl group (e.g., benzyl, trityl), a phenyl group, a trisubstituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group, a nitro group and the like.

Examples of the hydroxy-protecting group include a $C_{1-6}$ alkyl group, a phenyl group, a trityl group, a $C_{7-13}$ aralkyl group (e.g., benzyl), a formyl group, a $C_{1-6}$ alkyl-carbonyl group (e.g., acetyl, propanoyl), a benzoyl group, a $C_{7-13}$ aralkyl-carbonyl group (e.g., benzylcarbonyl), a 2-tetrahydropyranyl group, a 2-tetrahydrofuranyl group, a trisubstituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group, a nitro group and the like.

Examples of the carbonyl-protecting group include cyclic acetal (e.g., 1,3-dioxane), noncyclic acetal (e.g., di-$C_{1-6}$ alkylacetal) and the like.

These protecting groups can be introduced or removed by a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyliodide, trimethylsilylbromide etc.) and the like, a reduction method and the like.

The compound (I) obtained by each of the above-mentioned production methods can be subjected to a means known per se, such as solvent extraction, concentration, neutralization, filtration, crystallization, recrystallization, chromatography and the like, whereby the object compound can be isolated and purified. On the other hand, the starting material compound may be directly used as a starting material of the next step in the form of a reaction mixture without isolation. In addition, when the starting material compound used for each of the above-mentioned production method is commercially available, the commercially available product can be directly used.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

Here, the optical isomer can be produced by a method known per se.

Compound (I) and a prodrug thereof (hereinafter sometimes to be simply referred to as the compound of the present invention) show low toxicity and can be used as an agent for the prophylaxis or treatment of various diseases to be mentioned later for mammals (e.g., human, mouse, rat, rabbit, dog, cat, cattle, horse, swine, simian) as they are or by admixing with a pharmacologically acceptable carrier and the like to give a pharmaceutical composition.

Here, various organic or inorganic carriers conventionally used as materials for pharmaceutical compositions are used as a pharmacologically acceptable carrier, which are added as an excipient, a lubricant, a binder, a disintegrant and the like for solid preparations; and a solvent, a solubilizing agent, a suspending agent, an isotonicity agent, a buffer, a soothing agent and the like for liquid preparations. Where necessary, an additive for pharmaceutical compositions such as a preservative, an antioxidant, a colorant, a sweetening agent and the like can be used.

Preferable examples of the excipient include lactose, sucrose, D-mannitol, D-sorbitol, starch, pregelatinized starch, dextrin, crystalline cellulose, low-substituted hydroxypropyl cellulose, sodium carboxymethylcellulose, powdered acacia, pullulan, light anhydrous silicic acid, synthetic aluminum silicate, magnesium aluminate metasilicate and the like.

Preferable examples of the lubricant include magnesium stearate, calcium stearate, talc, colloidal silica and the like.

Preferable examples of the binder include pregelatinized starch, saccharose, gelatin, powdered acacia, methylcellulose, carboxymethylcellulose, sodium carboxymethylcellulose, crystalline cellulose, sucrose, D-mannitol, trehalose, dextrin, pullulan, hydroxypropyl cellulose, hydroxypropyl methylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethyl starch, light anhydrous silicic acid, low-substituted hydroxypropyl cellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropyl cellulose and the like; polysorbates, polyoxyethylene hydrogenated castor oil, and the like.

Preferable examples of the isotonicity agent include sodium chloride, glycerol, D-mannitol, D-sorbitol, glucose and the like.

Preferable examples of the buffer include phosphate buffer, acetate buffer, carbonate buffer, citrate buffer and the like.

Preferable examples of the soothing agent include benzyl alcohol and the like.

Preferable examples of the preservative include p-oxybenzoates, chlorobutanol, benzyl alcohol, phenethyl alcohol, dehydroacetic acid, sorbic acid and the like.

Preferable examples of the antioxidant include sulfite, ascorbate and the like.

Preferable examples of the colorant include water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., beta carotene, chlorophil, red iron oxide) and the like.

Preferable examples of the sweetening agent include saccharin sodium, dipotassium glycyrrhizinate, aspartame, stevia and the like.

While the content of the compound of the present invention in the pharmaceutical composition varies depending on the dosage form, dose of the compound of the present invention and the like, it is, for example, about 0.1-100 wt %.

For production of an oral preparation, the aforementioned pharmaceutical composition administered orally may be coated with a coating base as necessary for the purpose of masking taste, enteric property or sustained release.

Examples of the coating base used for coating include a sugar-coating base, a water-soluble film coating base, an enteric film coating base, a sustained-release film coating base and the like.

As the sugar-coating base, sucrose may be used, if necessary, along with one or more species selected from talc, precipitated calcium carbonate, gelatin, powdered acacia, pullulan, carnauba wax and the like.

As the water-soluble film coating base, for example, cellulose polymers such as hydroxypropyl cellulose, hydroxypropyl methylcellulose, hydroxyethylcellulose, methylhydroxyethylcellulose and the like; synthetic polymers such as polyvinyl acetal diethylaminoacetate, aminoalkyl methacrylate copolymer E [Eudragit E, trade name], polyvinylpyrrolidone and the like; and polysaccharides such as pullulan and the like are used.

As the enteric film coating base, for example, cellulose polymers such as hydroxypropyl methylcellulose phthalate, hydroxypropyl methylcellulose acetate succinate, carboxymethylethylcellulose, cellulose acetate phthalate and the like; acrylic acid polymers such as methacrylic acid copolymer L [Eudragit L, trade name], methacrylic acid copolymer LD [Eudragit L-30D55, trade name], methacrylic acid copolymer S [Eudragit S, trade name] and the like; and natural products such as shellac and the like are used.

As the sustained-release film coating base, for example, cellulose polymers such as ethylcellulose and the like; and acrylic acid polymers such as aminoalkyl methacrylate copolymer RS [Eudragit RS, trade name], ethyl acrylate-methyl methacrylate copolymer suspension [Eudragit Nebr., trade name] and the like are used.

Two or more kinds of the above-mentioned coating bases may be mixed in an appropriate ratio for use. In addition, a light shielding agent such as titanium oxide, ferric oxide and the like may be used during coating.

A pharmaceutical composition comprising compound (I) may be safely administered orally or parenterally (e.g., intravenous, intramuscular, subcutaneous, intraorgan, intranasal, intradermal, ocular, intracerebral, intrarectal, vaginal, intraperitoneal or intratumoral administration, administration proximal to tumor or directly to the lesion), for example, as a tablet (including sugar-coated tablet, film-coated tablet, sublingual tablet, orally-disintegrating tablet, buccal tablet or the like), a pill, a powder, a granule, a capsule (including soft capsule, microcapsule), a lozenge, syrup, solution, an emulsion, a suspension, a controlled-release preparation (e.g., quick-release preparation, sustained-release preparation, sustained-release microcapsule), aerosol, a film (e.g., orally-disintegrating film, film applicable to oral mucosa), an injection (e.g., subcutaneous injection, intravenous injection, intramuscular injection, intraperitoneal injection, intraocular injection, subretinal injection, intravitreal injection, periocular administration, subconjuctival injection, retrobulbar injection, intracameral injection (including into the anterior or vitreous chamber), sub-Tenon's injection or implantation such as depot injection), drops, a transdermally absorbed preparation, an ointment, lotion, a gel, a patch, pack, a suppository (e.g., rectal suppository, vaginal suppository), pellets, a inhalation, eye-drops, use of iontophoresis, incorporation in surgical irrigating solution or the like, by administering compound (I) alone or together with a pharmacologically acceptable carrier according to a method known per se as a method for producing a drug preparation (e.g., methods described in the Japanese Pharmacopoeia, etc.).

The compound of the present invention has a superior retinol binding protein 4 lowering action (retinol binding protein 4-TTR (transthyretin) binding-inhibitory action), and can be used as an agent for the prophylaxis or treatment of retinol binding protein 4 associated diseases.

The compound of the present invention can be used as an agent for the prophylaxis or treatment of diabetes (e.g., type 1 diabetes, type 2 diabetes, gestational diabetes, obese diabetes) borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

In addition, the compound of the present invention can be used as an agent for the prophylaxis or treatment of obesity, hyperlipidemia (e.g., hypertriglyceridemia, hypercholesterolemia, high LDL-cholesterolemia, low HDL-cholesterolemia, postprandial hyperlipemia), hypertension, heart failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular disorder, peripheral blood circulation disorder], metabolic syndrome (according to the diagnostic criteria for Japanese people reported in the Japan Society for the Study of Obesity and the like in 2005, the metabolic syndrome refers to the condition showing abdominal girth of 85 cm or above for male and 90 cm or above for female, as well as 2 out of 3 items of systolic blood pressure of 130 mmHg or above and diastolic blood pressure of 85 mmHg or above; triglyceride of 150 mg/dl or above or HDLc of less than 40 mg/dl; and fasting blood glucose level (glucose concentration of intravenous plasma) of 110 mg/dl or above), sarcopenia and the like.

As for the diagnostic criteria of diabetes, the Japan Diabetes Society reported new diagnostic criteria in 1999. According to the report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type". In addition, ADA (American Diabetes Association) reported new diagnostic criteria of diabetes in 1997 and WHO in 1998. According to the report of ADA, diabetes is a condition showing diabetes-like symptoms (polyuria, polydipsia, hyperphagia, overwork, body weight decrease, blurred vision, growth disorder), as well as any of a non-fasting blood glucose level (glucose concentration of intravenous plasma) of not less than 200 mg/dl, a fasting blood glucose level (glucose concentration of intravenous plasma) of not less than 126 mg/dl, and a 75 g oral glucose tolerance test 2 h level (glucose concentration of intravenous plasma) of not less than 200 mg/dl. According to the report of WHO, diabetes is a condition showing a fasting blood glucose level (glucose concentration of intravenous plasma) of not less than 126 mg/dl, or a 75 g oral glucose tolerance test 2 hr value (glucose concentration of intravenous plasma) of not less than 200 mg/dl. According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can be also used as an agent for the prophylaxis or treatment of, for example, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, polycystic ovary syndrome, kidney disease (e.g., diabetic nephropathy, glomerular nephritis, glomerulosclerosis, nephrotic syndrome, hypertensive nephrosclerosis, end stage kidney disease), muscular dystrophy, myocardial infarction, angina pectoris, cerebrovascular accident (e.g., cerebral infarction, cerebral apoplexy), Alzheimer's disease, Parkinson's disease, anxiety, dementia, insulin resistance syndrome, Syndrome X, hyperinsulinemia, hyperinsulinemia-induced sensory disorder, tumor (e.g., leukemia, breast cancer, prostatic cancer, skin cancer), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, swelling, neuralgia, pharyngolaryngitis, cystitis, hepatitis (inclusive of nonalcoholic steatohepatitis), pneumonia, pancreatitis, enteritis, inflammatory bowel diseases (including inflammatory disease of large intestine), ulcerative colitis, gastric mucosal injury (inclusive of gastric mucosal injury caused by aspirin)), small intestine mucous membrane trauma, malabsorption, testis function disorder, visceral obesity syndrome, sarcopenia and the like.

The compound of the present invention can be also used as an agent for the prophylaxis or treatment of, for example, retinol-related diseases, such as macular degenerations, macular dystrophies and retinal dystrophies, including dry (atrophic or nonvascular) form age-related macular degenerations, geographic atrophy, and/or photoreceptor degeneration.

The compound of the present invention can be also used as an agent for, for example, lowering levels of serum retinol, a serum RBP (reinol binding protein), and/or a serum TTR (transthyretin), and also used as an agent for the prophylaxis or treatment of, for example, hyperretinolemia (excess serum retinol revels).

The compound of the present invention can be also used as an agent for the prophylaxis or treatment of, for example, diabetic retinopathy, wet form of macular degeneration, retinopathy of prematurity, retinitis pigmentosa, retinal vein occlusion, retinal artery occlusion and/or glaucoma.

The compound of the present invention can be also used for secondary prophylaxis and prevention of progression of the above-mentioned various diseases (e.g., cardiovascular event such as myocardial infarction and the like).

While the dose of the compound of the present invention varies depending on the subject of administration, administration route, target disease, symptom and the like, it is, for example, generally about 0.01-100 mg/kg body weight, preferably 0.05-30 mg/kg body weight, more preferably 0.1-10 mg/kg body weight, more preferably 0.5-10 mg/kg body weight, for a single administration to adult diabetes patients or patients of age-related macular degeneration by oral administration. The dose is preferably administered in one to 3 portions a day.

To enhance the action of the compound of the present invention or reduce the dose of the compound and the like, the compound can be used in combination with pharmaceutical agents such as other therapeutic agents for diabetes, therapeutic agents for diabetic complications, therapeutic agents for hyperlipidemia, antihypertensive agents, antiobesitic agents, diuretics, therapeutic agents for macular degeneration, the antioxidant agents, the nitric oxide inducers, the matrix metalloproteinases, the antiangiogenic or anti-VEGF agents, chemotherapeutic agents, immunotherapeutic agents, antithrombotic agents, therapeutic agents for osteoporosis, antidementia agents, erectile dysfunction-improving agents, therapeutic agents for incontinence or frequent urination, therapeutic agents for dysuria and the like (hereinafter to be abbreviated as concomitant drug). These concomitant drugs may be low-molecular-weight compounds, or high-molecular-weight proteins, polypeptides, antibodies, vaccines and the like.

The administration time of the compound of the present invention and the concomitant drug is not restricted, and the compound of the present invention and the concomitant drug can be administered to an administration subject simultaneously, or may be administered at staggered times.

The administration mode is not particularly limited as long as the compound of the present invention and a concomitant drug are combined. Examples of the administration mode include the following.

(1) The compound of the present invention and the concomitant drug are simultaneously formulated to give a single preparation which is administered.

(2) The compound of the present invention and the concomitant drug are separately formulated to give two kinds of preparations which are administered simultaneously by the same administration route.

(3) The compound of the present invention and the concomitant drug are separately formulated to give two kinds of preparations which are administered by the same administration route at staggered times.

(4) The compound of the present invention and the concomitant drug are separately formulated to give two kinds of preparations which are administered simultaneously by the different administration routes.

(5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

The dose of the concomitant drug can be appropriately determined based on the clinically-employed doses. In addition, the mixing ratio of the compound of the present invention and the concomitant drug can be appropriately determined according to the subject of administration, administration route, target disease, symptom, combination and the like. For example, when the subject of administration is a human, 0.01-100 parts by weight of a concomitant drug can be used per 1 part by weight of the compound of the present invention.

The compound can be used in combination with procedures that provides additional or synergistic benefit to the patient, such as the use of extracorporeal rheopheresis, the use of implantable miniature telescopes, laser photocoagulation of drusen, microstimulation therapy and the like.

Examples of the agent for treating diabetes include insulin preparations (e.g., animal insulin preparations extracted from bovine or swine pancreas; human insulin preparations synthesized by genetic engineering using *E. coli* or yeast; insulin zinc; protamine insulin zinc; insulin fragments or derivatives (e.g., INS-1), oral insulin preparation), insulin-resistance improving agents (e.g., pioglitazone or salts thereof (preferably, hydrochloride salt), rosiglitazone or salts thereof (preferably, maleate salt), Netoglitazone (MCC-555), Rivoglitazone (CS-011), FK-614, compounds described in WO01/38325, Tesaglitazar (AZ-242), Ragaglitazar (N,N-622), Muraglitazar (BMS-298585), Edaglitazone (BM-13-1258), Metaglidasen (MBX-102), Naveglitazar (LY-519818), MX-6054, LY-510929, AMG131(T-131) or salts thereof, THR-0921), α-glucosidase inhibitor (e.g., voglibose, acarbose, miglitol, emiglitate), biguanides (e.g., phenformin, metformin, buformin or salts thereof (e.g., hydrochloride salt, fumarate salt, succinate salt)), insulin secretion promoters (sulphonylurea agents (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrates thereof), dipeptidyl peptidase-IV inhibitors (e.g., Vildagliptin (LAF237), P32/98, Sitagliptin (MK-431), alogliptin, P93/01, PT-100, Saxagliptin (BMS-477118), BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or salts thereof), β3-agonists (e.g., AJ-9677), GPR40 agonists, GLP-1 receptor agonists (e.g., GLP-1, GLP-1MR agent, N,N-2211, AC-2993 (exendin-4), BIM-51077, Aib(8,35)hGLP-1 (7,37)NH2, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095, dapagliflozin, remogliflozin), 11β-hydroxysteroid dehydrogenase inhibitors (e.g., BVT-3498), adiponectin or agonists thereof, IKK inhibitors (e.g., AS-2868), leptin-resistant improving drugs, somatostatin receptor agonists (e.g., compounds described in WO01/25228, WO03/42204, WO98/44921, WO98/45285, WO99/22735, etc.), glucokinase activators (e.g., Ro-28-1675), ACC2 (acetyl-CoA carboxylase 2) inhibitors and the like.

Examples of the therapeutic agent for diabetic complications include aldose reductase inhibitors (e.g., tolrestat, epalrestat, zenarestat, zopolrestat, minalrestat, fidarestat, CT-112, ranirestat (AS-3201)), neurotrophic factors and augmenting agents thereof (e.g., NGF, NT-3, BDNF, neurotrophin production/secretion promoters described in WO01/14372 (e.g., 4-(4-chlorophenyl)-2-(2-methyl-1-imidazolyl)-5-(3-(2-methylphenoxy)propyl)oxazole)), PKC inhibitors (e.g., ruboxistaurin mesylate), AGE inhibitors (e.g., ALT946, pimagedine, N-phenacylthiazolium bromide (ALT766), EXO-226, Pyridorin, pyridoxamine), active oxygen scavenging agents (e.g., thioctic acid), cerebral vasodilators (e.g., tiapride, mexiletine), somatostatin receptor agonists (e.g., BIM23190), and apoptosis signal-regulating kinase-1 (ASK-1) inhibitors.

Examples of the antihyperlipidemic agent include statin compounds as cholesterol synthesis inhibitors (e.g., cerivastatin, pravastatin, simvastatin, lovastatin, rosuvastatin, atorvastatin, fluvastatin, pitavastatin or salts thereof (e.g., sodium salt, etc.) etc.), squalene synthetase inhibitors or fibrate compounds with hypotriglyceride action (e.g., bezafibrate, clofibrate, simfibrate, clinofibrate, etc.), cholesterol absorption inhibitors (e.g., zetia), anion-exchange resins (e.g., cholestyramine), probucol, nicotinic drugs (e.g., nicomol, niceritrol), phytosterols (e.g., soysterol, γ-oryzanol)), fish oil preparations (EPA, DHA, omacor, etc.), PPAR α-agonists, PPAR γ-agonists, PPAR δ-agonists, LXR agonists, FXR antagonists, FXR agonists, DGAT inhibitors, MGAT inhibitors, MTP inhibitors (e.g., lomitapide), nucleic acid drugs including ApoB antisense (e.g., mipomersen) or PCSK9 siRNA antisense oligonucleotides, and the like.

Examples of the antihypertensive agent include angiotensin-converting enzyme inhibitors (e.g., captopril, enalapril, delapril, etc.), angiotensin II antagonists (e.g., candesartan cilexetil, candesartan, azilsartan, azilsartan medoxomil, losartan, losartan potassium, eprosartan, valsartan, telmisartan, irbesartan, tasosartan, olmesartan, olmesartan medoxomil, etc.), calcium antagonists (e.g., manidipine, nifedipine, amlodipine, efonidipine, nicardipine, etc.), β-blockers (e.g., propranolol, nadolol, timolol, nipradilol, bunitrolol, indenolol, penbutolol, carteolol, carvedilol, pindolol, acebutolol, atenolol, bisoprolol, metoprolol, labetalol, amosulalol, arotinolol, etc.), clonidine and the like.

Examples of the antiobestic agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA modulators (e.g., topiramate), neuropeptide Y antagonists (e.g., velneperit), cannabinoid receptor antagonists (e.g., rimonabant, taranabant), ghrelin antagonists, ghrelin receptor antagonists, ghrelin-acylating enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3-agonists (e.g., N-5984), diacylglycerol acyltransferase1 (DGAT1) inhibitors, acetyl CoA carboxylase (ACC) inhibitors, stearate CoA desaturase inhibitors, microsome triglyceride transfer protein inhibitors (e.g., R-256918), Na-glucose cotransport carrier inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., meterleptin), CNTFs (ciliary neurotrophic factors), BDNFs (brain-derived neurotrophic factors), cholecystokinin agonists, glucagon-like peptide-1 (GLP-1) preparations (e.g., animal GLP-1 preparations extracted from bovine or swine pancreas; human GLP-1 preparations synthesized by genetic engineering using E. coli or yeast; GLP-1 fragments or derivatives (e.g., exenatide, liraglutide)), amylin preparations (e.g., pramlintide, AC-2307), neuropeptide Y agonists (e.g., PYY3-36, PYY3-36 derivatives, obinepitide, TM-30339, TM-30335), oxyntomodulin preparations: FGF21 preparations (e.g., animal FGF21 preparations extracted from bovine or swine pancreas; human FGF21 preparations synthesized by genetic engineering using E. coli or yeast; FGF21 fragments or derivatives)), appetite suppressors (e.g., P-57) and the like.

Examples of the diuretic include xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, bentyl hydrochlorothiazide, penfluthiazide, poly 5 thiazide, methychlothiazide, etc.), anti-aldosterone preparations (e.g., spironolactone, eplerenone, triamterene, etc.), carbonate dehydratase inhibitors (e.g., acetazolamide, etc.), chlorobenzenesulfonamide preparations (e.g., chlortalidone, mefruside, indapamide, etc.), azosemide, isosorbide, ethacrynic acid, piretanide, bumetanide, furosemide and the like.

Examples of the therapeutic agent for macular degenerations include fenretinide (4-hydroxy(phenyl)retinamide), compound described in WO2009/042444, negatively-charged phospholipids, certain minerals (e.g., copper-containing minerals such as cupric oxide, zinc-containing minerals such as zinc oxide, selenium-containing compounds) and the like.

Examples of the antioxidant agent include vitamin C, vitamin E, beta-carotene and other carotenoids, coenzyme Q, 4-hydroxy-2,2,6,6-tetramethylpiperidine-N-oxyl (also known as Tempol), lutein, butylated hydroxytoluene, resveratrol, a trolox analogue (PNU-83836-E), bilberry extract and the like.

Examples of the nitric oxide inducers include L-arginine, L-homoarginine, and N-hydroxy-L-arginine (e.g., nitrosated L-arginine, nitrosylated L-arginine, nitrosated N-hydroxy-L-arginine, nitrosylated N-hydroxy-L-arginine, nitrosated L-homoarginine, nitrosylated L-homoarginine), precursors of L-arginine and/or physiolosically acceptable salt thereof (e.g., citrulline, ornithine, glutamine, lysine, polypeptides comprising at least one of the above-mentioned amino acid, inhibitors of the enzyme arginase (e.g., N-hydroxy-L-arginine and 2(S)-amino-6-boronohexanoic acid), the substrates for nitric oxide or a closely related derivative thereof and the like.

Examples of the matrix metalloproteinases (MMPs) inhibitors include Tissue Inhibitors of Metalloproteinases (TIMPs) (e.g., TIMP-1, TIMP-2, TIMP-3, TIMP-4), α2-macroglobulin, tetracyclines (e.g., tetracycline, minocycline, doxycycline), hydroxamates (e.g., BATIMASTAT, MARIMISTAT, TROCADE), chelators (e.g., EDTA, cysteine, acetylcysteine, D-penicillamine, gold salts), synthetic MMP fragments, succinyl mercaptopurines, phosphonamidates, hydroxaminic acids and the like.

Examples of the antiangiogenic or anti-VEGF agents include Rhufab V2 (Lucentis), Tryptophanyl-tRNA synthetase (TrpRS), Eye001 (Anti-VERG Pegylated Aptamer), squalamine, Retaane 15 mg (anecortave acetate for depot suspension; Alcon, inc.), Combretastain A4 Prodrug (CA4P), Macugen, Mifeprex (mifepristone-ru486), subtenon triamcinolone acetonide, intravitreal crystalline triamcinolone acetonide, Prinomastat (AG3340), fluocinolone acetonide (including fluocinolone intraocular implant), VEGFR inhibitors, VEGF-Trap and the like.

Examples of the chemotherapeutic agent include alkylation agents (e.g., cyclophosphamide, ifosfamide), metabolic antagonists (e.g., methotrexate, 5-fluorouracil or its derivative), anti-cancer antibiotics (e.g., mitomycin, adriamycin), plant-derived anti-cancer agents (e.g., vincristin, vindesine, taxol), cisplatin, carboplatin, etoposide and the like. Of these, furtulon and neofurtulon, which are 5-fluorouracil derivatives, and the like are preferable.

Examples of the immunotherapeutic agent include microorganism or bacterial components (e.g., muramyl dipeptide derivative, picibanil), polysaccharides having immunity potentiating activity (e.g., lentinan, sizofuran, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agent include heparin (e.g., heparin sodium, heparin calcium, dalteparin sodium), warfarin (e.g., warfarin potassium), anti-thrombin drugs (e.g., aragatroban, dabigatran), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride, prasugrel, E5555, SHC530348), FXa inhibitors (e.g., 1-(1-{(2S)-3-[(6-chloronaphthalen-2-yl)sulfonyl]-2-hydroxypropanoyl}piperidin-4-yl)tetrahydropyrimidin-2 (1H)-one, rivaroxaban, apixaban, DU-156, YM150) and the like.

Examples of the therapeutic agent of osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agent include tacrine, donepezil, rivastigmine, galanthamine and the like.

Examples of the agent for improving erectile dysfunction include apomorphine, sildenafil citrate and the like.

Examples of the therapeutic agent for incontinentia or pollakiuria include flavoxate hydrochloride, oxybutynin hydrochloride, propiverine hydrochloride and the like.

Examples of the therapeutic agent for dysurea include acetylcholine esterase inhibitors (e.g., distigmine) and the like.

In addition, examples of the concomitant drug include drugs having a cachexia-improving action established in animal models and clinical situations, such as cyclooxygenase inhibitors (e.g., Indometacin), Progesterone derivatives (e.g., Megesterol acetate), glucosteroid (e.g., dexamethasone), metoclopramide agents, tetrahydrocannabinol agents, fat metabolism improving agents (e.g., eicosapentaenoic acid), growth hormones, IGF-1, or antibodies to a cachexia-induced factor such as TNF-α, LIF, IL-6, Oncostatin M and the like.

Moreover, examples of the concomitant drug include nerve regeneration stimulators (e.g., Y-128, VX-853, prosaptide), antidepressants (e.g., desipramine, amitriptyline, imipramine), antiepileptic drugs (e.g., lamotrigine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin), α2 receptor agonists (e.g., clonidine), topical analgesic drugs (e.g., capsaicin), antianxiety drugs (e.g., benzodiazepine), dopamine agonists (e.g., apomorphine), midazolam, ketoconazole and the like.

The present invention is explained in detail in the following by referring to Reference Examples, Examples, Experimental Examples and Formulation Examples, which are not to be construed as limitative.

EXAMPLES

Unless otherwise specified, the room temperature means a temperature of 1-30° C. in the following Reference Examples and Examples.

In the following Reference Examples and Examples, unless particularly specified, the melting point, mass spectrum (MS) and nuclear magnetic resonance spectrum (NMR) were measured under the following conditions.
melting point measuring apparatus: a micro melting point apparatus of Yanagimoto Mfg. Co., Ltd., or Buchi melting point apparatus B-545 was used.
MS measuring apparatus: Waters Corporation, ZMD; Waters Corporation, ZQ2000; or Micromass Ltd., platform II;
ionization method: electrospray ionization method (ESI) or atmospheric pressure chemical ionization method (APCI). Unless particularly specified, ESI was used.
NMR measurement apparatus: Varian Inc., Varian Gemini 200 (200 MHz), Varian Mercury-300 (300 MHz), Varian INOVA-400 (400 MHz); or Bruker BioSpin Corp., AVANCE 300. The chemical shift is shown by ppm using tetramethylsilane as the internal standard, and the coupling constant (J) is shown by hertz (Hz).

The abbreviations in Reference Examples and Examples follow those generally used in the technical field, and mean, for example, the following.
s: singlet
d: doublet
t: triplet
q: quartet
quin: quintet
dd: double doublet
dt: double triplet
dq: double quartet
ddd: double double doublet
td: triple doublet
tt: triple triplet
m: multiplet
br: broad
brs: broad singlet
J: coupling constant
THF: tetrahydrofuran
DMF: dimethylformamide
DMSO: dimethyl sulfoxide
$CDCl_3$: deuterated chloroform
EDCI: 1-ethyl-3-(3-dimethylaminopropyl)carbodiimide
HOBt: 1-hydroxybenzotriazole
m-CPBA: m-chlorobenzoic acid
DIPEA: N,N-diisopropylethylamine
p-TsCl: p-toluenesulfonylchloride
MeOH: methanol
EtOH: ethanol HBTU: O-(benzotriazol-1-yl)-N,N,N',N'-tetramethyluroniumhexafluorophosphate
quant: quantitatively

Reference Example 1

1-(2-tert-Butylphenyl)piperazine dihydrochloride

A solution of 2-tert-butylaniline (35.7 g, 0.240 mol) and di(2-chloroethyl)amine hydrochloride (47.0 g, 0.264 mol) in diethylene glycol dimethyl ether (350 mL) was refluxed for 12 h. Then the mixture was cooled to room temperature, and 2 M NaOH solution (50 mL) was added. The mixture was extracted with ether, the combined organic layer was dried over anhydrous sodium sulfate, and the solvent was evaporated under reduced pressure to give crude product as a colorless oil. The product was purified by re-crystallization in petroleum ether to afford 1-[2-(tert-butyl)phenyl]piperazine (22.6 g, 43%) as a white solid. To the mixture of [2-(tert-butyl)phenyl]piperazine and ethyl acetate was added dropwise 4 M HCl solution in ethyl acetate (50 mL), keeping stirring for 0.5 h. Then the resulting solid was collected by filtration to give 1-[2-(tert-butyl)phenyl]piperazine dihydrochloride (30 g, quant.) as a white solid, which was re-crystalized in ethanol to give 1-(2-tert-butylphenyl)piperazine dihydrochloride.

$^1$H NMR (300 MHz, DMSO-$d_6$) δ 1.38 (s, 9H), 2.82-2.85 (m, 2H), 3.04-3.14 (m, 4H), 3.33-3.35 (m, 2H), 7.16-7.21 (m, 1H), 7.26-7.35 (m, 3H), 9.30 (br s, 2H).

Reference Example 2

Ethyl [(4-formyl-1,3-dimethyl-1H-pyrazol-5-yl)sulfanyl]acetate

A mixture of 5-chloro-1,3-dimethyl-1H-pyrazole-4-carbaldehyde (5.0 g), ethyl thioglycolate (3.97 g), potassium carbonate (5.53 g), and N,N-dimethylformamide (150 mL) was stirred at 80° C. for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (silica gel, 90:10-50:50 hexane/ethyl acetate) to provide the title compound (2.12 g, 28%) as an oil.

$^1$H NMR (300 MHz, CDCl$_3$) δ 1.20 (t, J=7.2 Hz, 3H), 2.47 (s, 3H), 3.60 (s, 3H), 3.96 (s, 2H), 4.10 (q, J=7.2 Hz, 2H), 9.98 (s, 1H).

Reference Example 3

[(4-Formyl-1,3-dimethyl-1H-pyrazol-5-yl)sulfanyl]acetic acid

A mixture of ethyl [(4-formyl-1,3-dimethyl-1H-pyrazol-5-yl)sulfanyl]acetate obtained in Reference Example 2 (2.12 g), 8 M sodium hydroxide solution (5 mL), methanol (50 mL), and tetrahydrofuran (50 mL) was stirred at room temperature for 2 h. 6 M Hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure, and the residue was recrystallized from ethyl acetate-diisopropyl ether to provide the title compound (1.09 g, 58%) as a solid.

$^1$H NMR (300 MHz, DMSO-$d_6$) δ 2.35 (s, 3H), 3.74 (s, 2H), 3.88 (s, 3H), 9.88 (s, 1H), 12.93 (br, 1H).

Reference Example 4 tert-Butyl 4-({[(4-methylphenyl)sulfonyl]oxy}methyl)piperidine-1-carboxylate

A mixture of tert-butyl 4-(hydroxymethyl)piperidine-1-carboxylate (11.6 g), tosyl chloride (11.44 g), and pyridine (60 mL) was stirred at room temperature for over-night. The solvent was evaporated under reduced pressure, and the residue was dissolved in ethyl acetate. The ethyl acetate layer was washed with 1 M hydrochloric acid solution, water, and saturated brine, and dried over anhydrous magnesium sulfate. The solvent was evaporated under reduced pressure to provide the title compound (16.94 g, 85%) as an oil.

$^1$H NMR (300 MHz, CDCl$_3$) δ 1.07-1.16 (m, 2H), 1.46 (s, 9H), 1.63-1.67 (m, 2H), 1.77-2.04 (m, 1H), 2.46 (s, 3H), 2.61-2.69 (m, 2H), 3.84 (d, J=6.3 Hz, 2H), 4.08-4.15 (m, 2H), 7.33-7.36 (m, 2H), 7.75-7.79 (m, 2H).

Reference Example 5 tert-Butyl 4-{[4-(methoxycarbonyl)phenoxy]methyl}piperidine-1-carboxylate

A mixture of tert-butyl 4-({[(4-methylphenyl)sulfonyl]oxy}methyl)piperidine-1-carboxylate obtained in Reference Example 4 (8.0 g), methyl 4-hydroxybenzoate (3.1 g), potassium carbonate (5.53 g), and N,N-dimethylformamide (80 mL) was stirred at 60° C. for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (7.12 g, 100%) as crystals.

$^1$H NMR (300 MHz, CDCl$_3$) δ 1.21-1.35 (m, 2H), 1.47 (s, 9H), 1.80-1.84 (m, 2H), 1.92-1.98 (m, 1H), 2.70-2.79 (m, 2H), 3.85 (d, J=6.3 Hz, 2H), 3.88 (s, 3H), 4.14-4.17 (m, 2H), 6.88 (d, J=8.4 Hz, 2H), 7.97 (d, J=8.4 Hz, 2H).

Reference Example 6

4-{[1-(tert-Butoxycarbonyl)piperidin-4-yl]methoxy}benzoic acid

A mixture of tert-butyl 4-{([4-(methoxycarbonyl)phenoxy]methyl}piperidine-1-carboxylate obtained in Reference Example 5 (7.12 g), 8 M sodium hydroxide solution (15 mL), methanol (20 mL), and tetrahydrofuran (200 mL) was stirred at 70° C. for 4 h. 1 M Hydrochloric acid solution was added to the reaction solution at 0° C., and the mixture was extracted with ethyl acetate. The ethyl acetate layer was washed with saturated brine, and dried over anhydrous magnesium sulfate. The solvent was evaporated under reduced pressure to provide the title compound (6.6 g, 96%) as crystals.

$^1$H NMR (300 MHz, DMSO-$d_6$) δ 1.09-1.22 (m, 2H), 1.40 (s, 9H), 1.73-1.77 (m, 2H), 1.90-1.98 (m, 1H), 2.70-2.80 (m, 2H), 3.90 (d, J=6.3 Hz, 2H), 3.95-4.00 (m, 2H), 6.98-7.01 (m, 2H), 7.86-7.88 (m, 2H), 12.59 (d, 1H).

Reference Example 7

1-Phenylproline

A mixture of D,L-proline (5.00 g, 43.4 mmol), iodobenzene (7.39 g, 36.2 mmol), copper(I) iodide (0.41 g, 2.17 mmol), K₃PO₄ (15.4 g, 72.4 mmol), and ethylene glycol (4.49 g, 72.4 mmol) in 2-propanol (36 mL) was stirred at 85° C. for 24 h under argon atmosphere. The reaction mixture was cooled to room temperature and diluted with water. The mixture was acidified with 6 M hydrochloric acid solution (pH 3), and extracted with diethyl ether (300 mL), and the extract was washed with water, and saturated brine, dried over anhydrous magnesium sulfate, filtered and concentrated under reduced pressure to afford a light brown solid. This solid was triturated with ethyl acetate and washed with diisopropyl ether successively to give the title compound (2.23 g, 27%) as a yellow solid.

$^1$H NMR (300 MHz, DMSO-d₆) δ 1.89-2.12 (m, 3H), 2.16-2.35 (m, 1H), 3.19-3.52 (m, 2H), 4.13 (dd, J=8.7, 2.3 Hz, 1H), 6.47 (d, J=7.9 Hz, 2H), 6.61 (t, J=7.2 Hz, 1H), 7.08-7.22 (m, 2H), 12.52 (br. s., 1H).

Reference Example 8

4-Bromo-2-tert-butylaniline

To a solution of 2-tert-butylaniline (50 g, 335 mmol) in THF (500 mL) was added tetrabutylammonium tribromide (234.5 g, 335 mmol) at 0° C. After the solution was stirred for 30 minutes at that temperature, it was poured into water and extracted with ethyl acetate. The organic layer was washed with saturated Na₂S₂O₃ solution and brine, dried over anhydrous magnesium sulfate, and concentrated under reduced pressure to give the crude product. The product was purified by flash column chromatography (silica gel, n-hexane/ethyl acetate=100:0 to 20:80) to provide 4-bromo-2-tert-butylaniline (74.6 g, 98%) as a pink oil.

$^1$H NMR (300 MHz, CDCl₃) δ 1.39 (s, 9H), 3.81 (br. s., 2H), 6.51 (d, J=8.3 Hz, 1H), 7.11 (dd, J=8.3, 2.3 Hz, 1H), 7.30 (d, J=2.3 Hz, 1H).

Reference Example 9

1-(4-Bromo-2-tert-butylphenyl)piperazine dihydrochloride

A suspension of 4-bromo-2-tert-butylaniline (Reference Example 8, 25.0 g, 110 mmol) and bis(2-chloroethyl)amine hydrochloride (21.5 g, 120 mmol) in diethylene glycol dimethyl ether (157 mL) was stirred for 3 days at 170° C. It was cooled to room temperature, added 1 M sodium hydroxide solution (50 mL), and extracted with ethyl acetate. The extract was washed with brine, dried over anhydrous magnesium sulfate, and concentrated under reduced pressure to give crude product. It was diluted with ethyl acetate and ether (50:50) and added 1 M hydrochloric acid solution to provide 1-(4-bromo-2-tert-butylphenyl)piperazine dihydrochloride (16.2 g, 40%) as a gray solid.

$^1$H NMR (300 MHz, DMSO-d₆) δ 1.37 (s, 9H), 2.81 (d, J=11.7 Hz, 2H), 2.87-3.09 (m, 2H), 3.09-3.21 (m, 2H), 3.33 (d, J=11.7 Hz, 2H), 7.27 (d, J=8.7 Hz, 1H), 7.42 (d, J=2.3 Hz, 1H), 7.49 (dd, J=8.3, 2.3 Hz, 1H), 9.50 (br. s., 2H).

Reference Example 10

1-(2-tert-Butyl-4-methylphenyl)piperazine dihydrochloride

To a solution of n-BuLi (1.6 M in n-hexane, 5.7 mL, 9.1 mmol) in THF (30 mL) was added a solution of tert-butyl 4-(4-bromo-2-tert-butylphenyl)piperazine-1-carboxylate (Example 85, 3.0 g, 7.55 mmol) in THF (10 mL) at −80° C. After stirred for 30 minutes at that temperature, it was added methyl iodide (1.61 g, 11.3 mmol) and allowed to be warmed to room temperature. After 16 h, it was added water and extracted with ethyl acetate. The organic layer was washed with brine, and dried over MgSO₄, and the solvent was evaporated under reduced pressure to get crude product. The product was purified by flash column chromatography (silica gel, n-hexane/ethyl acetate=97:3 to 90:10) to provide a white solid. It was added 4 M hydrochloric acid in ethyl acetate solution (7.5 mL). After 16 h, it was concentrated under reduced pressure to give a pale yellow powder, which was re-crystallized from methanol, ethyl acetate and hexane to provide a white powder. It was subjected to purification by high performance liquid chromatography [Column: Gilson, Ltd. High throughput purification system, YMC Combiprep ODS-A, S-5 μm, 50 mm×20 mm; Gradient cycle: H₂O (contains 0.1% CF₃COOH)-acetonitrile (contains 0.1% CF₃COOH), 90:10 (0 min)-90:10 (1 min)-10:90 (4.2 min)-10:90 (5.4 min)-90:10 (5.5 min)-90:10 (5.6 min); Flow rate: 25 mL/min; detection wavelength: UV 220 nm] to give a white solid. It was added 4 M hydrochloric acid ethyl acetate solution (7.5 mL). The solvent was removed under reduced pressure to give 1-(2-tert-butyl-4-methylphenyl)piperazine dihydrochloride (1.08 g, 47%) as a white powder.

$^1$H NMR (300 MHz, DMSO-d₆) δ 1.37 (s, 9H), 2.26 (s, 3H), 2.79 (d, J=10.6 Hz, 2H), 2.91-3.21 (m, 4H), 3.32 (d, J=11.0 Hz, 2H), 7.04-7.21 (m, 3H), 8.96-9.37 (m, 2H).

Reference Example 11

Methyl 5-oxo-1-phenylprolinate

A mixture of 5-oxo-pyrrolidine-2-carboxylic acid methyl ester (5.00 g, 34.9 mmol), bromobenzene (5.48 g, 34.9 mmol), tris(dibenzylideneacetone)dipalladium(0) (0.96 g, 1.05 mmol), Xantphos™ (1.21 g, 2.09 mmol), and cecium carbonate (15.9 g, 48.9 mmol) in toluene (100 mL) was stirred at 120° C. for 20 h under argon atmosphere. The reaction mixture was cooled to room temperature, and partitioned between ethyl acetate and 2 M HCl solution. The organic layer was washed with saturated NaHCO₃ solution, and brine, dried over anhydrous magnesium sulfate, filtered and concentrated under reduced pressure. The residue was purified by silica gel column chromatography (hexane/ethyl acetate 70:30 to 0:100) to give a yellow solid. The solid was triturated with hexane-diisopropyl ether to give the title compound (3.74 g, 49%) as a yellow solid.

$^1$H NMR (300 MHz, CHLOROFORM-d) δ ppm 2.11-2.27 (m, 1H), 2.40-2.65 (m, 2H), 2.65-2.84 (m, 1H), 3.73 (s, 3H), 4.68-4.79 (m, 1H), 7.15-7.22 (m, 1H), 7.32-7.41 (m, 2H), 7.43-7.50 (m, 2H). LC/MS; ESI(+) m/z: 220 (M+H)⁺.

Reference Example 12

5-Oxo-1-phenylproline

To a stirred solution of methyl 5-oxo-1-phenylprolinate (3.50 g, 15.96 mmol) in methanol (200 mL) was added 1 M NaOH solution (40 mL). After being stirred at room temperature for 2 h, the reaction mixture was acidified with 1 M HCl solution and the mixture was concentrated under reduced pressure. The resulting residue was partitioned between ethyl acetate and water. The organic layer was washed with brine, dried over anhydrous magnesium sulfate, filtered and concentrated under reduced pressure. The resulting light yellow solid was triturated with hexane to give the title compound (2.47 g, 75%) as a light yellow solid.

¹H NMR (300 MHz, DMSO-d₆) δ ppm 1.97-2.15 (m, 1H), 2.34-2.75 (m, 3H), 4.72-4.92 (m, 1H), 7.10-7.19 (m, 1H), 7.36 (t, J=7.9 Hz, 2H), 7.51 (d, J=7.5 Hz, 2H), 13.12 (br. s., 1H).

Reference Example 13

Methyl 5-cyclohexyl-1,3-oxazole-4-carboxylate

To an ice-cold mixture of cyclohexanecarboxylic acid (5.40 g, 42.1 mmol) and $K_2CO_3$ (23.3 g, 168.4 mmol) in N,N-dimethylformamide (60 mL) were added diphenylphosphoryl azide (16.1 g, 58.5 mmol) and methyl isocyanoacetate (5.0 g, 50.5 mmol). After being stirred at room temperature for 16 h, the reaction mixture was partitioned between ethyl acetate and water. The organic layer was washed with water, saturated $NaHCO_3$ solution, and brine, dried over anhydrous magnesium sulfate, filtered and concentrated under reduced pressure. The resulting light yellow solid was recrystallized from hexane-ethyl acetate to give the title compound (4.47 g, 51%) as an off-white solid. The mother liquid was concentrated under reduced pressure and the residue was purified by silica gel column chromatography (hexane/ethyl acetate 90:10 to 30:70) to give a light yellow solid. This solid was triturated with hexane-diisopropyl ether to give the title compound (2.05 g, 23%) as a light yellow solid.
¹H NMR (300 MHz, CHLOROFORM-d) δ ppm 1.21-1.62 (m, 5H), 1.71-1.98 (m, 5H), 3.38-3.58 (m, 1H), 3.91 (s, 3H), 7.74 (s, 1H). LC/MS; ESI(+) m/z: 210 (M+H)⁺.

Reference Example 14

5-Cyclohexyl-1,3-oxazole-4-carboxylic acid

To a stirred solution of methyl 5-cyclohexyl-1,3-oxazole-4-carboxylate (6.40 g, 30.6 mmol) in methanol (370 mL) was added 1 M NaOH solution (92 mL). After being stirred at room temperature for 2 h, and at 50° C. for 1 h, the reaction mixture was cooled to 0° C., and then acidified with 1 M HCl solution. The mixture was concentrated under reduced pressure and the resulting residue was partitioned between ethyl acetate and water. The organic layer was washed with brine, dried over anhydrous magnesium sulfate, filtered and concentrated under reduced pressure. The resulting light yellow solid was triturated with hexane to give the title compound (5.29 g, 89%) as a white solid.
¹H NMR (300 MHz, DMSO-d₆) δ ppm 1.11-1.92 (m, 10H), 3.27-3.48 (m, 1H), 8.29 (s, 1H), 12.93 (s, 1H).

Reference Example 15 tert-Butyl 4-[4-(methoxycarbonyl)-1,3-oxazol-5-yl]piperidine-1-carboxylate

To an ice-cold mixture of 1-Boc-4-piperidinecarboxylic acid (9.65 g, 42.1 mmol) and $K_2CO_3$ (23.3 g, 168.4 mmol) in N,N-dimethylformamide (60 mL) were added diphenylphosphoryl azide (16.1 g, 58.5 mmol) and methyl isocyanoacetate (5.0 g, 50.5 mmol). After being stirred at room temperature for 16 h, the reaction mixture was partitioned between ethyl acetate and water. The organic layer was washed with water, saturated $NaHCO_3$ solution, and brine, dried over anhydrous magnesium sulfate, filtered and concentrated under reduced pressure. The resulting residue was purified by silica gel column chromatography (hexane/ethyl acetate 80:20 to 20:80) to give the title compound (9.07 g, 69%) as a yellow solid.
¹H NMR (300 MHz, CHLOROFORM-d) δ ppm 1.48 (s, 9H), 1.70-1.94 (m, 4H), 2.77-2.92 (m, 2H), 3.56-3.74 (m, 1H), 3.93 (s, 3H), 4.14-4.34 (m, 2H), 7.77 (s, 1H).

Reference Example 16

5-[1-(tert-Butoxycarbonyl)piperidin-4-yl]-1,3-oxazole-4-carboxylic acid

To a stirred solution of tert-butyl 4-[4-(methoxycarbonyl)-1,3-oxazol-5-yl]piperidine-1-carboxylate (8.90 g, 28.7 mmol) in methanol (340 mL) was added 1 M NaOH solution (86 mL). After being stirred at room temperature for 2 h, the reaction mixture was concentrated to about one quarter. To this mixture was added ethyl acetate (80 mL) and the mixture was acidified with 10% $KHSO_4$ solution under ice-cooling. The organic layer was separated, washed with brine, dried over anhydrous magnesium sulfate, filtered and concentrated under reduced pressure. The resulting light yellow solid was triturated with diisopropyl ether to give the title compound (7.32 g, 86%) as a light yellow solid.
¹H NMR (300 MHz, DMSO-d₆) δ ppm 1.41 (s, 9H), 1.47-1.68 (m, 2H), 1.73-1.84 (m, 2H), 2.84 (br. s., 2H), 3.50-3.67 (m, 1H), 3.95-4.10 (m, 2H), 8.33 (s, 1H), 12.99 (br. s., 1H).

Reference Example 17

N-(2-tert-Butylphenyl)acetamide

To a solution of 2-tert-butylaniline (5.0 g, 33.5 mmol) and triethylamine (11.2 g, 110.6 mmol) in THF (350 mL) was added acetyl chloride (2.89 g, 36.9 mmol). After being stirred at room temperature for 3 h, the reaction mixture was partitioned between ethyl acetate and water. The organic layer was washed with saturated brine, dried over anhydrous magnesium sulfate, filtered and concentrated under reduced pressure. The resulting white solid was triturated with hexane/ethyl acetate to give the title compound (6.13 g) as a white crystalline powder.
¹H NMR (300 MHz, CDCl₃) δ ppm 1.41 (s, 9H), 1.89 (s, 1H), 2.21 (s, 3H), 7.04-7.26 (m, 2H), 7.35-7.46 (m, 1H), 7.53 (d, J=7.2 Hz, 1H).

Reference Example 18

N-(2-tert-Butyl-4-chlorophenyl)acetamide

A mixture of N-(2-tert-butylphenyl)acetamide (Reference Example 17, 5.93 g, 31.0 mmol) and sulfuryl chloride (10.5 g, 77.5 mmol) in acetic acid (190 mL) was stirred at 50° C. for 16 h. The reaction mixture was partitioned between ethyl acetate and water, and the organic layer was washed with 10% aqueous $NaHCO_3$, and saturated brine, dried over anhydrous magnesium sulfate, filtered and concentrated under reduced pressure. The resulting solid was recrystallized from toluene/diethyl ether to give the title compound (3.73 g) as a white solid. The mother liquid was concentrated under reduced pressure and the residue was purified by flash column chromatography (silica gel, 4:1-1:4 hexane/ethyl acetate) to provide the title compound (1.05 g) as a white solid.
¹H NMR (300 MHz, CDCl₃) δ ppm 1.40 (s, 9H), 2.21 (s, 3H), 7.05 (br. s., 1H), 7.20 (dd, J=8.3, 2.0 Hz, 1H), 7.35 (d, J=2.0 Hz, 1H), 7.50 (d, J=8.3 Hz, 1H).

Reference Example 19

2-tert-Butyl-4-chloroaniline

A mixture of N-(2-tert-butyl-4-chlorophenyl)acetamide (Reference Example 18, 4.78 g, 21.2 mmol), concentrated HCl (50 mL) and EtOH (10 mL) was stirred at 110° C. for 5 h. After cooling, the reaction mixture was basified with 8 M NaOH under ice-cooling. The mixture was extracted with ethyl acetate and the organic layer was washed with water, and saturated brine, dried over anhydrous magnesium sulfate, filtered and concentrated under reduced pressure to give the title compound (4.29 g) as a colorless oil.

$^1$H NMR (300 MHz, CDCl$_3$) δ ppm 1.40 (s, 9H), 3.80 (br. s., 2H), 6.56 (d, J=8.3 Hz, 1H), 6.95-7.01 (m, 1H), 7.17 (d, J=2.3 Hz, 1H).

Reference Example 20

1-(2-tert-Butyl-4-chlorophenyl)piperazine dihydrochloride

A mixture of 2-tert-butyl-4-chloroaniline (Reference Example 19, 16.7 g, 90.8 mmol) and bis(2-chloroethyl)amine hydrochloride (17.8 g, 99.9 mmol) in diglyme (170 mL) was stirred at 170° C. for 3 days under nitrogen atmosphere. After this time, the reaction mixture was cooled to room temperature and partitioned between ethyl acetate and 1 M NaOH. The organic layer was washed with water, and saturated brine, dried over anhydrous magnesium sulfate, filtered and concentrated under reduced pressure. The resulting brown oil was purified by flash column chromatography (NH-silica gel, 1:1-0:100 hexane/ethyl acetate, 10:1 ethyl acetate/MeOH) to provide an impure brown oil and a brown solid. The solid was dissolved in ethyl acetate and the solution was treated with 4 M HCl in ethyl acetate to give the title compound (2.17 g) as a brown solid. The impure brown oil was partitioned between ethyl acetate and 1 M HCl and the resulting white precipitate was collected by filtration, and washed with diethyl ether to give the title compound (2.98 g) as a white solid.

$^1$H NMR (300 MHz, DMSO-d$_6$) δ ppm 1.38 (s, 9H), 2.77-2.89 (m, 2H), 2.96-3.20 (m, 4H), 3.27-3.38 (m, 1H), 3.44 (br. s., 2H), 7.29 (d, J=2.3 Hz, 1H), 7.33-7.37 (m, 2H), 9.24 (br. s., 2H). LC/MS; ESI(+) m/z: 253 (M+H)$^+$.

Reference Example 21

Methyl 5-(3-tert-butoxy-3-oxopropyl)-1,3-oxazole-4-carboxylate

To an ice-cooled mixture of mono-tert-butyl succinate (5.0 g, 28.7 mmol) and K$_2$CO$_3$ (15.9 g, 114.8 mmol) in DMF (40 mL) were added diphenylphosphoryl azide (11.06 g, 40.2 mmol) and methyl isocyanoacetate (3.41 g, 34.4 mmol). After being stirred at room temperature for 16 h, the reaction mixture was partitioned between ethyl acetate and water. The organic layer was washed with brine, dried over anhydrous magnesium sulfate, filtered and concentrated under reduced pressure. The resulting residue was purified by flash column chromatography (silica-gel, 9:1-3:7 hexane/ethyl acetate) to give the title compound (6.20 g) as a brown oil.

$^1$H NMR (300 MHz, CDCl$_3$) δ ppm 1.43 (s, 9H), 2.64 (t, J=7.5 Hz, 2H), 3.35 (t, J=7.5 Hz, 2H), 3.92 (s, 3H), 7.77 (s, 1H).

Reference Example 22

5-(3-tert-Butoxy-3-oxopropyl)-1,3-oxazole-4-carboxylic acid

A mixture of methyl 5-(3-tert-butoxy-3-oxopropyl)-1,3-oxazole-4-carboxylate (Reference Example 21, 6.20 g, 24.3 mmol) and 2 M NaOH (73 mL) in MeOH (290 mL) was stirred at room temperature for 5 h. The reaction mixture was concentrated under reduced pressure and the resulting residue was partitioned between diethyl ether and water. The water layer was acidified with 1 M HCl and extracted with ethyl acetate. The organic layer was washed with saturated brine, dried over anhydrous magnesium sulfate, filtered and concentrated under reduced pressure to give the title compound (1.92 g) as a light brown oil.

$^1$H NMR (300 MHz, CDCl$_3$) δ ppm 1.43 (s, 9H), 2.67 (t, J=7.5 Hz, 2H), 3.37 (t, J=7.3 Hz, 2H), 7.83 (s, 1H).

Reference Example 23

1-[3,5-Bis(trifluoromethyl)phenyl]-2-bromoethanone

To a stirred solution of 3,5-bis(trifluoromethyl)acetophenone (50.0 g, 195.2 mmol) in acetic acid (200 mL) was added dropwise at 90° C. bromine (31.2 g, 195.2 mmol). After the initiation of the reaction (3-4 drops), the oil bath was removed and the mixture was stirred at room temperature for 1 h. To this mixture was added water (50 mL) and the mixture was concentrated under reduced pressure. The resulting residue was partitioned between ethyl acetate (500 mL) and water (500 mL). The organic layer was separated and washed with saturated sodium hydrogen carbonate (250 mL×2), and saturated sodium chloride (250 mL), dried (MgSO$_4$), filtered and concentrated under reduced pressure to give 1-[3,5-bis(trifluoromethyl)phenyl]-2-bromoethanone (57.65 g, 88%) as a colorless solid.

$^1$H NMR (300 MHz, CDCl$_3$) δ ppm 4.47 (s, 2H), 8.12 (s, 1H), 8.43 (s, 2H).

Reference Example 24

Methyl Succinamate

A mixture of succinamic acid (100 g, 763 mmol) and DOWEX 50WX8-100 (washed with methanol, 50 g) in methanol (200 mL) was stirred at room temperature for 16 h. The reaction mixture was filtered and to the filtrate was added Amberlyst A-21 (washed with methanol, 50 g). After being stirred at room temperature for 3 h, the reaction mixture was filtered and concentrated under reduced pressure. The resulting white solid was triturated with diisopropyl ether to afford methyl succinamate (94.6 g, 85%) as a white solid.

$^1$H NMR (300 MHz, DMSO-d$_6$) δ ppm 2.31-2.35 (m, 2H), 2.45-2.49 (m, 2H), 3.57 (s, 3H), 6.79 (br. s., 1H), 7.32 (br. s., 1H).

Reference Example 25

Methyl 3-{4-[3,5-bis(trifluoromethyl)phenyl]-1,3-oxazol-2-yl}propanoate

A mixture of 1-[3,5-bis(trifluoromethyl)phenyl]-2-bromoethanone (Reference Example 23, 16.0 g, 35.8 mmol) and methyl succinamate (Reference Example 24, 25.0 g, 191 mmol) was stirred at 140° C. for 2 h. After this time, the reaction mixture was cooled to room temperature, and partitioned between ethyl acetate (500 mL) and water (500 mL). The organic layer was separated, washed with water (500 mL), and saturated sodium chloride (200 mL), dried (MgSO$_4$), filtered and concentrated under reduced pressure. The resulting residue was purified by silica-gel column chromatography (silica-gel 150 g, hexane/ethyl acetate 9:1-4:1) to give a brown solid (12.6 g). This solid was recrystallized from hexane to afford methyl 3-{4-[3,5-bis(trifluoromethyl)phenyl]-1,3-oxazol-2-yl}propanoate (6.76 g, 51%) as yellow crystals.

$^1$H NMR (300 MHz, CDCl$_3$) δ ppm 2.90 (t, J=7.3 Hz, 2H), 3.17 (t, J=7.3 Hz, 2H), 3.73 (s, 3H), 7.79 (s, 1H), 7.98 (s, 1H), 8.14 (s, 2H).

Reference Example 26

3-{4-[3,5-bis(trifluoromethyl)phenyl]-1,3-oxazol-2-yl}propanoic acid

To an ice-cold stirred solution of methyl 3-{4-[3,5-bis(trifluoromethyl)phenyl]-1,3-oxazol-2-yl}propanoate (Reference Example 25, 19.8 g, 53.8 mmol) in methanol (800 mL) was added dropwise 1M solution of lithium hydroxide (161.4 mL, 161.4 mmol). The mixture was stirred at 0° C. for 30 min, then at room temperature for 4 h. The reaction mixture was acidified with 1N solution of hydrochloric acid (170 mL, pH 2) under ice-cooling and concentrated under reduced pressure. The residue was partitioned between ethyl acetate (400 mL) and water (400 mL). The organic layer was separated and the water layer was extracted with ethyl acetate (200 mL). The extract was combined to the organic layer and the mixture was washed with water (400 mL), and saturated sodium chloride (200 mL), dried (MgSO$_4$), filtered and concentrated under reduced pressure to give a light brown solid (18.8 g). This solid was recrystallized from hexane/acetone (10:1, 200 mL) to give 3-{4-[3,5-bis(trifluoromethyl)phenyl]-1,3-oxazol-2-yl}propanoic acid (18.04 g, 95%) as light yellow crystals.

$^1$H NMR (300 MHz, CDCl$_3$) δ ppm 2.88-3.03 (m, 2H), 3.11-3.23 (m, 2H), 7.79 (s, 1H), 7.98 (s, 1H), 8.13 (s, 2H).

Reference Example 27

Methyl 3-nitro-5-(trifluoromethyl)benzoate

To an ice cooled stirred solution of 3-nitro-5-(trifluoromethyl)benzoic acid (25.00 g, 106.3 mmol) in methanol (500 mL) was added acetyl chloride (22.00 g, 280.2 mmol) dropwise over 20 min. After the addition was complete, the reaction mixture was stirred for 20 min at 0° C., then heated at reflux for 6 h and then cooled to room temperature. The reaction mixture was concentrated under reduced pressure and the residue was dissolved in ethyl acetate, washed with saturated aqueous sodium bicarbonate, filtered through a silica gel and concentrated under reduced pressure to provide methyl 3-nitro-5-(trifluoromethyl)benzoate (24.65 g, 93%) as a pale yellow oil.

$^1$H NMR (500 MHz, CDCl$_3$) δ ppm 4.04 (s, 3H), 8.63 (s, 1H), 8.68 (s, 1H), 9.05 (t, J=1.60 Hz, 1H).

Reference Example 28

Methyl 3-amino-5-(trifluoromethyl)benzoate

A solution of methyl 3-nitro-5-(trifluoromethyl)benzoate (Reference Example 27, 24.6 g, 98.9 mmol) in ethanol (1500 mL) was sparged in a Parr bottle with nitrogen for 10 min. After this time, 10 wt % Pd/C (5.0 g, 5.0 mmol) was added and the reaction mixture was subjected to 40 psi of hydrogen on Parr shaker at room temperature for 1 h. After this time, the reaction mixture was filtered through a pad of celite and concentrated under reduced pressure to provide Methyl 3-amino-5-(trifluoromethyl)benzoate (20.6 g, 95%) as a light purple oil.

$^1$H NMR (500 MHz, CDCl$_3$) δ ppm 3.92 (s, 3H), 4.02 (br s, 2H), 7.05 (s, 1H), 7.48 (s, 1H), 7.64 (s, 1H).

Reference Example 29

Methyl 3-chloro-5-(trifluoromethyl)benzoate

To a stirred solution of methyl 3-amino-5-(trifluoromethyl)benzoate (Reference Example 28, 2.15 g, 9.81 mmol) in acetonitrile (50.0 mL) was added tert-butyl nitrite (3.04 g, 29.48 mmol) at room temperature. After 15 min copper(II) chloride (2.38 g, 17.70 mmol) was added and the reaction mixture was stirred overnight. After this time, the mixture was diluted with ethyl acetate, washed with water, saturated ammonium hydrochloride, and saturated sodium chloride, dried (Na$_2$SO$_4$), filtered and concentrated under reduced pressure to provide methyl 3-chloro-5-(trifluoromethyl)benzoate (2.20 g, 94%) as a brown oil, which was used without further purification or characterization.

Reference Example 30

(3-Chloro-5-(trifluoromethyl)phenyl)methanol

To a stirred solution of methyl 3-chloro-5-(trifluoromethyl)benzoate (Reference Example 29, 2.20 g, 9.22 mmol) in THF (100.0 mL) at −78° C. was added disobutylaluminum hydride solution (28.00 mL, 1.0 M in methylene chloride, 28.00 mmol) and the resulting reaction mixture was stirred at this temperature for 4 h. After this time, the reaction was quenched with 1.0 M hydrochloric acid (100 mL) and warmed to room temperature. The reaction mixture was diluted with ethyl acetate, washed with aqueous 1.0 M hydrochloric acid, water, and saturated sodium chloride, dried (Na$_2$SO$_4$), filtered, concentrated under reduced pressure to provide (3-chloro-5-(trifluoromethyl)phenyl)methanol (1.98 g, >99%) as a brown oil, which was used without further purification or characterization.

Reference Example 31

3-Chloro-5-(trifluoromethyl)benzaldehyde

To a stirred suspension of (3-chloro-5-(trifluoromethyl)phenyl)methanol (Reference Example 30, 1.98 g, 9.40 mmol) and celite 545 (6.00 g) in methylene chloride (60.0 mL) was added pyridinium chlorochromate (6.10 g, 28.30 mmol) at room temperature. After 1 h, the reaction mixture was diluted with diethyl ether (200 mL), and filtered through silica gel and the filter cake was washed with 1:1 solution of diethyl ether/hexanes. The filtrate was concentrated under reduced pressure and the residue was purified by flash column chromatography (silica gel, hexanes/ethyl acetate 49:1) to provide 3-chloro-5-(trifluoromethyl)benzaldehyde (1.15 g, 56% (overall for 3 steps)) as a pale yellow oil.

$^1$H NMR (500 MHz, CDCl$_3$) δ ppm 7.87 (s, 1H), 8.03-8.05 (m, 2H), 10.04 (s, 1H).

Reference Example 32

1-(3-Chloro-5-(trifluoromethyl)phenyl)ethanol

To a stirred solution at −10° C. of 3-chloro-5-(trifluoromethyl)benzaldehyde (Reference Example 31, 1.15 g, 5.51 mmol) in THF (20.0 mL) was added dropwise methyl magnesium bromide (2.30 mL, 3.0 M in ethyl ether, 6.90 mmol). After the addition was complete, the reaction mixture was stirred for an additional 1.5 h, then the reaction was quenched with saturated ammonium hydrochloride (30.0 mL), and the mixture was warmed to room temperature. The reaction mixture was diluted with ethyl acetate, washed with water, and saturated sodium chloride, dried ($Na_2SO_4$), filtered and concentrated under reduced pressure to provide 1-(3-chloro-5-(trifluoromethyl)phenyl)ethanol (1.17 g, 94%) as a pale yellow oil, which was used without further purification or characterization.

Reference Example 33

1-(3-Chloro-5-(trifluoromethyl)phenyl)ethanone

The title compound was prepared from 1-(3-chloro-5-(trifluoromethyl)phenyl)ethanol (Reference Example 32) by a procedure similar to the one described for 3-chloro-5-(trifluoromethyl)benzaldehyde (Reference Example 31) to provide 1-(3-chloro-5-(trifluoromethyl)phenyl)ethanone (0.998 g, 86%) as a pale yellow oil.

$^1$H NMR (500 MHz, $CDCl_3$) δ ppm 2.65 (s, 3H), 7.81 (s, 1H), 8.07-8.10 (m, 2H).

Reference Example 34

2-Bromo-1-(3-chloro-5-(trifluoromethyl)phenyl)ethanone

A stirred suspension of 1-(3-chloro-5-(trifluoromethyl)phenyl)ethanone (Reference Example 33, 0.990 g, 4.45 mmol), and copper(II) bromide (1.79 g, 8.01 mmol) in 1:1 chloroform/ethyl acetate (100 mL) was heated at reflux for 4 h. After this time, the reaction mixture was cooled to room temperature, diluted with diethyl ether, washed with water, saturated ammonium hydrochloride, and saturated sodium chloride, dried ($Na_2SO_4$), filtered and concentrated under reduced pressure to provide 2-bromo-1-(3-chloro-5-(trifluoromethyl)phenyl)ethanone (1.05 g, 78%) as a viscous yellow oil, which was used without further purification or characterization.

Reference Example 35

2-(3-Chloro-5-(trifluoromethyl)phenyl)-2-oxoethyl methyl succinate

A stirred suspension of 2-bromo-1-(3-chloro-5-(trifluoromethyl)phenyl)ethanone (Reference Example 34, 1.05 g, 3.48 mmol) and sodium 4-methoxy-4-oxobutanoate (0.805 g, 5.22 mmol) in acetone (50.0 mL) was heated at reflux overnight. After that time the reaction mixture was cooled to room temperature and adsorbed onto silica gel (4.30 g). The residue was purified by flash column chromatography (silica gel, hexanes/ethyl acetate 4:1) to provide 2-(3-chloro-5-(trifluoromethyl)phenyl)-2-oxoethyl methyl succinate (1.12 g, 91%) as a pale yellow oil.

$^1$H NMR (500 MHz, $CDCl_3$) δ ppm 2.71 (t, J=6.8 Hz, 2H), 2.83 (t, J=6.8 Hz, 2H), 3.71 (s, 3H), 5.32 (s, 2H), 7.85 (s, 1H), 8.02-8.05 (m, 2H).

Reference Example 36

Methyl 3-(4-(3-chloro-5-(trifluoromethyl)phenyl)oxazol-2-yl)propanoate

A stirred solution of 2-(3-chloro-5-(trifluoromethyl)phenyl)-2-oxoethyl methyl succinate (Reference Example 35, 1.10 g, 3.12 mmol), acetamide (0.921 g, 15.59 mmol) and boron trifluoride diethyl etherate (0.565 g, 3.98 mmol) was heated at 140° C. for 2 h. After this time, the reaction mixture was cooled to room temperature, diluted with ethyl acetate, washed with saturated sodium bicarbonate, water, and saturated sodium chloride, dried ($Na_2SO_4$), filtered and concentrated under reduced pressure. The residue was purified by flash column chromatography (silica gel, hexanes/ethyl acetate 4:1) to provide methyl 3-(4-(3-chloro-5-(trifluoromethyl)phenyl)oxazol-2-yl)propanoate (0.401 g, 39%) as a yellow viscous oil.

$^1$H NMR (500 MHz, $CDCl_3$) δ ppm 2.89 (t, J=7.4 Hz, 2H), 3.15 (t, J=7.4 Hz, 2H), 3.73 (s, 3H), 7.53 (s, 1H), 7.84 (s, 1H), 7.88 (s, 1H), 7.91 (s, 1H).

Reference Example 37

Methyl 3-bromo-5-(trifluoromethyl)benzoate

The title compound was prepared from methyl 3-amino-5-(trifluoromethyl)benzoate (Reference Example 28) and copper(II) bromide by a procedure similar to the one described for methyl 3-chloro-5-(trifluoromethyl)benzoate (Reference Example 29) to provide methyl 3-bromo-5-(trifluoromethyl)benzoate (26.35 g, >99%) as a brown gum, which was used without further purification or characterization.

Reference Example 38

(3-Bromo-5-(trifluoromethyl)phenyl)methanol

The title compound was prepared from methyl 3-bromo-5-(trifluoromethyl)benzoate (Reference Example 37) by a procedure similar to the one described for (3-chloro-5-(trifluoromethyl)phenyl)methanol (Reference Example 30) to provide (3-bromo-5-(trifluoromethyl)phenyl)methanol (7.42 g, 35% (2 steps)) as a yellow oil.

$^1$H NMR (500 MHz, $CDCl_3$) δ ppm 1.96 (br s, 1H), 4.76 (s, 2H), 7.56 (s, 1H), 7.68 (s, 1H), 7.71 (s, 1H).

Reference Example 39

3-Bromo-5-(trifluoromethyl)benzaldehyde

The title compound was prepared from (3-bromo-5-(trifluoromethyl)phenyl)methanol (Reference Example 38) by a procedure similar to the one described for 3-chloro-5-(trifluoromethyl)benzaldehyde (Reference Example 31) to provide 3-bromo-5-(trifluoromethyl)benzaldehyde (22.03 g, 85%) as a pale yellow oil.

$^1$H NMR (500 MHz, $CDCl_3$) δ ppm 8.02 (s, 1H), 8.07 (s, 1H), 8.20 (s, 1H), 10.02 (s, 1H).

Reference Example 40

1-(3-Bromo-5-(trifluoromethyl)phenyl)ethanol

To a stirred solution at −10° C. of methyl magnesium bromide (38.00 mL, 3.0 M in ethyl ether, 114.0 mmol) in THF (200.0 mL) was added dropwise a solution of 3-bromo-5-(trifluoromethyl)benzaldehyde (Reference Example 39, 22.01 g, 86.98 mmol) in THF (100 mL) and after the addition was complete, the reaction mixture was held at −10° C. for 2 h. After this time, the reaction was quenched with saturated ammonium hydrochloride (300.0 mL) and warmed to room temperature. The reaction mixture was diluted with ethyl acetate, washed with water, and saturated sodium chloride, dried (Na$_2$SO$_4$), filtered and concentrated under reduced pressure to provide 1-(3-bromo-5-(trifluoromethyl)phenyl) ethanol (21.30 g, 91%) as a pale yellow oil.

$^1$H NMR (500 MHz, CDCl$_3$) δ ppm 1.51 (d, J=6.5 Hz, 3H), 1.96 (br s, 1H), 4.94 (q, J=6.5 Hz, 1H), 7.57 (s, 1H), 7.65-7.72 (m, 1H), 7.82 (s, 1H).

Reference Example 41

1-(3-Bromo-5-(trifluoromethyl)phenyl)ethanone

The title compound was prepared from 1-(3-bromo-5-(trifluoromethyl)phenyl)ethanol (Reference Example 40) by a procedure similar to the one described for 3-chloro-5-(trifluoromethyl)benzaldehyde (Reference Example 31) to provide 1-(3-bromo-5-(trifluoromethyl)-phenyl)ethanone (17.94 g, 85%) as a pale yellow oil.

$^1$H NMR (500 MHz, CDCl$_3$) δ ppm 2.64 (s, 3H), 7.96 (s, 1H), 8.12 (d, J=0.4 Hz, 1H), 8.26 (s, 1H).

Reference Example 42

2-Bromo-1-(3-bromo-5-(trifluoromethyl)phenyl) ethanone

The title compound was prepared from 1-(3-bromo-5-(trifluoromethyl)phenyl)ethanone (Reference Example 41) by a procedure similar to the one described for 2-bromo-1-(3-chloro-5-(trifluoromethyl)phenyl)ethanone (Reference Example 34) to provide 2-bromo-1-(3-bromo-5-(trifluoromethyl)phenyl)ethanone (23.17 g, >99%) as a yellow oil.

$^1$H NMR (500 MHz, CDCl$_3$) δ ppm 4.42 (s, 2H), 8.00 (s, 1H), 8.15 (s, 1H), 8.29 (s, 1H).

Reference Example 43

2-(3-Bromo-5-(trifluoromethyl)phenyl)-2-oxoethyl methyl succinate

The title compound was prepared from 2-bromo-1-(3-bromo-5-(trifluoromethyl)phenyl)ethanone (Reference Example 42) by a procedure similar to the one described for 2-(3-chloro-5-(trifluoromethyl)phenyl)-2-oxoethyl methyl succinate (Reference Example 35) to provide 2-(3-bromo-5-(trifluoromethyl)phenyl)-2-oxoethyl methyl succinate (16.05 g, 60%) as a pale yellow oil.

$^1$H NMR (500 MHz, CDCl$_3$) δ ppm 2.71 (t, J=6.8 Hz, 2H), 2.82-2.85 (m, 2H), 3.71 (s, 3H), 5.32 (s, 2H), 8.01 (s, 1H), 8.06 (d, J=0.5 Hz, 1H), 8.21 (s, 1H).

Reference Example 44

Methyl 3-(4-(3-bromo-5-(trifluoromethyl)phenyl) oxazol-2-yl)propanoate

The title compound was prepared from 2-(3-bromo-5-(trifluoromethyl)phenyl)-2-oxoethyl methyl succinate (Reference Example 43) by a procedure similar to the one described for methyl 3-(4-(3-chloro-5-(trifluoromethyl)phenyl)oxazol-2-yl)propanoate (Reference Example 36) to provide methyl 3-(4-(3-bromo-5-(trifluoromethyl)phenyl)oxazol-2-yl)propanoate (3.62 g, 47%) as a yellow solid.

$^1$H NMR (500 MHz, CDCl$_3$) δ ppm 2.89 (t, J=7.4 Hz, 2H), 3.15 (t, J=7.4 Hz, 2H), 3.73 (s, 3H), 7.68 (s, 1H), 7.88 (s, 1H), 7.91 (s, 1H), 8.03 (s, 1H).

Reference Example 45

Methyl 3-(4-(3-methyl-5-(trifluoromethyl)phenyl) oxazol-2-yl)propanoate

A stirred solution of methyl 3-(4-(3-bromo-5-(trifluoromethyl)phenyl)oxazol-2-yl)propanoate (Reference Example 44, 0.150 g, 0.397 mmol), methylboronic acid (0.071 g, 1.19 mmol), and triethylamine (0.402 g, 3.97 mmol) in DMF (10.0 mL) was degassed and then purged with nitrogen. To this reaction mixture was added tetrakis(triphenylphosphine)palladium(0) (0.024 g, 0.0203 mmol) and the resulting reaction mixture was heated at 100° C. for 6 h. After this time, the mixture was cooled to room temperature, diluted with ethyl acetate (50 mL), washed with water and saturated sodium chloride, dried (Na$_2$SO$_4$), filtered, and concentrated under reduced pressure. The residue was purified by flash column chromatography (silica gel, hexanes/ethyl acetate 9:1) to provide methyl 3-(4-(3-methyl-5-(trifluoromethyl)phenyl)oxazol-2-yl)propanoate (0.097 g, 78%) as a viscous yellow oil.

$^1$H NMR (500 MHz, CDCl$_3$) δ ppm 2.44 (s, 3H), 2.89 (t, J=7.5 Hz, 2H), 3.16 (t, J=7.5 Hz, 2H), 3.73 (s, 3H), 7.26 (s, 1H), 7.70 (s, 1H), 7.74 (s, 1H), 7.87 (s, 1H).

Reference Example 46

Methyl 3-(4-(3-cyano-5-(trifluoromethyl)phenyl) oxazol-2-yl)propanoate

A suspension of methyl 3-(4-(3-bromo-5-(trifluoromethyl)phenyl)oxazol-2-yl)-propanoate (Reference Example 44, 0.645 g, 1.71 mmol) and zinc cyanide (0.120 g, 1.02 mmol) in DMF (15.0 mL) was evacuated and purged with nitrogen. To this reaction mixture was added tetrakis(triphenylphosphine)palladium(0) (0.197 g, 0.170 mmol) and the resulting reaction mixture was heated at 100° C. for 8 h. After this time, the reaction mixture was cooled to room temperature, diluted with ethyl acetate, washed with water and saturated sodium chloride, dried (Na$_2$SO$_4$), filtered and concentrated under reduced pressure. The resulting residue was purified by flash column chromatography (silica gel, hexanes/ethyl acetate 4:1) to provide methyl 3-(4-(3-cyano-5-(trifluoromethyl)phenyl)-oxazol-2-yl)propanoate (0.417 g, 75%) as a white solid.

$^1$H NMR (500 MHz, CDCl$_3$) δ ppm 2.90 (t, J=7.3 Hz, 2H), 3.16 (t, J=7.3 Hz, 2H), 3.74 (s, 3H), 7.82 (s, 1H), 7.98 (s, 1H), 8.17 (s, 1H), 8.18 (s, 1H).

Reference Example 47

Methyl 3-(4-(3-(thiophen-2-yl)-5-(trifluoromethyl) phenyl)oxazol-2-yl)propanoate A suspension of methyl 3-(4-(3-bromo-5-(trifluoromethyl)phenyl)oxazol-2-yl)propanoate (Reference Example 44, 0.454 g, 1.20 mmol), thiophene-2-boronic acid (0.230 g, 1.80 mmol) and sodium carbonate (0.954 g, 9.00 mmol) in toluene (30.0 mL) was evacuated and purged with nitrogen. To this mixture was added tetrakis(triphenylphosphine)palladium(0) (0.208 g, 0.180 mmol) and the resulting reaction mixture was heated at 100° C. for 7 h. After this time, the reaction mixture was cooled to room temperature, quenched with 1.0 M hydrochloric acid (20.0 mL), diluted with ethyl acetate and separated. The organic layer was washed with water and saturated sodium chloride, dried (Na$_2$SO$_4$), filtered and concentrated under reduced pressure. The resultant residue was purified by flash column chromatography (silica gel, hexanes/ethyl acetate 9:1) to provide methyl 3-(4-(3-(thiophen-2-yl)-5-(trifluoromethyl)phenyl)oxazol-2-yl)propanoate (0.145 g, 32%) as a yellow solid.

$^1$H NMR (500 MHz, CDCl$_3$) δ ppm 2.91 (t, J=7.5 Hz, 2H), 3.17 (t, J=7.5 Hz, 2H), 3.74 (s, 3H), 7.12 (dd, J=4.0, 3.8 Hz, 1H), 7.36 (dd, J=5.1, 1.1 Hz, 1H), 7.43 (dd, J=3.6, 1.1 Hz, 1H), 7.76 (s, 1H), 7.85 (s, 1H), 7.94 (s, 1H), 8.09 (s, 1H).

Reference Example 48

Methyl 3-(4-(3-(thiophen-3-yl)-5-(trifluoromethyl)phenyl)oxazol-2-yl)propanoate

The title compound was prepared from methyl 3-(4-(3-bromo-5-(trifluoromethyl)phenyl)oxazol-2-yl)propanoate (Reference Example 44) and thiophene-3-boronic acid by a procedure similar to the one described for methyl 3-(4-(3-(thiophen-2-yl)-5-(trifluoromethyl)phenyl)oxazol-2-yl)propanoate (Reference Example 47) to provide methyl 3-(4-(3-(thiophen-3-yl)-5-(trifluoromethyl)phenyl)oxazol-2-yl) propanoate (0.371 g, 81%) as a yellow solid.

$^1$H NMR (500 MHz, CDCl$_3$) δ ppm 2.91 (t, J=7.4 Hz, 2H), 3.17 (t, J=7.4 Hz, 2H), 3.73 (s, 3H), 7.45-7.43 (m, 2H), 7.57-7.58 (m, 1H), 7.74 (s, 1H), 7.86 (s, 1H), 7.93 (s, 1H), 8.10 (s, 1H).

Reference Example 49

Methyl 3-(4-(3-(prop-1-en-2-yl)-5-(trifluoromethyl)phenyl)oxazol-2-yl)propanoate A suspension of methyl 3-(4-(3-bromo-5-(trifluoromethyl)phenyl)oxazol-2-yl)propanoate (Reference Example 44, 0.605 g, 1.60 mmol), 4,4,5,5-tetramethyl-2-(prop-1-en-2-yl)-1,3,2-dioxaborolane (0.404 g, 2.40 mmol) and potassium acetate (2.36 g, 24.0 mmol) in toluene (50.0 mL) and water (1.00 mL) was evacuated and purged with nitrogen. To this reaction mixture was added tetrakis(triphenylphosphine)palladium(0) (0.277 g, 0.240 mmol) and the resulting reaction mixture was heated at 100° C. for 10 h. After this time, the reaction mixture was cooled to room temperature, diluted with ethyl acetate, washed with water and saturated sodium chloride, dried (Na$_2$SO$_4$), filtered and concentrated under reduced pressure. The resultant residue was purified by flash column chromatography (silica gel, hexanes/ethyl acetate 9:1) to provide methyl 3-(4-(3-(prop-1-en-2-yl)-5-(trifluoromethyl)phenyl)oxazol-2-yl)propanoate (0.377 g, 68%) as a pale yellow solid.

$^1$H NMR (500 MHz, CDCl$_3$) δ ppm 2.20 (s, 3H), 2.90 (t, J=7.4 Hz, 2H), 3.16 (t, J=7.4 Hz, 2H), 3.73 (s, 3H), 5.20-5.21 (m, 1H), 5.46 (s, 1H), 7.61 (s, 1H), 7.84 (s, 1H), 7.90 (s, 1H), 7.94 (s, 1H).

Reference Example 50

Methyl 3-(4-(3-isopropyl-5-(trifluoromethyl)phenyl)oxazol-2-yl)propanoate

To a nitrogen sparged solution of methyl 3-(4-(3-(prop-1-en-2-yl)-5-(trifluoromethyl)phenyl)oxazol-2-yl)propanoate (Reference Example 49, 0.200 g, 0.589 mmol) in ethanol (50.0 mL) was added 10% Pd/C (0.025 g) in a Parr bottle, and the mixture was vigorously shaken under an atmosphere of hydrogen (40 psi) at room temperature for 4 h. After this time, the reaction mixture was filtered through a pad of Celite, the filter cake was washed with ethanol and the filtrate was concentrated under reduced pressure to provide methyl 3-(4-(3-isopropyl-5-(trifluoromethyl)phenyl)oxazol-2-yl)propanoate (0.191 g, 95%) as a colorless oil.

$^1$H NMR (500 MHz, CDCl$_3$) δ ppm 1.30 (d, J=6.9 Hz, 6H), 2.89 (t, J=7.5 Hz, 2H), 2.97-3.03 (m, 1H), 3.16 (t, J=7.5 Hz, 2H), 3.73 (s, 3H), 7.70 (s, 1H), 7.74 (s, 1H), 7.76 (s, 1H), 7.87 (s, 1H).

Reference Example 51

Methyl 3-(4-(3-acetyl-5-(trifluoromethyl)phenyl)oxazol-2-yl)propanoate

To a stirred solution of methyl 3-(4-(3-(prop-1-en-2-yl)-5-(trifluoromethyl)phenyl)oxazol-2-yl)propanoate (Reference Example 49, 0.175 g, 0.516 mmol), and osmium tetroxide solution (0.21 g, 4 wt % in water, 0.033 mmol) in acetone (10.0 mL) and water (3.0 mL) was added sodium periodate (0.331 g, 1.55 mmol) at room temperature and the mixture was stirred at room temperature for 2 h. After this time, the reaction mixture was diluted with ethyl acetate, washed with water and saturated sodium chloride, dried (Na$_2$SO$_4$), filtered and concentrated under reduced pressure. The resultant residue was purified by flash column chromatography (silica gel, hexanes/ethyl acetate 9:1) to provide methyl 3-(4-(3-acetyl-5-(trifluoromethyl)phenyl)oxazol-2-yl)propanoate (0.128 g, 73%) as a white solid: ESI MS m/z 342 [M+H]$^+$.

Reference Example 52

3-(4-(3-Chloro-5-(trifluoromethyl)phenyl)oxazol-2-yl)propanoic acid

To a stirred solution of methyl 3-(4-(3-chloro-5-(trifluoromethyl)phenyl)oxazol-2-yl)propanoate (Reference Example 36, 0.386 g, 1.16 mmol) in methanol (10.0 mL) was added sodium hydroxide (1.50 mL, 1.0 M in water, 1.50 mmol) at room temperature. After 16 h, the reaction was quenched with 1.0 M hydrochloric acid (1.70 mL), diluted with ethyl acetate, washed with water, and saturated sodium chloride, dried (Na$_2$SO$_4$), filtered and concentrated under reduced pressure. The residue was triturated with methylene chloride and hexanes to provide 3-(4-(3-chloro-5-(trifluoromethyl)phenyl)oxazol-2-yl)propanoic acid (0.316 g, 85%) as a white powder.

$^1$H NMR (500 MHz, DMSO-d$_6$) δ ppm 2.76 (t, J=7.0 Hz, 2H), 3.03 (t, J=7.0 Hz, 2H), 7.80 (s, 1H), 8.05 (s, 1H), 8.12 (s, 1H), 8.79 (s, 1H), 12.33 (s, 1H).

Reference Example 53

3-(4-(3-Bromo-5-(trifluoromethyl)phenyl)oxazol-2-yl)propanoic acid

The title compound was prepared from methyl 3-(4-(3-bromo-5-(trifluoromethyl)phenyl)oxazol-2-yl)propanoate (Reference Example 44) by a procedure similar to the one described for 3-(4-(3-chloro-5-(trifluoromethyl)phenyl)oxazol-2-yl)propanoic acid (Reference Example 52) to provide 3-(4-(3-bromo-5-(trifluoromethyl)phenyl)oxazol-2-yl)propanoic acid (0.316 g, 85%) as an off-white powder.

$^1$H NMR (500 MHz, DMSO-d$_6$) δ ppm 2.76 (t, J=7.0 Hz, 2H), 3.03 (t, J=7.0 Hz, 2H), 7.91 (s, 1H), 8.08 (s, 1H), 8.26 (s, 1H), 8.78 (s, 1H), 12.33 (s, 1H).

Reference Example 54

3-(4-(3-Methyl-5-(trifluoromethyl)phenyl)oxazol-2-yl)propanoic acid

A solution of methyl 3-(4-(3-methyl-5-(trifluoromethyl)phenyl)oxazol-2-yl)propanoate (Reference Example 45, 0.091 g, 0.290 mmol) and sodium hydroxide (0.50 mL, 1.0 M in water, 0.50 mmol) in methanol (5.0 mL) was stirred for 6 h at room temperature. After this time, the reaction mixture was quenched with 1.0 M hydrochloric acid (0.60 mL), diluted with ethyl acetate and separated. The organic layer was washed with water, and saturated sodium chloride, dried ($Na_2SO_4$), filtered and concentrated under reduced pressure. The residue was purified by flash column chromatography (silica gel, methylene chloride/methanol 49:1) to provide 3-(4-(3-methyl-5-(trifluoromethyl)phenyl)oxazol-2-yl)propanoic acid (0.068 g, 75%) as a white solid.

$^1$H NMR (500 MHz, DMSO-$d_6$) δ ppm 2.43 (s, 3H), 2.75 (t, J=7.2 Hz, 2H), 3.02 (t, J=7.2 Hz, 2H), 7.49 (s, 1H), 7.86 (s, 1H), 7.88 (s, 1H), 8.66 (s, 1H), 12.39 (s, 1H).

Reference Example 55

3-(4-(3-Cyano-5-(trifluoromethyl)phenyl)oxazol-2-yl)propanoic acid

A solution of methyl 3-(4-(3-cyano-5-(trifluoromethyl)phenyl)oxazol-2-yl)propanoate (Reference Example 46, 0.276 g, 0.851 mmol), lithium hydroxide (0.024 g, 1.00 mmol) and water (0.016 g, 0.889 mmol) was stirred at 0° C. for 4 h and then warmed to room temperature overnight. After this time, the reaction mixture was quenched with 1.0 M hydrochloric acid (1.0 mL), diluted with ethyl acetate and separated. The organic layer was washed with saturated sodium chloride, dried ($Na_2SO_4$), filtered and concentrated under reduced pressure. The resultant residue was purified by preparative HPLC (95% water-acetonitrile with 0.05% v/v trifluoroacetic acid/95% acetonitrile-water with 0.05% v/v trifluoroacetic acid 1:1, 15 mL/min) to provide 3-(4-(3-cyano-5-(trifluoromethyl)phenyl)oxazol-2-yl)propanoic acid (0.035 g, 13%) as a white solid.

$^1$H NMR (500 MHz, DMSO-$d_6$) δ ppm 2.77 (br s, 2H), 3.04 (br s, 2H), 8.36 (s, 1H), 8.49 (s, 1H), 8.58 (s, 1H), 8.81 (s, 1H), 12.33 (s, 1H).

Reference Example 56

3-(4-(3-(Thiophen-2-yl)-5-(trifluoromethyl)phenyl)oxazol-2-yl)propanoic acid

The title compound was prepared from methyl 3-(4-(3-(thiophen-2-yl)-5-(trifluoromethyl)phenyl)oxazol-2-yl)propanoate (Reference Example 47) by a procedure similar to the one described for 3-(4-(3-chloro-5-(trifluoromethyl)phenyl)oxazol-2-yl)propanoic acid (Reference example 52) to provide 3-(4-(3-(thiophen-2-yl)-5-(trifluoromethyl)phenyl)oxazol-2-yl)propanoic acid (0.094 g, 71%) as a white solid.

$^1$H NMR (500 MHz, DMSO-$d_6$) δ ppm 2.78 (t, J=7.2 Hz, 2H), 3.05 (t, J=7.0 Hz, 2H), 7.22 (dd, J=5.0, 4.0 Hz, 1H), 7.68-7.70 (m, 1H), 7.77 (dd, J=3.5, 1.0 Hz, 1H), 7.89 (s, 1H), 7.99 (s, 1H), 8.27 (s, 1H), 8.81 (s, 1H), 12.34 (s, 1H).

Reference Example 57

3-(4-(3-(Thiophen-3-yl)-5-(trifluoromethyl)phenyl)oxazol-2-yl)propanoic acid

The title compound was prepared from methyl 3-(4-(3-(thiophen-3-yl)-5-(trifluoromethyl)phenyl)oxazol-2-yl)propanoate (Reference Example 48) by a procedure similar to the one described for 3-(4-(3-chloro-5-(trifluoromethyl)phenyl)oxazol-2-yl)propanoic acid (Reference example 52) to provide 3-(4-(3-(thiophen-3-yl)-5-(trifluoromethyl)phenyl)oxazol-2-yl)propanoic acid (0.268 g, 77%) as a white solid.

$^1$H NMR (500 MHz, DMSO-$d_6$) δ ppm 2.78 (t, J=7.0 Hz, 2H), 3.05 (t, J=7.2 Hz, 2H), 7.71-7.74 (m, 2H), 7.98 (s, 1H), 8.15-8.16 (m, 1H), 8.36 (s, 1H), 8.77 (s, 1H), 12.32 (s, 1H).

Reference Example 58

3-(4-(3-Isopropyl-5-(trifluoromethyl)phenyl)oxazol-2-yl)propanoic acid

The title compound was prepared from methyl 3-(4-(3-isopropyl-5-(trifluoromethyl)phenyl)oxazol-2-yl)propanoate (Reference Example 50) by a procedure similar to the one described for 3-(4-(3-chloro-5-(trifluoromethyl)phenyl)oxazol-2-yl)propanoic acid (Reference example 52) to provide 3-(4-(3-isopropyl-5-(trifluoromethyl)phenyl)oxazol-2-yl)propanoic acid (0.132 g, 76%) as a white solid.

$^1$H NMR (500 MHz, DMSO-$d_6$) δ ppm 1.26 (d, J=7.0 Hz, 6H), 2.76 (t, J=7.2 Hz, 2H), 3.01-3.08 (m, 3H), 7.52 (s, 1H), 7.88 (s, 1H), 7.93 (s, 1H), 8.69 (s, 1H), 12.28 (s, 1H).

Reference Example 59

3-(4-(3-Acetyl-5-(trifluoromethyl)phenyl)oxazol-2-yl)propanoic acid

The title compound was prepared from methyl 3-(4-(3-acetyl-5-(trifluoromethyl)phenyl)oxazol-2-yl)propanoate (Reference Example 51) by a procedure similar to the one described for 3-(4-(3-chloro-5-(trifluoromethyl)phenyl)oxazol-2-yl)propanoic acid (Reference example 52) to provide 3-(4-(3-acetyl-5-(trifluoromethyl)phenyl)oxazol-2-yl)propanoic acid (0.081 g, 70%) as a white solid.

$^1$H NMR (500 MHz, DMSO-$d_6$) δ ppm 2.70 (s, 3H), 2.78 (t, J=7.0 Hz, 2H), 3.05 (t, J=7.0 Hz, 2H), 8.14 (s, 1H), 8.32 (s, 1H), 8.55 (s, 1H), 8.84 (s, 1H), 12.32 (s, 1H).

Example 1

3-{[4-(2-tert-Butylphenyl)piperazin-1-yl]carbonyl}adamantane-1-carboxylic acid

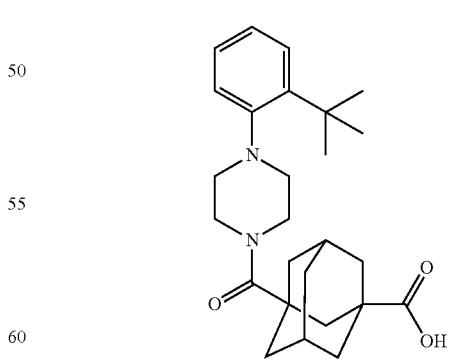

A mixture of 1-(2-tert-butylphenyl)piperazine dihydrochloride obtained in Reference Example 1 (400 mg), 1,3-adamantanedicarboxylic acid (628 mg), 1-ethyl-3-(3-dimethylaminopropyl)carbodiimide hydrochloride (316 mg), 1-hydroxy-1H-benzotriazole monohydrate (253 mg), triethylamine (0.697 mL), and N,N-dimethylformamide (5 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was subjected to purification by high performance liquid chromatography [Column: Gilson, Ltd. High throughput purification system, YMC Combiprep ODS-A, S-5 µm, 50 mm×20 mm; Gradient cycle: $H_2O$ (contains 0.1% $CF_3COOH$)-acetonitrile (contains 0.1% $CF_3COOH$), 90:10 (0 min)-90:10 (1 min)-10:90 (4.2 min)-10:90 (5.4 min)-90:10 (5.5 min)-90:10 (5.6 min); Flow rate: 25 mL/min; detection wavelength: UV 220 nm] to give the title compound (352 mg, 61%) as a white solid.

$^1$H-NMR (300 MHz, DMSO-$d_6$) δ 1.41 (s, 9H), 1.51-1.77 (m, 6H), 1.82-1.87 (m, 2H), 1.95-1.98 (m, 4H), 2.07-2.08 (m, 2H), 2.72-2.75 (m, 4H), 2.96-3.02 (m, 2H), 4.42-4.46 (m, 2H), 7.09-7.23 (m, 2H), 7.29-7.36 (m, 2H), 12.08 (br, 1H).

Example 2

[5-({2-[4-(2-tert-Butylphenyl)piperazin-1-yl]-2-oxoethyl}sulfanyl)-1H-tetrazol-1-yl]acetic acid

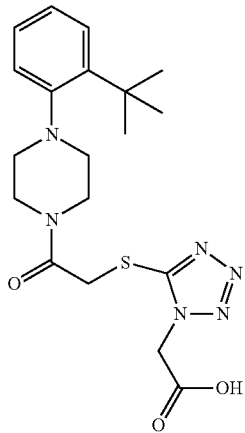 [SMILES: CC(C)(C)c1ccccc1N1CCN(C(=O)CSc2nnnn2CC(=O)O)CC1]

A mixture of 1-(2-tert-butylphenyl)piperazine dihydrochloride obtained in Reference Example 1 (500 mg), acetyl chloride (253 mg), triethylamine (0.836 mL), and tetrahydrofuran (10 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure. Sodium (5-sulfanyl-1H-tetrazol-1-yl)acetate (1.00 g) and N,N-dimethylformamide (5 mL) were added to the obtained residue, and the mixture was stirred at 60° C. for 6 h. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was subjected to purification by high performance liquid chromatography [Column: Gilson, Ltd. High throughput purification system, YMC Combiprep ODS-A, S-5 µm, 50 mm×20 mm; Gradient cycle: $H_2O$ (contains 0.1% $CF_3COOH$)-acetonitrile (contains 0.1% $CF_3COOH$), 90:10 (0 min)-90:10 (1 min)-10:90 (4.2 min)-10:90 (5.4 min)-90:10 (5.5 min)-90:10 (5.6 min); Flow rate: 25 mL/min; detection wavelength: UV 220 nm] to give the title compound (555 mg, 77%.) as a white solid.

$^1$H-NMR (300 MHz, DMSO-$d_6$) δ 1.41 (s, 9H), 2.74-2.95 (m, 4H), 3.27-3.35 (m, 2H), 3.90-3.94 (m, 1H), 4.35-4.38 (m, 1H), 4.45-4.62 (m, 2H), 5.37 (s, 2H), 7.11-7.24 (m, 2H), 7.30-7.37 (m, 2H), 13.01 (br, 1H).

Example 3

1-(2-tert-Butylphenyl)-4-(1H-imidazol-4-ylcarbonyl)piperazine

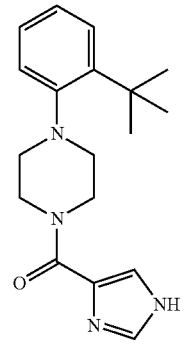 [SMILES: CC(C)(C)c1ccccc1N1CCN(C(=O)c2c[nH]cn2)CC1]

A mixture of 1-(2-tert-butylphenyl)piperazine dihydrochloride obtained in Reference Example 1 (400 mg), 1H-imidazole-4-carboxylic acid (191 mg), 1-ethyl-3-(3-dimethylaminopropyl)carbodiimide hydrochloride (326 mg), 1-hydroxy-1H-benzotriazole monohydrate (260 mg), triethylamine (0.697 mL), and N,N-dimethylformamide (5 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was subjected to purification by high performance liquid chromatography [Column: Gilson, Ltd. High throughput purification system, YMC Combiprep ODS-A, S-5 µm, 50 mm×20 mm; Gradient cycle: $H_2O$ (contains 0.1% $CF_3COOH$)-acetonitrile (contains 0.1% $CF_3COOH$), 90:10 (0 min)-90:10 (1 min)-10:90 (4.2 min)-10:90 (5.4 min)-90:10 (5.5 min)-90:10 (5.6 min); Flow rate: 25 mL/min; detection wavelength: UV 220 nm] to give the title compound (322 mg, 75%.) as a white solid.

$^1$H-NMR (300 MHz, CDCl$_3$) δ 1.47 (s, 9H), 2.93-3.00 (m, 5H), 3.12-3.58 (m, 2H), 4.74 (br, 2H), 7.12-7.28 (m, 3H), 7.37-7.39 (m, 1H), 7.46 (s, 1H), 7.62 (s, 1H).

Example 4

Ethyl N-{[4-(2-tert-butylphenyl)piperazin-1-yl]carbonyl}glycinate

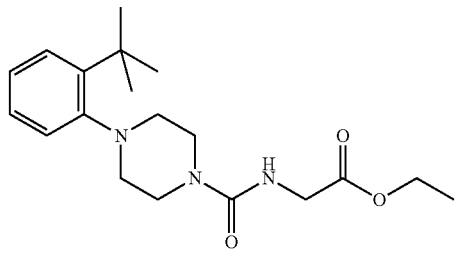 [SMILES: CCOC(=O)CNC(=O)N1CCN(c2ccccc2C(C)(C)C)CC1]

A mixture of 1-(2-tert-butylphenyl)piperazine dihydrochloride obtained in Reference Example 1 (400 mg), ethyl isocyanatoacetate (258 mg), triethylamine (0.418 mL), and tetrahydrofuran (20 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (430 mg, 90%) as a colorless solid.

$^1$H NMR (300 MHz, CDCl$_3$) δ 1.30 (t, J=7.2 Hz, 3H), 1.44 (s, 9H), 2.83-2.93 (m, 4H), 3.12-3.21 (m, 2H), 3.92-3.96 (m, 2H), 4.04 (d, J=5.1 Hz, 2H), 4.19 (q, J=7.2 Hz, 2H), 5.03-5.05 (m, 1H), 7.11-7.28 (m, 3H), 7.35-7.38 (m, 1H).

Example 5

Ethyl N-{[4-(2-tert-butylphenyl)piperazin-1-yl]carbonyl}-beta-alaninate

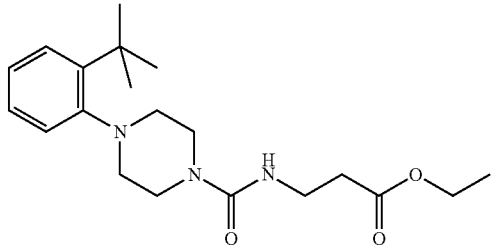 [SMILES: CCOC(=O)CCNC(=O)N1CCN(c2ccccc2C(C)(C)C)CC1]

A mixture of 1-(2-tert-butylphenyl)piperazine dihydrochloride obtained in Reference Example 1 (400 mg), ethyl 3-isocyanatopropionate (286 mg), triethylamine (0.418 mL), and tetrahydrofuran (20 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (470 mg, 95%) as a colorless solid.

$^1$H NMR (300 MHz, CDCl$_3$) δ 1.28 (t, J=7.2 Hz, 3H), 1.43 (s, 9H), 2.57 (t, J=5.7 Hz, 2H), 2.84-2.91 (m, 3H), 3.06-3.15 (m, 2H) 3.40-3.48 (m, 1H), 3.51-3.57 (m, 2H), 3.85-3.90 (m, 2H), 4.16 (q, J=7.2 Hz, 2H), 5.26-5.30 (m, 1H), 7.11-7.28 (m, 3H), 7.35-7.38 (m, 1H).

Example 6

N-{[4-(2-tert-Butylphenyl)piperazin-1-yl]carbonyl}glycine

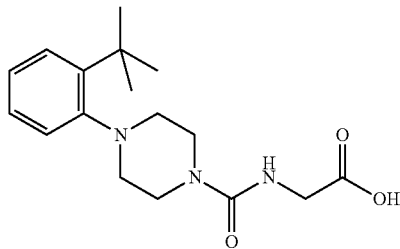 [SMILES: CC(C)(C)c1ccccc1N1CCN(C(=O)NCC(=O)O)CC1]

A mixture of ethyl N-{[4-(2-tert-butylphenyl)piperazin-1-yl]carbonyl}glycinate obtained in Example 4 (430 mg), lithium hydroxide monohydrate (420 mg), water (50 mL), and tetrahydrofuran (50 mL) was stirred at room temperature for 3 h. 6 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (350 mg, 89%) as a colorless solid.

$^1$H NMR (300 MHz, DMSO-d$_6$) δ 1.40 (s, 9H), 2.68-2.81 (m, 4H), 2.86-2.93 (m, 2H), 3.67-3.69 (m, 2H), 3.95-3.99 (m, 2H), 6.94 (br, 1H), 7.12-7.14 (m, 1H), 7.18-7.20 (m, 1H), 7.29-7.36 (m, 2H), 12.34 (s, 1H).

Example 7

N-{[4-(2-tert-Butylphenyl)piperazin-1-yl]carbonyl}-beta-alanine

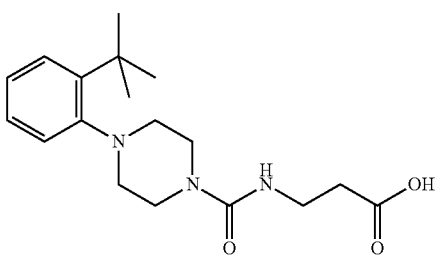 [SMILES: CC(C)(C)c1ccccc1N1CCN(C(=O)NCCC(=O)O)CC1]

A mixture of ethyl N-{[4-(2-tert-butylphenyl)piperazin-1-yl]carbonyl}-beta-alaninate obtained in Example 5 (470 mg), lithium hydroxide monohydrate (420 mg), water (50 mL), and tetrahydrofuran (50 mL) was stirred at room temperature for 3 h. 6 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (298 mg, 69%) as a colorless solid.

$^1$H-NMR (300 MHz, DMSO-d$_6$) δ 1.40 (s, 9H), 2.41 (t, J=6.9 Hz, 2H), 2.66-2.89 (m, 5H), 3.23-2.34 (m, 3H), 3.92-3.96 (m, 2H), 6.62-6.64 (m, 1H), 7.09-7.14 (m, 1H), 7.18-7.23 (m, 1H), 7.29-7.37 (m, 2H), 12.13 (br, 1H).

Example 8

Ethyl 3-[4-(2-tert-butylphenyl)piperazin-1-yl]-3-oxopropanoate

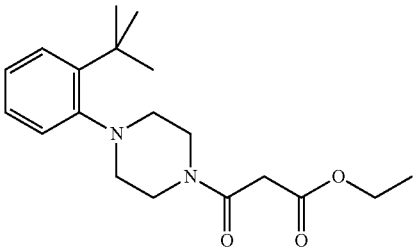 [SMILES: CCOC(=O)CC(=O)N1CCN(c2ccccc2C(C)(C)C)CC1]

A mixture of 1-(2-tert-butylphenyl)piperazine dihydrochloride obtained in Reference Example 1 (400 mg), ethyl hydrogen malonate (225 mg), 1-ethyl-3-(3-dimethylaminopropyl)carbodiimide hydrochloride (326 mg), 1-hydroxy-1H-benzotriazole monohydrate (260 mg), triethylamine (0.697 mL), and N,N-dimethylformamide (5 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (silica gel, 90:10-70:30 hexane/ethyl acetate) to provide the title compound (312 mg, 69%) as a colorless oil.

$^1$H NMR (300 MHz, CDCl$_3$) δ 1.31 (t, J=7.2 Hz, 3H), 1.44 (s, 9H), 2.83-2.98 (m, 4H), 3.40-3.49 (m, 2H), 3.55 (s, 2H), 3.71-3.75 (m, 1H), 4.23 (q, J=7.2 Hz, 2H), 4.61-4.65 (m, 1H), 7.12-7.26 (m, 3H), 7.36-7.38 (m, 1H).

Example 9

3-[4-(2-tert-Butylphenyl)piperazin-1-yl]-3-oxopropanoic acid

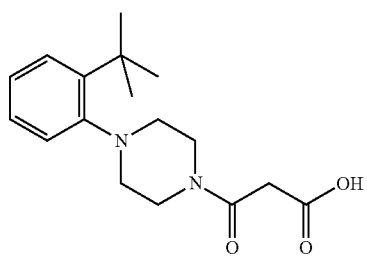 [SMILES: CC(C)(C)c1ccccc1N1CCN(C(=O)CC(=O)O)CC1]

A mixture of ethyl 3-[4-(2-tert-butylphenyl)piperazin-1-yl]-3-oxopropanoate obtained in Example 8 (300 mg), lithium hydroxide monohydrate (840 mg), water (10 mL), and tetrahydrofuran (10 mL) was stirred at room temperature for 3 h. 6 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (199 mg, 73%) as a colorless solid.

$^1$H NMR (300 MHz, DMSO-d$_6$) δ 1.41 (s, 9H), 2.74-2.86 (m, 4H), 3.19-3.23 (m, 2H), 3.42-3.51 (m, 2H), 3.81-3.86 (m, 1H), 4.39-4.42 (m, 1H), 7.13-7.22 (m, 2H), 7.30-7.34 (m, 2H), 12.63 (br, 1H).

Example 10

4-[4-(2-tert-Butylphenyl)piperazin-1-yl]-N-[(cyclopropylmethyl)sulfamoyl]-4-oxobutanamide

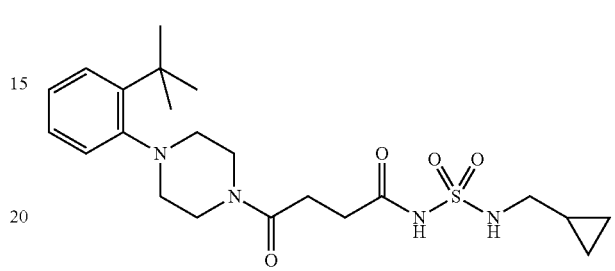

A mixture of 4-[4-(2-tert-butylphenyl)piperazin-1-yl]-4-oxobutanoic acid obtained in Example 53 (500 mg), N-(cyclopropylmethyl)sulfamide (248 mg), 2-methyl-6-nitrobenzoic anhydride (692 mg), N,N-dimethylaminopyridine (192 mg), triethylamine (0.656 mL), and acetonitrile (10 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (148 mg, 21%) as a colorless solid.

$^1$H NMR (300 MHz, DMSO-d$_6$) δ 0.13-0.18 (m, 2H), 0.38-0.44 (m, 2H), 0.91-0.96 (m, 1H), 1.41 (s, 9H), 2.57-2.83 (m, 11H), 3.19-3.26 (m, 1H), 3.91-4.03 (m, 1H), 4.37-4.40 (m, 1H), 7.10-7.16 (m, 1H), 7.18-7.24 (m, 1H), 7.29-7.35 (m, 2H), 7.51 (t, J=6.0 Hz, 1H), 11.31 (s, 1H).

Example 11

5-({2-[4-(2-tert-Butylphenyl)piperazin-1-yl]-2-oxoethyl}sulfanyl)-1,3-dimethyl-1H-pyrazole-4-carboxylic acid

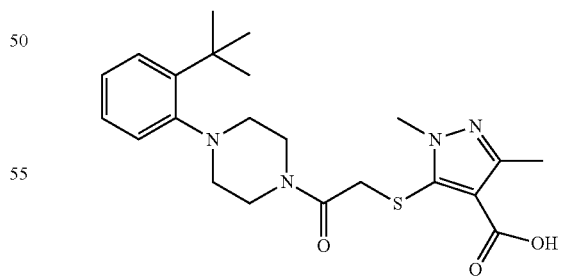

A mixture of 1-(2-tert-butylphenyl)piperazine dihydrochloride obtained in Reference Example 1 (1.0 g), [(4-formyl-1,3-dimethyl-1H-pyrazol-5-yl)sulfanyl]acetic acid obtained in Reference Example 3 (736 mg), 1-ethyl-3-(3-dimethylaminopropyl)carbodiimide hydrochloride (786 mg), 1-hydroxy-1H-benzotriazole monohydrate (628 mg), triethylamine (1.39 mL), and N,N-dimethylformamide (50 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (silica gel, 80:20-30:70 hexane/ethyl acetate) to provide 5-({2-[4-(2-tert-butylphenyl)piperazin-1-yl]-2-oxoethyl}sulfanyl)-1,3-dimethyl-1H-pyrazole-4-carbaldehyde (900 mg, 64%) as a colorless oil.

$^1$H NMR (300 MHz, CDCl$_3$) δ 1.43 (s, 9H), 2.49 (s, 3H), 2.71-2.94 (m, 5H), 3.35-3.44 (m, 1H), 3.68-3.72 (m, 1H), 3.75-3.92 (m, 2H), 4.00 (s, 3H), 4.52-4.56 (m, 1H), 7.12-7.25 (m, 3H), 7.35-7.38 (m, 1H), 10.00 (s, 1H).

To a mixture of 5-({2-[4-(2-tert-butylphenyl)piperazin-1-yl]-2-oxoethyl}sulfanyl)-1,3-dimethyl-1H-pyrazole-4-carbaldehyde (900 mg), sodium dihydrogen phosphate (1.19 g), 2-methyl-2-butene (1.17 mL), tetrahydrofuran (10 mL), tert-butanol (3 mL), and water (1.5 mL) was added sodium chlorite (393 mg) at 0° C. and stirred at room temperature for 1 h. Aqueous sodium hydrogen sulfite was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (550 mg, 59%) as a colorless solid.

$^1$H NMR (300 MHz, DMSO-d$_6$) δ 1.40 (s, 9H), 2.31 (s, 3H), 2.62-2.79 (m, 5H), 3.21-3.26 (m, 1H), 3.88 (s, 3H), 3.83-4.06 (m, 3H), 4.32-4.35 (m, 1H), 7.11-7.16 (m, 1H), 7.19-7.24 (m, 1H), 7.30-7.32 (m, 2H), 12.49 (s, 1H).

Example 12

6-{[4-(2-tert-Butylphenyl)piperazin-1-yl]carbonyl}-5H-[1,3]thiazolo[3,2-a]pyrimidin-5-one

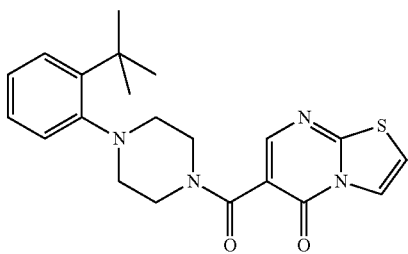 [SMILES: CC(C)(C)c1ccccc1N1CCN(C(=O)c2cnc3sccn3c2=O)CC1]

A mixture of 1-(2-tert-butylphenyl)piperazine dihydrochloride obtained in Reference Example 1 (500 mg), 5-oxo-5H-[1,3]thiazolo[3,2-a]pyrimidine-6-carboxylic acid (371 mg), 1-ethyl-3-(3-dimethylaminopropyl)carbodiimide hydrochloride (395 mg), 1-hydroxy-1H-benzotriazole monohydrate (315 mg), triethylamine (0.558 mL), and N,N-dimethylformamide (10 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (320 mg, 47%) as a colorless solid.

$^1$H NMR (300 MHz, DMSO-d$_6$) δ 1.42 (s, 9H), 2.65-2.72 (m, 1H), 2.78-2.99 (m, 4H), 3.30-3.32 (m, 1H), 3.65-3.69 (m, 1H), 4.53-4.56 (m, 1H), 7.13-7.16 (m, 1H), 7.20-7.25 (m, 1H), 7.30-7.38 (m, 2H), 7.66 (d, J=4.8 Hz, 1H), 8.15 (d, J=4.8 Hz, 1H), 8.21 (s, 1H).

Example 13

6-{[4-(2-tert-Butylphenyl)piperazin-1-yl]carbonyl}piperidin-2-one

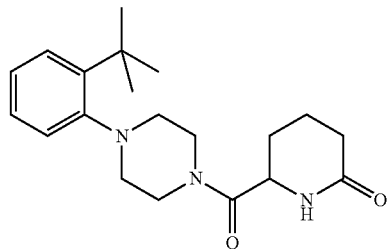 [SMILES: CC(C)(C)c1ccccc1N1CCN(C(=O)C2CCCC(=O)N2)CC1]

A mixture of 1-(2-tert-butylphenyl)piperazine dihydrochloride obtained in Reference Example 1 (500 mg), 6-oxopiperidine-2-carboxylic acid (261 mg), 1-ethyl-3-(3-dimethylaminopropyl)carbodiimide hydrochloride (403 mg), 1-hydroxy-1H-benzotriazole monohydrate (322 mg), triethylamine (0.627 mL), and N,N-dimethylformamide (5 mL) was stirred at room temperature for over-night. Water was added to the reaction solution, and the mixture was extracted with ethyl acetate. The ethyl acetate layer was washed with 1 M sodium hydroxide solution, saturated brine, and dried over anhydrous magnesium sulfate. The solvent was evaporated under reduced pressure to provide the title compound (280 mg, 47%) as a colorless solid.

$^1$H NMR (300 MHz, DMSO-d$_6$) δ 1.41 (s, 9H), 1.66-1.70 (m, 3H), 1.92-1.99 (m, 1H), 2.12-2.15 (m, 2H), 2.74-2.82 (m, 5H), 3.23-3.28 (m, 1H), 3.97-4.02 (m, 1H), 4.45-4.53 (m, 2H), 7.11-7.33 (m, 5H).

Example 14

4-{2-[4-(2-tert-Butylphenyl)piperazin-1-yl]-2-oxoethyl}piperidine-2,6-dione

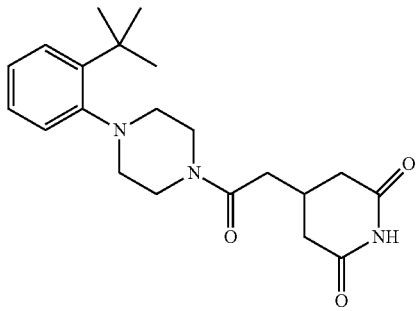 [SMILES: CC(C)(C)c1ccccc1N1CCN(C(=O)CC2CC(=O)NC(=O)C2)CC1]

A mixture of 1-(2-tert-butylphenyl)piperazine dihydrochloride obtained in Reference Example 1 (500 mg), (2,6-dioxopiperidin-4-yl)acetic acid (311 mg), 1-ethyl-3-(3-dimethylaminopropyl)carbodiimide hydrochloride (403 mg), 1-hydroxy-1H-benzotriazole monohydrate (322 mg), triethylamine (0.627 mL), and N,N-dimethylformamide (5 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was subjected to purification by high performance liquid chromatography [Column: Gilson, Ltd. High throughput purification system, YMC Combiprep ODS-A, S-5 μm, 50 mm×20 mm; Gradient cycle: H$_2$O (contains 0.1% CF$_3$COOH)-acetonitrile (contains 0.1% CF$_3$COOH), 90:10 (0 min)-90:10 (1 min)-10:90 (4.2 min)-10:90 (5.4 min)-90:10 (5.5 min)-90:10 (5.6 min); Flow rate: 25 mL/min; detection wavelength: UV 220 nm] to give the title compound (47 mg, 13%) as a white solid.

$^1$H NMR (300 MHz, DMSO-d$_6$) δ 1.41 (s, 9H), 2.35-2.74 (m, 12H), 3.20-3.31 (m, 1H), 3.85-3.98 (m, 1H), 4.40-4.50 (m, 1H), 7.13-7.21 (m, 2H), 7.30-7.34 (m, 2H), 10.72 (br, 1H).

Example 15

4-[4-(2-tert-Butylphenyl)piperazin-1-yl]-2,2-dimethyl-4-oxobutanoic acid

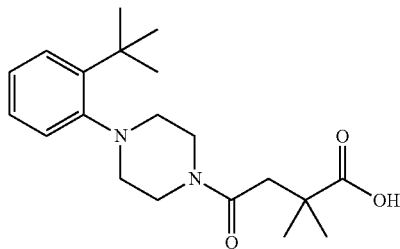 [SMILES: CC(C)(CC(=O)N1CCN(c2ccccc2C(C)(C)C)CC1)C(=O)O]

A mixture of 1-(2-tert-butylphenyl)piperazine dihydrochloride obtained in Reference Example 1 (400 mg), 2,2-dimethylsuccinic anhydride (400 mg), triethylamine (1.39 mL), and tetrahydrofuran (20 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (1.03 g, 95%) as a colorless solid.

$^1$H NMR (300 MHz, DMSO-d$_6$) δ 1.17 (s, 3H), 1.19 (s, 3H), 1.41 (s, 9H), 2.54-2.84 (m, 7H), 3.06-3.23 (m, 1H), 3.90-3.95 (m, 1H), 4.38-4.40 (m, 1H), 7.11-7.16 (m, 1H), 7.19-7.24 (m, 1H), 7.30-7.36 (m, 2H), 11.79 (br, 1H).

Example 16

4-{[4-(2-tert-Butylphenyl)piperazin-1-yl]carbonyl}benzonitrile

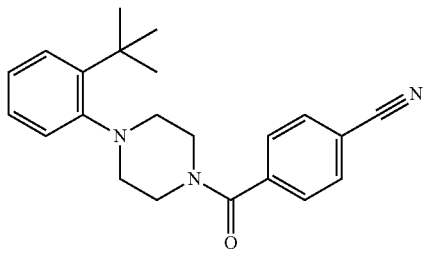 [SMILES: CC(C)(C)c1ccccc1N1CCN(C(=O)c2ccc(C#N)cc2)CC1]

A mixture of 1-(2-tert-butylphenyl)piperazine dihydrochloride obtained in Reference Example 1 (1.0 g), 4-cyanobenzoyl chloride (662 mg), triethylamine (1.67 mL), and tetrahydrofuran (30 mL) was stirred at room temperature for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (NH-silica gel, ethyl acetate) to provide the title compound (1200 mg, quant.) as a solid.

$^1$H NMR (300 MHz, CDCl$_3$) δ 1.44 (s, 9H), 2.81-2.97 (m, 4H), 3.12-3.16 (m, 1H), 3.44-3.56 (m, 2H), 4.71-4.75 (m, 1H), 7.13-7.28 (m, 3H), 7.38 (dd, J=7.5, 1.5 Hz, 1H), 7.55-7.58 (m, 2H), 7.72-7.75 (m, 2H). Anal. Calcd for C$_{22}$H$_{25}$N$_3$O-0.1H$_2$O: C, 75.66; H, 7.27; N, 12.03. Found: C, 75.61; H, 7.37; N, 11.85.

Example 17

1-{[4-(Benzyloxy)phenyl]carbonyl}-4-(2-tert-butylphenyl)piperazine

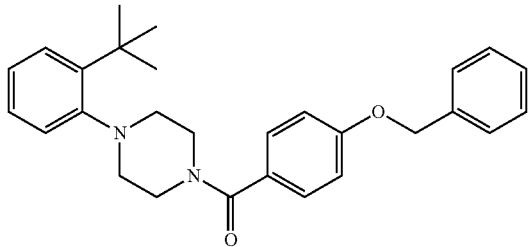 [SMILES: CC(C)(C)c1ccccc1N1CCN(C(=O)c2ccc(OCc3ccccc3)cc2)CC1]

To a stirred solution of 4-(benzyloxy)benzoic acid (913 mg) and N,N-dimethylformamide (0.01 mL) in tetrahydrofuran (30 mL) was added oxalyl chloride (0.508 mL) at room temperature. After 1 h the reaction mixture was concentrated under reduced pressure to provide the residue and the residue was dissolved in tetrahydrofuran (30 mL). A mixture of 1-(2-tert-butylphenyl)piperazine dihydrochloride obtained in Reference Example 1 (1.0 g) and triethylamine (1.67 mL) was added to the solution and stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (NH-silica gel, ethyl acetate) to provide the title compound (1360 mg, 79%) as a solid.

$^1$H NMR (300 MHz, CDCl$_3$) δ 1.45 (s, 9H), 2.84-2.90 (m, 4H), 3.10-3.38 (m, 2H), 3.80-4.00 (m, 1H), 4.60-4.70 (m, 1H), 5.09 (s, 2H), 6.90-7.02 (m, 2H), 7.12-7.46 (m, 11H). Anal. Cald. for C$_{22}$H$_{32}$N$_2$O$_2$: C, 78.47; H, 7.53; N, 6.54. Found: C, 78.40; H, 7.67; N, 6.52.

Example 18

1-(2-tert-Butylphenyl)-4-[(6-chloropyridin-3-yl)carbonyl]piperazine

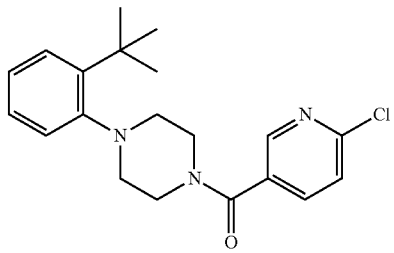 [SMILES: CC(C)(C)c1ccccc1N1CCN(C(=O)c2ccc(Cl)nc2)CC1]

A mixture of 1-(2-tert-butylphenyl)piperazine dihydrochloride obtained in Reference Example 1 (0.5 g), 6-chloropyridine-3-carbonyl chloride (352 mg), triethylamine (0.835 mL), and tetrahydrofuran (30 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (NH-silica gel, 0:100 hexane/ethyl acetate) to provide the title compound (635 mg, quant.) as a solid.

$^1$H NMR (300 MHz, CDCl$_3$) δ 1.45 (s, 9H), 2.85-2.96 (m, 4H), 3.10-3.20 (m, 1H), 3.44-3.48 (m, 1H), 3.64-3.69 (m, 1H), 4.70-4.74 (m, 1H), 7.14-7.28 (m, 3H), 7.37-7.43 (m, 2H), 7.76-7.80 (m, 1H), 8.50-8.51 (m, 1H).

Example 19

3-(4-{[4-(2-tert-Butylphenyl)piperazin-1-yl]carbonyl}phenyl)-1,2,4-oxadiazol-5(4H)-one

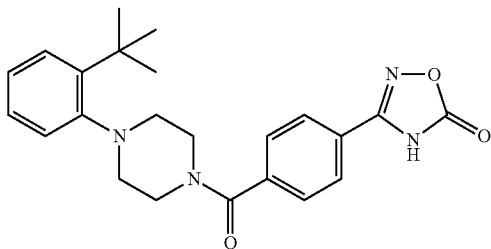 [SMILES: CC(C)(C)c1ccccc1N1CCN(C(=O)c2ccc(-c3noc(=O)[nH]3)cc2)CC1]

A mixture of hydroxylammonium chloride (1.04 g) in DMSO (10.0 mL) was stirred at 40° C. After stirred at 40° C. for 1 h, a mixture of 4-{[4-(2-tert-butylphenyl)piperazin-1-yl]carbonyl}benzonitrile obtained in Example 16 (1.1 g) and sodium hydrogen carbonate (1.26 g) was added to the mixture. After stirred at 90° C. for 1 h, the reaction mixture was partitioned between ethyl acetate and water and separated. The organic layer was washed with saturated sodium chloride, dried (Na$_2$SO$_4$), filtered and concentrated under reduced pressure. The residue was dissolved in THF (30.0 mL), added to a mixture of 1,1'-carbonyl bis-1H-imidazole (0.568 g) and 1,8-diazabicyclo[5.4.0]undec-7-ene (0.522 mL) and the resulting reaction mixture was stirred at room temperature for 3 h. After this time, the reaction mixture was poured into 1 M HCl water solution and extracted with ethyl acetate. The combined organics were washed with saturated sodium chloride, dried (MgSO$_4$), filtered, and concentrated under reduced pressure to provide the title compound (1.01 g, 78%) as a solid.

$^1$H NMR (300 MHz, DMSO-d$_6$) δ 1.41 (s, 9H), 2.67-2.89 (m, 4H), 3.00-3.04 (m, 1H), 3.33-3.36 (m, 1H), 3.49-3.54 (m, 1H), 4.50-4.60 (m, 1H), 7.14 (t, J=7.5 Hz, 1H), 7.23 (t, J=7.5 Hz, 1H), 7.31 (dd, J=8.1, 1.5 Hz, 1H), 7.43 (dd, J=7.8, 1.5 Hz, 1H), 7.68 (d, J=7.8 Hz, 2H), 7.89 (d, J=8.1 Hz, 2H), 13.07 (br, 1H). Anal. Calcd. for C$_{23}$H$_{26}$N$_4$O$_3$·0.25H$_2$O: C, 67.22; H, 6.50; N, 13.63. Found: C, 67.40; H, 6.64; N, 13.47.

Example 20

4-{[4-(2-tert-Butylphenyl)piperazin-1-yl]carbonyl}phenol

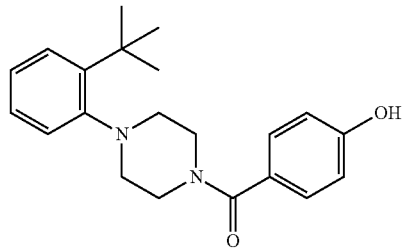 [SMILES: CC(C)(C)c1ccccc1N1CCN(C(=O)c2ccc(O)cc2)CC1]

A mixture of 1-{[4-(benzyloxy)phenyl]carbonyl}-4-(2-tert-butylphenyl)piperazine obtained in Example 17 (1.3 g), palladium carbon (contains 50% H$_2$O, 300 mg), methanol (120 mL), and tetrahydrofuran (30 mL) was stirred at room temperature under hydrogen atmosphere (5 atm). The mixture was filtered and evaporated under reduced pressure to provide the title compound (1.03 g, quant.) as a solid.

$^1$H NMR (300 MHz, CDCl$_3$) δ 1.41 (s, 9H), 2.75-2.86 (m, 4H), 3.10-3.17 (m, 2H), 4.02-4.20 (m, 2H), 6.79 (d, J=8.7 Hz, 2H), 7.13 (t, J=7.5 Hz, 1H), 7.22 (t, J=7.5 Hz, 1H), 7.30-7.34

(m, 3H), 7.40 (t, J=7.2 Hz, 1H), 9.85 (s, 1H). Anal. Calcd. for C$_{21}$H$_{26}$N$_2$O$_2$·0.25H$_2$O: C, 73.55; H, 7.79; N, 8.17. Found: C, 73.73; H, 7.90; N, 8.15.

Example 21

Ethyl [(5-{[4-(2-tert-butylphenyl)piperazin-1-yl]carbonyl}pyridin-2-yl)sulfanyl]acetate

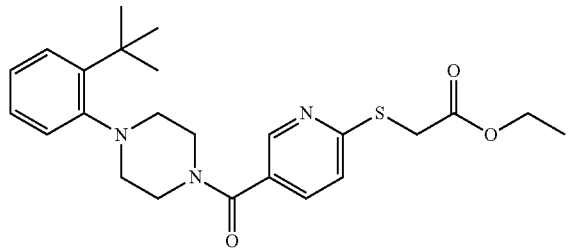 [SMILES: CCOC(=O)CSc1ccc(C(=O)N2CCN(c3ccccc3C(C)(C)C)CC2)cn1]

A mixture of 1-(2-tert-butylphenyl)-4-[(6-chloropyridin-3-yl)carbonyl]piperazine obtained in Example 18 (590 mg), ethyl thioglycolate (361 mg), potassium carbonate (691 mg), and N,N-dimethylformamide (10 mL) was stirred at 80° C. for 2 h. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (silica gel, 50:50-0:100 hexane/ethyl acetate) to provide the title compound (430 mg, 59%) as a solid.

$^1$H NMR (300 MHz, CDCl$_3$) δ 1.27 (t, J=6.9 Hz, 3H), 1.45 (s, 9H), 2.80-3.00 (m, 4H), 3.15-3.40 (m, 2H), 3.70-3.80 (m, 1H), 3.99 (s, 2H), 4.20 (q, J=6.9 Hz, 2H), 4.68-4.70 (m, 1H), 7.13-7.30 (m, 4H), 7.38 (dd, J=7.8, 1.5 Hz, 1H), 7.62 (dd, J=8.4, 2.1 Hz, 1H), 8.50-8.51 (m, 1H). Anal. Calcd. for C$_{24}$H$_{31}$N$_3$O$_3$S: C, 65.28; H, 7.08; N, 9.52. Found: C, 65.24; H, 7.03; N, 9.48.

Example 22

Methyl (4-{[4-(2-tert-butylphenyl)piperazin-1-yl]carbonyl}phenoxy)acetate

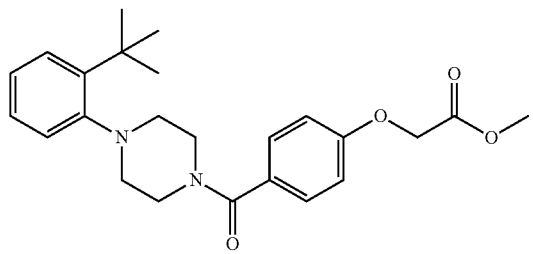 [SMILES: COC(=O)COc1ccc(C(=O)N2CCN(c3ccccc3C(C)(C)C)CC2)cc1]

A mixture of 4-{[4-(2-tert-Butylphenyl)piperazin-1-yl]carbonyl}phenol obtained in Example 20 (1.0 g), methyl bromoacetate (542 mg), potassium carbonate (1.38 g), and N,N-dimethylformamide (30 mL) was stirred at 50° C. for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (430 mg, 59%) as white crystals.

$^1$H NMR (300 MHz, CDCl$_3$) δ 1.45 (s, 9H), 2.80-3.00 (m, 4H), 3.15-3.30 (m, 2H), 3.76-3.87 (m, 1H), 3.81 (s, 3H), 4.61-4.69 (m, 1H), 4.67 (s, 2H), 6.90-6.95 (m, 2H), 7.12-7.30 (m, 3H), 7.36-7.46 (m, 3H). Anal. Calcd. for C$_{24}$H$_{30}$N$_2$O$_4$: C, 70.22; H, 7.37; N, 6.82. Found: C, 70.16; H, 7.31; N, 6.77.

Example 23

5-(Benzyloxy)-2-{[4-(2-tert-butylphenyl)piperazin-1-yl]carbonyl}-1H-indole

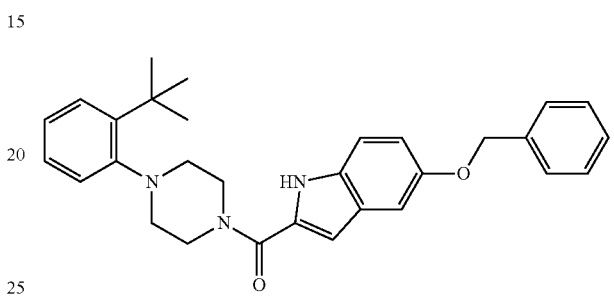

A mixture of 1-(2-tert-butylphenyl)piperazine dihydrochloride obtained in Reference Example 1 (2.0 g), 5-(benzyloxy)-1H-indole-2-carboxylic acid (2.03 g), 1-ethyl-3-(3-dimethylaminopropyl)carbodiimide hydrochloride (1.92 g), 1-hydroxy-1H-benzotriazole monohydrate (1.53 g), triethylamine (2.79 mL), and N,N-dimethylformamide (30 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (2.6 g, 81%) as crystals.

$^1$H NMR (300 MHz, DMSO-d$_6$) δ 1.44 (s, 9H), 2.82-2.89 (m, 4H), 3.20-3.40 (m, 2H), 4.50-4.54 (m, 2H), 5.09 (s, 2H), 6.74 (s, 1H), 6.92 (dd, J=9.0, 1.8 Hz, 1H), 7.13-7.46 (m, 11H), 11.50 (s, 1H). LC/MS (ESI+) m/z: 468 (M+H)$^+$.

Example 24

(4-{[4-(2-tert-Butylphenyl)piperazin-1-yl]carbonyl}phenoxy)acetic acid

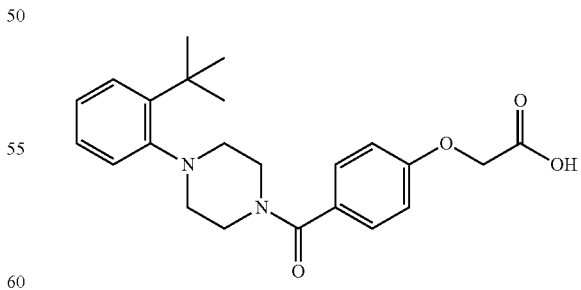

A mixture of methyl (4-{[4-(2-tert-butylphenyl)piperazin-1-yl]carbonyl}phenoxy)acetate obtained in Example 22 (1.11 g), 1 M sodium hydroxide solution (12 mL), methanol (50 mL), and tetrahydrofuran (50 mL) was stirred at room temperature for 3 h. 1 M hydrochloric acid solution was added to the reaction solution, and the solvent was evaporated under reduced pressure to afford crystals. Crystals were washed with water, diethyl ether and dried under reduced pressure to provide the title compound (1.05 g, 98%) as crystals.

¹H-NMR (300 MHz, DMSO-d₆) δ 1.41 (s, 9H), 2.76-2.87 (m, 4H), 3.10-3.20 (m, 2H), 3.70-3.85 (m, 1H), 4.40-4.48 (m, 1H), 4.73 (s, 2H), 6.96 (d, J=8.7 Hz, 2H), 7.13 (t, J=7.2 Hz, 1H), 7.22 (t, J=7.8 Hz, 1H), 7.29-7.32 (m, 1H), 7.40-7.44 (m, 3H), 13.06 (s, 1H). Anal. Calcd. for C₂₃H₂₈N₂O₄:C, 69.67; H, 7.12; N, 7.07. Found: C, 69.51; H, 7.20; N, 6.98.

Example 25

[(5-{[4-(2-tert-Butylphenyl)piperazin-1-yl]carbonyl}pyridin-2-yl)sulfanyl]acetic acid

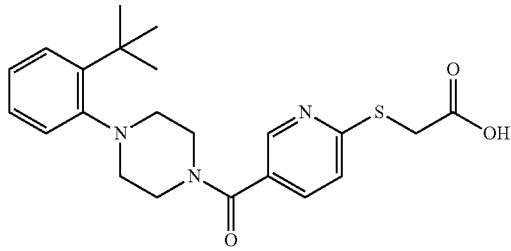 [SMILES: CC(C)(C)c1ccccc1N1CCN(C(=O)c2ccc(SCC(=O)O)nc2)CC1]

A mixture of ethyl [(5-{[4-(2-tert-butylphenyl)piperazin-1-yl]carbonyl}pyridin-2-yl)sulfanyl]acetate obtained in Example 21 (390 mg), 1 M sodium hydroxide solution (12 mL), methanol (30 mL), and tetrahydrofuran (30 mL) was stirred at room temperature for 3 h. 1 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (336 mg, 99%) as crystals.

¹H NMR (300 MHz, DMSO-d₆) δ 1.41 (s, 9H), 2.72-2.99 (m, 4H), 3.10-3.14 (m, 1H), 3.20-3.38 (m, 1H), 3.58-3.62 (m, 1H), 3.84 (s, 2H), 4.40-4.60 (m, 1H), 7.11-7.41 (m, 5H), 7.72 (d, J=8.4 Hz, 1H), 8.48 (s, 1H), 13.41 (br, 1H). Anal. Calcd. for C₂₂H₂₇N₃O₃S-2.5H₂O: C, 57.62; H, 7.03; N, 9.16. Found: C, 57.54; H, 6.75; N, 8.86.

Example 26

5-(Benzyloxy)-2-{[4-(2-tert-butylphenyl)piperazin-1-yl]carbonyl}-1-methyl-1H-indole

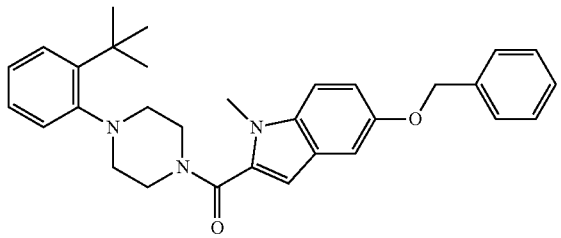 [SMILES: Cn1c(C(=O)N2CCN(c3ccccc3C(C)(C)C)CC2)cc2cc(OCc3ccccc3)ccc21]

A mixture of 5-(benzyloxy)-2-{[4-(2-tert-butylphenyl)piperazin-1-yl]carbonyl}-1H-indole obtained in Example 23 (880 mg), iodomethane (0.143 mL), sodium hydride (92 mg, 60% in oil dispersion), and N,N-dimethylformamide (5 mL) was stirred at room temperature for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (860 mg, 95%) as crystals.

¹H-NMR (300 MHz, DMSO-d₆) δ 1.43 (s, 9H), 2.80-2.91 (m, 4H), 3.10-3.27 (m, 2H), 3.77 (s, 3H), 4.30-4.44 (m, 2H), 5.11 (s, 2H), 6.62 (s, 1H), 6.96-7.00 (m, 1H), 7.11-7.47 (m, 11H). LC/MS (ESI+) m/z: 482 (M+H)⁺.

Example 27

5-{[4-(2-tert-Butylphenyl)piperazin-1-yl]carbonyl}-1H-benzimidazole-2-thiol

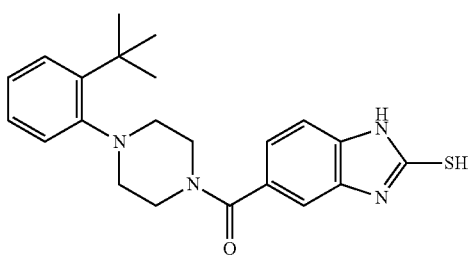 [SMILES: CC(C)(C)c1ccccc1N1CCN(C(=O)c2ccc3[nH]c(S)nc3c2)CC1]

A mixture of 1-(2-tert-butylphenyl)piperazine dihydrochloride obtained in Reference Example 1 (582 mg), 2 mercapto-1H-benzimidazole-5-carboxylic acid (466 mg), 1-ethyl-3-(3-dimethylaminopropyl)carbodiimide hydrochloride (460 mg), 1-hydroxy-1H-benzotriazole monohydrate (368 mg), triethylamine (1.39 mL), and N,N-dimethylformamide (5 mL) was stirred at room temperature for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (800 mg, quant.) as crystals.

¹H-NMR (300 MHz, DMSO-d₆) δ 1.41 (s, 9H), 2.73-2.89 (m, 4H), 3.18-3.28 (m, 2H), 3.50-3.64 (m, 1H), 4.30-4.50 (m, 1H), 7.12-7.32 (m, 6H), 7.42 (d, J=7.8 Hz, 1H), 12.69 (s, 2H). LC/MS (ESI+) m/z: 395 (M+H)⁺.

Example 28

2-{[4-(2-tert-Butylphenyl)piperazin-1-yl]carbonyl}-1-methyl-1H-indol-5-ol

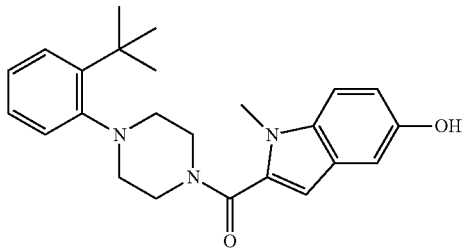 [SMILES: Cn1c(C(=O)N2CCN(c3ccccc3C(C)(C)C)CC2)cc2cc(O)ccc21]

A mixture of 5-(benzyloxy)-2-{[4-(2-tert-butylphenyl) piperazin-1-yl]carbonyl}-1-methyl-1H-indole obtained in Example 26 (830 mg), palladium carbon (contains 50% H₂O, 100 mg), methanol (100 mL), and tetrahydrofuran (50 mL) was stirred at room temperature under hydrogen atmosphere (5 atm). The mixture was filtered and evaporated under reduced pressure to provide the title compound (540 mg, 80%) as a solid.

¹H NMR (300 MHz, DMSO-d₆) δ 1.43 (s, 9H), 2.73-2.91 (m, 4H), 3.15-3.34 (m, 2H), 3.73 (s, 3H), 4.20-4.50 (m, 2H), 6.53 (s, 1H), 6.77 (dd, J=8.7, 2.4 Hz, 1H), 6.89 (d, J=2.4 Hz, 1H), 7.11-7.33 (m, 4H), 7.42 (dd, J=7.5, 1.5 Hz, 1H), 8.89 (br, 1H). Anal. Calcd. for C₂₄H₂₉N₃O₂·0.25H₂O: C, 72.79; H, 7.51; N, 10.61. Found: C, 72.86; H, 7.56; N, 10.38.

Example 29 tert-Butyl [(5-{[4-(2-tert-butylphenyl)piperazin-1-yl] carbonyl}-1H-benzimidazol-2-yl)sulfanyl]acetate

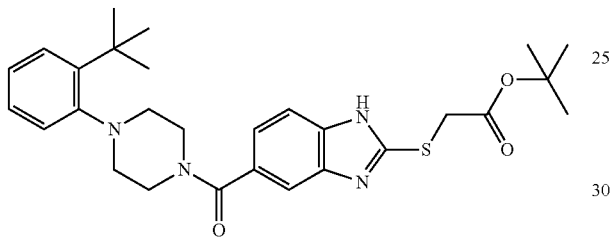

A mixture of 5-{[4-(2-tert-butylphenyl)piperazin-1-yl] carbonyl}-1H-benzimidazole-2-thiol obtained in Example 27 (750 mg), tert-butyl bromoacetate (429 mg), potassium carbonate (415 mg), and N,N-dimethylformamide (5 mL) was stirred at room temperature for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (silica gel, 90:10-50:50 hexane/ethyl acetate) to provide the title compound (785 mg, 81%) as an amorphous.

¹H NMR (300 MHz, CDCl₃) δ 1.45 (s, 9H), 1.50 (s, 9H), 2.80-2.96 (m, 4H), 3.10-3.35 (m, 2H), 3.89 (s, 2H), 3.89-3.91 (m, 1H), 4.70-4.80 (m, 1H), 7.13-7.74 (m, 7H), 11.23 (s, 1H).

Example 30

Methyl [(2-{[4-(2-tert-Butylphenyl)piperazin-1-yl] carbonyl}-1-methyl-1H-indol-5-yl)oxy]acetate

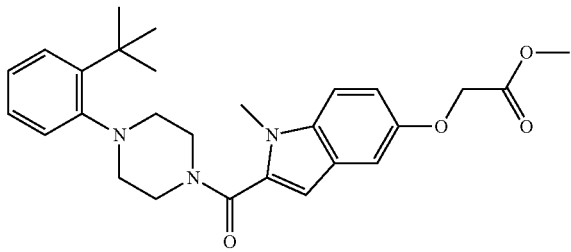 [SMILES: COC(=O)COc1ccc2c(c1)cc(C(=O)N1CCN(c3ccccc3C(C)(C)C)CC1)n2C]

A mixture of 2-{[4-(2-tert-butylphenyl)piperazin-1-yl] carbonyl}-1-methyl-1H-indol-5-ol obtained in Example 28 (510 mg), methyl bromoacetate (239 mg), potassium carbonate (276 mg), and N,N-dimethylformamide (5 mL) was stirred at 60° C. for 3 h. Water was added to the reaction solution, and the mixture was extracted with ethyl acetate. The ethyl acetate layer was washed with saturated brine, and dried over anhydrous magnesium sulfate. The solvent was evaporated under reduced pressure to afford crystals. Crystals were washed with diethyl ether and dried under reduced pressure to provide the title compound (509 mg, 84%) as crystals.

¹H-NMR (300 MHz, DMSO-d₆) δ 1.43 (s, 9H), 2.81-2.91 (m, 4H), 3.20-3.39 (m, 2H), 3.69 (s, 3H), 3.77 (s, 3H), 4.10-4.20 (m, 1H), 4.50-4.60 (m, 1H), 4.78 (s, 2H), 6.63 (s, 1H), 6.94 (dd, J=9.0, 2.4 Hz, 1H), 7.05 (d, J=2.4 Hz, 1H), 7.14 (t, J=7.8 Hz, 1H), 7.23 (t, J=6.9 Hz, 1H), 7.32 (d, J=7.8 Hz, 1H), 7.42-7.45 (m, 2H). Anal. Calcd. for C₂₇H₃₃N₃O₄: C, 69.95; H, 7.18; N, 9.16. Found: C, 69.74; H, 7.24; N, 9.05.

Example 31

[(5-{[4-(2-tert-Butylphenyl)piperazin-1-yl]carbonyl}-1H-benzimidazol-2-yl)sulfanyl]acetic acid

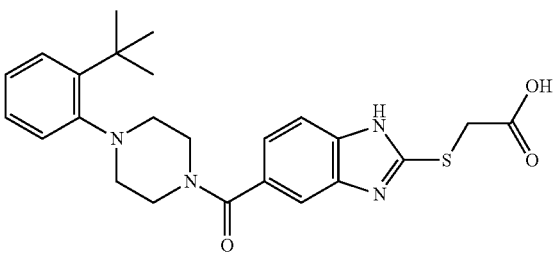 [SMILES: CC(C)(C)c1ccccc1N1CCN(C(=O)c2ccc3[nH]c(SCC(=O)O)nc3c2)CC1]

A mixture of tert-butyl [(5-{[4-(2-tert-butylphenyl)piperazin-1-yl]carbonyl}-1H-benzimidazol-2-yl)sulfanyl]acetate obtained in Example 29 (763 mg) and trifluoroacetic acid (3 mL) was stirred at room temperature for 3 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (475 mg, 70%) as crystals.

¹H NMR (300 MHz, DMSO-d₆) δ 1.41 (s, 9H), 2.76-2.90 (m, 4H), 3.12-3.24 (m, 2H), 3.54-3.66 (m, 1H), 4.16 (s, 2H), 4.36-4.40 (m, 1H), 7.11-7.32 (m, 4H), 7.43-7.55 (m, 3H), 12.87 (br, 2H).

Example 32

[(2-{[4-(2-tert-Butylphenyl)piperazin-1-yl]carbonyl}-1-methyl-1H-indol-5-yl)oxy]acetic acid

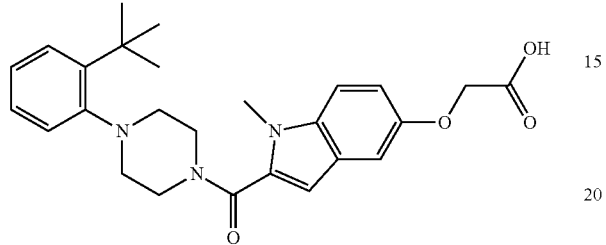

A mixture of methyl [(2-{[4-(2-tert-butylphenyl)piperazin-1-yl]carbonyl}-1-methyl-1H-indol-5-yl)oxy]acetate obtained in Example 30 (470 mg), 1 M sodium hydroxide solution (5 mL), methanol (50 mL), and tetrahydrofuran (50 mL) was stirred at room temperature for 2 h. 1 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (455 mg, 100%) as crystals.

¹H NMR (300 MHz, DMSO-d₆) δ 1.43 (s, 9H), 2.81-2.91 (m, 4H), 3.20-3.40 (m, 3H), 3.77 (s, 3H), 4.04-4.16 (m, 1H), 4.65 (s, 2H), 6.63 (s, 1H), 6.91 (dd, J=9.0, 2.4 Hz, 1H), 7.02 (d, J=2.4 Hz, 1H), 7.14 (t, J=7.2 Hz, 1H), 7.23 (t, J=7.2 Hz, 1H), 7.31 (d, J=7.5 Hz, 1H), 7.43 (d, J=9.0 Hz, 2H), 12.91 (br, 1H). Anal. Calcd. for $C_{26}H_{31}N_3O_4 \cdot 0.2H_2O$: C, 68.91; H, 6.98; N, 9.27. Found: C, 69.12; H, 7.09; N, 9.12.

Example 33

Methyl 4-{[4-(2-tert-butylphenyl)piperazin-1-yl]carbonyl}benzoate

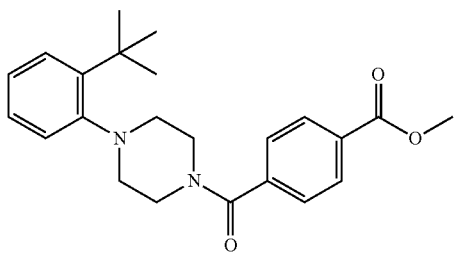 [SMILES: COC(=O)c1ccc(C(=O)N2CCN(c3ccccc3C(C)(C)C)CC2)cc1]

A mixture of 1-(2-tert-butylphenyl)piperazine dihydrochloride obtained in Reference Example 1 (0.5 g), methyl 4-(chlorocarbonyl)benzoate (397 mg), triethylamine (0.836 mL), and tetrahydrofuran (10 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (NH-silica gel, 90:10-50:50 hexane/ethyl acetate) to provide the title compound (628 mg, 96%) as crystals.

¹H NMR (300 MHz, CDCl₃) δ 1.44 (s, 9H), 2.70-2.90 (m, 2H), 2.93-2.98 (m, 2H), 3.10-3.20 (m, 1H), 3.30-3.50 (m, 1H), 3.60-3.70 (m, 1H), 3.93 (s, 3H), 4.73-4.77 (m, 1H), 7.13-7.30 (m, 3H), 7.37 (dd, J=7.8, 1.8 Hz, 1H), 7.50-7.54 (m, 2H), 8.07-8.11 (m, 2H). Anal. Calcd. for $C_{23}H_{28}N_2O_3$: C, 72.60; H, 7.42; N, 7.36. Found: C, 72.46; H, 7.56; N, 7.31.

Example 34

4-{[4-(2-tert-Butylphenyl)piperazin-1-yl]carbonyl}benzoic acid

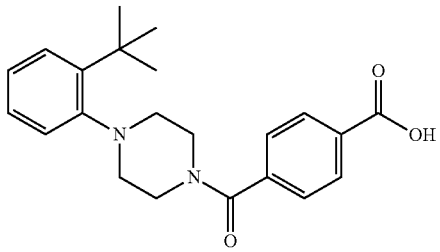 [SMILES: CC(C)(C)c1ccccc1N1CCN(C(=O)c2ccc(C(=O)O)cc2)CC1]

A mixture of methyl 4-{[4-(2-tert-butylphenyl)piperazin-1-yl]carbonyl}benzoate obtained in Example 33 (608 mg), 1 M sodium hydroxide solution (5 mL), methanol (20 mL), and tetrahydrofuran (5 mL) was stirred at 50° C. for 4 h. 1 M hydrochloric acid solution was added to the reaction solution, and the solvent was evaporated under reduced pressure to afford crystals. Crystals were washed with water, diethyl ether and dried under reduced pressure to provide the title compound (580 mg, 99%) as colorless crystals.

¹H NMR (300 MHz, CDCl₃) δ 1.44 (s, 9H), 2.80-2.99 (m, 4H), 3.10-3.20 (m, 1H), 3.40-3.50 (m, 1H), 3.60-3.70 (m, 1H), 4.75-4.78 (m, 1H), 7.13-7.29 (m, 3H), 7.37 (d, J=7.5 Hz, 1H), 7.56 (d, J=8.1 Hz, 2H), 8.16 (d, J=8.1 Hz, 2H), 13.56 (br, 1H).

Example 35 tert-Butyl [(5-{[4-(2-tert-butylphenyl)piperazin-1-yl]carbonyl}pyridin-3-yl)oxy]acetate

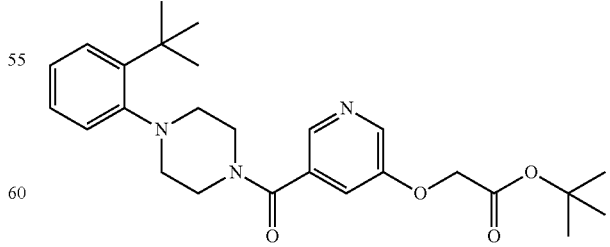

A mixture of 1-(2-tert-butylphenyl)piperazine dihydrochloride obtained in Reference Example 1 (500 mg), 5-hydroxypyridine-3-carboxylic acid (287 mg), 1-ethyl-3-(3-dimethylaminopropyl)carbodiimide hydrochloride (403 mg), 1-hydroxy-1H-benzotriazole monohydrate (322 mg), triethylamine (0.488 mL), and N,N-dimethylformamide (5 mL) was stirred at room temperature for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide a powder (LC/MS (ESI+) m/z: 340 (M+H)$^+$). A mixture of the powder, tert-butyl bromoacetate (683 mg), potassium carbonate (691 mg), and N,N-dimethylformamide (10 mL) was stirred at 60° C. for 5 h. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (silica gel, 90:10-50:50 hexane/ethyl acetate) to provide the title compound (530 mg, 68%) as crystals.

$^1$H NMR (300 MHz, CDCl$_3$) δ 1.45 (s, 9H), 1.51 (s, 9H), 2.84-2.95 (m, 4H), 3.10-3.20 (m, 1H), 3.40-3.50 (m, 1H), 3.65-3.75 (m, 1H), 4.60 (s, 2H), 4.67-4.73 (m, 1H), 7.13-7.30 (m, 4H), 7.37 (dd, J=7.8, 1.5 Hz, 1H), 8.34-8.37 (m, 2H).

Example 36

[(5-{[4-(2-tert-Butylphenyl)piperazin-1-yl]carbonyl}pyridin-3-yl)oxy]acetic acid

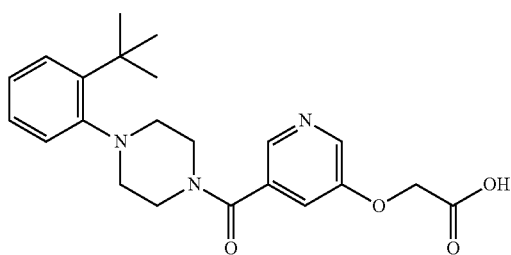 [SMILES: CC(C)(C)c1ccccc1N1CCN(C(=O)c2cncc(OCC(=O)O)c2)CC1]

A mixture of tert-butyl [(5-{[4-(2-tert-butylphenyl)piperazin-1-yl]carbonyl}pyridin-3-yl)oxy]acetate obtained in Example 35 (500 mg) and trifluoroacetic acid (7 mL) was stirred at room temperature for 3 h. Water was added to the reaction solution, and subsequently 1 M sodium hydroxide solution was added to the mixture to pH 5-6. The resulting precipitate was collected and dried under reduced pressure to provide the title compound (405 mg, 93%) as crystals.

$^1$H NMR (300 MHz, DMSO-d$_6$) δ 1.42 (s, 9H), 2.60-2.70 (m, 1H), 2.85-3.03 (m, 4H), 3.40-3.62 (m, 2H), 4.50-4.60 (m, 1H), 4.85 (s, 2H), 7.13 (t, J=6.3 Hz, 1H), 7.23 (t, J=6.3 Hz, 1H), 7.32 (d, J=6.6 Hz, 1H), 7.42-7.47 (m, 2H), 8.27 (s, 1H), 8.35 (d, J=2.7 Hz, 1H), 13.11 (br, 1H). Anal. Calcd. for C$_{22}$H$_{27}$N$_3$O$_4$·2.3H$_2$O: C, 60.20; H, 7.26; N, 9.57. Found: C, 60.47; H, 7.21; N, 9.26. LC/MS (ESI+) m/z: 398 (M+H)$^+$.

Example 37 tert-Butyl 4-[(4-{[4-(2-tert-butylphenyl)piperazin-1-yl]carbonyl}phenoxy)methyl]piperidine-1-carboxylate

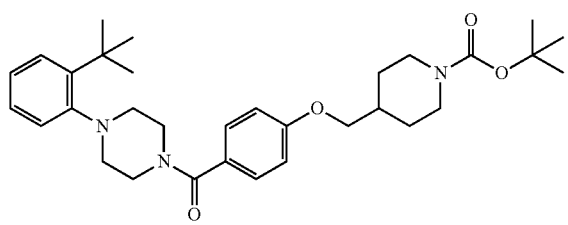 [SMILES: CC(C)(C)OC(=O)N1CCC(COc2ccc(C(=O)N3CCN(c4ccccc4C(C)(C)C)CC3)cc2)CC1]

A mixture of 1-(2-tert-butylphenyl)piperazine dihydrochloride obtained in Reference Example 1 (1.0 g), 4-{[1-(tert-butoxycarbonyl)piperidin-4-yl]methoxy}benzoic acid obtained in Reference Example 6 (1.41 g), 1-ethyl-3-(3-dimethylaminopropyl)carbodiimide hydrochloride (824 mg), 1-hydroxy-1H-benzotriazole monohydrate (659 mg), triethylamine (1.53 mL), and N,N-dimethylformamide (10 mL) was stirred at room temperature for over-night. Water was added to the reaction solution, and the mixture was extracted with ethyl acetate. The ethyl acetate layer was washed with saturated brine, and dried over anhydrous magnesium sulfate. The solvent was evaporated under reduced pressure, and the residue was purified by flash column chromatography (NH-silica gel, 10:90-0:100 hexane/ethyl acetate) to provide the title compound (1.6 g, 87%) as crystals.

$^1$H NMR (300 MHz, CDCl$_3$) δ 1.20-1.40 (m, 2H), 1.45 (s, 9H), 1.47 (s, 9H), 1.80-1.85 (m, 2H), 1.92-1.98 (m, 1H), 2.71-2.95 (m, 6H), 3.10-3.30 (m, 3H), 3.82 (d, J=6.3 Hz, 2H), 4.11-4.15 (m, 2H), 4.60-4.80 (m, 1H), 6.87-6.92 (m, 2H), 7.12-7.30 (m, 3H), 7.36-7.45 (m, 3H). Anal. Calcd. for C$_{32}$H$_{45}$N$_3$O$_4$: C, 71.74; H, 8.47; N, 7.84. Found: C, 71.48; H, 8.49; N, 7.75.

Example 38

2-[4-(2-tert-Butylphenyl)piperazin-1-yl]-2-oxo-N-(pentylsulfonyl)acetamide

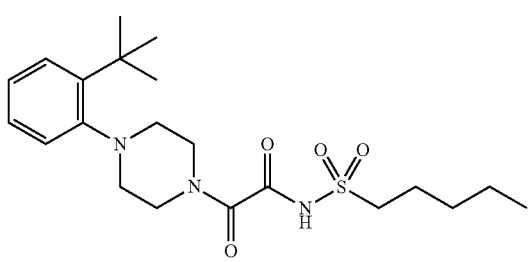 [SMILES: CCCCCS(=O)(=O)NC(=O)C(=O)N1CCN(c2ccccc2C(C)(C)C)CC1]

A mixture of [4-(2-tert-butylphenyl)piperazin-1-yl](oxo)acetic acid obtained in Example 44 (450 mg), pentane-1-sulfonamide (247 mg), 2-methyl-6-nitrobenzoic anhydride (689 mg), N,N-dimethylaminopyridine (189 mg), triethylamine (0.648 mL), and acetonitrile (5 mL) was stirred at room temperature for over-night. 1 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure, and the residue was subjected to purification by high performance liquid chromatography [Column: Gilson, Ltd. High throughput purification system, YMC Combiprep ODS-A, S-5 μm, 50 mm×20 mm; Gradient cycle: H₂O (contains 0.1% CF₃COOH)-acetonitrile (contains 0.1% CF₃COOH), 90:10 (0 min)-90:10 (1 min)-10:90 (4.2 min)-10:90 (5.4 min)-90:10 (5.5 min)-90:10 (5.6 min); Flow rate: 25 mL/min; detection wavelength: UV 220 nm]. 1 M sodium hydroxide solution (20 mL) was added to the mixture obtained by HPLC purification and subsequently 1 M hydrochloric acid solution (10.5 ml) was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (410 mg, 62%) as crystals.

¹H NMR (300 MHz, DMSO-d₆) δ 0.86 (t, J=7.2 Hz, 3H), 1.20-1.36 (m, 4H), 1.41 (s, 9H), 1.62-1.73 (m, 2H), 2.81-2.93 (m, H), 3.33-3.58 (m, 4H), 4.25-4.29 (m, 1H), 7.12-7.17 (m, 1H), 7.21-7.26 (m, 1H), 7.31-7.35 (m, 2H), 12.48 (br, 1H). Anal. Calcd. for $C_{21}H_{33}N_3O_4S$: C, 59.55; H, 7.85; N, 9.92. Found: C, 59.51; H, 7.85; N, 9.78. LC/MS (ESI+) m/z: 424 (M+H)⁺.

Example 39

2-[4-(2-tert-Butylphenyl)piperazin-1-yl]-N-[(cyclopropylmethyl)sulfamoyl]-2-oxoacetamide

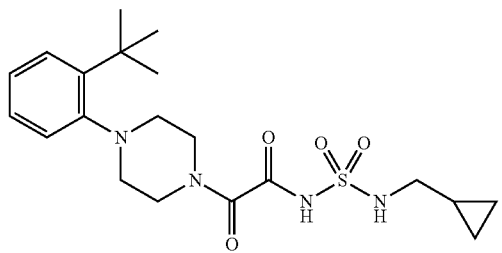 [SMILES: CC(C)(C)c1ccccc1N1CCN(C(=O)C(=O)NS(=O)(=O)NCC2CC2)CC1]

A mixture of [4-(2-tert-butylphenyl)piperazin-1-yl](oxo)acetic acid obtained in Example 44 (450 mg), N-(cyclopropylmethyl)sulfamide (249 mg), 2-methyl-6-nitrobenzoic anhydride (689 mg), N,N-dimethylaminopyridine (189 mg), triethylamine (0.648 mL), and acetonitrile (5 mL) was stirred at room temperature for 16 h. 1 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure, and the residue was subjected to purification by high performance liquid chromatography [Column: Gilson, Ltd. High throughput purification system, YMC Combiprep ODS-A, S-5 μm, 50 mm×20 mm; Gradient cycle: H₂O (contains 0.1% CF₃COOH)-acetonitrile (contains 0.1% CF₃COOH), 90:10 (0 min)-90:10 (1 min)-10:90 (4.2 min)-10:90 (5.4 min)-90:10 (5.5 min)-90:10 (5.6 min); Flow rate: 25 mL/min; detection wavelength: UV 220 nm]. 1 M sodium hydroxide solution (10 mL) was added to the mixture obtained by HPLC purification and subsequently 1 M hydrochloric acid solution (10 ml) was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (255 mg, 39%) as crystals.

¹H NMR (300 MHz, DMSO-d₆) δ 0.16-0.26 (m, 2H), 0.35-0.46 (m, 2H), 0.86-1.01 (m, 1H), 1.41 (s, 9H), 2.79-3.00 (m, 7H), 3.33-3.40 (m, 1H), 3.53-3.57 (m, 1H), 4.25-4.29 (m, 1H), 7.12-7.18 (m, 1H), 7.21-7.27 (m, 1H), 7.31-7.37 (m, 2H), 8.16 (br, 1H), 12.23 (br, 1H). Anal. Calcd. for $C_{20}H_{30}N_4O_4S \cdot 0.2H_2O$: C, 56.37; H, 7.19; N, 23.15. Found: C, 56.44; H, 7.14; N, 12.95. LC/MS (ESI+) m/z: 423 (M+H)⁺.

Example 40

1-(2-tert-Butylphenyl)-4-{[4-(chloromethyl)phenyl]carbonyl}piperazine

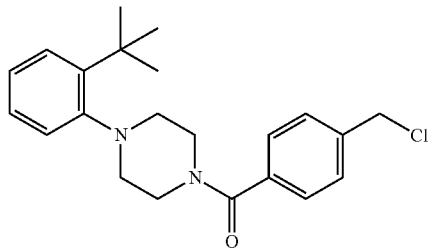 [SMILES: CC(C)(C)c1ccccc1N1CCN(C(=O)c2ccc(CCl)cc2)CC1]

A mixture of 1-(2-tert-butylphenyl)piperazine dihydrochloride obtained in Reference Example 1 (1.0 g), 4-(chloromethyl)benzoyl chloride (756 mg), triethylamine (1.53 mL), and tetrahydrofuran (30 mL) was stirred at room temperature for 16 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (1.35 g, quant.) as crystals.

¹H NMR (300 MHz, CDCl₃) δ 1.45 (s, 9H), 2.81-2.95 (m, 4H), 3.08-3.11 (m, 1H), 3.29-3.49 (m, 1H), 3.61-3.81 (m, 1H), 4.60 (s, 2H), 4.67-4.83 (m, 1H), 7.13-7.30 (m, 3H), 7.36-7.42 (m, 1H), 7.45-7.48 (m, 4H).

Example 41

1-(2-tert-Butylphenyl)-4-{[4-(piperidin-4-ylmethoxy)phenyl]carbonyl}piperazine

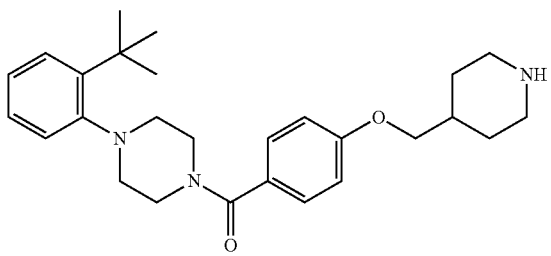 [SMILES: CC(C)(C)c1ccccc1N1CCN(C(=O)c2ccc(OCC3CCNCC3)cc2)CC1]

A mixture of tert-butyl 4-[(4-{[4-(2-tert-butylphenyl)piperazin-1-yl]carbonyl}phenoxy)methyl]piperidine-1-carboxylate obtained in Example 37 (1.5 g), 4 M hydrochloric acid-ethyl acetate solution (20 mL), ethyl acetate (100 mL), and methanol (100 mL) was stirred at room temperature for 16 h. The solvent was evaporated. 1 M sodium hydroxide solution was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (1.1 g, 90%) as crystals.

$^1$H NMR (300 MHz, DMSO-d$_6$) δ 1.08-1.21 (m, 2H), 1.41 (s, 9H), 1.66-1.70 (m, 2H), 1.74-1.81 (m, 1H), 2.21 (br, 1H), 2.42-2.46 (m, 2H), 2.76-2.87 (m, 4H), 2.92-2.96 (m, 2H), 3.10-3.38 (m, 3H), 3.83 (d, J=6.3 Hz, 2H), 4.38-4.44 (m, 1H), 6.97 (d, J=8.4 Hz, 2H), 7.13 (t, J=7.5 Hz, 1H), 7.19-7.24 (m, 1H), 7.29-7.34 (m, 1H), 7.40-7.43 (m, 3H). Anal. Calcd. for $C_{27}H_{37}N_3O_2$: C, 74.45; H, 8.56; N, 9.65. Found: C, 74.23; H, 8.55; N, 9.54.

From Example 42 to Example 58, mass spectra were obtained on a Finnigan LCQ Duo LCMS ion trap electrospray ionization (ESI) mass spectrometer.

$^1$H NMR spectra were obtained on a Bruker AVANCE 300 spectrometer at 300 MHz or Bruker AVANCE 500 spectrometer at 500 MHz. Spectra are given in ppm (δ) and coupling constants, J values, are reported in hertz. Tetramethylsilane was used as an internal standard.

Example 42

(4-(2-tert-Butylphenyl)piperazin-1-yl)(pyridin-2-yl)methanone

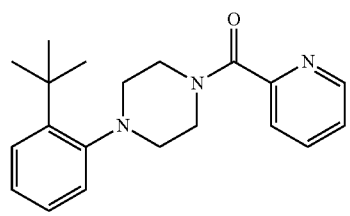 [SMILES: CC(C)(C)c1ccccc1N1CCN(C(=O)c2ccccn2)CC1]

To a stirred solution of 1-(2-tert-butylphenyl)piperazine dihydrochloride (0.064 g, 0.22 mmol) and diisopropylethylamine (0.089 g, 0.69 mmol) in methylene chloride stirring at 0° C. was added picolinoyl chloride hydrochloride (0.043 g, 0.24 mmol) at room temperature. After 2 h the reaction mixture was concentrated under reduced pressure and the residue purified by flash column chromatography (silica gel, 95:5 to 90:10 dichloromethane/methanol) to provide (4-(2-tert-butylphenyl)piperazin-1-yl)(pyridin-2-yl)methanone (0.057 g, 80%) as a brown solid, mp 140-145° C.

$^1$H NMR (500 MHz, DMSO-d$_6$) δ 1.41 (s, 9H), 2.68 (d, J=11.5 Hz, 1H), 2.82-2.90 (m, 3H), 2.99-3.05 (m, 1H), 3.28-3.30 (m, 1H), 3.68-3.76 (m, 1H), 4.57 (d, J=12.5 Hz, 1H), 7.14 (t, J=7.5 Hz, 1H), 7.23 (t, J=7.5 Hz, 1H), 7.32 (d, J=7.5 Hz, 1H), 7.40 (d, J=7.5 Hz, 1H), 7.47-7.49 (m, 1H), 7.63 (d, J=7.5 Hz, 1H), 7.94 (t, J=7.5 Hz, 1H), 8.61 (d, J=4.5 Hz, 1H). LC/MS (ESI+) m/z: 324 (M+H)$^+$.

Example 43

Ethyl 2-[4-(2-tert-butylphenyl)piperazin-1-yl]-2-oxoacetate

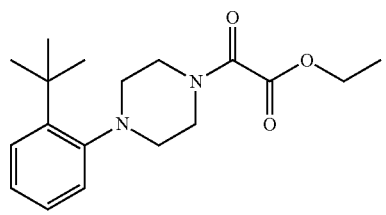 [SMILES: CCOC(=O)C(=O)N1CCN(c2ccccc2C(C)(C)C)CC1]

To a stirred suspension at 0° C. of 1-(2-tert-butylphenyl)piperazine dihydrochloride (0.150 g, 0.51 mmol) in methylene chloride (6.0 mL) was added diisopropylethylamine (0.208 g, 1.61 mmol) followed by ethyl oxalyl chloride (0.073 g, 0.54 mmol) and the reaction mixture was warmed to room temperature. After 16 h the reaction mixture was concentrated under reduced pressure and the residue was purified by flash chromatography (silica, 90:10 to 70:30 heptanes/ethyl acetate; gradient elution) to provide ethyl 2-[4-(2-tert-butylphenyl)piperazin-1-yl]-2-oxoacetate (0.103 g, 64%) as a white solid, mp 95-98° C.

$^1$H NMR (500 MHz, DMSO-d$_6$) δ 1.28 (t, J=7.5 Hz, 3H), 1.41 (s, 9H), 2.81 (br s, 4H), 2.94-3.00 (m, 1H), 3.34-3.40 (m, 1H), 3.59 (d, J=13.0 Hz, 1H), 4.28-4.33 (m, 3H), 7.13-7.17 (m 1H), 7.20-7.24 (m, 1H), 7.31-7.33 (m, 1H), 7.40-7.38 (m, 1H). LC/MS (ESI+) m/z: 319 (M+H)$^+$.

Example 44

2-[4-(2-tert-Butylphenyl)piperazin-1-yl]-2-oxoacetic acid

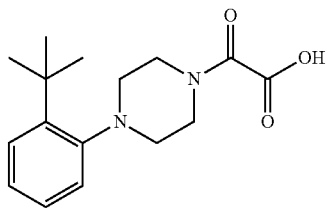 [SMILES: CC(C)(C)c1ccccc1N1CCN(C(=O)C(=O)O)CC1]

To a stirred solution of ethyl 2-[4-(2-tert-butylphenyl)piperazin-1-yl]-2-oxoacetate (0.067 g, 0.21 mmol) in THF (3.0 mL) was added a solution of lithium hydroxide (0.025 g, 1.04 mmol) in water (2.0 mL) at room temperature. After 1 h the reaction mixture was extracted with ethyl acetate (1×5.0 mL) and the aqueous solution acidified with 1 M hydrochloric acid to pH 6. The aqueous layer was extracted with 3:1 chloroform/2-propanol (2×10.0 mL). The combined organics were dried (Na$_2$SO$_4$), filtered, and concentrated under reduced pressure providing 2-[4-(2-tert-butylphenyl)piperazin-1-yl]-2-oxoacetic acid (0.031 g, 51%) as a white solid.

$^1$H NMR (500 MHz, DMSO-d$_6$) δ 1.41 (s, 9H), 2.75-2.81 (m, 5H), 3.19-3.25 (m, 1H), 3.70 (d, J=12.0 Hz, 1H), 4.28-

Example 45

(4-(2-tert-Butylphenyl)piperazin-1-yl)(4-fluorophenyl)methanone

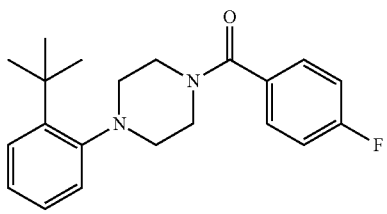 [SMILES: CC(C)(C)c1ccccc1N1CCN(C(=O)c2ccc(F)cc2)CC1]

To a stirred solution of 1-(2-tert-butylphenyl)piperazine dihydrochloride (0.125 g, 0.43 mmol) and diisopropylethylamine (0.171 g, 1.32 mmol) in methylene chloride (5.0 mL) at 0° C. was added 4-fluorobenzoyl chloride (0.080 g, 0.51 mmol) and the reaction mixture was warmed to room temperature. After 2 h the reaction mixture was concentrated under reduced pressure and the residue purified by flash column chromatography (silica gel, 100:0 to 95:5 dichloromethane/methanol) to provided (4-(2-tert-butylphenyl)piperazin-1-yl)(4-fluorophenyl)methanone (0.044 g, 30%) as a white solid, mp 137-139° C.

$^1$H NMR (500 MHz, DMSO-$d_6$) δ 1.41 (s, 9H), 2.68-3.20 (m, 6H), 3.52-3.63 (br s, 1H), 4.57 (br s, 1H), 7.14 (t, J=7.5 Hz, 1H), 7.23 (t, J=7.5 Hz, 1H), 7.26-7.33 (m, 3H), 7.42 (d, J=7.5 Hz, 1H), 8.61 (dd, J=5.5, 3.0 Hz, 2H). LC/MS (ESI+) m/z: 341 (M+H)$^+$.

Example 46

2-(4-(2-tert-Butylphenyl)piperazin-1-yl)-2-oxo-N-(pyridin-2-yl)acetamide

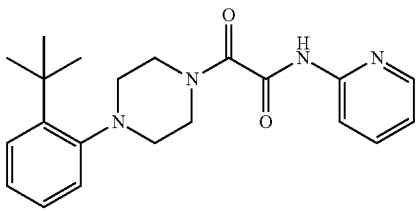 [SMILES: CC(C)(C)c1ccccc1N1CCN(C(=O)C(=O)Nc2ccccn2)CC1]

To a stirred solution of 2-(4-(2-tert-butylphenyl)piperazin-1-yl)-2-oxo-acetic acid (0.086 g, 0.30 mmol) in methylene chloride (4.0 mL) was added EDCI (0.75 g, 0.39 mmol) and HOBt (0.053 g, 0.39 mmol) at room temperature. After 30 min 2-aminopyridine (0.031 g, 0.33 mmol) was added and the reaction mixture was stirred at room temperature for 16 h. After this time, the reaction mixture was concentrated under reduced pressure and the residue purified by flash column chromatography (silica gel, 80:20 heptane/ethyl acetate) to provided 2-(4-(2-tert-butylphenyl)piperazin-1-yl)-2-oxo-N-(pyridin-2-yl)acetamide (0.043 g, 39%) as a white solid, mp 168-172° C.

$^1$H NMR (500 MHz, DMSO-$d_6$) δ 1.41 (s, 9H), 2.75-2.94 (m, 5H), 3.34-3.37 (m, 1H), 3.65-3.75 (m, 1H), 4.33-4.35 (m, 1H), 7.12-7.38 (m, 5H), 7.84 (br s, 1H), 8.06 (br s, 1H), 8.38 (br s, 1H), 11.16 (br s, 1H). LC/MS (ESI+) m/z: 367 (M+H)$^+$.

Example 47

N-Benzyl-2-(4-(2-tert-butylphenyl)piperazin-1-yl)-N-isopropyl-2-oxoacetamide

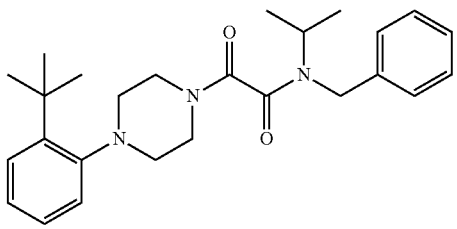 [SMILES: CC(C)N(Cc1ccccc1)C(=O)C(=O)N1CCN(c2ccccc2C(C)(C)C)CC1]

To a stirred solution of 2-(4-(2-tert-butylphenyl)piperazin-1-yl)-2-oxo-acetic acid (0.091 g, 0.31 mmol) in methylene chloride (5.0 mL) was added EDCI (0.078 g, 0.41 mmol) and HOBt (0.055 g, 0.41 mmol) at room temperature. After 40 min N-benzylpropan-2-amine (0.054 g, 0.36 mmol) was added at room temperature. After 16 h the reaction mixture was concentrated under reduced pressure and the residue was purified by flash column chromatography (silica gel, 80:20 to 70:30 heptane/ethyl acetate, gradient elution) to provide N-benzyl-2-(4-(2-tert-butylphenyl)-piperazin-1-yl)-N-isopropyl-2-oxoacetamide as a mixture of cis and trans isomers (0.041 g, 32%) as a white solid, mp 65-68° C.

$^1$H NMR (500 MHz, DMSO-$d_6$) δ 1.11-1.15 (m, 6H), 1.38-1.42 (m, 9H), 2.66-2.83 (m, 4H), 2.91-3.11 (m, 1H), 3.39-3.42 (m, 1H), 3.58-3.61 (m, 1H), 3.98 (br s, 1H), 4.36-4.39 (m, 1H), 4.47-4.54 (m, 2H), 7.13-7.41 (m, 9H). LC/MS (ESI+) m/z: 422 (M+H)$^+$.

Example 48

N-Benzyl-2-(4-(2-tert-butylphenyl)piperazin-1-yl)-N-ethyl-2-oxoacetamide

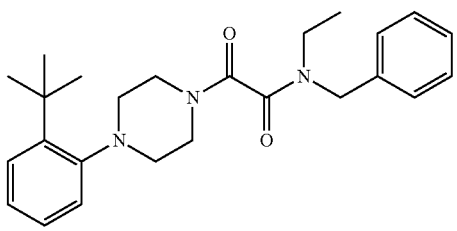 [SMILES: CCN(Cc1ccccc1)C(=O)C(=O)N1CCN(c2ccccc2C(C)(C)C)CC1]

To a stirred solution of 2-(4-(2-tert-butylphenyl)piperazin-1-yl)-2-oxo-acetic acid (0.100 g, 0.34 mmol) in methylene chloride (6.0 mL) was added EDCI (0.085 g, 0.44 mmol) and HOBt (0.060 g, 0.44 mmol) at room temperature. After 1 h N-benzyl-N-ethyl amine (0.050 g, 0.37 mmol) was added at room temperature. After 16 h the reaction mixture was concentrated under reduced pressure and the residue was purified by flash column chromatography (silica gel, 90:10 to 0:100 heptane/ethyl acetate, gradient elution) to provide N-benzyl-2-(4-(2-tert-butylphenyl)piperazin-1-yl)-N-ethyl-2-oxoacetamide as a mixture of cis and trans isomers (0.026 g, 19%) as a white foam.

$^1$H NMR (500 MHz, DMSO-d$_6$) δ 1.01-1.15 (m, 3H), 1.38-1.42 (m, 9H), 2.61-2.97 (m, 4H), 3.20-3.38 (m, 4H), 3.49-3.56 (m, 1H), 4.30-4.50 (m, 1H), 4.58-4.59 (m, 2H), 7.12-7.41 (m, 9H). LC/MS (ESI+) m/z: 408 (M+H)$^+$.

Example 49

[4-(2-tert-Butylphenyl)piperazin-1-yl](5-phenyloxazol-4-yl)methanone

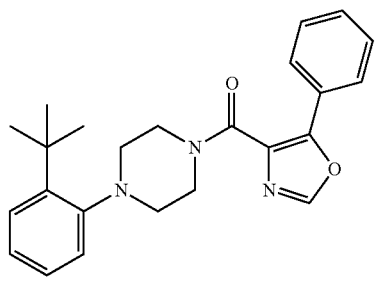 [SMILES: CC(C)(C)c1ccccc1N1CCN(C(=O)c2ncoc2-c2ccccc2)CC1]

To a stirred solution at 0° C. of 1-(2-tert-butylphenyl)piperazine dihydrochloride (0.399 g, 1.37 mmol) and pyridine (0.342 g, 4.33 mmol) in methylene chloride (8.0 mL) was added 5-phenyloxazole-4-carbonyl chloride (0.300 g, 1.45 mmol) and the reaction mixture was warmed to room temperature. After 16 h the reaction mixture was concentrated under reduced pressure, the residue was dissolved in ethyl acetate, washed with 0.5 N hydrochloric acid, water, saturated sodium bicarbonate, dried (Na$_2$SO$_4$), filtered and concentrated under reduced pressure. The residue was purified by flash column chromatography (silica, 30 to 100% ethyl acetate/heptane) to provide a residue. The residue was further purified by preparative HPLC (Column: Phenomenex Luna C18 (2) 10μ 250×21.2 mm, Eluant: 10:90 [95:5:0.05 CH$_3$CN:H$_2$O:TFA]/[95:5:0.05H$_2$O:CH$_3$CN:TFA], isocratic, Flow rate: 15 mL/min, Detection wave length: 254 nm) to provide a solid. The solid was dissolved in ethyl acetate, washed with 1.0 M sodium hydroxide, dried (Na$_2$SO$_4$), filtered and concentrated under reduced pressure to provide [4-(2-tert-butylphenyl)piperazin-1-yl](5-phenyloxazol-4-yl)methanone (0.025 g, 4.7%) as an off-white solid, mp 146-148° C.

$^1$H NMR (500 MHz, DMSO-d$_6$) δ 1.40 (s, 9H), 2.66-2.73 (m, 2H), 2.85-2.87 (m, 2H), 3.01-3.06 (m, 1H), 3.26-3.27 (m, 1H), 3.78 (d, J=13.5 Hz, 1H), 4.60 (d, J=13.5 Hz, 1H), 7.12-7.22 (m, 2H), 7.29-7.32 (m, 2H), 7.45-7.58 (m, 3H), 7.77 (d, J=7.5 Hz, 2H), 8.58 (s, 1H). LC/MS (ESI+) m/z: 390 (M+H)$^+$.

Example 50

[4-(2-tert-Butylphenyl)piperazin-1-yl](phenyl)methanone

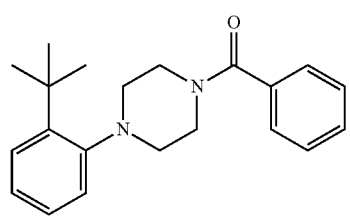 [SMILES: CC(C)(C)c1ccccc1N1CCN(C(=O)c2ccccc2)CC1]

To a stirred solution of 1-(2-tert-butylphenyl)piperazine dihydrochloride (0.150 g, 0.52 mmol) and pyridine (0.166 g, 2.13 mmol) in dichloromethane (5 mL) was added benzoyl chloride (0.079 g, 0.56 mmol) at room temperature. After 16 h the reaction mixture was concentrated under reduced pressure and the residue was purified by flash column chromatography (silica gel, 90:10 to 70:30 heptanes/ethyl acetate, gradient elution) to provide [4-(2-tert-butylphenyl)piperazin-1-yl](phenyl)methanone (0.140 g, 83%) as a white powder, mp 104-106° C.

$^1$H NMR (500 MHz, DMSO-d$_6$) δ 1.41 (s, 9H), 2.49-2.99 (m, 6H), 3.59 (br s, 1H), 4.56 (br s, 1H), 7.14 (t, J=7.0 Hz, 1H), 7.22 (t, J=7.0 Hz, 1H), 7.31 (d, J=8.0 Hz, 1H), 7.42-7.46 (m, 6H). LC/MS (ESI+) m/z: 323 (M+H)$^+$.

Example 51

4-(2-tert-Butylphenyl)-N-ethylpiperazine-1-carboxamide

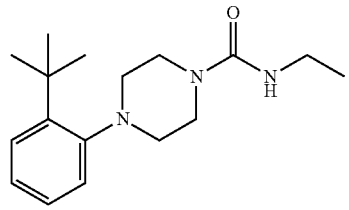 [SMILES: CCNC(=O)N1CCN(c2ccccc2C(C)(C)C)CC1]

To a stirred solution of 1-(2-tert-butylphenyl)piperazine dihydrochloride (0.12 g, 0.41 mmol) in pyridine (4.0 mL) was added ethyl isocyanate (0.036 g, 0.51 mmol) at room temperature and the reaction mixture was heated at 50° C. for 16 h. After this time, the reaction mixture was cooled to room temperature and concentration under reduced pressure. The residue was partitioned between ethyl acetate and 0.5 N hydrochloric acid (2×10 mL), separated and the organic layer was concentrated under reduced pressure. The residue was purified by flash column chromatography (silica gel, 1:9 to 1:1 ethyl acetate/heptanes) to provide 4-(2-tert-butylphenyl)-N-ethylpiperazine-1-carboxamide (0.092 g, 77%) as a white solid, mp 196-198° C.

$^1$H NMR (500 MHz, DMSO-d$_6$) δ 1.03 (t, J=7.0 Hz, 3H), 1.40 (s, 9H), 2.67-2.87 (m, 6H), 3.04-3.10 (m, 2H), 3.96 (d, J=12.5 Hz, 2H), 6.51 (t, J=5.5 Hz, 1H), 7.11-7.14 (m, 1H), 7.19-7.23 (m, 1H), 7.30-7.37 (m, 2H). LC/MS (ESI+) m/z: 290 (M+H)$^+$.

Example 52

Methyl 4-(4-(2-tert-butylphenyl)piperazin-1-yl)-4-oxobutanoate

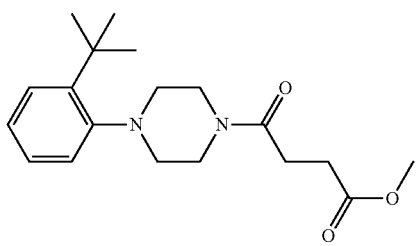 [SMILES: COC(=O)CCC(=O)N1CCN(c2ccccc2C(C)(C)C)CC1]

To a stirred solution at 0° C. of 1-(2-tert-butylphenyl)piperazine (0.218 g, 1.00 mmol) and triethylamine (0.303 g, 3.00 mmol) in methylene chloride (5.0 mL) was added methyl 4-chloro-4-oxobutanoate (0.171 g, 1.10 mmol) and the resulting reaction mixture was warmed to room temperature. After 2 h the reaction mixture was diluted with methylene chloride (10.0 mL), washed with water (20.0 mL), dried (Na$_2$SO$_4$), filtered and concentrated under reduced pressure. The residue was purified by flash column chromatography (silica gel, 50% ethyl acetate/heptanes) to provide methyl 4-(4-(2-tert-butylphenyl)-piperazin-1-yl)-4-oxobutanoate (0.245 g, 74%) as an off-white solid.

$^1$H NMR (500 MHz, CDCl$_3$) δ 1.45 (s, 9H), 2.65-2.92 (m, 9H), 3.36-3.42 (m, 1H), 3.72 (s, 3H), 3.85-3.87 (m, 1H), 4.59-4.61 (m, 1H), 7.14-7.17 (m, 1H), 7.10-7.23 (m, 1H), 7.24 (d, J=1.8 Hz, 1H), 7.38 (dd, J=1.5, 7.9, Hz 1H). LC/MS (ESI+) m/z: 333 (M+H)$^+$.

Example 53

4-(4-(2-tert-Butylphenyl)piperazin-1-yl)-4-oxobutanoic acid

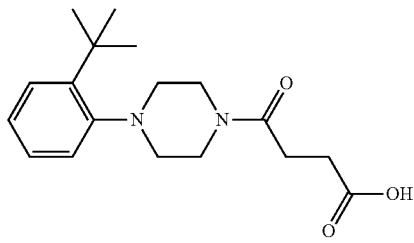 [SMILES: CC(C)(C)c1ccccc1N1CCN(C(=O)CCC(=O)O)CC1]

To a stirred solution of methyl 4-(4-(2-tert-butylphenyl)-piperazin-1-yl)-4-oxobutanoate obtained in Example 52 (0.245 g, 0.74 mmol) in THF (2.0 mL) was added a solution of lithium hydroxide (0.053 g, 2.20 mmol) in 4:1 MeOH/H$_2$O (2.5 mL) at room temperature. After 2 h the reaction mixture was concentrate under reduced pressure. The residue was acidified to pH 1-2 with 1.0 M hydrochloric acid and extracted with ethyl acetate (3×20 mL). The combined organics were washed with saturated sodium chloride (20 mL), dried (Na$_2$SO$_4$), filtered and concentrated under reduced pressure to provide a residue. Trituration of the residue with 1:3 CH$_3$CN/H$_2$O provided 4-(4-(2-tert-butylphenyl)piperazin-1-yl)-4-oxobutanoic acid (0.217 g, 92%) as a white solid, mp 175-176° C.

$^1$H NMR (300 MHz, DMSO-d$_6$) δ 1.41 (s, 9H), 2.44-2.46 (m, 2H), 2.54-2.63 (m, 2H), 2.66-2.87 (m, 5H), 3.19-3.26 (m, 1H), 3.94 (d, J=12.6 Hz, 1H), 4.41 (d, J=9.9 Hz, 1H), 7.11-7.16 (m, 1H), 7.19-7.24 (m, 1H), 7.33-7.37 (m, 2H), 12.04 (br s, 1H). LC/MS (ESI–) m/z: 317 (M–H)$^-$.

Example 54

4-(4-(2-tert-Butylphenyl)piperazin-1-yl)-4-oxobutanenitrile

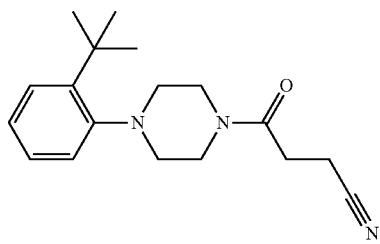 [SMILES: CC(C)(C)c1ccccc1N1CCN(C(=O)CCC#N)CC1]

To a stirred solution at 0° C. of provide 3-cyanopropanoic acid (0.110 g, 1.11 mmol) and DMF (2 drops) in THF (4.0 mL) was added oxalyl chloride (0.144 g, 1.13 mmol) dropwise and the reaction mixture was warmed to room temperature. After 1 h the reaction mixture was concentrated under reduced pressure. To a stirred solution at 0° C. of 1-(2-tert-butylphenyl)piperazine (0.218 g, 1.00 mmol) and triethylamine (0.303 g, 3.00 mmol) in methylene chloride (2.0 mL) was added a solution of the freshly prepared 3-cyanopropanoyl chloride in methylene chloride (2.0 mL) and the reaction mixture was warmed to room temperature. After 2 h the reaction mixture was diluted with methylene chloride (10.0 mL), washed with water (20.0 mL), dried (Na$_2$SO$_4$), filtered and concentrated under reduced pressure. The residue was purified by flash column chromatography (silica gel, 50% ethyl acetate/heptanes) to provide 4-(4-(2-tert-butyl-phenyl) piperazin-1-yl)-4-oxobutanenitrile (0.170 g, 57%) as an off-white solid, mp 109-110° C.

$^1$H NMR (300 MHz, DMSO-d$_6$) δ 1.41 (s, 9H), 2.62-2.88 (m, 9H), 3.19-3.29 (m, 1H), 3.94 (d, J=12.0 Hz, 1H), 4.42 (d, J=11.6 Hz, 1H), 7.10-7.17 (m, 1H), 7.19-7.27 (m, 1H), 7.30-7.36 (m, 2H). LC/MS (ESI+) m/z: 300 (M+H)$^+$.

Example 55

4-(4-(2-tert-Butylphenyl)piperazin-1-yl)-N-(methylsulfonyl)-4-oxobutanamide

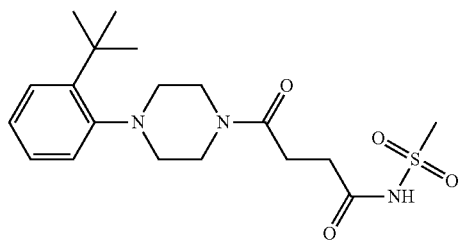 [SMILES: CC(C)(C)c1ccccc1N1CCN(C(=O)CCC(=O)NS(C)(=O)=O)CC1]

To a stirred solution of 4-(4-(2-tert-butylphenyl)piperazin-1-yl)-4-oxobutanoic acid obtained in Example 53 (0.100 g, 0.31 mmol), EDCI (0.090 g, 0.47 mmol), HOBt (0.064 g, 0.47 mmol) and diisopropylethylamine (0.163 g, 1.26 mmol) in methylene chloride (2.0 mL) was added methane-sulfonamide (0.031 g, 0.31 mmol) at room temperature. After 18 h the reaction mixture was diluted with ethyl acetate, washed with 1.0 M hydrochloric acid (5.0 mL), water (5.0 mL), dried (Na$_2$SO$_4$), filtered and concentrated under reduced pressure. The residue was purified by flash column chromatography (silica gel, 95:5 methylene chloride/MeOH) to provide 4-(4-(2-tert-butylphenyl)piperazin-1-yl)-N-(methylsulfonyl)-4-oxobutanamide (0.051 g, 41%) as an off-white solid, mp: 89-90° C.

$^1$H NMR (500 MHz, DMSO-d$_6$) δ 1.41 (s, 9H), 2.51-2.54 (m, 2H), 2.60-2.75 (m, 6H), 2.82-2.86 (m, 1H), 3.20 (s, 3H), 3.20-3.25 (m, 1H), 3.93 (d, J=12.8 Hz, 1H), 4.39 (d, J=11.0 Hz, 1H), 7.12-7.15 (m, 1H), 7.20-7.23 (m, 1H), 7.32 (dd, J=7.9, 1.4 Hz, 1H), 7.35 (dd, J=7.7, 1.1 Hz, 1H), 11.69 (br s, 1H). LC/MS (ESI+) m/z: 396 (M+H)$^+$.

Example 56

4-(2-tert-Butylphenyl)-N-phenylpiperazine-1-carboxamide

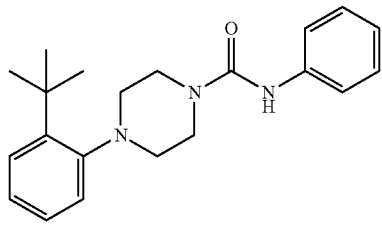 [SMILES: CC(C)(C)c1ccccc1N1CCN(C(=O)Nc2ccccc2)CC1]

To a stirred solution of 1-(2-tert-butylphenyl)piperazine dihydrochloride (0.120 g, 0.41 mmol) in pyridine (4.0 mL) was added phenyl isocyanate (0.055 g, 0.46 mmol) and the reaction mixture was heated to 50° C. After 18 h the reaction mixture was concentrated under reduced pressure and the residue was purified by flash column chromatography (silica gel, 90:10 to 0:100 heptane/ethyl acetate, gradient elution) to provide 4-(2-tert-butylphenyl)-N-phenylpiperazine-1-carboxamide (0.093 g, 67%) as an off-white solid, mp 68-72° C.

$^1$H NMR (500 MHz, DMSO-d$_6$) δ 1.43 (s, 9H), 2.75-2.77 (m, 2H), 2.82-2.87 (m, 2H), 2.98-3.03 (m, 2H), 4.17 (d, J=12.5 Hz, 2H), 6.92-6.96 (m, 1H), 7.12-7.16 (m, 1H), 7.21-7.25 (m, 3H), 7.33 (dd, J=1.5, 8.0 Hz, 1H), 7.40 (dd, J=1.5, 8.0 Hz, 1H), 7.48 (dd, J=1.0, 9.0 Hz, 2H), 8.55 (s, 1H). LC/MS (ESI+) m/z: 338 (M+H)$^+$.

Example 57

3-(4-(2-tert-Butylphenyl)piperazin-1-yl)-3-oxopropanenitrile

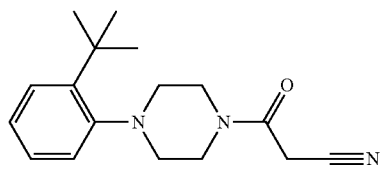 [SMILES: CC(C)(C)c1ccccc1N1CCN(C(=O)CC#N)CC1]

To a stirred solution of provide 1-(2-tert-butylphenyl)piperazine (0.203 g, 0.69 mmol), 2-cyanoacetic acid (0.065 g, 0.77 mmol) and triethylamine (0.279 g, 2.76 mmol) in methylene chloride (5.0 mL) was added bis(2-oxo-3-oxazolidinyl)phosphinic chloride (0.202 g, 0.77 mmol) at room temperature. After 2.5 h the reaction mixture was diluted with methylene chloride (10.0 mL), washed with water (20.0 mL), dried (Na$_2$SO$_4$), filtered and concentrated under reduced pressure. The residue was purified by flash column chromatography (silica gel, 50% ethyl acetate/heptanes) to provide 3-(4-(2-tert-butylphenyl)piperazin-1-yl)-3-oxopropanenitrile (0.114 g, 58%) as an off-white solid, mp 163-164° C.

$^1$H NMR (500 MHz, DMSO-d$_6$) δ 1.41 (s, 9H), 2.71-2.89 (m, 5H), 3.21-3.27 (m, 1H), 3.69-3.72 (m, 1H), 4.03 (d, J=18.8 Hz, 1H), 4.14 (d, J=18.8 Hz, 1H), 4.35-4.38 (m, 1H), 7.12-7.16 (m, 1H), 7.21-7.24 (m, 1H), 7.31-7.35 (m, 2H). LC/MS (ESI+) m/z: 286 (M+H)$^+$.

Example 58

1-(4-(2-tert-Butylphenyl)piperazin-1-yl)-2-(1H-tetrazol-5-yl)ethanone

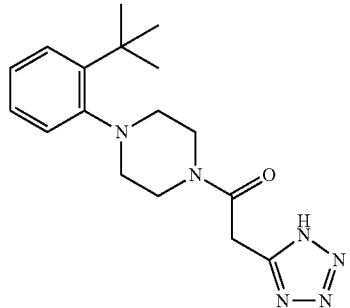 [SMILES: CC(C)(C)c1ccccc1N1CCN(C(=O)Cc2nnn[nH]2)CC1]

A stirred suspension of 3-(4-(2-tert-butylphenyl)piperazin-1-yl)-3-oxopropanenitrile (0.060 g, 0.21 mmol), sodium azide (0.015 g, 0.23 mmol) and zinc bromide (0.055 g, 0.21 mmol) in water (1.0 mL) was heated at 150° C. for 24 h. After this time, the reaction mixture was cooled to room temperature, acidified with 1.0 M hydrochloric acid to pH 1-2 and extracted with ethyl acetate (3×15 mL). The combined organics were washed with water, dried (Na$_2$SO$_4$), filtered and concentrated under reduced pressure. The residue was triturated with acetonitrile to provide 1-(4-(2-tert-butylphenyl)piperazin-1-yl)-2-(1H-tetrazol-5-yl)ethanone (0.018 g, 27%) as an off-white solid, mp 236-237° C.

$^1$H NMR (300 MHz, DMSO-d$_6$) δ 1.42 (s, 9H), 2.32-2.93 (m, 5H), 3.32-3.38 (m, 1H), 4.03-4.08 (m, 1H), 4.17-4.33 (m, 2H), 4.40-4.44 (m, 1H), 7.12-7.17 (m, 1H), 7.21-7.26 (m, 1H), 7.31-7.37 (m, 2H). LC/MS (ESI+) m/z: 329 (M+H)$^+$.

Example 59

1-(2-tert-Butylphenyl)-4-(1H-1,2,4-triazol-3-ylcarbonyl)piperazine

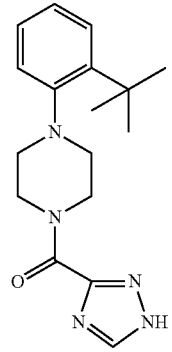 [SMILES: CC(C)(C)c1ccccc1N1CCN(C(=O)c2nc[nH]n2)CC1]

A mixture of 1-(2-tert-butylphenyl)piperazine dihydrochloride obtained in Reference Example 1 (0.30 g, 1.03 mmol), 1H-1,2,4-triazole-3-carboxylic acid (0.12 g, 1.08 mmol), triethylamine (0.22 g, 2.16 mmol), EDCI (0.21 g, 1.08 mmol) and HOBt (0.17 g, 1.08 mmol) in N,N-dimethylformamide (10 mL) was stirred at room temperature for 16 h. The reaction mixture was concentrated under reduced pressure and the resulting residue was partitioned between ethyl acetate and water, and the suspension of white precipitate in ethyl acetate was washed with 10% sodium hydrogen carbonate solution, water, saturated brine, dried over anhydrous magnesium sulfate, filtered and concentrated under reduced pressure to afford white solid. This solid was triturated with diisopropyl ether to give the title compound (0.18 g, 56%) as a white solid, mp 295° C.

$^1$H NMR (300 MHz, DMSO-$d_6$) δ 1.42 (s, 9H), 2.63-3.11 (m, 5H), 3.18-3.47 (m, 1H), 4.38-4.79 (m, 2H), 7.02-7.29 (m, 2H), 7.28-7.47 (m, 2H), 8.46 (s, 1H), 14.46 (br. s., 1H). LC/MS (ESI+) m/z: 313 (M+H)$^+$.

Example 60

2,2,2-Trichloroethyl 4-(2-tert-butylphenyl)piperazine-1-carboxylate

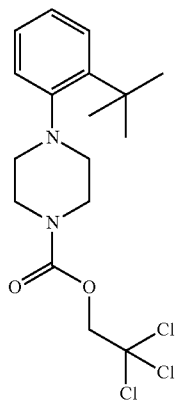 [SMILES: CC(C)(C)c1ccccc1N1CCN(C(=O)OCC(Cl)(Cl)Cl)CC1]

To an ice-cold mixture of 1-(2-tert-butylphenyl)piperazine dihydrochloride obtained in Reference Example 1 (4.00 g, 3.43 mmol), and triethylamine (4.43 g, 43.8 mmol) in tetrahydrofuran (70 mL) was added 2,2,2-trichloroethyl chloroformate (3.06 g, 14.4 mmol) and the mixture was stirred at room temperature for 48 h. The reaction mixture was partitioned between ethyl acetate and water, and the organic layer was washed with water, saturated brine, dried over anhydrous magnesium sulfate, filtered and concentrated under reduced pressure. The resulting residue was filtered through a pad of silica gel eluted with ethyl acetate to afford a white solid. The solid was triturated with hexane to give the title compound (2.54 g, 47%) as a white solid.

$^1$H NMR (300 MHz, CDCl$_3$) δ 1.45 (s, 9H), 2.75-2.98 (m, 4H), 3.04-3.42 (m, 2H), 4.12-4.25 (m, 2H), 4.80 (s, 2H), 7.10-7.21 (m, 1H), 7.21-7.30 (m, 2H), 7.38 (dd, J=7.7, 1.7 Hz, 1H). LC/MS (ESI+) m/z: 393 (M+H)$^+$.

Example 61

1-(2-tert-Butylphenyl)-4-[(1-phenyl-1H-pyrrol-2-yl)carbonyl]piperazine

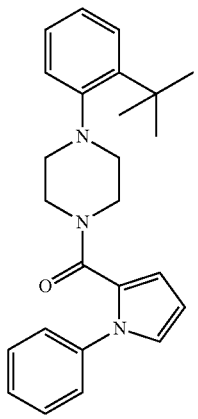 [SMILES: CC(C)(C)c1ccccc1N1CCN(C(=O)c2cccn2-c2ccccc2)CC1]

A mixture of 1-(2-tert-butylphenyl)piperazine dihydrochloride obtained in Reference Example 1 (0.30 g, 1.03 mmol), 1-phenylproline obtained in Reference example 7 (0.21 g, 1.08 mmol), triethylamine (0.22 g, 2.16 mmol), EDCI (0.21 g, 1.08 mmol) and HOBt (0.17 g, 1.08 mmol) in acetonitrile (10 mL) was stirred at room temperature for 16 h. The reaction mixture was concentrated under reduced pressure and the resulting residue was partitioned between ethyl acetate and water, and the suspension of white precipitate in ethyl acetate was washed with 10% sodium hydrogen carbonate solution, water, saturated brine, dried over anhydrous magnesium sulfate, filtered and concentrated under reduced pressure. The resulting residue was purified by silica gel column chromatography (hexane/ethyl acetate 90:10 to 30:70) to afford the title compound (0.10 g, 25%) as a light brown amorphous powder.

$^1$H NMR (300 MHz, CDCl$_3$) δ 1.38 (s, 9H), 2.36-3.25 (m, 8H), 6.26-6.34 (m, 1H), 6.57 (dd, J=3.6, 1.7 Hz, 1H), 6.92-6.97 (m, 1H), 7.00 (dd, J=7.6, 1.9 Hz, 1H), 7.08-7.22 (m, 2H), 7.30-7.43 (m, 4H), 7.44-7.51 (m, 2H). LC/MS (ESI+) m/z: 388 (M+H)$^+$.

Example 62

5-{[4-(2-tert-Butylphenyl)piperazin-1-yl]carbonyl}pyrrolidin-2-one

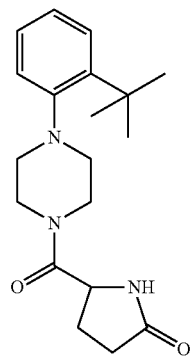 [SMILES: CC(C)(C)c1ccccc1N1CCN(C(=O)C2CCC(=O)N2)CC1]

A mixture of 1-(2-tert-butylphenyl)piperazine dihydrochloride obtained in Reference Example 1 (1.00 g, 3.43 mmol), DL-pyroglutamic acid (0.49 g, 3.78 mmol), triethylamine (0.73 g, 7.20 mmol), EDCI (0.72 g, 3.78 mmol) and HOBt (0.58 g, 3.78 mmol) in acetonitrile (30 mL) was stirred at room temperature for 16 h. The reaction mixture was concentrated under reduced pressure and the resulting residue was partitioned between ethyl acetate and 10% sodium hydrogen carbonate solution. The resulting white precipitate was collected by filtration and washed with diethyl ether to afford the title compound (1.03 g, 91%) as a off-white solid, mp 290° C.

$^1$H NMR (300 MHz, DMSO-d$_6$) δ 1.42 (s, 9H), 1.83-2.22 (m, 3H), 2.24-2.42 (m, 1H), 2.69-2.94 (m, 5H), 3.30 (br. s., 1H), 3.93 (br. s., 1H), 4.41 (br. s., 1H), 4.49-4.68 (m, 1H), 7.10-7.27 (m, 2H), 7.28-7.48 (m, 2H), 7.73 (br. s., 1H). LC/MS (ESI+) m/z: 330 (M+H)$^+$.

Example 63

1-Benzyl-5-{[4-(2-tert-butylphenyl)piperazin-1-yl]carbonyl}pyrrolidin-2-one

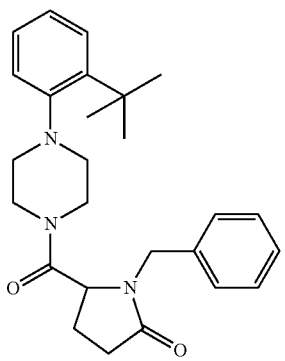 [SMILES: CC(C)(C)c1ccccc1N1CCN(C(=O)C2CCC(=O)N2Cc2ccccc2)CC1]

To a stirring solution of 5-{[4-(2-tert-butylphenyl)piperazin-1-yl]carbonyl}pyrrolidin-2-one obtained in Example 62 (0.30 g, 0.91 mmol) in DMF (5 mL) was added sodium hydride (40 mg, 60% in mineral oil, 1.00 mmol) and the mixture was stirred at room temperature for 30 min. After this time, to the mixture was added benzyl bromide (0.17 g, 1.00 mmol) and the mixture was stirred at room temperature for 2 h. The reaction was quenched with saturated ammonium chloride solution, and the mixture was partitioned between ethyl acetate and water, and the organic layer was washed with water, saturated brine, dried over anhydrous magnesium sulfate, filtered and concentrated under reduced pressure. The resulting solid was triturated with hexane-diisopropyl ether solution to give the title compound (0.30 g, 79%) as a white solid, mp 164° C.

$^1$H NMR (300 MHz, CDCl$_3$) δ 1.43 (d, J=4.2 Hz, 9H), 1.87-2.35 (m, 2H), 2.39-2.99 (m, 7H), 3.12-3.36 (m, 1H), 3.41-3.54 (m, 1H), 3.76-4.01 (m, 1H), 4.20-4.33 (m, 1H), 4.55-4.69 (m, 1H), 5.23 (dd, J=14.8, 9.5 Hz, 1H), 7.13-7.24 (m, 3H), 7.26-7.43 (m, 6H). LC/MS (ESI+) m/z: 420 (M+H)$^+$.

Example 64

Methyl (2-{[4-(2-tert-butylphenyl)piperazin-1-yl]carbonyl}-5-oxopyrrolidin-1-yl)acetate

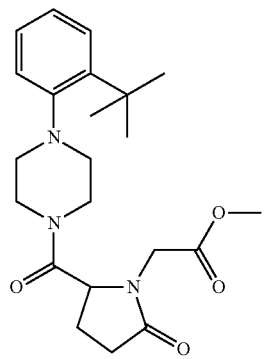 [SMILES: COC(=O)CN1C(=O)CCC1C(=O)N1CCN(c2ccccc2C(C)(C)C)CC1]

To a stirring solution of 5-{[4-(2-tert-butylphenyl)piperazin-1-yl]carbonyl}pyrrolidin-2-one obtained in Example 62 (0.40 g, 1.21 mmol) in DMF (7 mL) was added sodium hydride (54 mg, 60% in mineral oil, 1.34 mmol) and the mixture was stirred at room temperature for 30 min. After this time, to the mixture was added methyl bromoacetate (0.20 g, 1.34 mmol) and the mixture was stirred at room temperature for 2 h. The reaction was quenched with saturated ammonium chloride solution, and the mixture was partitioned between ethyl acetate and water, and the organic layer was washed with water, saturated brine, dried over anhydrous magnesium sulfate, filtered and concentrated under reduced pressure. The resulting residue was washed with hexane-diisopropyl ether solution to give the title compound (0.41 g, 84%) as a white amorphous solid.

$^1$H NMR (300 MHz, CDCl$_3$) δ ppm 1.45 (s, 9H), 1.94-2.17 (m, 1H), 2.37-2.62 (m, 3H), 2.76-3.04 (m, 5H), 3.33-3.55 (m, 1H), 3.66-3.83 (m, 5H), 4.53-4.65 (m, 1H), 4.72-4.95 (m, 2H), 7.11-7.26 (m, 3H), 7.39 (d, J=6.8 Hz, 1H). LC/MS (ESI+) m/z: 402 (M+H)$^+$.

Example 65

(2-{[4-(2-tert-Butylphenyl)piperazin-1-yl]carbonyl}-5-oxopyrrolidin-1-yl)acetic acid

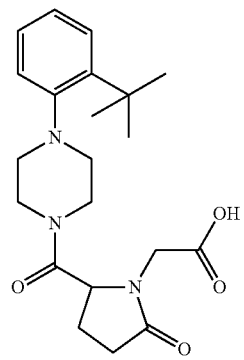 [SMILES: CC(C)(C)c1ccccc1N1CCN(C(=O)C2CCC(=O)N2CC(=O)O)CC1]

To a stirring solution of methyl (2-{[4-(2-tert-butylphenyl) piperazin-1-yl]carbonyl}-5-oxopyrrolidin-1-yl)acetate obtained in Example 64 (0.39 g, 0.97 mmol) in methanol (12 mL) was added 1 M lithium hydroxide (2.9 mmol, 2.9 mL) and the mixture was stirred at room temperature for 1 h. The reaction mixture was acidified with 1 M hydrochloric acid (pH 3) and concentrated under reduced pressure. The resulting residue was partitioned between ethyl acetate and water, and the organic layer was washed with saturated brine, dried over anhydrous magnesium sulfate, filtered and concentrated under reduced pressure. The resulting solid was recrystallized from hexane-diethyl ether to give the title compound (0.24 g, 64%) as a white solid, mp 273° C.

$^1$H NMR (300 MHz, DMSO-$d_6$) δ ppm 1.41 (s, 9H), 1.80-2.04 (m, 1H), 2.14-2.45 (m, 3H), 2.67-2.93 (m, 4H), 3.18-3.38 (m, 2H), 3.40-3.60 (m, 1H), 3.81-3.99 (m, 1H), 4.14-4.34 (m, 1H), 4.35-4.45 (m, 1H), 4.66-4.92 (m, 1H), 7.07-7.29 (m, 2H), 7.27-7.47 (m, 2H), 12.77 (br. s., 1H). LC/MS (ESI+) m/z: 388 (M+H)$^+$.

Example 66

Ethyl [4-(4-bromo-2-tert-butylphenyl)piperazin-1-yl](oxo)acetate

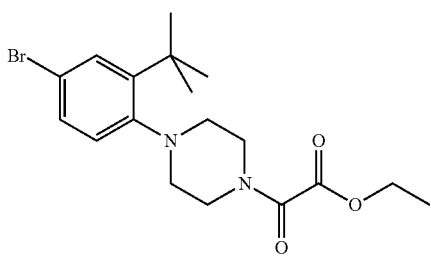

To a stirred suspension of 1-(4-bromo-2-tert-butylphenyl) piperazine dihydrochloride (Reference Example 9, 0.300 g, 0.81 mmol) and triethylamine (564 µl, 4.05 mmol) in THF (10 mL) stirring at 0° C. was added ethyl chloro(oxo)acetate (0.144 mg, 1.05 mmol). The mixture was warmed to room temperature. After 16 h the reaction mixture was poured into water and extracted with ethyl acetate. The organic layer was washed with saturated sodium hydrogen carbonate and brine, dried over MgSO$_4$, and the solvent was evaporated under reduced pressure to give the crude product. The product was purified by flash column chromatography (silica gel, n-hexane/ethyl acetate=80:20 to 50:50) to provide ethyl [4-(4-bromo-2-tert-butylphenyl)piperazin-1-yl](oxo)acetate (0.328 g, quant) as a white solid.

$^1$H NMR (300 MHz, CDCl$_3$) δ 1.38 (t, J=7.19 Hz, 3H), 1.42 (s, 9H), 2.78-2.96 (m, 4H), 2.96-3.09 (m, 1H), 3.38-3.53 (m, 1H), 3.68 (dq, J=12.9, 2.2 Hz, 1H), 4.36 (q, J=7.2 Hz, 2H), 4.52 (dq, J=13.1 2.1 Hz, 1H), 7.13 (d, J=8.3 Hz, 1H), 7.35 (dd, J=8.5, 2.46 Hz, 1H), 7.49 (d, J=2.3 Hz, 1H).

Example 67

[4-(4-Bromo-2-tert-butylphenyl)piperazin-1-yl](oxo) acetic acid

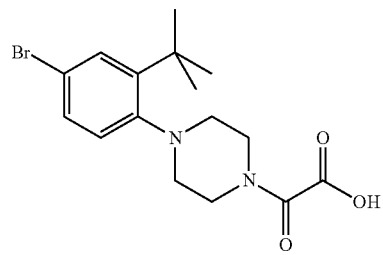

To a stirred solution of ethyl [4-(4-bromo-2-tert-butylphenyl)piperazin-1-yl](oxo)acetate (Example 66, 0.280 g, 0.705 mmol) in THF (5 mL) stirring at 0° C. was added 1 M lithium hydroxide solution (5 mL, 5 mmol). After 2 h the reaction mixture was acidified with 1 M hydrochloric acid solution and extracted with ethyl acetate. The organic layer was washed with brine, dried over MgSO$_4$, and the solvent was evaporated under reduced pressure to provide [4-(4-bromo-2-tert-butylphenyl)piperazin-1-yl](oxo)acetic acid (0.241 g, 92%) as a white powder.

$^1$H NMR (300 MHz, CDCl$_3$) δ 1.43 (s, 9H), 2.79-3.02 (m, 4H), 3.13 (td, J=12.1, 3.8 Hz, 1H), 3.48 (ddd, J=13.3, 9.9, 5.1 Hz, 1H), 4.56 (dd, J=12.6, 1.7 Hz, 1H), 5.09 (dd, J=13.0, 1.7 Hz, 1H), 7.12 (d, J=8.3 Hz, 1H), 7.35 (dd, J=8.5, 2.5 Hz, 1H), 7.49 (d, J=2.3 Hz, 1H).

Example 68

Ethyl 3-[4-(4-bromo-2-tert-butylphenyl)piperazin-1-yl]-3-oxopropanoate

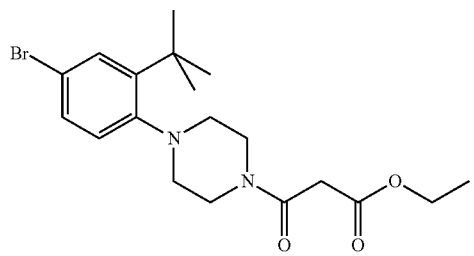

A suspension of 1-(4-bromo-2-tert-butylphenyl)piperazine dihydrochloride (Reference Example 9, 0.300 g, 0.81 mmol), 3-ethoxy-3-oxopropanoic acid (0.128 g, 0.97 mmol), EDCI (0.186 g, 0.972 mmol), HOBt (0.131 g, 0.972 mmol) and triethylamine (339 4.05 mmol) in acetonitrile (10 mL) was stirred at room temperature for 16 h. The reaction mixture was poured into saturated sodium hydrogen carbonate solution and extracted with ethyl acetate. The organic layer was washed with saturated sodium hydrogen carbonate solution and brine, dried over MgSO$_4$, and the solvent was evaporated under reduced pressure to give the crude product. The product was purified by flash column chromatography (silica gel, n-hexane/ethyl acetate=80:20 to 50:50) to provide ethyl 3-[4-(4-bromo-2-tert-butylphenyl)piperazin-1-yl]-3-oxopropanoate (0.308 g, 93%) as a white solid.

¹H NMR (300 MHz, CDCl₃) δ 1.31 (t, J=7.2 Hz, 3H), 1.42 (s, 9H), 2.71-3.00 (m, 5H), 3.36-3.49 (m, 1H), 3.51 (s, 2H), 3.72 (dd, J=12.9, 2.3 Hz, 1H), 4.23 (q, J=7.2 Hz, 2H), 4.63 (dd, J=12.7, 1.7 Hz, 1H), 7.12 (d, J=8.3 Hz, 1H), 7.34 (dd, J=8.3, 2.3 Hz, 1H), 7.48 (d, J=2.3 Hz, 1H).

Example 69

3-[4-(4-Bromo-2-tert-butylphenyl)piperazin-1-yl]-3-oxopropanoic acid

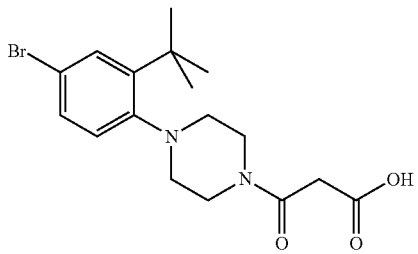

To a stirred solution of ethyl 3-[4-(4-bromo-2-tert-butylphenyl)piperazin-1-yl]-3-oxopropanoate (Example 68, 0.280 g, 0.681 mmol) in THF (5 mL) stirring at 0° C. was added 1 M lithium hydroxide solution (5 mL, 5 mmol). After 2 h the reaction mixture was acidified with 1 M hydrochloric acid solution and extracted with ethyl acetate. The organic layer was washed with brine, dried over MgSO₄, and the solvent was evaporated under reduced pressure to provide 3-[4-(4-bromo-2-tert-butylphenyl)piperazin-1-yl]-3-oxopropanoic acid (0.267 g, quant) as a white powder.

¹H NMR (300 MHz, CDCl₃) δ 1.43 (s, 9H), 2.73-3.09 (m, 5H), 3.33-3.54 (m, 3H), 3.77 (dd, J=12.8, 2.3 Hz, 1H), 4.66 (dd, J=12.8, 1.9 Hz, 1H), 7.10 (d, J=8.3 Hz, 1H), 7.35 (dd, J=8.7, 2.3 Hz, 1H), 7.50 (d, J=2.3 Hz, 1H).

Example 70

Methyl 1-{[4-(2-tert-butylphenyl)piperazin-1-yl]carbonyl}cyclopropanecarboxylate

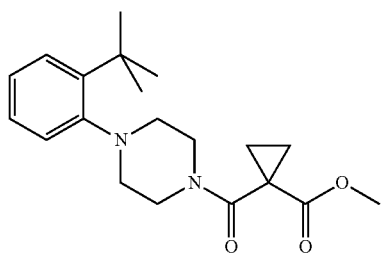 [SMILES: COC(=O)C1(C(=O)N2CCN(c3ccccc3C(C)(C)C)CC2)CC1]

A suspension of 1-(2-tert-butylphenyl)piperazine dihydrochloride (Reference Example 1, 0.500 g, 1.72 mmol), 1-(methoxycarbonyl)cyclopropanecarboxylic acid (0.297 g, 2.06 mmol), EDCI (0.395 g, 2.06 mmol), HOBt (0.278 g, 2.06 mmol) and triethylamine (719 µl, 5.16 mmol) in acetonitrile (10 mL) was stirred at room temperature for 16 h. The reaction mixture was poured into saturated sodium hydrogen carbonate solution and extracted with ethyl acetate. The organic layer was washed with saturated sodium hydrogen carbonate solution and brine, dried over MgSO₄, and the solvent was evaporated under reduced pressure to give the crude product. The product was purified by flash column chromatography (silica gel, n-hexane/ethyl acetate=90:10 to 65:35) to provide methyl 1-{[4-(2-tert-butylphenyl)piperazin-1-yl]carbonyl}cyclopropanecarboxylate (0.485 g, 82%) as a white solid.

¹H NMR (300 MHz, CDCl₃) δ 1.21-1.63 (m, 13H), 2.78-2.92 (m, 4H), 2.93-3.05 (m, 1H), 3.28-3.45 (m, 1H), 3.77 (s, 3H), 3.93 (dd, J=13.1, 2.1 Hz, 1H), 4.59 (dd, J=12.7, 1.7 Hz, 1H), 7.12-7.28 (m, 3H), 7.39 (dd, J=7.8, 1.3 Hz, 1H).

Example 71

1-{[4-(2-tert-Butylphenyl)piperazin-1-yl]carbonyl}cyclopropanecarboxylic acid

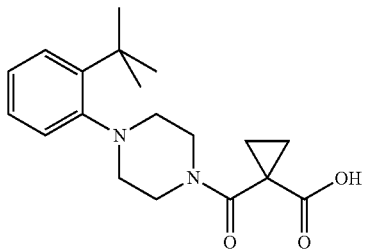 [SMILES: CC(C)(C)c1ccccc1N1CCN(C(=O)C2(C(=O)O)CC2)CC1]

To a stirred solution of methyl 1-{[4-(2-tert-butylphenyl)piperazin-1-yl]carbonyl}cyclopropanecarboxylate (Example 70, 0.417 g, 1.21 mmol) in THF (5 mL) stirring at 0° C. was added 1 M lithium hydroxide solution (5 mL, 5 mmol). After 3 h, it was warmed to room temperature and kept stirring for another 3 h. The reaction mixture was acidified with 1 M hydrochloric acid solution and extracted with ethyl acetate. The organic layer was washed with brine, dried over MgSO₄, and the solvent was evaporated in vacuum to provide 1-{[4-(2-tert-butylphenyl)piperazin-1-yl]carbonyl}cyclopropanecarboxylic acid. (0.307 g, 77%) as a white powder.

¹H NMR (300 MHz, CDCl₃) δ 1.35-1.56 (m, 11H), 1.56-1.69 (m, 2H), 2.87 (d, J=5.3 Hz, 4H), 3.22 (br. s., 2H), 4.30 (br. s., 1H), 6.01 (br. s., 1H), 7.11-7.30 (m, 3H), 7.38 (dd, J=7.6, 1.9 Hz, 1H).

Example 72

Methyl (4-{2-[4-(2-tert-butylphenyl)piperazin-1-yl]-2-oxoethyl}-2,6-dioxopiperidin-1-yl)acetate

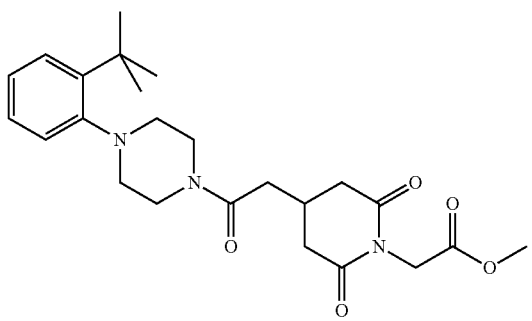 [SMILES: COC(=O)CN1C(=O)CC(CC(=O)N2CCN(c3ccccc3C(C)(C)C)CC2)CC1=O]

A suspension of 4-{2-[4-(2-tert-butylphenyl)piperazin-1-yl]-2-oxoethyl}piperidine-2,6-dione (Example 14, 0.500 g, 1.35 mmol), methyl bromoacetate (0.247 g, 1.62 mmol), and potassium carbonate (0.56 g, 4.05 mmol) in DMF (6 mL) was stirred at 60° C. for 16 h. The reaction mixture was poured into water and extracted with ethyl acetate. The organic layer was washed with saturated sodium hydrogen carbonate solution and brine, dried over MgSO$_4$, and the solvent was evaporated under reduced pressure to give the crude product. The product was purified by flash column chromatography (silica gel, n-hexane/ethyl acetate=50:50 to 0:100) to provide methyl (4-{2-[4-(2-tert-butylphenyl)piperazin-1-yl]-2-oxoethyl}-2,6-dioxopiperidin-1-yl)acetate (0.474 g, 79%) as a white amorphous.

$^1$H NMR (300 MHz, CDCl$_3$) δ 1.44 (s, 9H), 2.42-2.76 (m, 4H), 2.77-2.98 (m, 8H), 3.30-3.43 (m, 1H), 3.72 (s, 3H), 3.84 (dd, J=12.8, 2.3 Hz, 1H), 4.55 (s, 2H), 4.62 (dd, J=12.6, 1.7 Hz, 1H), 7.11-7.30 (m, 3H), 7.38 (dd, J=7.9, 1.5 Hz, 1H).

Example 73

5-[4-(2-tert-Butylphenyl)piperazin-1-yl]-3-{2-[(carboxymethyl)amino]-2-oxoethyl}-5-oxopentanoic acid

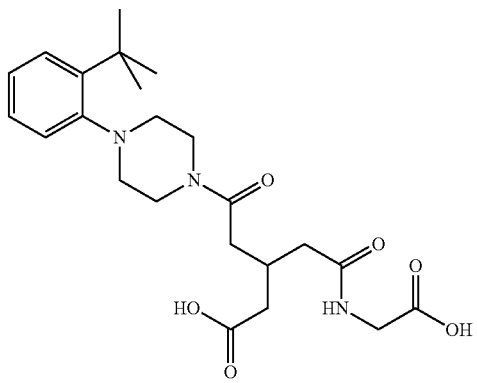 [SMILES: CC(C)(C)c1ccccc1N1CCN(C(=O)CC(CC(=O)O)CC(=O)NCC(=O)O)CC1]

To a stirred solution of methyl (4-{2-[4-(2-tert-butylphenyl)piperazin-1-yl]-2-oxoethyl}-2,6-dioxopiperidin-1-yl)acetate (Example 72, 0.463 g, 1.04 mmol) in THF (5 mL) stirring at 0° C. was added 1 M lithium hydroxide solution (5 mL, 5 mmol). After 3 h the reaction mixture was acidified with 1 M hydrochloric acid solution and extracted with ethyl acetate. The organic layer was washed with brine, dried over MgSO$_4$, and the solvent was evaporated under reduced pressure to provide 5-[4-(2-tert-butylphenyl)piperazin-1-yl]-3-{2-[(carboxymethyl)amino]-2-oxoethyl}-5-oxopentanoic acid (0.505 g, quant) as a pale brown solid.

$^1$H NMR (300 MHz, DMSO-d$_6$) δ 1.41 (s, 9H), 2.24 (d, J=5.7 Hz, 2H), 2.30-2.42 (m, 3H), 2.53-2.65 (m, 1H), 2.65-2.94 (m, 5H), 3.13-3.27 (m, 1H), 3.32 (br. s., 1H), 3.72 (d, J=5.7 Hz, 2H), 3.88-4.01 (m, 1H), 4.43 (br. s., 1H), 7.08-7.18 (m, 1H), 7.22 (td, J=7.4, 1.5 Hz, 1H), 7.27-7.42 (m, 2H), 8.22 (t, J=5.8 Hz, 1H), 12.29 (br. s., 2H).

Example 74

Methyl 4-[(4-{2-[4-(2-tert-butylphenyl)piperazin-1-yl]-2-oxoethyl}-2,6-dioxopiperidin-1-yl)methyl]benzoate

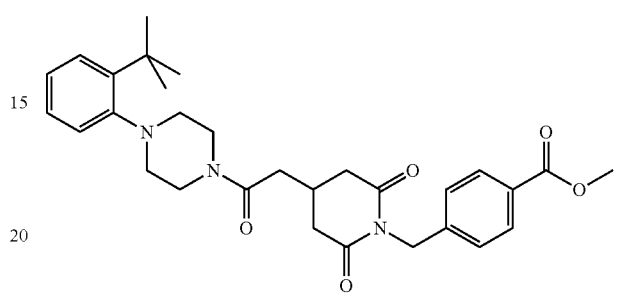

A suspension of 4-{2-[4-(2-tert-butylphenyl)piperazin-1-yl]-2-oxoethyl}piperidine-2,6-dione (Example 14, 0.500 g, 1.35 mmol), methyl 4-(bromomethyl)benzoate (0.370 g, 1.62 mmol), and potassium carbonate (0.56 g, 4.05 mmol) in DMF (6 mL) was stirred at room temperature for 16 h. The reaction mixture was poured into water and extracted with ethyl acetate. The organic layer was washed with saturated sodium hydrogen carbonate solution and brine, dried over MgSO$_4$, and the solvent was evaporated under reduced pressure to give the crude product. The product was purified by flash column chromatography (silica gel, n-hexane/ethyl acetate=90:10 to 20:80) to provide methyl 4-[(4-{2-[4-(2-tert-butylphenyl)piperazin-1-yl]-2-oxoethyl}-2,6-dioxopiperidin-1-yl)methyl]benzoate (0.604 g, 86%) as a white amorphous.

$^1$H NMR (300 MHz, CDCl$_3$) δ 1.44 (s, 9H), 2.27-2.59 (m, 4H), 2.69-3.01 (m, 8H), 3.26-3.38 (m, 1H), 3.60 (dd, J=13.2, 1.5 Hz, 1H), 3.85 (s, 3H), 4.59 (d, J=10.9 Hz, 1H), 5.01 (s, 2H), 7.13-7.25 (m, 3H), 7.34-7.46 (m, 3H), 7.95 (m, 2H).

Example 75

4-[({5-[4-(2-tert-Butylphenyl)piperazin-1-yl]-3-(carboxymethyl)-5-oxopentanoyl}amino)methyl]benzoic acid

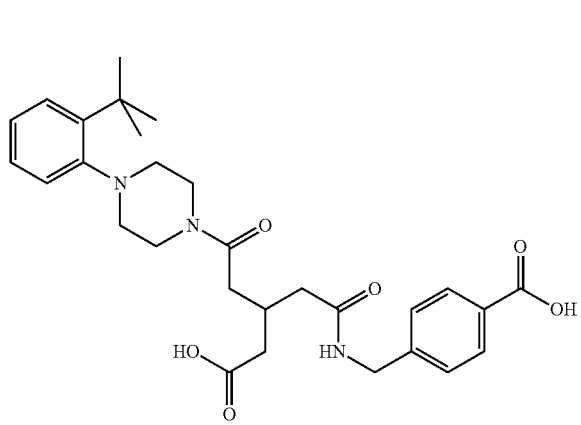 [SMILES: CC(C)(C)c1ccccc1N1CCN(C(=O)CC(CC(=O)O)CC(=O)NCc2ccc(C(=O)O)cc2)CC1]

To a stirred solution of methyl 4-[(4-{2-[4-(2-tert-butylphenyl)piperazin-1-yl]-2-oxoethyl}-2,6-dioxopiperidin-1-yl)methyl]benzoate (Example 74, 0.575 g, 1.11 mmol) in THF (5 mL) stirring at 0° C. was added 1 M lithium hydroxide solution (5 mL, 5 mmol). After 1 h the reaction mixture was warmed to room temperature and kept stirring for 3 h. The mixture was acidified with 1 M hydrochloric acid solution and extracted with ethyl acetate. The organic layer was washed with brine, dried over MgSO$_4$, and the solvent was evaporated under reduced pressure to provide the crude product. The product was purified by flash column chromatography (silica gel, n-hexane/ethyl acetate=90:10 to 20:80) to provide 4-[({5-[4-(2-tert-butylphenyl)piperazin-1-yl]-3-(carboxymethyl)-5-oxopentanoyl}amino)methyl]benzoic acid (0.608 g, quant) as a white solid.

$^1$H NMR (300 MHz, DMSO-d$_6$) δ 1.41 (s, 9H), 2.21-2.46 (m, 6H), 2.55-2.88 (m, 6H), 3.19 (t, J=10.8 Hz, 1H), 3.92 (d, J=12.5 Hz, 1H), 4.33 (d, J=5.7 Hz, 2H), 4.44 (d, J=8.0 Hz, 1H), 7.09-7.17 (m, 1H), 7.21 (td, J=7.5, 1.3 Hz, 1H), 7.27-7.41 (m, 4H), 7.88 (m, 2H), 8.47 (t, J=5.1 Hz, 1H), 12.47 (br. s., 2H).

Example 76

2-[4-(2-tert-Butylphenyl)piperazin-1-yl]-N-(2-hydroxy-2-methylpropyl)-2-oxoacetamide

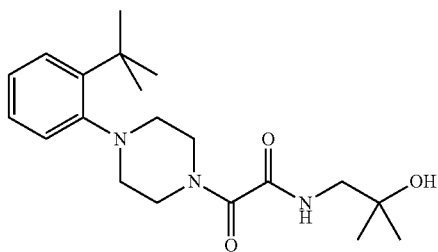 [SMILES: CC(C)(O)CNC(=O)C(=O)N1CCN(c2ccccc2C(C)(C)C)CC1]

A solution of [4-(2-tert-butylphenyl)piperazin-1-yl](oxo)acetic acid (Example 44, 0.300 g, 1.03 mmol), 1-amino-2-methylpropan-2-ol (0.111 g, 1.24 mmol), EDCI (0.238 g, 1.24 mmol) and HOBt (0.168 g, 1.24 mmol) in acetonitrile (5 mL) was stirred at room temperature for 16 h. The reaction mixture was poured into saturated sodium hydrogen carbonate solution and extracted with ethyl acetate. The organic layer was washed with saturated sodium hydrogen carbonate solution and brine, dried over MgSO$_4$, and the solvent was evaporated under reduced pressure to provide 2-[4-(2-tert-butylphenyl)piperazin-1-yl]-N-(2-hydroxy-2-methylpropyl)-2-oxoacetamide (0.380 g, quant) as a white amorphous.

$^1$H NMR (300 MHz, CDCl$_3$) δ 1.27 (s, 6H), 1.45 (s, 9H), 2.01 (br. s., 1H), 2.82-3.13 (m, 5H), 3.34 (d, J=6.4 Hz, 2H), 3.36-3.47 (m, 1H), 4.57 (dq, J=12.6 2.1 Hz, 1H), 5.03 (dq, J=12.9, 2.4 Hz, 1H), 7.11-7.31 (m, 3H), 7.38 (dd, J=7.7, 1.7 Hz, 1H), 7.56 (br. s., 1H).

Example 77

2-[4-(2-tert-Butylphenyl)piperazin-1-yl]-N-(2-hydroxy-1,1-dimethylethyl)-2-oxoacetamide

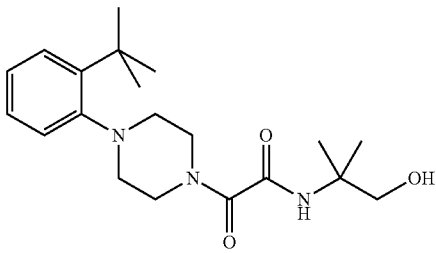 [SMILES: CC(C)(CO)NC(=O)C(=O)N1CCN(c2ccccc2C(C)(C)C)CC1]

A solution of [4-(2-tert-butylphenyl)piperazin-1-yl](oxo)acetic acid (Example 44, 0.300 g, 1.03 mmol), 2-amino-2-methylpropan-1-ol (0.111 g, 1.24 mmol), EDCI (0.238 g, 1.24 mmol) and HOBt (0.168 g, 1.24 mmol) in acetonitrile (5 mL) was stirred at room temperature for 16 h. The reaction mixture was poured into saturated sodium hydrogen carbonate solution and extracted with ethyl acetate. The organic layer was washed with saturated sodium hydrogen carbonate solution and brine, dried over MgSO$_4$, and the solvent was evaporated under reduced pressure to give the crude product. The product was purified by flash column chromatography (silica gel, n-hexane/ethyl acetate=80:20 to 40:60) to provide 2-[4-(2-tert-butylphenyl)piperazin-1-yl]-N-(2-hydroxy-1,1-dimethylethyl)-2-oxoacetamide (0.302 g, 81%) as a white amorphous.

$^1$H NMR (300 MHz, CDCl$_3$) δ ppm 1.35-1.38 (m, 6H), 1.45 (s, 9H), 2.83-3.11 (m, 5H), 3.41 (ddd, J=13.0, 11.3, 3.4 Hz, 1H), 3.66 (d, J=6.1 Hz, 2H), 3.81-3.88 (m, 1H), 4.54 (dq, J=12.5, 2.0 Hz, 1H), 5.02 (dq, J=13.2, 2.2 Hz, 1H), 7.12-7.29 (m, 3H), 7.31 (br. s., 1H), 7.38 (dd, J=7.8, 1.7 Hz, 1H).

Example 78

Benzyl (4-{2-[4-(2-tert-butylphenyl)piperazin-1-yl]-2-oxoethyl}-2,6-dioxopiperidin-1-yl)acetate

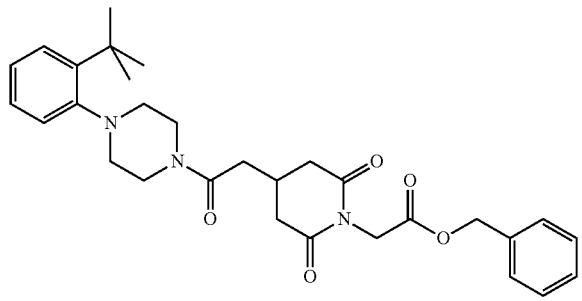 [SMILES: CC(C)(C)c1ccccc1N1CCN(C(=O)CC2CC(=O)N(CC(=O)OCc3ccccc3)C(=O)C2)CC1]

A suspension of 4-{2-[4-(2-tert-butylphenyl)piperazin-1-yl]-2-oxoethyl}piperidine-2,6-dione (Example 14, 0.300 g, 0.81 mmol), benzyl bromoacetate (0.236 g, 0.97 mmol), and potassium carbonate (0.335 g, 2.42 mmol) in DMF (5 mL)

was stirred at 60° C. for 16 h. The reaction mixture was poured into water and extracted with ethyl acetate. The organic layer was washed with saturated sodium hydrogen carbonate solution and brine, dried over MgSO$_4$, and the solvent was evaporated under reduced pressure to give a pale yellow powder, which was re-crystallized from hexane and ethyl acetate to provide benzyl (4-{2-[4-(2-tert-butylphenyl)piperazin-1-yl]-2-oxoethyl}-2,6-dioxopiperidin-1-yl)acetate (0.474 g, 79%) as an off-white powder.

$^1$H NMR (300 MHz, CDCl$_3$) δ 1.44 (s, 9H), 2.42-2.57 (m, 1H), 2.57-2.78 (m, 3H), 2.78-3.01 (m, 8H), 3.25-3.43 (m, 1H), 3.79 (dd, J=12.8, 1.9 Hz, 1H), 4.54-4.67 (m, 3H), 5.15 (s, 2H), 7.10-7.47 (m, 9H).

Example 79

(4-{2-[4-(2-tert-Butylphenyl)piperazin-1-yl]-2-oxoethyl}-2,6-dioxopiperidin-1-yl)acetic acid

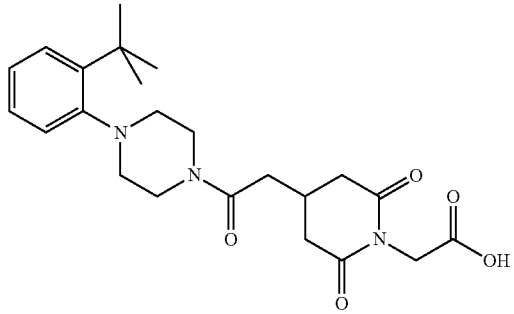 [SMILES: CC(C)(C)c1ccccc1N1CCN(C(=O)CC2CC(=O)N(CC(=O)O)C(=O)C2)CC1]

A suspension of benzyl (4-{2-[4-(2-tert-butylphenyl)piperazin-1-yl]-2-oxoethyl}-2,6-dioxopiperidin-1-yl)acetate (Example 78, 0.28 g, 0.539 mmol) and palladium hydroxide (20% on carbon, wetted with ca. 50% water, 30 mg) in ethyl acetate (25 mL) was stirred under hydrogen atmosphere at room temperature for 3 h. The reaction mixture was filtered and the filtrate was concentrated under reduced pressure to provide (4-{2-[4-(2-tert-butylphenyl)piperazin-1-yl]-2-oxoethyl}-2,6-dioxopiperidin-1-yl)acetic acid (0.21 g, 91%) as a white powder.

$^1$H NMR (300 MHz, CDCl$_3$) δ 1.44 (s, 9H), 2.41-2.73 (m, 4H), 2.74-3.01 (m, 8H), 3.28-3.44 (m, 1H), 3.78 (d, J=12.9 Hz, 1H), 4.52-4.68 (m, 3H), 7.10-7.34 (m, 3H), 7.38 (d, J=7.6 Hz, 1H).

Example 80 tert-Butyl 4-[2-tert-butyl-4-(1-hydroxy-1-methylethyl)phenyl]piperazine-1-carboxylate

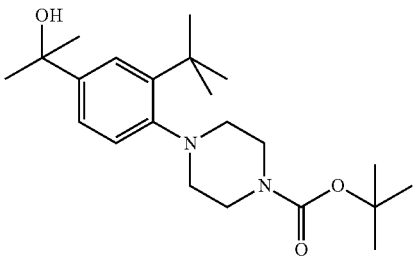 [SMILES: CC(C)(C)OC(=O)N1CCN(c2ccc(C(C)(C)O)cc2C(C)(C)C)CC1]

To a solution of n-BuLi (1.6 M in n-hexane, 10.6 mL, 6.62 mmol) in THF (30 mL) was added a solution of tert-butyl 4-(4-bromo-2-tert-butylphenyl)piperazine-1-carboxylate (Example 85, 4.5 g, 11.3 mmol) in THF (15 mL) at −80° C. After stirred for 2 h at that temperature, it was added acetone (4 mL) and allowed to be warmed to room temperature. After 16 h, it was added saturated ammonium chloride solution and extracted with ethyl acetate. The organic layer was washed with brine, dried over MgSO$_4$, and the solvent was evaporated under reduced pressure to give the crude product. The product was purified by flash column chromatography (silica gel, n-hexane/ethyl acetate=98:2 to 80:20) to provide tert-butyl 4-[2-tert-butyl-4-(1-hydroxy-1-methylethyl)phenyl]piperazine-1-carboxylate (3.1 g, 73%) as a pale yellow solid.

$^1$H NMR (300 MHz, CDCl$_3$) δ 1.44 (s, 9H), 1.49 (s, 9H), 1.58 (s, 6H), 1.76 (s, 1H), 2.69-2.89 (m, 4H), 3.05 (br. s., 2H), 4.04 (br. s., 2H), 7.23 (d, J=8.3 Hz, 1H), 7.31 (dd, J=8.3, 2.3 Hz, 1H), 7.51 (d, J=2.3 Hz, 1H).

Example 81

Ethyl [4-(2-tert-butyl-4-methylphenyl)piperazin-1-yl](oxo)acetate

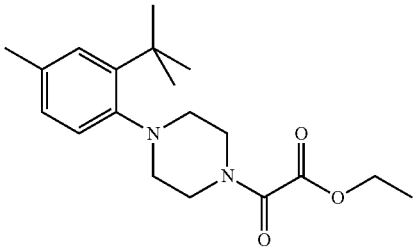 [SMILES: CCOC(=O)C(=O)N1CCN(c2ccc(C)cc2C(C)(C)C)CC1]

To a stirred suspension of 1-(2-tert-butyl-4-methylphenyl)piperazine dihydrochloride (Reference Example 10, 0.300 g, 0.98 mmol) and triethylamine (548 μl, 3.93 mmol) in THF (10 mL) stirring at 0° C. was added ethyl chloro(oxo)acetate (0.175 mg, 1.28 mmol). The mixture was warmed to room temperature. After 3 days the reaction mixture was poured into water and extracted with ethyl acetate. The organic layer was washed with brine, dried over MgSO$_4$, and the solvent was evaporated under reduced pressure to give the crude product. The product was purified by flash column chromatography (silica gel, n-hexane/ethyl acetate=90:10 to 50:50) to provide ethyl [4-(2-tert-butyl-4-methylphenyl)piperazin-1-yl](oxo)acetate (0.233 g, 71%) as a white solid.

$^1$H NMR (300 MHz, CDCl$_3$) δ 1.38 (t, J=7.19 Hz, 3H), 1.43 (s, 9H), 2.32 (s, 3H), 2.80-2.94 (m, 4H), 2.94-3.09 (m, 1H), 3.46 (ddd, J=13.1, 10.8, 4.2 Hz, 1H), 3.60-3.70 (m, 1H), 4.36 (q, J=7.19 Hz, 2H), 4.51 (dq, J=12.5, 2.1 Hz, 1H), 6.99-7.07 (m, 1H), 7.11-7.21 (m, 2H).

Example 82

[4-(2-tert-Butyl-4-methylphenyl)piperazin-1-yl](oxo)acetic acid

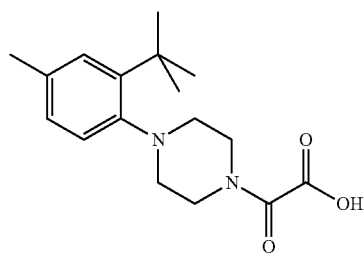 [SMILES: Cc1ccc(N2CCN(C(=O)C(=O)O)CC2)c(C(C)(C)C)c1]

To a stirred solution of ethyl [4-(2-tert-butyl-4-methylphenyl)piperazin-1-yl](oxo)acetate (Example 81, 0.210 g, 0.63 mmol) in THF (5 mL) stirring at 0° C. was added 1 M lithium hydroxide solution (5 mL, 5 mmol). After 2 h the reaction mixture was acidified with 1 M hydrochloric acid solution and extracted with ethyl acetate. The organic layer was washed with brine, dried over MgSO$_4$, and the solvent was evaporated in vacuum to provide [4-(2-tert-butyl-4-methylphenyl)piperazin-1-yl](oxo)acetic acid (0.171 g, 89%) as a white solid.

$^1$H NMR (300 MHz, CDCl$_3$) δ 1.44 (s, 9H), 2.32 (s, 3H), 2.83-3.02 (m, 4H), 3.14 (ddd, J=12.5, 10.8, 4.7 Hz, 1H), 3.48 (ddd, J=13.2, 10.3, 4.9 Hz, 1H), 4.56 (dq, J=12.8, 2.2 Hz, 1H), 5.24 (dq, J=13.2, 2.3 Hz, 1H), 6.98-7.08 (m, 1H), 7.14 (d, J=8.0 Hz, 1H), 7.18 (d, J=1.9 Hz, 1H).

Example 83

Ethyl 3-[4-(2-tert-butyl-4-methylphenyl)piperazin-1-yl]-3-oxopropanoate

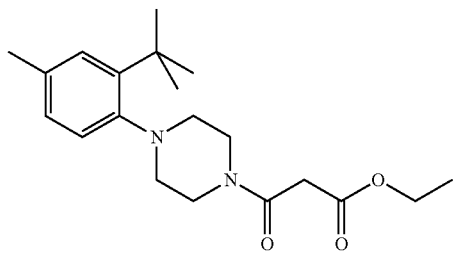 [SMILES: CCOC(=O)CC(=O)N1CCN(c2ccc(C)cc2C(C)(C)C)CC1]

A suspension of 1-(2-tert-butyl-4-methylphenyl)piperazine dihydrochloride (Reference Example 10, 0.300 g, 0.98 mmol), 3-ethoxy-3-oxopropanoic acid (0.169 g, 1.28 mmol), EDCI (0.245 g, 1.28 mmol), HOBt (0.173 g, 1.28 mmol) and triethylamine (411 µl, 2.95 mmol) in acetonitrile (10 mL) was stirred at room temperature for 3 days. The reaction mixture was poured into saturated sodium hydrogen carbonate solution and extracted with ethyl acetate. The organic layer was washed with saturated sodium hydrogen carbonate solution and brine, dried over MgSO$_4$, and the solvent was evaporated in vacuum to give the crude product. The product was purified by flash column chromatography (silica gel, n-hexane/ethyl acetate=90:20 to 50:50) to provide ethyl 3-[4-(2-tert-butyl-4-methylphenyl)piperazin-1-yl]-3-oxopropanoate (0.234 g, 69%) as a colorless gum.

$^1$H NMR (300 MHz, CDCl$_3$) δ 1.31 (t, J=7.2 Hz, 3H), 1.43 (s, 9H), 2.32 (s, 3H), 2.76-3.03 (m, 5H), 3.36-3.50 (m, 1H), 3.51 (s, 2H), 3.71 (dd, J=12.9, 1.9 Hz, 1H), 4.23 (q, J=7.2 Hz, 2H), 4.62 (dd, J=12.1, 1.89 Hz, 1H), 7.00-7.06 (m, 1H), 7.11-7.20 (m, 2H).

Example 84

3-[4-(2-tert-Butyl-4-methylphenyl)piperazin-1-yl]-3-oxopropanoic acid

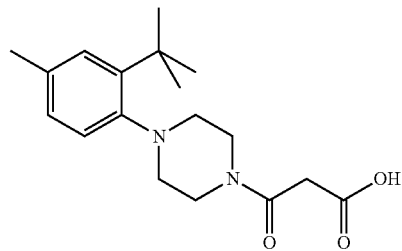 [SMILES: Cc1ccc(N2CCN(C(=O)CC(=O)O)CC2)c(C(C)(C)C)c1]

To a stirred solution of ethyl 3-[4-(2-tert-butyl-4-methylphenyl)piperazin-1-yl]-3-oxopropanoate (Example 83, 0.210 g, 0.61 mmol) in THF (5 mL) stirring at 0° C. was added 1 M lithium hydroxide solution (5 mL, 5 mmol). After 2 h the reaction mixture was acidified with 1 M hydrochloric acid solution and extracted with ethyl acetate. The organic layer was washed with brine, dried over MgSO$_4$, and the solvent was to evaporated under reduced pressure to provide 3-[4-(2-tert-butyl-4-methylphenyl)piperazin-1-yl]-3-oxopropanoic acid (0.186 g, 96%) as a white solid.

$^1$H NMR (300 MHz, CDCl$_3$) δ 1.43 (s, 9H), 2.33 (s, 3H), 2.78-3.10 (m, 5H), 3.32-3.53 (m, 3H), 3.76 (dq, J=13.4, 2.4

Hz, 1H), 4.65 (dq, J=12.9, 2.3 Hz, 1H), 7.00-7.09 (m, 1H), 7.12 (d, J=8.0 Hz, 1H), 7.18 (d, J=1.5 Hz, 1H).

Example 85 tert-Butyl 4-(4-bromo-2-tert-butylphenyl)piperazine-1-carboxylate

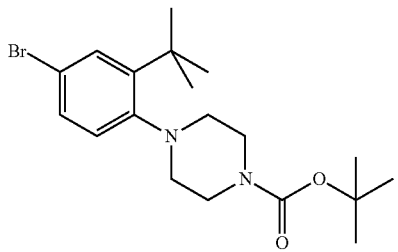 [SMILES: CC(C)(C)OC(=O)N1CCN(c2ccc(Br)cc2C(C)(C)C)CC1]

To a solution of 1-(4-bromo-2-tert-butylphenyl)piperazine dihydrochloride (Reference Example 9, 19.3 g, 52.3 mmol) and triethylamine (18.1 mL, 130 mmol) in THF (120 mL) was added di-tert-butyl dicarbonate (12.9 g, 59.1 mmol) at room temperature. After 16 h, it was added water and extracted with ethyl acetate. The organic layer was washed with saturated sodium hydrogen carbonate solution and brine, dried over MgSO$_4$, and the solvent was evaporated under reduced pressure to provide tert-butyl 4-(4-bromo-2-tert-butylphenyl)piperazine-1-carboxylate (18.75 g, 90%) as a gray solid.

$^1$H NMR (300 MHz, CDCl$_3$) δ 1.41 (s, 9H), 1.49 (s, 9H), 2.67-2.86 (m, 4H), 3.04 (br. s., 2H), 4.05 (br. s., 2H), 7.14 (d, J=8.3 Hz, 1H), 7.33 (dd, J=8.3, 2.3 Hz, 1H), 7.47 (d, J=2.3 Hz, 1H).

Example 86

Benzyl N-{[4-(2-tert-butylphenyl)piperazin-1-yl](oxo)acetyl}glycinate

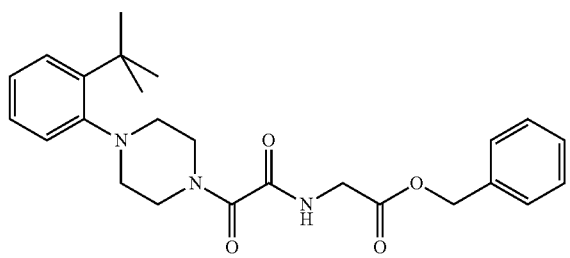 [SMILES: CC(C)(C)c1ccccc1N1CCN(C(=O)C(=O)NCC(=O)OCc2ccccc2)CC1]

A solution of [4-(2-tert-butylphenyl)piperazin-1-yl](oxo) acetic acid (Example 44, 0.300 g, 1.03 mmol), benzyl glycinate hydrochloride (0.250 g, 1.24 mmol), EDCI (0.238 g, 1.24 mmol), HOBt (0.168 g, 1.24 mmol) and triethylamine (201 μL, 1.44 mmol) in acetonitrile (10 mL) was stirred at room temperature for 2 days. The reaction mixture was poured into saturated sodium hydrogen carbonate solution and extracted with ethyl acetate. The organic layer was washed with saturated sodium hydrogen carbonate solution and brine, dried over MgSO$_4$, and the solvent was evaporated under reduced pressure to give the crude product. The product was purified by flash column chromatography (silica gel, n-hexane/ethyl acetate=90:10 to 50:50) to provide benzyl N-{[4-(2-tert-butylphenyl)piperazin-1-yl](oxo) acetyl}glycinate (0.375 g, 83%) as a white powder.

$^1$H NMR (300 MHz, CDCl$_3$) δ 1.45 (s, 9H), 2.81-2.96 (m, 4H), 2.96-3.12 (m, 1H), 3.40 (ddd, J=13.1, 11.2, 3.4 Hz, 1H), 4.14 (d, J=5.7 Hz, 2H), 4.56 (dq, J=12.6, 2.0 Hz, 1H), 4.98 (dq, J=12.9, 2.3 Hz, 1H), 5.22 (s, 2H), 7.09-7.29 (m, 4H), 7.32-7.43 (m, 5H), 7.63 (t, J=5.3 Hz, 1H).

Example 87

N-{[4-(2-tert-Butylphenyl)piperazin-1-yl](oxo)acetyl}glycine

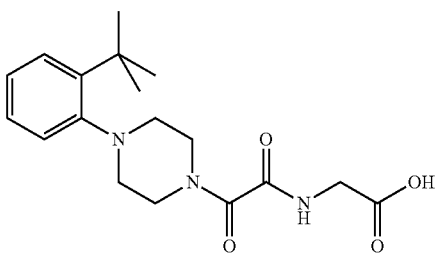 [SMILES: CC(C)(C)c1ccccc1N1CCN(C(=O)C(=O)NCC(=O)O)CC1]

A suspension of benzyl N-{[4-(2-tert-butylphenyl)piperazin-1-yl](oxo)acetyl}glycinate (Example 86, 350 mg, 0.80 mmol) and palladium hydroxide (20% on carbon, wetted with ca. 50% water, 30 mg) in ethyl acetate (25 mL) was stirred under hydrogen atmosphere at room temperature for 3 h. The reaction mixture was filtered and the filtrate was concentrated under reduced pressure to provide N-{[4-(2-tert-butylphenyl)piperazin-1-yl](oxo)acetyl}glycine (0.273 g, 98%) as a white solid.

$^1$H NMR (300 MHz, CDCl$_3$) δ 1.45 (s, 9H), 2.83-2.99 (m, 4H), 2.98-3.16 (m, 1H), 3.43 (ddd, J=13.1, 11.4, 3.4 Hz, 1H), 4.16 (d, J=5.7 Hz, 2H), 4.56 (dd, J=12.6, 1.7 Hz, 1H), 4.93 (dd, J=13.0, 1.7 Hz, 1H), 7.10-7.29 (m, 3H), 7.38 (dd, J=7.7, 1.7 Hz, 1H), 7.90 (t, J=5.46 Hz, 1H).

Example 88

Methyl 1-{[4-(2-tert-butylphenyl)piperazin-1-yl](oxo)acetyl}piperidine-4-carboxylate

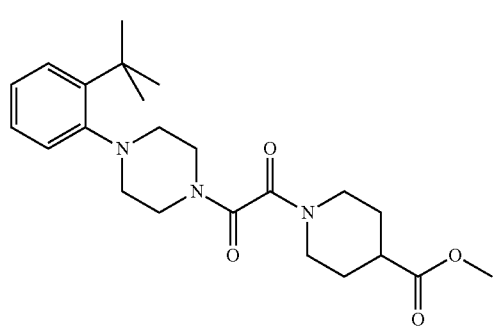 [SMILES: COC(=O)C1CCN(C(=O)C(=O)N2CCN(c3ccccc3C(C)(C)C)CC2)CC1]

A solution of [4-(2-tert-butylphenyl)piperazin-1-yl](oxo) acetic acid (Example 44, 0.300 g, 1.03 mmol), methyl piperidine-4-carboxylate (0.178 g, 1.24 mmol), EDCI (0.238 g, 1.24 mmol) and HOBt (0.168 g, 1.24 mmol) in acetonitrile (10 mL) was stirred at room temperature for 2 days. The reaction mixture was poured into saturated sodium hydrogen carbonate solution and extracted with ethyl acetate. The organic layer was washed with saturated sodium hydrogen carbonate solution and brine, dried over MgSO₄, and the solvent was evaporated in vacuum to give the crude product. The product was purified by flash column chromatography (silica gel, n-hexane/ethyl acetate=90:10 to 50:50) to provide methyl 1-{[4-(2-tert-butylphenyl)piperazin-1-yl](oxo)acetyl}piperidine-4-carboxylate (0.173 g, 40%) as a white amorphous.

$^1$H NMR (300 MHz, CDCl₃) δ 1.44 (s, 9H), 1.62-1.90 (m, 2H), 1.95-2.11 (m, 2H), 2.54-2.73 (m, 1H), 2.80-3.13 (m, 6H), 3.15-3.32 (m, 1H), 3.37-3.54 (m, 1H), 3.56-3.80 (m, 5H), 4.21-4.44 (m, 1H), 4.55 (d, J=12.4 Hz, 1H), 7.12-7.29 (m, 3H), 7.38 (dd, J=7.5, 1.5 Hz, 1H).

Example 89

1-{[4-(2-tert-Butylphenyl)piperazin-1-yl](oxo)acetyl}piperidine-4-carboxylic acid

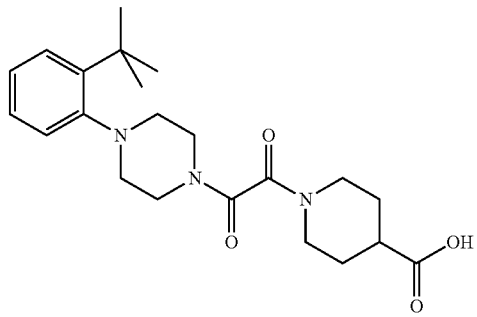 [SMILES: CC(C)(C)c1ccccc1N1CCN(C(=O)C(=O)N2CCC(C(=O)O)CC2)CC1]

To a stirred solution of methyl 1-{[4-(2-tert-butylphenyl)piperazin-1-yl](oxo)acetyl}piperidine-4-carboxylate (Example 88, 0.159 g, 0.383 mmol) in THF (3 mL) stirring at 0° C. was added 1 M lithium hydroxide solution (3 mL, 3 mmol). After 2 h the reaction mixture was acidified with 1 M hydrochloric acid solution and extracted with ethyl acetate. The organic layer was washed with brine, dried over MgSO₄, and the solvent was evaporated under reduced pressure to provide 1-{[4-(2-tert-butylphenyl)piperazin-1-yl](oxo)acetyl}piperidine-4-carboxylic acid (0.147 g, 96%) as a white amorphous.

$^1$H NMR (300 MHz, CDCl₃) δ 1.44 (s, 9H), 1.63-1.93 (m, 2H), 1.97-2.14 (m, 2H), 2.58-2.75 (m, 1H), 2.79-3.16 (m, 6H), 3.18-3.34 (m, 1H), 3.38-3.54 (m, 1H), 3.57-3.68 (m, 1H), 3.68-3.80 (m, 1H), 4.23-4.41 (m, 1H), 4.55 (d, J=12.9 Hz, 1H), 7.10-7.30 (m, 3H), 7.38 (dd, J=7.8, 1.3 Hz, 1H).

Example 90

5-{2-[4-(2-tert-Butylphenyl)piperazin-1-yl]-2-oxoethyl}imidazolidine-2,4-dione

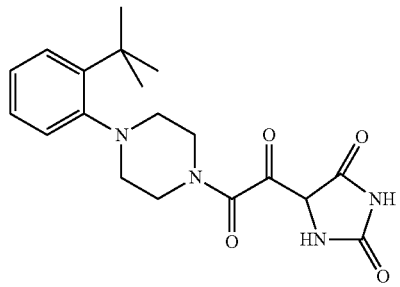 [SMILES: CC(C)(C)c1ccccc1N1CCN(C(=O)C(=O)C2NC(=O)NC2=O)CC1]

A suspension of 1-(2-tert-butylphenyl)piperazine dihydrochloride (Reference Example 1, 0.400 g, 1.37 mmol), (2,5-dioxoimidazolidin-4-yl)acetic acid (0.261 g, 1.65 mmol), EDCI (0.311 g, 1.65 mmol), HOBt (0.223 g, 1.65 mmol) and triethylamine (496 µl, 3.56 mmol) in DMF (13 mL) was stirred at room temperature for 16 h. The reaction mixture was poured into saturated ammonium chloride solution and extracted with ethyl acetate. The organic layer was washed with saturated sodium hydrogen carbonate solution and brine, dried over MgSO₄, and the solvent was evaporated under reduced pressure to give crude product. The product was purified by re-crystallization from THF and n-hexane to provide 5-{2-[4-(2-tert-butylphenyl)piperazin-1-yl]-2-oxoethyl}imidazolidine-2,4-dione (0.344 g, 70%) as a white powder.

$^1$H NMR (300 MHz, CDCl₃) δ 1.42 (s, 9H), 2.47-2.73 (m, 1H), 2.76-3.02 (m, 5H), 3.05-3.27 (m, 1H), 3.31-3.50 (m, 1H), 3.71 (d, J=12.1 Hz, 1H), 4.43-4.64 (m, 2H), 6.08 (d, J=10.2 Hz, 1H), 7.12-7.21 (m, 1H), 7.21-7.25 (m, 2H), 7.39 (d, J=7.2 Hz, 1H), 7.54 (br. s., 1H).

From Example 91 to Example 134 and Example 135 to Example 158, compounds were synthesized sequentially and purified by Preparative HPLC system [Apparatus: Gilson High Throughput Purification System; Column: CombiPrep, Pro C18 RS S-5 µm, 20×50 mm (YMC); Solvent: A phase=0.1% TFA in water, B phase=0.1% TFA in MeCN; Gradient Cycle: 0 min. (A phase/B phase=98/2), 1.10 min. (A phase/B phase=98/2), 5.00 min. (A phase/B phase=0/100), 6.40 min. (A phase/B phase=0/100), 6.50 min. (A phase/B phase=98/2); Flow rate: 20 mL/min; Detection Wavelength: UV 220, 254 nm]. Purity and mass spectra were obtained by LC-MS system [Apparatus: Waters MUX 4-ch LC/MS system; Column: CAPCELL PAK c18UG120 S-3 µm, 1.5×35 mm (Shisendo); Solvent: A phase=5 mM ammonium acetate water solution, B phase=5 mM ammonium acetate MeCN solution; Gradient Cycle: 0 min. (A phase/B phase=100/0), 2.00 min. (A phase/B phase=0/100), 3.00 min. (A phase/B phase=0/100), 3.01 min. (A phase/B phase=100/0), 3.30 min. (A phase/B phase=100/0); Injection volume: 2 µL; Flow rate: 0.5 mL/min; Detection Wavelength: UV 220 nm; Ionization method: ESI, Measurement mode; Full Scan (positive and negative); MS range: m/z=150-750].

$^1$H NMR spectra were obtained at 400 MHz on a Brucker AV400 (400 MHz). Chemical shifts are given in δ values (ppm) using trimethylsilane as an internal standard. LC-MS

Example 91

1-(2-tert-Butylphenyl)-4-(tetrahydrofuran-2-ylcarbonyl)piperazine

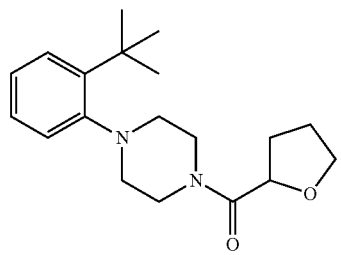 [SMILES: CC(C)(C)c1ccccc1N1CCN(C(=O)C2CCCO2)CC1]

To a stirred solution of 2-tetrahydrofuroic acid (23 mg, 0.2 mmol) in DMF (0.5 mL) was added N-(3-dimethylaminopropyl)-N'-ethylcarbodiimide hydrochloride (38 mg, 0.2 mmol) and HOBt (27 mg, 0.2 mmol) in DMF (0.25 mL) followed by 1 (2-(tert-butylphenyl)piperazine dihydrochloride (29 mg, 0.1 mmol) with triethylamine (0.014 mL, 0.2 mmol) in DMF (0.25 mL). After stirring for 15 h at room temperature, saturated sodium hydrogen carbonate solution (1.5 mL) was added to the mixture, and the mixture was extracted with ethyl acetate (2 mL). The organic layer was separated by phase separation filter kit and the filtrate was evaporated under reduced pressure. The resulting residue was dissolved in dimethylsulfoxide (1 mL) and the solution was purified by preparative HPLC. The eluted fraction was evaporated by air blowing at 60° C. to give the title compound (18.7 mg, 59%). LC/MS (ESI+) m/z: 317 (M+H)$^+$. purity 100%.

Example 92

N-{2-[4-(2-tert-Butylphenyl)piperazin-1-yl]-2-oxoethyl}acetamide

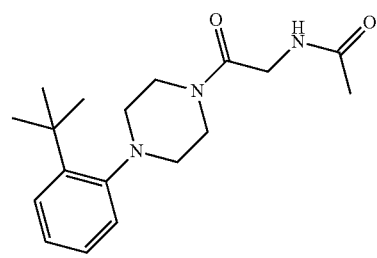 [SMILES: CC(=O)NCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 318 [M+H], 11.3 mg, yield 36%, purity 100%.

Example 93

4-[4-(2-tert-Butylphenyl)piperazin-1-yl]-4-oxobutanamide

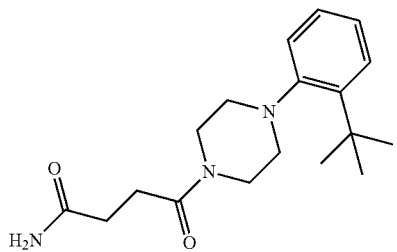 [SMILES: CC(C)(C)c1ccccc1N1CCN(C(=O)CCC(N)=O)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 318 [M+H], 6.1 mg, yield 19%, purity 100%.

Example 94

1-(2-tert-Butylphenyl)-4-(1H-tetrazol-1-ylacetyl)piperazine

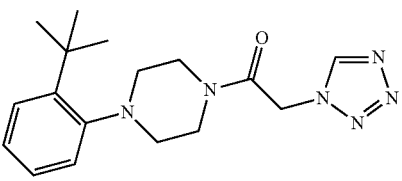 [SMILES: CC(C)(C)c1ccccc1N1CCN(C(=O)Cn2cnnn2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 329 [M+H], 9.3 mg, yield 28%, purity 100%.

Example 95

(5S)-5-{[4-(2-tert-Butylphenyl)piperazin-1-yl]carbonyl}pyrrolidin-2-one

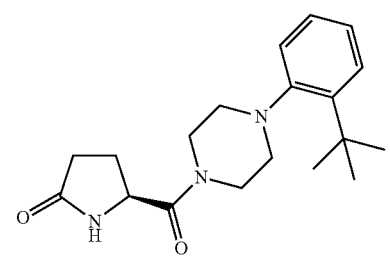 [SMILES: CC(C)(C)c1ccccc1N1CCN(C(=O)[C@@H]2CCC(=O)N2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 330 [M+H], 8.7 mg, yield 26%, purity 100%.

Example 96

N-{2-[4-(2-tert-Butylphenyl)piperazin-1-yl]-1-methyl-2-oxoethyl}acetamide

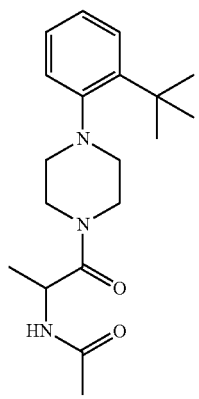 [SMILES: CC(=O)NC(C)C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 332 [M+H], 8.3 mg, yield 25%, purity 100%.

Example 97

N-{4-[4-(2-tert-Butylphenyl)piperazin-1-yl]-4-oxobutyl}acetamide

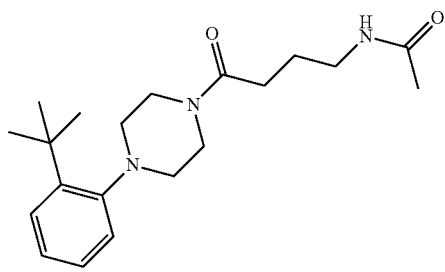 [SMILES: CC(=O)NCCCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 346 [M+H], 8.5 mg, yield 25%, purity 100%.

Example 98

(4R)-4-{[4-(2-tert-Butylphenyl)piperazin-1-yl]carbonyl}-1,3-thiazolidin-2-one

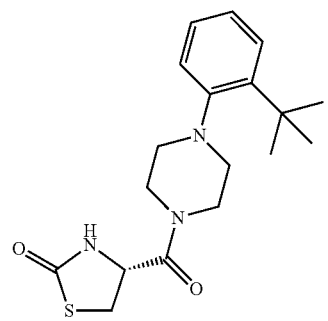 [SMILES: CC(C)(C)c1ccccc1N1CCN(C(=O)[C@@H]2CSC(=O)N2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 348 [M+H], 7.8 mg, yield 23%, purity 100%.

Example 99

5-{2-[4-(2-tert-Butylphenyl)piperazin-1-yl]-2-oxoethyl}imidazolidine-2,4-dione

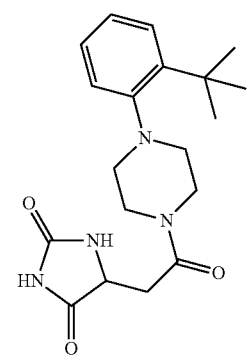 [SMILES: CC(C)(C)c1ccccc1N1CCN(C(=O)CC2NC(=O)NC2=O)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 359 [M+H], 10.6 mg, yield 30%, purity 100%.

Example 100

3-{2-[4-(2-tert-Butylphenyl)piperazin-1-yl]-2-oxoethyl}-1H-indole

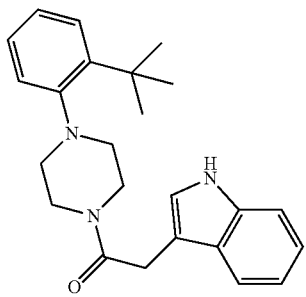 [SMILES: CC(C)(C)c1ccccc1N1CCN(C(=O)Cc2c[nH]c3ccccc23)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 376 [M+H], 22.1 mg, yield 59%, purity 100%.

Example 101

N-{2-[4-(2-tert-Butylphenyl)piperazin-1-yl]-2-oxoethyl}benzamide

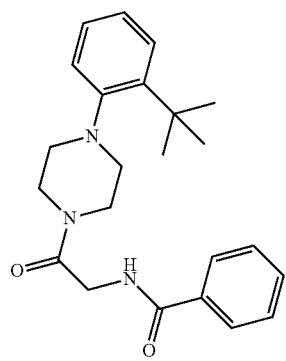 [SMILES: CC(C)(C)c1ccccc1N1CCN(C(=O)CNC(=O)c2ccccc2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 380 [M+H], 21.8 mg, yield 57%, purity 100%.

Example 102

3-{3-[4-(2-tert-Butylphenyl)piperazin-1-yl]-3-oxopropyl}-1H-indole

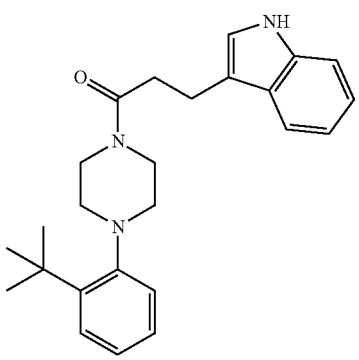 [SMILES: CC(C)(C)c1ccccc1N1CCN(C(=O)CCc2c[nH]c3ccccc23)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 390 [M+H], 20.6 mg, yield 53%, purity 100%.

Example 103

N-{3-[4-(2-tert-Butylphenyl)piperazin-1-yl]-3-oxopropyl}benzamide

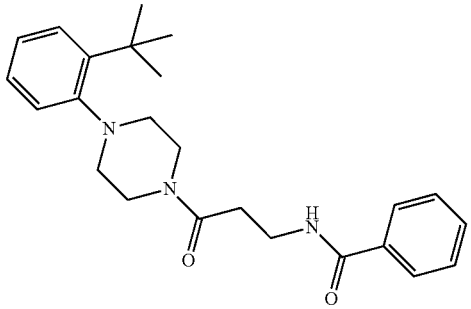 [SMILES: CC(C)(C)c1ccccc1N1CCN(C(=O)CCNC(=O)c2ccccc2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 394 [M+H], 19.4 mg, yield 49%, purity 100%.

Example 104

N-{1-Benzyl-2-[4-(2-tert-butylphenyl)piperazin-1-yl]-2-oxoethyl}acetamide

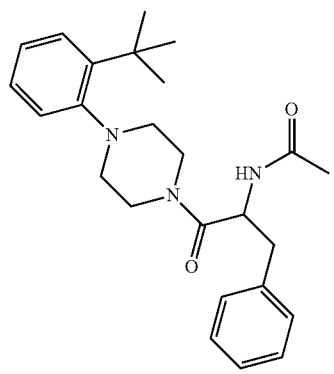 [SMILES: CC(=O)NC(Cc1ccccc1)C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 408 [M+H], 15.4 mg, yield 38%, purity 100%.

Example 105 tert-Butyl 4-{[4-(2-tert-butylphenyl)piperazin-1-yl]carbonyl}piperidine-1-carboxylate

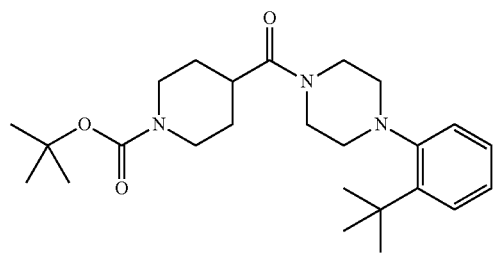 [SMILES: CC(C)(C)OC(=O)N1CCC(C(=O)N2CCN(c3ccccc3C(C)(C)C)CC2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 430 [M+H], 3.9 mg, yield 9%, purity 100%.

Example 106

2-[4-(2-tert-Butylphenyl)piperazin-1-yl]-2-oxoacetamide

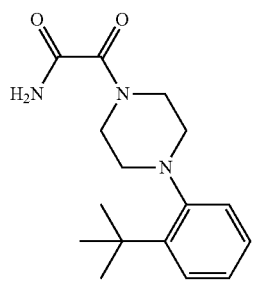 [SMILES: CC(C)(C)c1ccccc1N1CCN(C(=O)C(N)=O)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 290 [M+H], 8.1 mg, yield 28%, purity 100%.

Example 107

3-[4-(2-tert-Butylphenyl)piperazin-1-yl]-3-oxopropan-1-ol

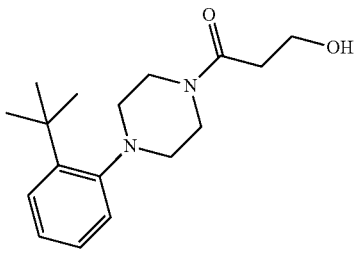 [SMILES: CC(C)(C)c1ccccc1N1CCN(C(=O)CCO)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 291 [M+H], 4.6 mg, yield 16%, purity 100%.

Example 108

1-(2-tert-Butylphenyl)-4-(3-methoxypropanoyl)piperazine

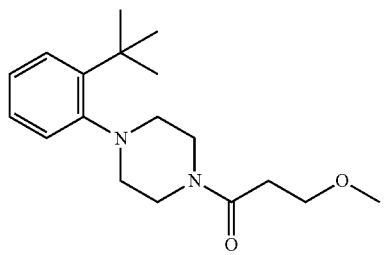 [SMILES: COCCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 305 [M+H], 8.6 mg, yield 28%, purity 100%.

Example 109

1-[4-(2-tert-Butylphenyl)piperazin-1-yl]-2-methyl-1-oxopropan-2-ol

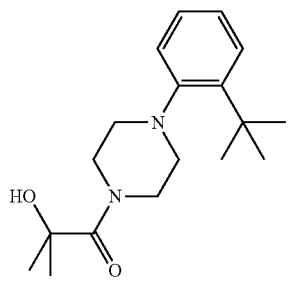 [SMILES: CC(C)(O)C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 305 [M+H], 8.9 mg, yield 29%, purity 100%.

Example 110

3-[4-(2-tert-Butylphenyl)piperazin-1-yl]-3-oxopropane-1,2-diol

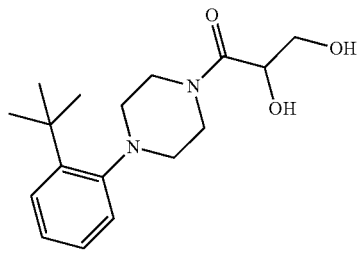 [SMILES: CC(C)(C)c1ccccc1N1CCN(C(=O)C(O)CO)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 307 [M+H], 4.6 mg, yield 15%, purity 100%.

Example 111

1-(2-tert-Butylphenyl)-4-(tetrahydrofuran-3-ylcarbonyl)piperazine

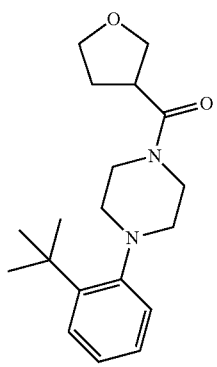 [SMILES: CC(C)(C)c1ccccc1N1CCN(C(=O)C2CCOC2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 317 [M+H], 12.5 mg, yield 40%, purity 100%.

Example 112

5-[4-(2-tert-Butylphenyl)piperazin-1-yl]-5-oxopentan-2-one

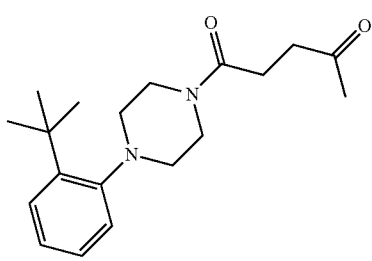 [SMILES: CC(=O)CCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 317 [M+H], 12.3 mg, yield 39%, purity 100%.

Example 113

1-(2-tert-Butylphenyl)-4-(3-ethoxypropanoyl)piperazine

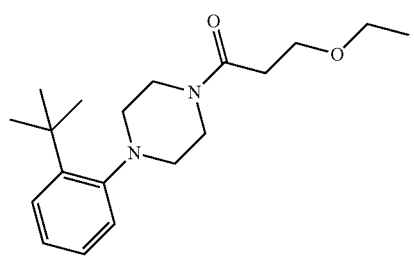 [SMILES: CCOCCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 319 [M+H], 8.7 mg, yield 27%, purity 100%.

Example 114

3-[4-(2-tert-Butylphenyl)piperazin-1-yl]-2,2-dimethyl-3-oxopropan-1-ol

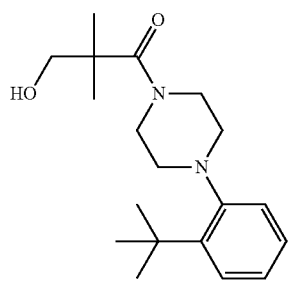 [SMILES: CC(C)(CO)C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 319 [M+H], 6.2 mg, yield 19%, purity 100%.

Example 115

(2Z)-4-[4-(2-tert-Butylphenyl)piperazin-1-yl]-N-methyl-4-oxobut-2-enamide

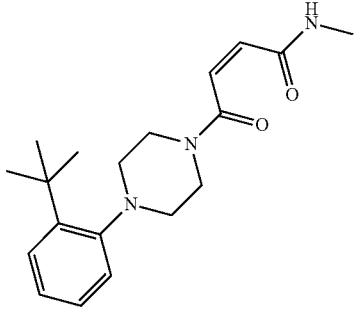 [SMILES: CNC(=O)/C=C\C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 330 [M+H], 6.7 mg, yield 20%, purity 100%, Example 116

(5S)-5-{[4-(2-tert-Butylphenyl)piperazin-1-yl] carbonyl}dihydrofuran-2(3H)-one

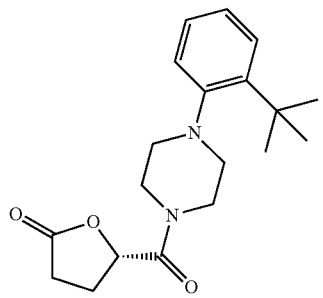 [SMILES: CC(C)(C)c1ccccc1N1CCN(C(=O)[C@@H]2CCC(=O)O2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 331[M+H], 9.7 mg, yield 29%, purity 100%.

Example 117

6-[4-(2-tert-Butylphenyl)piperazin-1-yl]-6-oxohexan-2-one

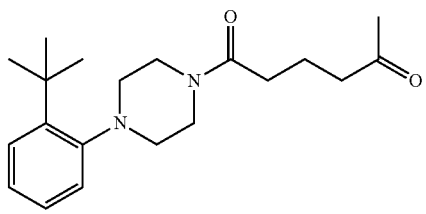 [SMILES: CC(=O)CCCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 331 [M+H], 22.6 mg, yield 68%, purity 100%.

Example 118

1-[4-(2-tert-Butylphenyl)piperazin-1-yl]-4-methyl-1-oxopentan-2-one

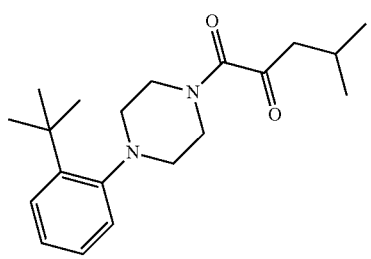 [SMILES: CC(C)CC(=O)C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 331 [M+H], 5.7 mg, yield 17%, purity 100%.

Example 119

2-{[4-(2-tert-Butylphenyl)piperazin-1-yl]carbonyl}-4H-pyran-4-one

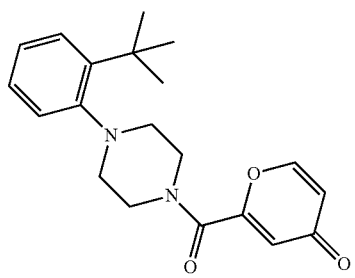 [SMILES: CC(C)(C)c1ccccc1N1CCN(C(=O)c2cc(=O)cco2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 341 [M+H], 11.6 mg, yield 34%, purity 100%.

Example 120

2-[4-(2-tert-Butylphenyl)piperazin-1-yl]-2-oxo-1-phenylethanone

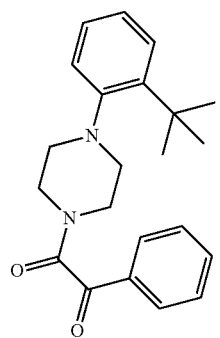 [SMILES: CC(C)(C)c1ccccc1N1CCN(C(=O)C(=O)c2ccccc2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 351 [M+H], 6.8 mg, yield 19%, purity 100%.

Example 121

1-(2-tert-Butylphenyl)-4-(phenoxyacetyl)piperazine

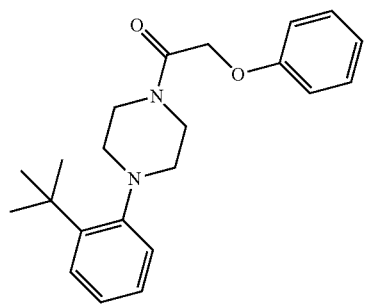 [SMILES: CC(C)(C)c1ccccc1N1CCN(C(=O)COc2ccccc2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 353 [M+H], 11.3 mg, yield 32%, purity 100%.

Example 122

2-{2-[4-(2-tert-Butylphenyl)piperazin-1-yl]-2-oxoethyl}phenol

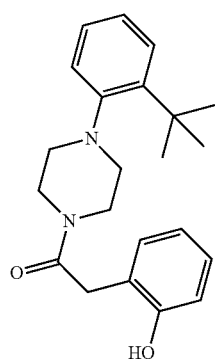 [SMILES: CC(C)(C)c1ccccc1N1CCN(C(=O)Cc2ccccc2O)CC1]

ran-2-ylcarbonyl)piperazine (Example 91). LC/MS (ESI+) m/z 353 [M+H], 8.9 mg, yield 25%, purity 100%.

Example 123

5-{[4-(2-tert-Butylphenyl)piperazin-1-yl]carbonyl}pyrimidine-2,4(1H,3H)-dione

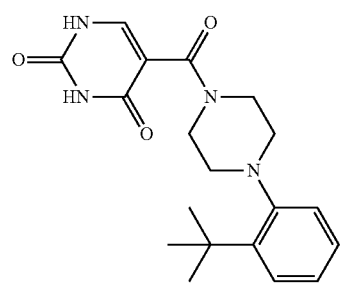 [SMILES: CC(C)(C)c1ccccc1N1CCN(C(=O)c2c[nH]c(=O)[nH]c2=O)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 357 [M+H], 12.9 mg, yield 36%, purity 100%.

Example 124

(6S)-6-{[4-(2-tert-Butylphenyl)piperazin-1-yl]carbonyl}dihydropyrimidine-2,4(1H,3H)-dione

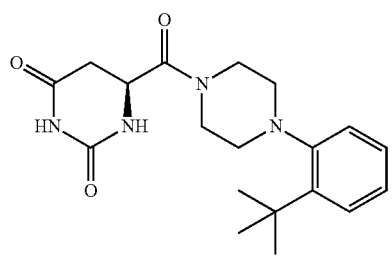 [SMILES: CC(C)(C)c1ccccc1N1CCN(C(=O)[C@@H]2CC(=O)NC(=O)N2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 359 [M+H], 9.4 mg, yield 26%, purity 100%.

Example 125

N-(1-{[4-(2-tert-Butylphenyl)piperazin-1-yl]carbonyl}-2-methylpropyl)acetamide

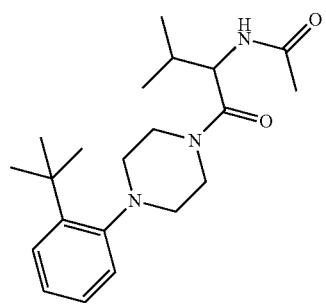 [SMILES: CC(=O)NC(C(=O)N1CCN(c2ccccc2C(C)(C)C)CC1)C(C)C]

The title compound was prepared by a procedure similar to the one described for 1-(2-tert-butylphenyl)-4-(tetrahydrofuran-2-ylcarbonyl)piperazine (Example 91).

$^1$H NMR (DMSO-d$_6$) δ 0.81-0.94 (m, 6H), 1.41 (s, 9H), 1.87 (d, J=13.4 Hz, 3H), 1.93-2.06 (m, 1H), 2.64-2.84 (m, 5H), 3.15-3.31 (m, 1H), 4.10-4.18 (m, 1H), 4.41-4.51 (m, 1H), 4.55-4.66 (m, 1H), 7.14 (t, J=7.3 Hz, 1H), 7.22 (t, J=7.1 Hz, 1H), 7.32 (d, J=7.8 Hz, 2H), 8.11 (t, J=6.1 Hz, 1H). LC/MS (ESI+) m/z 360 [M+H], 12.9 mg, yield 36%, purity 100%.

Example 126

N-[(1S)-1-{[4-(2-tert-Butylphenyl)piperazin-1-yl]carbonyl}-2-methylpropyl]acetamide

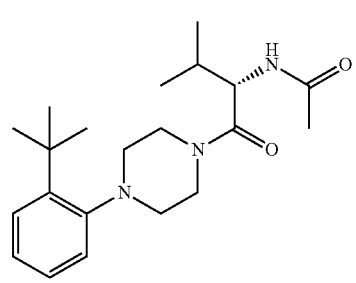 [SMILES: CC(=O)N[C@H](C(=O)N1CCN(c2ccccc2C(C)(C)C)CC1)C(C)C]

The title compound was prepared by a procedure similar to the one described for 1-(2-tert-butylphenyl)-4-(tetrahydrofuran-2-ylcarbonyl)piperazine (Example 91). LC/MS (ESI+) m/z 360[M+H], 12.6 mg, yield 35%, purity 100%.

Example 127

N-(1-{[4-(2-tert-Butylphenyl)piperazin-1-yl]carbonyl}pentyl)acetamide

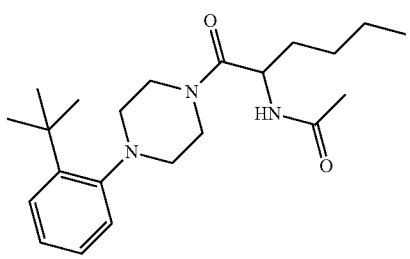 [SMILES: CCCCC(NC(C)=O)C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 374 [M+H], 13.5 mg, yield 36%, purity 100%.

Example 128

6-{[4-(2-tert-Butylphenyl)piperazin-1-yl]carbonyl}pyrimidine-2,4(1H,3H)-dione

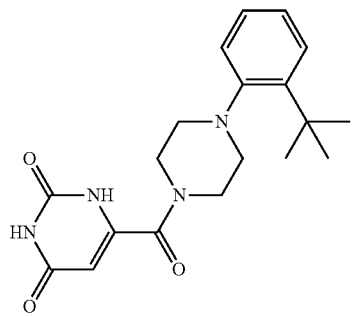 [SMILES: CC(C)(C)c1ccccc1N1CCN(C(=O)c2cc(=O)[nH]c(=O)[nH]2)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 357 [M+H], 4.0 mg, yield 11%, purity 100%.

Example 129 tert-Butyl {2-[4-(2-tert-butylphenyl)piperazin-1-yl]-2-oxoethyl}carbamate

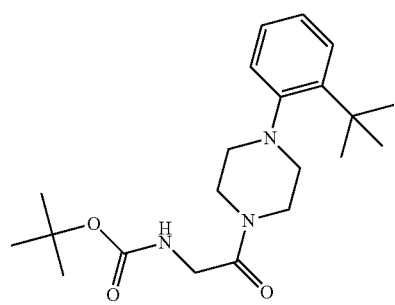 [SMILES: CC(C)(C)OC(=O)NCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 376 [M+H], 5.6 mg, yield 15%, purity 100%.

Example 130

1-(3-{2-[4-(2-tert-Butylphenyl)piperazin-1-yl]-2-oxoethyl}-2,2-dimethylcyclobutyl)ethanone

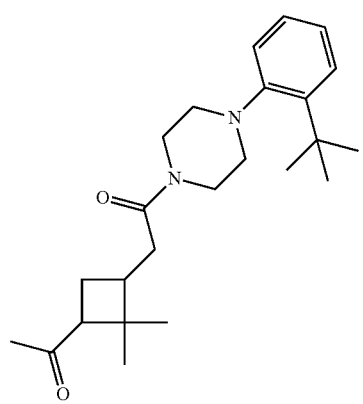 [SMILES: CC(=O)C1CC(CC(=O)N2CCN(c3ccccc3C(C)(C)C)CC2)C1(C)C]

The title compound was prepared by a procedure similar to the one described for 1-(2-tert-butylphenyl)-4-(tetrahydrofuran-2-ylcarbonyl)piperazine (Example 91). LC/MS (ESI+) m/z 385 [M+H], 17.8 mg, yield 46%, purity 100%.

Example 131 tert-Butyl {3-[4-(2-tert-butylphenyl)piperazin-1-yl]-3-oxopropyl}carbamate

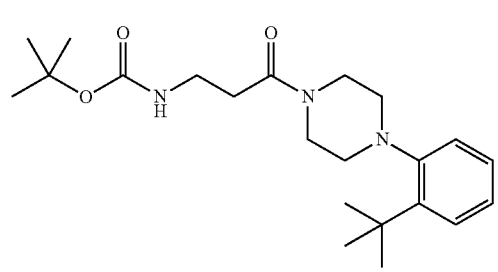 [SMILES: CC(C)(C)OC(=O)NCCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 390 [M+H], 2.6 mg, yield 7%, purity 100%.

Example 132 tert-Butyl {4-[4-(2-tert-butylphenyl)piperazin-1-yl]-4-oxobutyl}carbamate

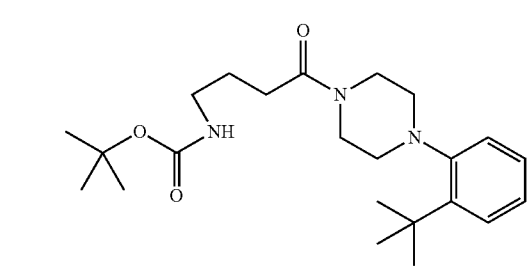 [SMILES: CC(C)(C)OC(=O)NCCCC(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 404 [M+H], 2.0 mg, yield 5%, purity 100%.

Example 133 tert-Butyl {2-[4-(2-tert-butylphenyl)piperazin-1-yl]-1,1-dimethyl-2-oxoethyl}carbamate

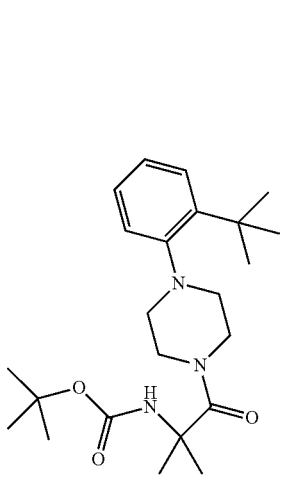 [SMILES: CC(C)(C)OC(=O)NC(C)(C)C(=O)N1CCN(c2ccccc2C(C)(C)C)CC1]

The title compound was prepared by a procedure similar to the one described for 1-(2-tert-butylphenyl)-4-(tetrahydrofuran-2-ylcarbonyl)piperazine (Example 91). LC/MS (ESI+) m/z 404 [M+H], 4.9 mg, yield 12%, purity 100%.

Example 134

3-{2-[4-(2-tert-Butylphenyl)piperazin-1-yl]-2-oxoethyl}-5-methoxy-2,3-dihydro-1H-inden-1-one

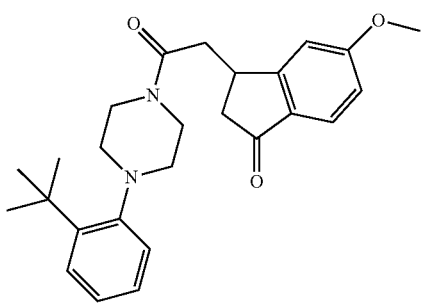 [SMILES: COc1ccc2c(c1)C(CC(=O)N1CCN(c3ccccc3C(C)(C)C)CC1)CC2=O]

The title compound was prepared by a procedure similar to the one described for 1-(2-tert-butylphenyl)-4-(tetrahydrofuran-2-ylcarbonyl)piperazine (Example 91).

$^1$H NMR (DMSO-d$_6$) δ 1.41 (s, 9H), 2.24-2.39 (m, 1H), 2.55-2.91 (m, 7H), 3.00-3.26 (m, 2H), 3.67-3.77 (m, 1H), 3.85-3.99 (m, 4H), 4.49 (t, J=6.0 Hz, 1H), 6.99 (d, J=7.6 Hz, 1H), 7.11-7.18 (m, 1H), 7.19-7.28 (m, 2H), 7.30-7.38 (m, 2H), 7.56 (d, J=8.5 Hz, 1H). LC/MS (ESI+) m/z 421 [M+H], 18.2 mg, yield 43%, purity 100%.

Example 135

4-{[4-(2-tert-Butylphenyl)piperazin-1-yl]carbonyl}benzoic acid

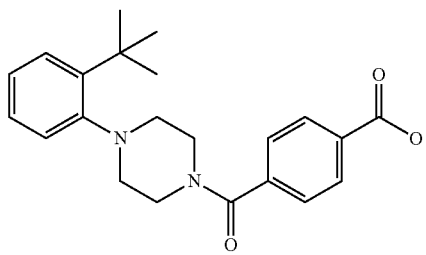 [SMILES: CC(C)(C)c1ccccc1N1CCN(C(=O)c2ccc(C(=O)O)cc2)CC1]

To a stirred suspension of 1 (2 tert-butylphenyl)piperazine dihydrochloride (29 mg, 0.1 mmol) and triethylamine (0.021 mL, 0.3 mmol) in THF (1.0 mL) was added terephthalic acid monomethyl ester chloride (59 mg, 0.3 mmol) at room temperature. After stirring for 2 h at room temperature, saturated sodium hydrogen carbonate solution (1.5 mL) was added to the mixture, and the mixture was extracted with ethyl acetate (2 mL). The organic layer was separated by phase separation filter kit and the filtrate was evaporated in vacuo. The resulting residue was dissolved in DMSO (1 mL) and the solution was purified by preparative HPLC. The eluted fraction was evaporated by air blowing at 60° C. to give a methyl ester of title compound. The obtained ester was dissolved in MeOH (0.5 mL) and THF (0.5 mL), and 1 M NaOH (0.5 mL) was added to the mixture. After stirring for 2 h at 60 deg C., the mixture was neutralized with 1 M hydrochloric acid solution, extracted with ethyl acetate. The organic layer was separated by phase separation filter kit and the filtrate was evaporated under reduced pressure to give a title compound (17.1 mg, 47%). LC/MS (ESI+) m/z 367 [M+H], purity 100%.

Example 136

1-Acetyl-4-(2-tert-butylphenyl)piperazine

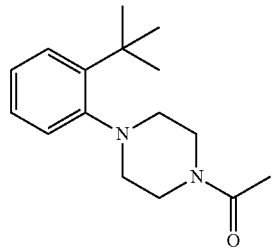 [SMILES: CC(=O)N1CCN(c2ccccc2C(C)(C)C)CC1]

To a stirred suspension of 1 (2 tert-butylphenyl)piperazine dihydrochloride (29 mg, 0.1 mmol) and triethylamine (0.021 mL, 0.3 mmol) in THF (1.0 mL) was added acetyl chloride (23 mg, 0.3 mmol) at rt. After stirring for 2 h at room temperature, saturated sodium hydrogen carbonate solution (1.5 mL) was added to the mixture, and the mixture was extracted with ethyl acetate (2 mL). The organic layer was separated by phase separation filter kit and the filtrate was evaporated under reduced pressure. The resulting residue was dissolved in DMSO (1 mL) and the solution was purified by preparative HPLC. The eluted fraction was evaporated by air blowing at 60° C. to give a title compound (20.5 mg, 79%). LC/MS (ESI+) m/z 261 [M+H], purity 100%.

Example 137

1-(2-tert-Butylphenyl)-4-(cyclopropylcarbonyl)piperazine

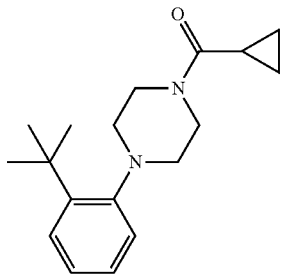 [SMILES: CC(C)(C)c1ccccc1N1CCN(C(=O)C2CC2)CC1]

The title compound was prepared by a procedure similar to the one described for 1-acetyl-4-(2-tert-butylphenyl)piperazine (Example 136). LC/MS (ESI+) m/z 287 [M+H], 24.3 mg, yield 85%, purity 100%.

Example 138

1-(2-tert-Butylphenyl)-4-(2-methylpropanoyl)piperazine

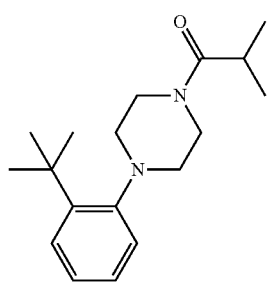 [SMILES: CC(C)C(=O)N1CCN(c2ccccc2C(C)(C)C)CC1]

The title compound was prepared by a procedure similar to the one described for 1-acetyl-4-(2-tert-butylphenyl)piperazine (Example 136). LC/MS (ESI+) m/z 289 [M+H], 26.3 mg, yield 91%, purity 100%.

Example 139

1-(2-tert-Butylphenyl)-4-(methoxyacetyl)piperazine

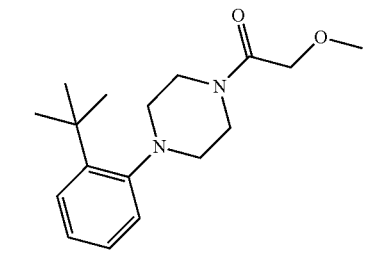 [SMILES: COCC(=O)N1CCN(c2ccccc2C(C)(C)C)CC1]

The title compound was prepared by a procedure similar to the one described for 1-acetyl-4-(2-tert-butylphenyl)piperazine (Example 136). LC/MS (ESI+) m/z 290 [M+H], 29.3 mg, yield quant., purity 100%.

Example 140

1-(2-tert-Butylphenyl)-4-(2,2-dimethylpropanoyl)piperazine

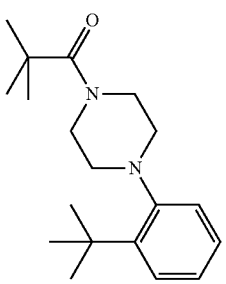 [SMILES: CC(C)(C)C(=O)N1CCN(c2ccccc2C(C)(C)C)CC1]

The title compound was prepared by a procedure similar to the one described for 1-acetyl-4-(2-tert-butylphenyl)piperazine (Example 136). LC/MS (ESI+) m/z 303 [M+H], 20.6 mg, yield 68%, purity 100%.

Example 141

1-(2-tert-Butylphenyl)-4-(isoxazol-5-ylcarbonyl)piperazine

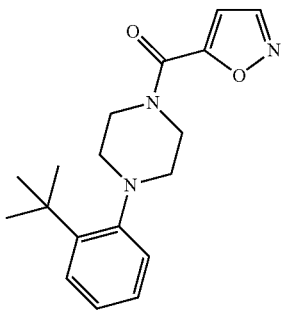 [SMILES: CC(C)(C)c1ccccc1N1CCN(C(=O)c2ccno2)CC1]

The title compound was prepared by a procedure similar to the one described for 1-acetyl-4-(2-tert-butylphenyl)piperazine (Example 136). LC/MS (ESI+) m/z 314 [M+H], 13.2 mg, yield 42%, purity 100%.

Example 142

1-(2-tert-Butylphenyl)-4-(pyridin-3-ylcarbonyl)piperazine

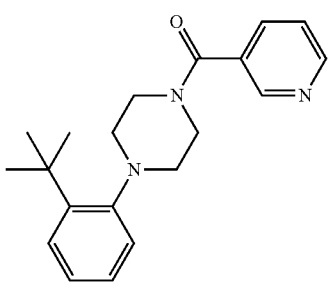 [SMILES: CC(C)(C)c1ccccc1N1CCN(C(=O)c2cccnc2)CC1]

The title compound was prepared by a procedure similar to the one described for 1-acetyl-4-(2-tert-butylphenyl)piperazine (Example 136). 25.2 mg, yield 78%, purity 100%.

Example 143

1-(2-tert-Butylphenyl)-4-(1,3-thiazol-2-ylcarbonyl)piperazine

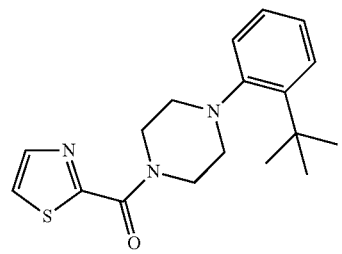 [SMILES: CC(C)(C)c1ccccc1N1CCN(C(=O)c2nccs2)CC1]

The title compound was prepared by a procedure similar to the one described for 1-acetyl-4-(2-tert-butylphenyl)piperazine (Example 136). LC/MS (ESI+) m/z 330 [M+H], 17.8 mg, yield 54%, purity 100%.

Example 144

1-(2-tert-Butylphenyl)-4-[(2,5-dimethylfuran-3-yl)carbonyl]piperazine

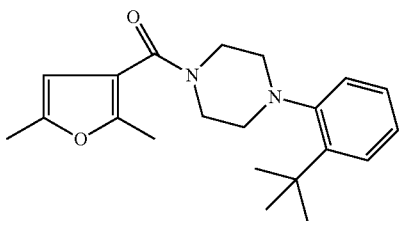 [SMILES: Cc1cc(C(=O)N2CCN(c3ccccc3C(C)(C)C)CC2)c(C)o1]

The title compound was prepared by a procedure similar to the one described for 1-acetyl-4-(2-tert-butylphenyl)piperazine (Example 136). LC/MS (ESI+) m/z 341 [M+H], 20.6 mg, yield 61%, purity 100%.

Example 145

1-(2-tert-Butylphenyl)-4-[(1,3-dimethyl-1H-pyrazol-5-yl)carbonyl]piperazine

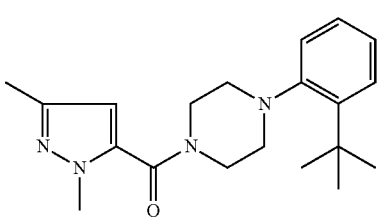 [SMILES: Cc1cc(C(=O)N2CCN(c3ccccc3C(C)(C)C)CC2)n(C)n1]

The title compound was prepared by a procedure similar to the one described for 1-acetyl-4-(2-tert-butylphenyl)piperazine (Example 136). LC/MS (ESI+) m/z 341 [M+H], 35.3 mg, yield quant., purity 100%.

Example 146

1-(2-tert-Butylphenyl)-4-[(2-methoxyphenyl)carbonyl]piperazine

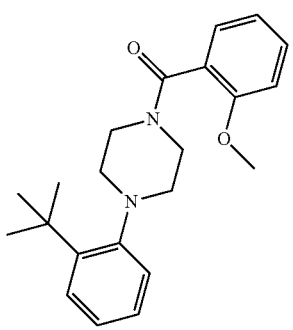 [SMILES: COc1ccccc1C(=O)N1CCN(c2ccccc2C(C)(C)C)CC1]

The title compound was prepared by a procedure similar to the one described for 1-acetyl-4-(2-tert-butylphenyl)piperazine (Example 136). LC/MS (ESI+) m/z 353 [M+H], 19.6 mg, yield 56%, purity 100%.

Example 147

1-(2-tert-Butylphenyl)-4-[(4-methoxyphenyl)carbonyl]piperazine

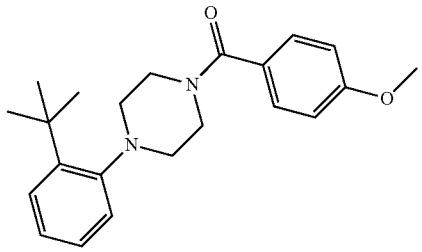 [SMILES: COc1ccc(C(=O)N2CCN(c3ccccc3C(C)(C)C)CC2)cc1]

The title compound was prepared by a procedure similar to the one described for 1-acetyl-4-(2-tert-butylphenyl)piperazine (Example 136). LC/MS (ESI+) m/z 353 [M+H], 14.5 mg, yield 41%, purity 100%.

Example 148

5-[4-(2-tert-Butylphenyl)piperazin-1-yl]-5-oxopentanoic acid

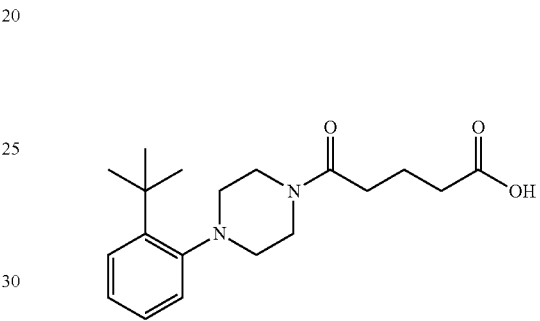

The title compound was prepared by a procedure similar to the one described for 4-{[4-(2-tert-butylphenyl)piperazin-1-yl]carbonyl}benzoic acid (Example 135). LC/MS (ESI+) m/z 333 [M+H], 8.9 mg, yield 27%, purity 100%.

Example 149

1-(2-tert-Butylphenyl)-4-[(4-methoxyphenyl)acetyl]piperazine

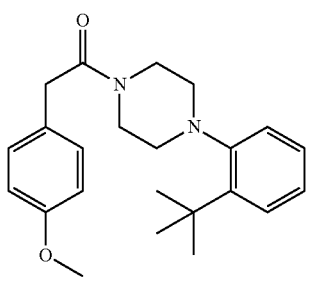 [SMILES: COc1ccc(CC(=O)N2CCN(c3ccccc3C(C)(C)C)CC2)cc1]

The title compound was prepared by a procedure similar to the one described for 1-acetyl-4-(2-tert-butylphenyl)piperazine (Example 136). LC/MS (ESI+) m/z 367 [M+H], 33.0 mg, yield 90%, purity 100%.

Example 150

1-[(Benzyloxy)acetyl]-4-(2-tert-butylphenyl)piperazine

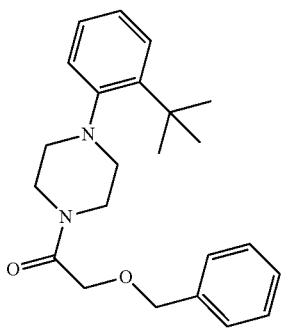 [SMILES: CC(C)(C)c1ccccc1N1CCN(C(=O)COCc2ccccc2)CC1]

The title compound was prepared by a procedure similar to the one described for 1-acetyl-4-(2-tert-butylphenyl)piperazine (Example 136). LC/MS (ESI+) m/z 367 [M+H], 19.7 mg, yield 54%, purity 100%.

Example 151

1-(2-tert-Butylphenyl)-4-[(4-chlorophenyl)acetyl]piperazine

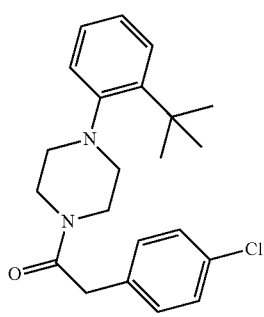 [SMILES: CC(C)(C)c1ccccc1N1CCN(C(=O)Cc2ccc(Cl)cc2)CC1]

The title compound was prepared by a procedure similar to the one described for 1-acetyl-4-(2-tert-butylphenyl)piperazine (Example 136). LC/MS (ESI+) m/z 371 [M+H], 25.9 mg, yield 70%, purity 100%.

Example 152

1-(2-tert-Butylphenyl)-4-{[6-(trifluoromethyl)pyridin-3-yl]carbonyl}piperazine

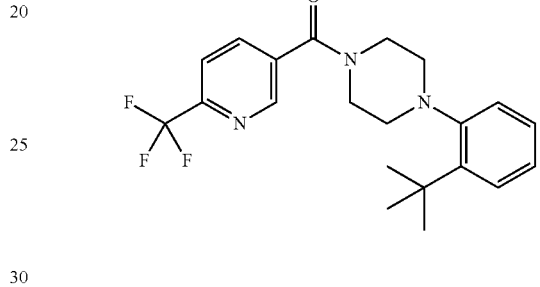

The title compound was prepared by a procedure similar to the one described for 1-acetyl-4-(2-tert-butylphenyl)piperazine (Example 136).

$^1$H NMR (DMSO-$d_6$) δ 1.42 (s, 9H), 2.62-2.70 (m, 1H), 2.81-2.96 (m, 3H), 3.00-3.09 (m, 1H), 3.35-3.56 (m, 2H), 4.58 (d, J=12.4 Hz, 1H), 7.15 (t, J=8.3 Hz, 1H), 7.24 (t, J=8.3 Hz, 1H), 7.32 (d, J=7.8 Hz, 1H), 7.44 (d, J=7.8 Hz, 1H), 8.03 (d, J=8.0 Hz, 1H), 8.23 (d, J=8.1 Hz, 1H), 8.90 (d, J=1.0 Hz, 1H). LC/MS (ESI+) m/z 392 [M+H], 15.2 mg, yield 39%, purity 100%.

Example 153

(1S,4R)-1-{[4-(2-tert-Butylphenyl)piperazin-1-yl]carbonyl}-4,7,7-trimethyl-2-oxabicyclo[2.2.1]heptan-3-one

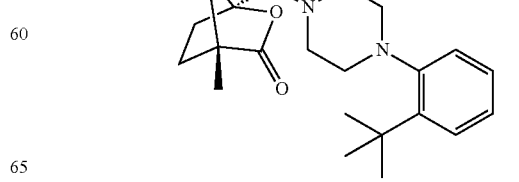

The title compound was prepared by a procedure similar to the one described for 1-acetyl-4-(2-tert-butylphenyl)piperazine (Example 136). LC/MS (ESI+) m/z 399 [M+H], 33.6 mg, yield 84%, purity 100%.

Example 154

1-[(1-Acetylpiperidin-4-yl)carbonyl]-4-(2-tert-butylphenyl)piperazine

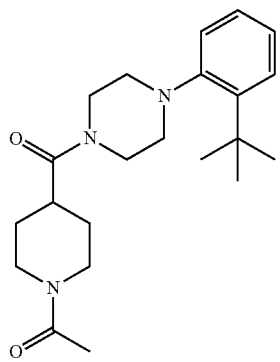 [SMILES: CC(=O)N1CCC(C(=O)N2CCN(c3ccccc3C(C)(C)C)CC2)CC1]

The title compound was prepared by a procedure similar to the one described for 1-acetyl-4-(2-tert-butylphenyl)piperazine (Example 136). LC/MS (ESI+) m/z 372 [M+H], 20.4 mg, yield 55%, purity 100%.

Example 155

2-{[4-(2-tert-Butylphenyl)piperazin-1-yl]carbonyl}quinoline

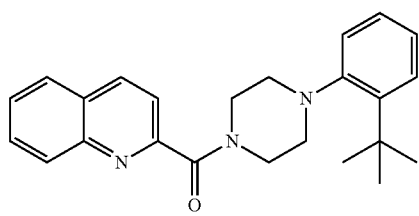 [SMILES: CC(C)(C)c1ccccc1N1CCN(C(=O)c2ccc3ccccc3n2)CC1]

The title compound was prepared by a procedure similar to the one described for 1-acetyl-4-(2-tert-butylphenyl)piperazine (Example 136). LC/MS (ESI+) m/z 374 [M+H], 16.3 mg, yield 44%, purity 100%.

Example 156

1-Methylethyl 4-(2-tert-butylphenyl)piperazine-1-carboxylate

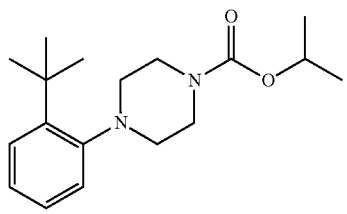 [SMILES: CC(C)OC(=O)N1CCN(c2ccccc2C(C)(C)C)CC1]

The title compound was prepared by a procedure similar to the one described for 1-acetyl-4-(2-tert-butylphenyl)piperazine (Example 136). LC/MS (ESI+) m/z 305 [M+H], 17.6 mg, yield 58%, purity 100%.

Example 157

Phenyl 4-(2-tert-butylphenyl)piperazine-1-carboxylate

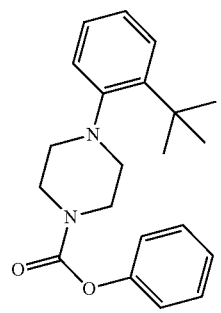 [SMILES: CC(C)(C)c1ccccc1N1CCN(C(=O)Oc2ccccc2)CC1]

The title compound was prepared by a procedure similar to the one described for 1-acetyl-4-(2-tert-butylphenyl)piperazine (Example 136). LC/MS (ESI+) m/z 339 [M+H], 20.8 mg, yield 62%, purity 100%.

Example 158

4-{[4-(2-tert-Butylphenyl)piperazin-1-yl]carbonyl}morpholine

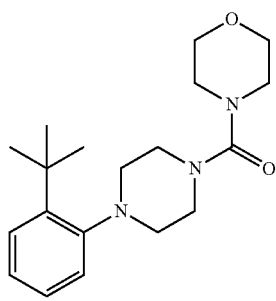 [SMILES: CC(C)(C)c1ccccc1N1CCN(C(=O)N2CCOCC2)CC1]

The title compound was prepared by a procedure similar to the one described for 1-acetyl-4-(2-tert-butylphenyl)piperazine (Example 136). LC/MS (ESI+) m/z 332 [M+H], 7.6 mg, yield 23%, purity 100%.

Example 159

(5R)-5-{[4-(2-tert-Butylphenyl)piperazin-1-yl]carbonyl}pyrrolidin-2-one

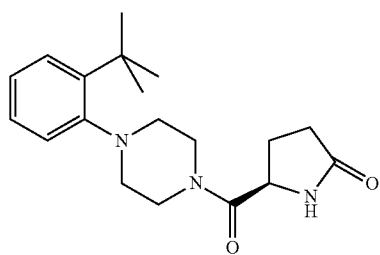 [SMILES: CC(C)(C)c1ccccc1N1CCN(C(=O)[C@H]2CCC(=O)N2)CC1]

A mixture of 1-(2-tert-butylphenyl)piperazine dihydrochloride obtained in Reference Example 1 (0.30 g, 1.03 mmol), (R)-(+)-2-pyrrolidone-5-carboxylic acid (0.15 g, 1.13 mmol), triethylamine (0.23 g, 2.26 mmol), EDCI (0.22 g, 1.13 mmol) and HOBt (0.17 g, 1.13 mmol) in acetonitrile (10 mL) was stirred at room temperature for 16 h. The reaction mixture was concentrated under reduced pressure and the resulting residue was partitioned between ethyl acetate and 10% sodium hydrogen carbonate solution. The organic layer was washed with brine, dried over anhydrous magnesium sulfate, filtered and concentrated under reduced pressure. The resulting light pink solid was triturated with hexane to afford the title compound (0.32 g, 94%) as a light pink solid.

$^1$H NMR (300 MHz, DMSO-d$_6$) δ ppm 1.42 (s, 9H), 1.83-2.22 (m, 3H), 2.24-2.42 (m, 1H), 2.64-2.97 (m, 5H), 3.30 (br. s., 1H), 3.93 (br. s., 1H), 4.41 (br. s., 1H), 4.49-4.72 (m, 1H), 7.06-7.19 (m, 1H), 7.22 (t, J=7.3 Hz, 1H), 7.28-7.46 (m, 2H), 7.73 (br. S., 1H). LC/MS; ESI(+) m/z: 330 (M+H)$^+$.

Example 160

1-(2-tert-Butylphenyl)-4-(1-phenylprolyl)piperazine

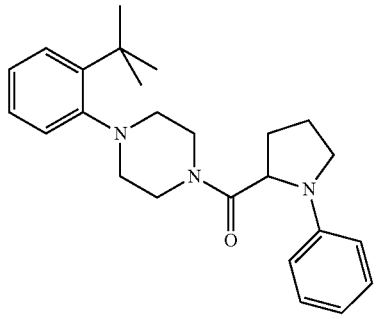 [SMILES: CC(C)(C)c1ccccc1N1CCN(C(=O)C2CCCN2c2ccccc2)CC1]

A mixture of 1-(2-tert-butylphenyl)piperazine dihydrochloride obtained in Reference Example 1 (0.30 g, 1.03 mmol), 1-phenylproline (Reference example 7, 0.22 g, 1.13 mmol), triethylamine (0.23 g, 2.26 mmol), EDCI (0.22 g, 1.13 mmol) and HOBt (0.17 g, 1.13 mmol) in N,N-dimethylformamide (10 mL) was stirred at room temperature for 16 h. The reaction mixture was concentrated under reduced pressure and the resulting residue was partitioned between ethyl acetate and 10% sodium hydrogen carbonate solution. The organic layer was washed with brine, dried over anhydrous magnesium sulfate, filtered and concentrated under reduced pressure. The resulting residue was purified by silica gel column chromatography (hexane/ethyl acetate 90:10 to 50:50) and the resulting yellow solid was triturated with hexane-ethyl acetate to give the title compound (0.10 g, 25%) as a white solid.

$^1$H NMR (300 MHz, CHLOROFORM-d) δ ppm 1.46 (s, 9H), 1.94-2.49 (m, 4H), 2.62-3.15 (m, 5H), 3.28-3.75 (m, 3H), 3.96-4.18 (m, 1H), 4.46-4.71 (m, 2H), 6.40-6.61 (m, 2H), 6.63-6.79 (m, 1H), 7.12-7.26 (m, 5H), 7.31-7.48 (m, 1H). LC/MS; ESI(+) m/z: 392 (M+H)$^+$.

Example 161

5-{[4-(2-tert-Butylphenyl)piperazin-1-yl]carbonyl}-1-phenylpyrrolidin-2-one

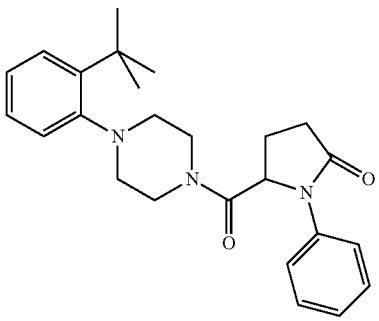 [SMILES: CC(C)(C)c1ccccc1N1CCN(C(=O)C2CCC(=O)N2c2ccccc2)CC1]

To an ice-cold stirred solution of 5-oxo-1-phenylproline (Reference Example 12, 0.22 g, 1.08 mmol) and N,N-dimethylformamide (3 drops) in tetrahydrofuran (10 mL) was added oxalyl chloride (0.14 g, 1.10 mmol). The mixture was stirred at 0° C. for 30 min, and then allowed to warm to room temperature. The reaction mixture was concentrated under reduced pressure, and the residue was dissolved in pyridine (10 mL). To this mixture was added 1-(2-tert-butylphenyl) piperazine dihydrochloride (Reference Example 1, 0.30 g, 1.03 mmol) and the mixture was stirred at room temperature for 16 h. The reaction mixture was concentrated under reduced pressure and the resulting residue was partitioned between ethyl acetate and 10% NaHCO$_3$ solution. The organic layer was washed with brine, dried over anhydrous magnesium sulfate, filtered and concentrated under reduced pressure. The resulting solid was dissolved in ethyl acetate and filtered through a pad of silica gel. The filtrate was concentrated under reduced pressure to give an orange solid. This solid was recrystallized from hexane-ethyl acetate to give the title compound (0.26 g, 59%) as a light yellow solid.

$^1$H NMR (300 MHz, CHLOROFORM-d) δ ppm 1.41-1.49 (m, 9H), 2.07-2.26 (m, 1H), 2.38-3.01 (m, 8H), 3.35-3.56 (m, 1H), 3.84 (d, J=12.9 Hz, 1H), 4.49-4.63 (m, 1H), 4.98-5.18 (m, 1H), 7.07-7.25 (m, 4H), 7.32-7.56 (m, 5H). LC/MS; ESI(+) m/z: 406 (M+H)$^+$.

Example 162

1-(2-tert-Butylphenyl)-4-[(5-cyclohexyl-1,3-oxazol-4-yl)carbonyl]piperazine

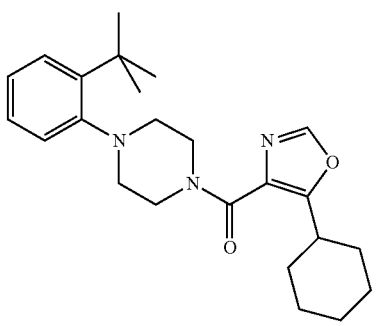 [SMILES: CC(C)(C)c1ccccc1N1CCN(C(=O)c2ncoc2C2CCCCC2)CC1]

A mixture of 1-(2-tert-butylphenyl)piperazine dihydrochloride (Reference Example 1, 0.30 g, 1.03 mmol), 5-cyclohexyl-1,3-oxazole-4-carboxylic acid (Reference Example 14, 0.22 g, 1.13 mmol), triethylamine (0.23 g, 2.26 mmol), EDCI (0.22 g, 1.13 mmol) and HOBt (0.17 g, 1.13 mmol) in acetonitrile (10 mL) was stirred at room temperature for 16 h. The reaction mixture was concentrated under reduced pressure and the resulting residue was partitioned between ethyl acetate and 10% sodium hydrogen carbonate solution. The organic layer was washed with brine, dried over anhydrous magnesium sulfate, filtered and concentrated under reduced pressure. The resulting residue was purified by silica gel column chromatography (hexane/ethyl acetate 80:20 to 50:50) and the resulting white solid was triturated with hexane to give the title compound (0.15 g, 37%) as a white solid.

$^1$H NMR (300 MHz, CHLOROFORM-d) δ ppm 1.19-2.00 (m, 20H), 2.79-3.16 (m, 4H), 3.18-3.53 (m, 2H), 4.47-4.79 (m, 2H), 7.11-7.25 (m, 2H), 7.27-7.33 (m, 1H), 7.38 (dd, J=7.8, 1.7 Hz, 1H), 7.71 (s, 1H). LC/MS; ESI(+) m/z: 396 (M+H)$^+$.

Example 163 tert-Butyl 4-(4-{[4-(2-tert-butylphenyl)piperazin-1-yl]carbonyl}-1,3-oxazol-5-yl)piperidine-1-carboxylate

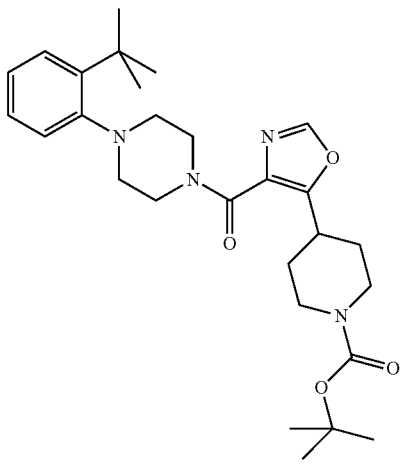 [SMILES: CC(C)(C)OC(=O)N1CCC(c2ocnc2C(=O)N2CCN(c3ccccc3C(C)(C)C)CC2)CC1]

A mixture of 1-(2-tert-butylphenyl)piperazine dihydrochloride (Reference Example 1, 0.30 g, 1.03 mmol), 5-[1-(tert-butoxycarbonyl)piperidin-4-yl]-1,3-oxazole-4-carboxylic acid (Reference Example 16, 0.33 g, 1.13 mmol), triethylamine (0.23 g, 2.26 mmol), EDCI (0.22 g, 1.13 mmol) and HOBt (0.17 g, 1.13 mmol) in acetonitrile (10 mL) was stirred at room temperature for 16 h. The reaction mixture was concentrated under reduced pressure and the resulting residue was partitioned between ethyl acetate and 10% sodium hydrogen carbonate solution. The organic layer was washed with brine, dried over anhydrous magnesium sulfate, filtered and concentrated under reduced pressure. The resulting residue was purified by silica gel column chromatography (hexane/ethyl acetate 80:20 to 50:50) to give the title compound (0.47 g, 92%) as a white amorphous powder.

$^1$H NMR (300 MHz, CHLOROFORM-d) δ ppm 1.45 (s, 9H), 1.48 (s, 9H), 1.66-2.00 (m, 4H), 2.68-3.23 (m, 7H), 3.34-3.67 (m, 2H), 4.11-4.37 (m, 2H), 4.59-4.80 (m, 2H), 7.10-7.25 (m, 2H), 7.27-7.32 (m, 1H), 7.38 (dd, J=8.0, 1.9 Hz, 1H), 7.73 (s, 1H). LC/MS; ESI(+) m/z: 497 (M+H)⁺.

Example 164

N-(4-{[4-(2-tert-Butylphenyl)piperazin-1-yl]carbonyl}benzyl)tetrahydro-2H-thiopyran-4-amine 1,1-dioxide

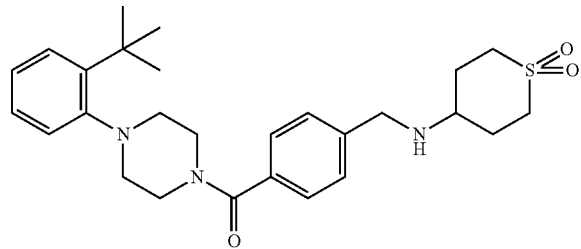 [SMILES: CC(C)(C)c1ccccc1N1CCN(C(=O)c2ccc(CNC3CCS(=O)(=O)CC3)cc2)CC1]

A mixture of 1-(2-tert-butylphenyl)-4-{[4-(chloromethyl)phenyl]carbonyl}piperazine obtained in Example (450 mg), N-(1,1-dioxidotetrahydro-2H-thiopyran-4-yl)-2-nitrobenzenesulfonamide (435 mg), potassium carbonate (415 mg), and N,N-dimethylformamide (5 mL) was stirred at 40° C. for 4 h. Water was added to the reaction solution, and the mixture was extracted with ethyl acetate. The ethyl acetate layer was washed with saturated brine, and dried over anhydrous magnesium sulfate. The solvent was evaporated under reduced pressure to provide a solid (820 mg).

LC/MS (ESI+) m/z: 669 (M+H)⁺.

A mixture of the solid (820 mg), sulfanylacetic acid (1.0 g), lithium hydroxide mono-hydrate (1.0 g), and N,N-dimethylformamide (10 mL) was stirred at 40° C. for 4 h. 6 M hydrochloric acid solution was added to the reaction solution, and the mixture was extracted with ethyl acetate. The ethyl acetate layer was washed with saturated brine, and dried over anhydrous magnesium sulfate. The solvent was evaporated under reduced pressure to provide the title compound (82 mg, 14%) as crystals.

¹H NMR (300 MHz, CHLOROFORM-d) δ ppm 1.16-1.69 (m, 2H), 1.49 (s, 9H), 1.96-2.18 (m, 2H), 2.18-2.37 (m, 2H), 2.65-3.23 (m, 9H), 3.22-3.51 (m, 2H), 3.81 (s, 2H), 4.74 (br. s., 1H), 7.10-7.41 (m, 6H), 7.42-7.50 (m, 2H). LC/MS; ESI (+) m/z: 484 (M+H)⁺.

Example 165

1-{[4-(2-tert-Butylphenyl)piperazin-1-yl]carbonyl}piperidin-4-ol

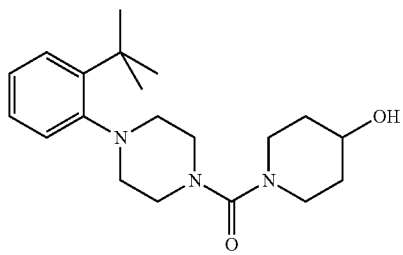 [SMILES: CC(C)(C)c1ccccc1N1CCN(C(=O)N2CCC(O)CC2)CC1]

A solution of 2,2,2-trichloroethyl 4-(2-tert-butylphenyl)piperazine-1-carboxylate (Example 60, 0.40 g, 1.02 mmol), piperidin-4-ol (0.50 g, 4.94 mmol), and N-ethyl-N-(1-methylethyl)propan-2-amine (0.158 g, 1.22 mmol) in DMSO (5 mL) was stirred for 3 days at 110° C. The reaction mixture was poured into saturated NaHCO₃ solution and extracted with ethyl acetate. The organic layer was washed with brine, dried over MgSO₄, and the solvent was evaporated under reduced pressure to give a crude product. The product was purified by flash column chromatography (silica gel, n-hexane/ethyl acetate=50:50 to 0:100 then ethyl acetate/methanol=100/0 to 70/30) to provide 1-{[4-(2-tert-butylphenyl)piperazin-1-yl]carbonyl}piperidin-4-ol (0.121 g, 34%) as a yellow solid.

¹H NMR (300 MHz, CHLOROFORM-d) δ ppm 1.37-1.70 (m, 12H), 1.85-2.01 (m, 2H), 2.74-2.85 (m, 2H), 2.91 (td, J=11.5, 2.5 Hz, 2H), 3.01 (ddd, J=13.2, 9.9, 3.0 Hz, 2H), 3.16 (td, J=11.9, 3.0 Hz, 2H), 3.55-3.72 (m, 4H), 3.87 (tt, J=8.6, 4.1 Hz, 1H), 7.10-7.18 (m, 1H), 7.21 (td, J=7.4, 1.5 Hz, 1H), 7.25-7.34 (m, 1H), 7.37 (dd, J=7.8, 1.7 Hz, 1H).

Example 166

Ethyl {4-[2-tert-butyl-4-(1-methylethenyl)phenyl]piperazin-1-yl}(oxo)acetate

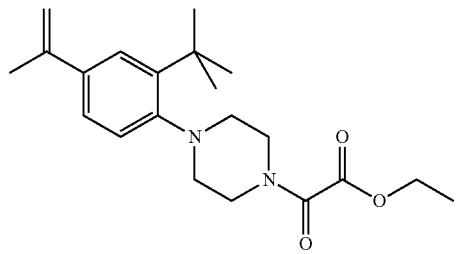

Example 167

Ethyl {4-[2-tert-butyl-4-(1-hydroxy-1-methylethyl)phenyl]piperazin-1-yl}(oxo)acetate

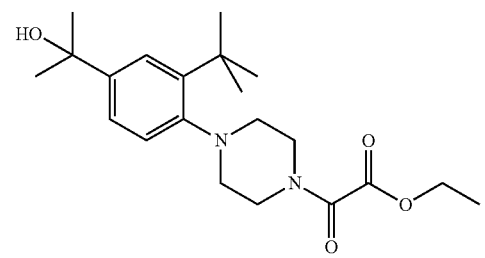 [SMILES: CCOC(=O)C(=O)N1CCN(c2ccc(C(C)(C)O)cc2C(C)(C)C)CC1]

A solution of tert-butyl 4-[2-tert-butyl-4-(1-hydroxy-1-methylethyl)phenyl]piperazine-1-carboxylate (Example 80, 2.5 g, 6.64 mmol) in 4 M HCl-EtOAc solution (15 mL) was stirred for 16 h at room temperature. It was concentrated under reduced pressure to provide a pale yellow powder (2.16 g). To a suspension of the powder (0.80 g) and triethylamine (1.28 mL, 9.16 mmol) in THF (15 mL) stirring at 0° C. was added ethyl chloro(oxo)acetate (0.41 g, 3.0 mmol). The mixture was warmed to room temperature. After 16 h the reaction mixture was poured into saturated NaHCO₃ solution and extracted with ethyl acetate. The organic layer was washed with saturated NaHCO₃ solution and brine, dried over MgSO₄, and the solvent was evaporated under reduced pressure to give the crude product. The product was purified by flash column chromatography (silica gel, n-hexane/ethyl acetate=90:10 to 50:50) to provide ethyl {4-[2-tert-butyl-4-(1-methylethenyl)phenyl]piperazin-1-yl}(oxo)acetate (0.246 g, 2 steps 27%) as a pale yellow oil and ethyl {4-[2-tert-butyl-4-(1-hydroxy-1-methylethyl)phenyl]piperazin-1-yl}(oxo)acetate (0.48 g, 2 steps 51%) as a yellow solid.

Ethyl {4-[2-tert-butyl-4-(1-methylethenyl)phenyl]piperazin-1-yl}(oxo)acetate

Example 166

¹H NMR (300 MHz, CHLOROFORM-d) δ ppm 1.39 (t, J=7.2 Hz, 3H), 1.45 (s, 9H), 2.14 (s, 3H), 2.81-3.13 (m, 5H), 3.40-3.56 (m, 1H), 3.67 (dd, J=12.9, 1.9 Hz, 1H), 4.36 (q, J=6.9 Hz, 2H), 4.53 (dd, J=12.5, 1.9 Hz, 1H), 5.05-5.09 (m, 1H), 5.33 (s, 1H), 7.21 (d, J=8.3 Hz, 1H), 7.32 (dd, J=8.3, 2.3 Hz, 1H), 7.49 (d, J=1.9 Hz, 1H).

Ethyl {4-[2-tert-butyl-4-(1-hydroxy-1-methylethyl)phenyl]piperazin-1-yl}(oxo)acetate Example 167

¹H NMR (300 MHz, CHLOROFORM-d) δ ppm 1.38 (t, J=7.2 Hz, 3H), 1.45 (s, 9H), 1.58 (s, 6H), 2.80-3.13 (m, 5H), 3.39-3.55 (m, 1H), 3.59-3.72 (m, 1H), 4.36 (q, J=7.2 Hz, 2H), 4.52 (dd, J=12.7, 2.1 Hz, 1H), 7.21 (d, J=8.3 Hz, 1H), 7.3 (dd, J=8.3, 2.3 Hz, 1H), 7.52 (d, J=2.3 Hz, 1H).

Example 168

{4-[2-tert-Butyl-4-(1-methylethenyl)phenyl]piperazin-1-yl}(oxo)acetic acid

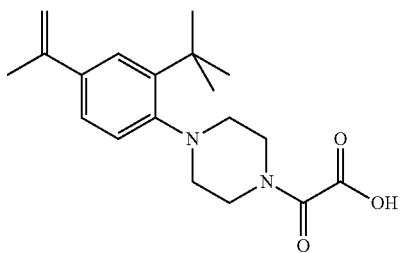 [SMILES: C=C(C)c1ccc(N2CCN(C(=O)C(=O)O)CC2)c(C(C)(C)C)c1]

To a stirred solution of ethyl {4-[2-tert-butyl-4-(1-methylethenyl)phenyl]piperazin-1-yl}(oxo)acetate (Example 166, 0.057 g, 0.158 mmol) in THF (5 mL) stirring at 0° C. was added 1 M lithium hydroxide solution (5 mL, 5 mmol). After 2 h the reaction mixture was acidified with 1 M HCl solution and extracted with ethyl acetate. The organic layer was washed with brine, dried over MgSO₄, and the solvent was evaporated under reduced pressure to provide {4-[2-tert-butyl-4-(1-methylethenyl)phenyl]piperazin-1-yl}(oxo)acetic acid (0.057 g, quant.) as a white powder.

¹H NMR (300 MHz, CHLOROFORM-d) δ ppm 1.46 (s, 9H), 2.14 (s, 3H), 2.86-3.04 (m, 4H), 3.08-3.25 (m, 1H), 3.50 (ddd, J=13.3, 10.3, 4.7 Hz, 1H), 4.57 (dd, J=12.6, 2.1 Hz, 1H), 5.07 (t, J=1.3 Hz, 1H), 5.26 (dd, J=13.0, 2.5 Hz, 1H), 5.33 (d, J=0.8 Hz, 1H), 7.20 (d, J=8.3 Hz, 1H), 7.32 (dd, J=8.3, 2.3 Hz, 1H), 7.50 (d, J=2.3 Hz, 1H).

Example 169

{4-[2-tert-Butyl-4-(1-hydroxy-1-methylethyl)phenyl]piperazin-1-yl}(oxo)acetic acid

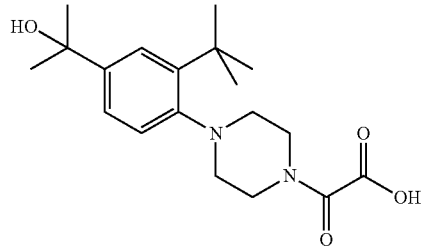 [SMILES: CC(C)(C)c1cc(C(C)(C)O)ccc1N1CCN(C(=O)C(=O)O)CC1]

To a stirred solution of ethyl {4-[2-tert-butyl-4-(1-hydroxy-1-methylethyl)phenyl]piperazin-1-yl}(oxo)acetate (Example 167, 0.38 g, 1.01 mmol) in THF (5 mL) stirring at 0° C. was added 1 M lithium hydroxide solution (5 mL, 5 mmol). After 2 h the reaction mixture was acidified with 1 M hydrochloric acid solution and extracted with ethyl acetate. The organic layer was washed with brine, dried over MgSO₄, and the solvent was evaporated under reduced pressure to provide {4-[2-tert-butyl-4-(1-hydroxy-1-methylethyl)phenyl]piperazin-1-yl}(oxo)acetic acid (0.333 g, 95%) as a pale yellow powder.

¹H NMR (300 MHz, DMSO-d₆) δ ppm 1.32-1.49 (m, 15H), 2.61-3.02 (m, 5H), 3.23-3.45 (m, 1H), 3.61 (d, J=12.8 Hz, 1H), 4.29 (d, J=12.8 Hz, 1H), 4.92 (br. s., 1H), 7.27 (s, 2H), 7.47 (s, 1H), 14.23 (br. s., 1H).

Example 170

Ethyl {4-[2-tert-butyl-4-(1-methylethyl)phenyl]piperazin-1-yl}(oxo)acetate

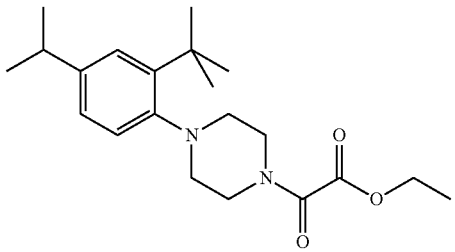 [SMILES: CCOC(=O)C(=O)N1CCN(c2ccc(C(C)C)cc2C(C)(C)C)CC1]

A suspension of ethyl {4-[2-tert-butyl-4-(1-methylethenyl)phenyl]piperazin-1-yl}(oxo)acetate (Example 166, 0.17 g, 0.474 mmol) and palladium hydroxide (20% on carbon, wetted with ca. 50% water, 20 mg) in ethyl acetate (3 mL) was stirred under hydrogen at room temperature for 30 minutes. The reaction mixture was filtered and the filtrate was concentrated under reduced pressure to provide ethyl {4-[2-tert-butyl-4-(1-methylethyl)phenyl]piperazin-1-yl}(oxo)acetate (0.133 g, 78%) as a colorless oil.

¹H NMR (300 MHz, CHLOROFORM-d) δ ppm 1.24 (d, J=7.2 Hz, 6H), 1.38 (t, J=7.2 Hz, 3H), 1.44 (s, 9H), 2.76-3.12

(m, 6H), 3.39-3.54 (m, 1H), 3.60-3.71 (m, 1H), 4.36 (q, J=7.2 Hz, 2H), 4.51 (dd, J=12.4, 1.8 Hz, 1H), 7.08 (dd, J=7.9, 1.8 Hz, 1H), 7.17 (d, J=7.9 Hz, 1H), 7.21 (d, J=2.3 Hz, 1H).

Example 171

{4-[2-tert-Butyl-4-(1-methylethyl)phenyl]piperazin-1-yl}(oxo)acetic acid

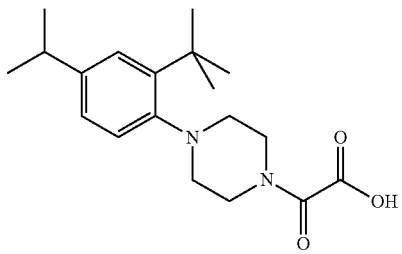 [SMILES: CC(C)c1ccc(N2CCN(C(=O)C(=O)O)CC2)c(C(C)(C)C)c1]

To a stirred solution of ethyl {4-[2-tert-butyl-4-(1-methylethyl)phenyl]piperazin-1-yl}(oxo)acetate (Example 170, 0.113 g, 0.34 mmol) in THF (5 mL) stirring at 0° C. was added 1 M lithium hydroxide solution (5 mL, 5 mmol). After 1 h the reaction mixture was acidified with 1 M hydrochloric acid solution and extracted with ethyl acetate. The organic layer was washed with brine, dried over MgSO$_4$, and the solvent was evaporated under reduced pressure to provide {4-[2-tert-butyl-4-(1-methylethyl)phenyl]piperazin-1-yl}(oxo)acetic acid (0.110 g, 97%) as a white powder.
$^1$H NMR (300 MHz, CHLOROFORM-d) δ ppm (d, J=6.8 Hz, 6H), 1.44 (s, 9H), 2.80-3.03 (m, 5H), 3.14 (td, J=12.1, 3.8 Hz, 1H), 3.49 (ddd, J=13.4, 9.2, 5.9 Hz, 1H), 4.55 (dd, J=12.5, 1.9 Hz, 1H), 5.16 (d, J=13.6 Hz, 1H), 7.08 (dd, J=8.0, 1.9 Hz, 1H), 7.16 (d, J=8.3 Hz, 1H), 7.21 (d, J=1.9 Hz, 1H).

Example 172 tert-Butyl 4-(2-tert-butyl-4-cyanophenyl)piperazine-1-carboxylate

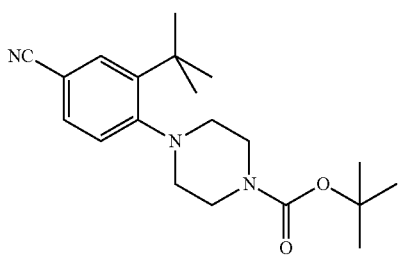 [SMILES: CC(C)(C)OC(=O)N1CCN(c2ccc(C#N)cc2C(C)(C)C)CC1]

A mixture of tert-butyl 4-(4-bromo-2-tert-butylphenyl)piperazine-1-carboxylate (Example 85, 3.0 g, 7.55 mmol), zinc cyanide (1.77 g, 15.1 mmol) and tetrakis(triphenylphosphine)palladium(0) (0.88 g, 0.76 mmol) in DMF (30 mL) was stirred at 100° C. for 4 h under argon atmosphere. The reaction mixture was cooled to room temperature, poured into saturated NaHCO$_3$ solution and extracted with ethyl acetate. The organic layer was washed with brine, dried over MgSO$_4$, and the solvent was evaporated under reduced pressure to give the crude product. The product was purified by flash column chromatography (silica gel, n-hexane/ethyl acetate=95:5 to 80:20) to provide tert-butyl 4-(2-tert-butyl-4-cyanophenyl)piperazine-1-carboxylate (2.29 g, 88%) as a white powder.
$^1$H NMR (300 MHz, CHLOROFORM-d) δ ppm 1.44 (s, 9H), 1.49 (s, 9H), 2.65-2.91 (m, 4H), 3.07 (br. s., 2H), 3.91-4.25 (m, 2H), 7.36 (d, J=8.3 Hz, 1H), 7.52 (dd, J=8.3, 2.3 Hz, 1H), 7.67 (d, J=2.3 Hz, 1H).

Example 173

N-[4-(Benzyloxy)phenyl]-4-(2-tert-butylphenyl)piperazine-1-carboxamide

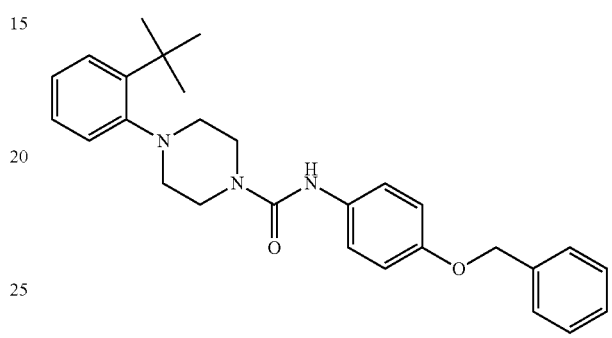

A suspension of 1-(2-tert-butylphenyl)piperazine dihydrochloride (Reference Example 1, 1.76 g, 6.05 mmol), 1-(benzyloxy)-4-isocyanatobenzene (1.50 g, 6.66 mmol) and triethylamine (2.11 mL, 15.1 mmol) in THF (15 mL) was stirred at room temperature for 16 h. The reaction mixture was poured into saturated NaHCO$_3$ solution and extracted with ethyl acetate. The organic layer was washed with saturated NaHCO$_3$ solution and brine, dried over MgSO$_4$, and the solvent was evaporated under reduced pressure to provide N-[4-(benzyloxy)phenyl]-4-(2-tert-butylphenyl)piperazine-1-carboxamide (2.65 g, 99%) as a off white solid.
$^1$H NMR (300 MHz, CHLOROFORM-d) δ ppm 1.45 (s, 9H), 2.81-3.01 (m, 4H), 3.14-3.29 (m, 2H), 4.01 (d, J=12.9 Hz, 2H), 5.04 (s, 2H), 6.32 (s, 1H), 6.86-6.99 (m, 2H), 7.11-7.48 (m, 11H).

Example 174

4-(2-tert-Butylphenyl)-N-(4-hydroxyphenyl)piperazine-1-carboxamide

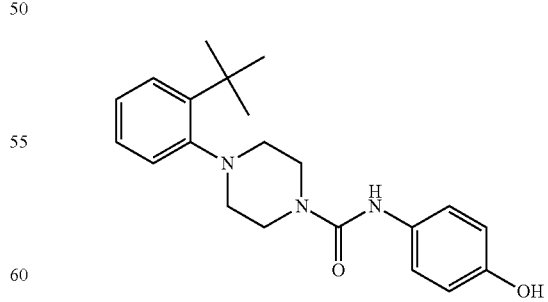

A suspension of N-[4-(benzyloxy)phenyl]-4-(2-tert-butylphenyl)piperazine-1-carboxamide (Example 173, 2.0 g, 4.51 mmol) and palladium hydroxide (20% on carbon, wetted with ca. 50% water, 100 mg) in ethyl acetate (100 mL) was stirred under hydrogen at 60° C. for 16 h. The reaction mixture was filtered and the filtrate was concentrated under reduced pressure. The residue was purified by flash column chromatography (silica gel, n-hexane/ethyl acetate=90:10 to 30:70) to provide 4-(2-tert-butylphenyl)-N-(4-hydroxyphenyl)piperazine-1-carboxamide (1.47 g, 92%) as a white solid.

$^1$H NMR (300 MHz, DMSO-$d_6$) δ ppm 1.42 (s, 9H), 2.66-2.90 (m, 4H), 2.90-3.08 (m, 2H), 4.13 (d, J=12.1 Hz, 2H), 6.65 (m, 2H), 7.10-7.28 (m, 3H), 7.28-7.46 (m, 3H), 8.29 (s, 1H), 9.01 (br. s., 1H).

Example 175

Methyl [4-({[4-(2-tert-butylphenyl)piperazin-1-yl]carbonyl}amino)phenoxy]acetate

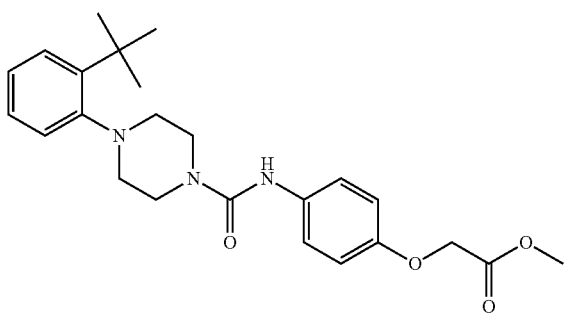 [SMILES: COC(=O)COc1ccc(NC(=O)N2CCN(c3ccccc3C(C)(C)C)CC2)cc1]

A suspension of 4-(2-tert-butylphenyl)-N-(4-hydroxyphenyl)piperazine-1-carboxamide (Example 174, 0.290 g, 0.82 mmol), methyl bromoacetate (0.163 g, 1.07 mmol), and potassium carbonate (0.227 g, 1.64 mmol) in DMF (3 mL) was stirred at room temperature for 24 h. The reaction mixture was poured into water and extracted with ethyl acetate. The organic layer was washed with saturated NaHCO$_3$ solution and brine, dried over MgSO$_4$, and the solvent was evaporated under reduced pressure to give the crude product, which was purified by flash column chromatography (silica gel, n-hexane/ethyl acetate=90:10 to 50:50) to provide methyl [4-({[4-(2-tert-butylphenyl)piperazin-1-yl]carbonyl}amino)phenoxy]acetate (0.260 g, 75%) as a white powder.

$^1$H NMR (300 MHz, CHLOROFORM-d) δ ppm 1.45 (s, 9H), 2.83-3.01 (m, 4H), 3.15-3.28 (m, 2H), 3.80 (s, 3H), 4.02 (d, J=12.5 Hz, 2H), 4.61 (s, 2H), 6.35 (s, 1H), 6.83-6.92 (m, 2H), 7.12-7.33 (m, 5H), 7.39 (dd, J=7.8, 1.7 Hz, 1H).

Example 176

[4-({[4-(2-tert-Butylphenyl)piperazin-1-yl]carbonyl}amino)phenoxy]acetic acid

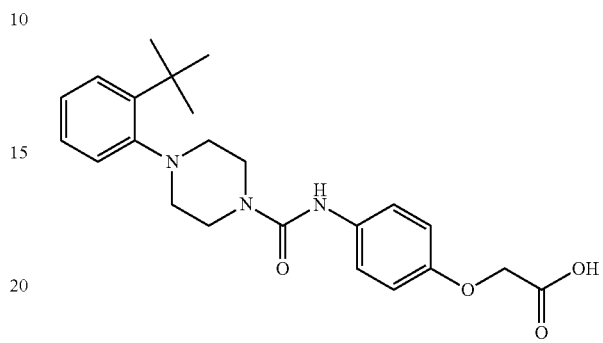

To an ice-cold stirred solution of methyl [4-({[4-(2-tert-butylphenyl)piperazin-1-yl]carbonyl}amino)phenoxy]acetate (Example 175, 0.240 g, 0.564 mmol) in THF (5 mL) was added 1 M lithium hydroxide solution (5 mL, 5 mmol). After 1 h the reaction mixture was acidified with 1 M HCl solution and extracted with ethyl acetate. The organic layer was washed with brine, dried over MgSO$_4$, filtered and concentrated under reduced pressure to provide [4-({[4-(2-tert-butylphenyl)piperazin-1-yl]carbonyl}amino)phenoxy]acetic acid (0.228 g, 98%) as a white powder.

$^1$H NMR (300 MHz, DMSO-$d_6$) δ ppm 1.43 (s, 9H), 2.69-2.91 (m, 4H), 2.91-3.07 (m, 2H), 4.14 (d, J=12.4 Hz, 2H), 4.60 (s, 2H), 6.72-6.91 (m, 2H), 7.10-7.18 (m, 1H), 7.19-7.27 (m, 1H), 7.28-7.46 (m, 4H), 8.43 (s, 1H), 12.88 (br. s., 1H).

Example 177 tert-Butyl 3-(4-{[4-(2-tert-butylphenyl)piperazin-1-yl]carbonyl}-1,3-oxazol-5-yl)propanoate

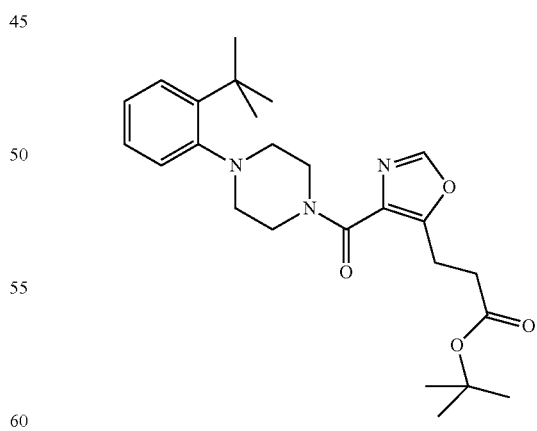

A mixture of 1-(2-tert-butylphenyl)piperazine dihydrochloride (Reference Example 1, 2.18 g, 7.50 mmol), 5-(3-tert-butoxy-3-oxopropyl)-1,3-oxazole-4-carboxylic acid (Reference Example 22, 1.90 g, 7.88 mmol), triethylamine (1.52 g, 7.88 mmol), EDCI (1.51 g, 7.88 mmol) and HOBt (1.21 g, 7.88 mmol) in MeCN (40 mL) was stirred at room temperature for 16 h. The reaction mixture was concentrated under reduced pressure, and the resulting residue was partitioned between ethyl acetate and water. The organic layer was washed with 10% NaHCO$_3$, saturated brine, dried over anhydrous magnesium sulfate, filtered and concentrated under reduced pressure. The resulting residue was purified by flash column chromatography (silica gel, 9:1-2:3 hexane/ethyl acetate) to give the title compound (2.81 g) as a light yellow oil.

$^1$H NMR (300 MHz, CDCl$_3$) δ ppm 1.45 (s, 9H), 1.46 (s, 9H), 2.66 (t, J=7.6 Hz, 2H), 2.86-3.04 (m, 5H), 3.27 (t, J=7.6 Hz, 2H), 3.43 (br. s., 1H), 4.68 (d, J=12.5 Hz, 2H), 7.12-7.33 (m, 3H), 7.38 (dd, J=7.8, 1.7 Hz, 1H), 7.73 (s, 1H).

Example 178

3-(4-{[4-(2-tert-Butylphenyl)piperazin-1-yl]carbonyl}-1,3-oxazol-5-yl)propanoic acid

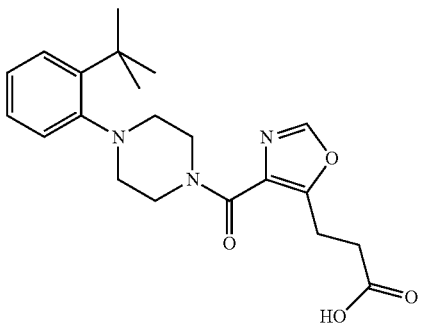 [SMILES: CC(C)(C)c1ccccc1N1CCN(C(=O)c2ncoc2CCC(=O)O)CC1]

A mixture of tert-butyl 3-(4-{[4-(2-tert-butylphenyl)piperazin-1-yl]carbonyl}-1,3-oxazol-5-yl)propanoate (Example 177, 0.60 g, 1.36 mmol) and trifluoroacetic acid (5.0 mL) was stirred at room temperature for 1 h. The reaction mixture was concentrated under reduced pressure and the resulting residue was suspended in water. The mixture was adjusted to pH 4 with 10% NaHCO$_3$ and then extracted with ethyl acetate. The extract was washed with saturated brine, dried over anhydrous magnesium sulfate, filtered and concentrated under reduced pressure. The resulting white solid was triturated with hexane and ethyl acetate successively to give the title compound (0.40 g) as a white solid: mp 180-181° C.

$^1$H NMR (300 MHz, DMSO-d$_6$) δ ppm 1.42 (s, 9H), 2.62 (t, J=7.3 Hz, 2H), 2.68-3.04 (m, 6H), 3.11 (t, J=7.3 Hz, 2H), 4.40-4.60 (m, 2H), 7.10-7.18 (m, 1H), 7.22 (td, J=7.4, 1.7 Hz, 1H), 7.32 (dd, J=7.7, 1.7 Hz, 1H), 7.35-7.42 (m, 1H), 8.36 (s, 1H), 12.29 (s, 1H). LC/MS; ESI(+) m/z: 386 (M+H)$^+$.

Example 179

Ethyl [4-(2-tert-butyl-4-chlorophenyl)piperazin-1-yl](oxo)acetate

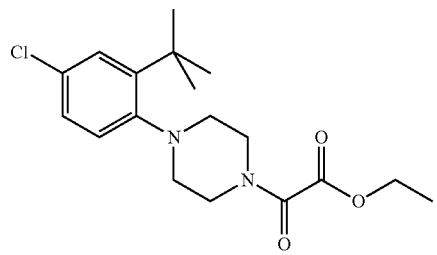 [SMILES: CCOC(=O)C(=O)N1CCN(c2ccc(Cl)cc2C(C)(C)C)CC1]

To a mixture of 1-(2-tert-butyl-4-chlorophenyl)piperazine dihydrochloride (Reference Example 20, 0.50 g, 1.54 mmol) and triethylamine (0.48 g, 4.77 mmol) in THF (30 mL) was added ethyl chloro(oxo)acetate (0.23 g, 1.69 mmol). The mixture was stirred at room temperature for 1 h, filtered and concentrated under reduced pressure. The resulting residue was partitioned between ethyl acetate and water. The organic layer was washed with saturated brine, died over anhydrous magnesium sulfate, filtered and concentrated under reduced pressure. The resulting residue was purified by flash column chromatography (silica gel, 9:1-3:7, hexane/ethyl acetate) to give the title compound (0.49 g) as a colorless solid.

$^1$H NMR (300 MHz, CDCl$_3$) δ ppm 1.38 (t, J=7.2 Hz, 3H), 1.42 (s, 9H), 2.81-2.92 (m, 4H), 2.94-3.15 (m, 1H), 3.34-3.54 (m, 1H), 3.68 (dd, J=13.0, 2.1 Hz, 1H), 4.36 (q, J=7.2 Hz, 2H), 4.53 (dd, J=12.6, 2.1 Hz, 1H), 7.15-7.22 (m, 2H), 7.33 (s, 1H).

Example 180

[4-(2-tert-Butyl-4-chlorophenyl)piperazin-1-yl](oxo)acetic acid

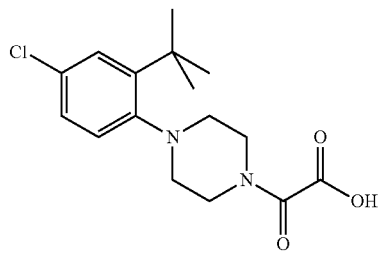 [SMILES: CC(C)(C)c1cc(Cl)ccc1N1CCN(C(=O)C(=O)O)CC1]

A mixture of ethyl [4-(2-tert-butyl-4-chlorophenyl)piperazin-1-yl](oxo)acetate (Example 179, 0.45 g, 1.28 mmol) and 1 M LiOH (3.8 mL) in EtOH (15 mL) was stirred at room temperature for 1 h. The reaction mixture was acidified with 1 M HCl, concentrated under reduced pressure, and partitioned between ethyl acetate and water. The organic layer was washed with saturated brine, dried over anhydrous magnesium sulfate, filtered and concentrated under reduced pressure. The resulting white solid was triturated with diisopropyl ether to give the title compound (0.29 g) as a white solid: mp 154-155° C.

¹H NMR (300 MHz, DMSO-d₆) δ ppm 1.40 (s, 9H), 2.70-3.06 (m, 5H), 3.21-3.52 (m, 1H), 3.55-3.69 (m, 1H), 4.19-4.36% (m, 1H), 7.23-7.33 (m, 2H), 7.39-7.48 (m, 1H), 14.18 (br. s., 1H). LC/MS; ESI(+) m/z: 325 (M+H)⁺.

Example 181 tert-Butyl 4-({[4-(2-tert-butylphenyl)piperazin-1-yl](oxo)acetyl}amino)piperidine-1-carboxylate

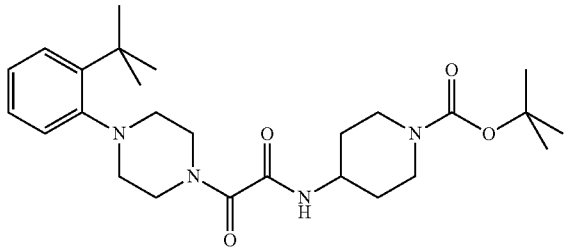 [SMILES: CC(C)(C)OC(=O)N1CCC(NC(=O)C(=O)N2CCN(c3ccccc3C(C)(C)C)CC2)CC1]

A mixture of 2-[4-(2-tert-butylphenyl)piperazin-1-yl]-2-oxoacetic acid (Example 44, 1.50 g, 5.12 mmol), tert-butyl 4-aminopiperidine-1-carboxylate (1.24 g, 6.2 mmol), EDCI (1.24 g, 6.2 mmol) and HOBt (0.95 g, 6.2 mmol) in N,N-dimethylformamide (20 mL) was stirred at room temperature for 16 h. The reaction mixture was added to saturated NaHCO₃ solution and extracted with ethyl acetate. The extract was washed with saturated NaHCO₃ solution, 1M HCl and brine, dried over anhydrous magnesium sulfate, filtered and concentrated under reduced pressure to give the title compound (2.52 g, quant.) as a yellow amorphous.

¹H NMR (300 MHz, CDCl₃) δ ppm 1.30-1.70 (m, 2H), 1.45 (s, 9H), 1.46 (s, 9H), 1.87-2.01 (m, 2H), 2.80-3.12 (m, 7H), 3.34-3.48 (m, 1H), 3.79-3.98 (m, 1H), 3.98-4.24 (m, 2H), 4.56 (dd, J=12.5, 1.9 Hz, 1H), 5.15 (dd, J=13.1, 2.1 Hz, 1H), 7.09-7.31 (m, 4H), 7.38 (dd, J=7.8, 1.7 Hz, 1H).

Example 182

4-({[4-(2-tert-Butylphenyl)piperazin-1-yl](oxo)acetyl}amino)-N-ethylpiperidine-1-carboxamide

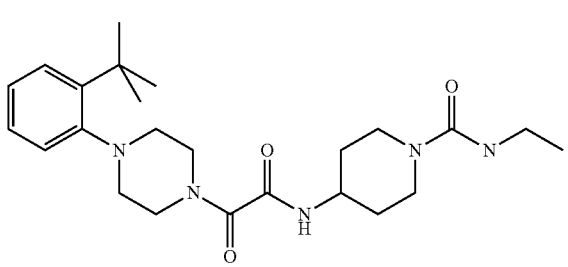 [SMILES: CCNC(=O)N1CCC(NC(=O)C(=O)N2CCN(c3ccccc3C(C)(C)C)CC2)CC1]

(A) 2-[4-(2-tert-Butylphenyl)piperazin-1-yl]-2-oxo-N-piperidin-4-ylacetamide dihydrochloride A solution of tert-butyl 4-({[4-(2-tert-butylphenyl)piperazin-1-yl](oxo)acetyl}amino)piperidine-1-carboxylate (Example 181, 2.5 g, 5.29 mmol) in 4 M HCl-EtOAc solution (20 mL) was stirred at room temperature for 3 h. The reaction mixture was concentrated under reduced pressure to give the title compound (2.94 g) as a yellow solid.

¹H NMR (300 MHz, CDCl₃) δ ppm 1.41 (s, 9H), 1.64-1.82 (m, 2H), 1.85-2.03 (m, 2H), 2.67-3.07 (m, 7H), 3.15-3.38 (m, 3H), 3.71 (d, J=12.4 Hz, 1H), 3.83-3.98 (m, 1H), 4.33 (d, J=10.2 Hz, 1H), 7.10-7.20 (m, 1H), 7.20-7.28 (m, 1H), 7.35 (dd, J=16.8, 7.3 Hz, 2H), 8.99 (d, J=7.5 Hz, 1H), 9.05-9.35 (m, 2H), 9.61 (br. s., 1H).

(B) 4-({[4-(2-tert-Butylphenyl)piperazin-1-yl](oxo)acetyl}amino)-N-ethylpiperidine-1-carboxamide A mixture of 2-[4-(2-tert-butylphenyl)piperazin-1-yl]-2-oxo-N-piperidin-4-ylacetamide dihydrochloride (0.35 g, 0.79 mmol), isocyanatoethane (72.5 mg, 1.02 mmol) and triethylamine (329 μL, 2.36 mmol) in tetrahydrofuran (10 mL) was stirred at room temperature for 16 h. The reaction mixture was poured into saturated NaHCO₃ solution and extracted with ethyl acetate. The extract was washed with brine, dried over anhydrous magnesium sulfate, filtered and concentrated under reduced pressure to give the title compound (0.34 g, 99%) as a white solid.

¹H NMR (300 MHz, CDCl₃) δ ppm 1.15 (t, J=7.2 Hz, 3H), 1.40-1.50 (m, 11H), 1.87-2.08 (m, 2H), 2.81-3.14 (m, 7H), 3.21-3.35 (m, 2H), 3.35-3.51 (m, 1H), 3.81-4.01 (m, 3H), 4.32-4.46 (m, 1H), 4.56 (dd, J=12.6, 2.1 Hz, 1H), 5.15 (dd, J=13.0, 2.1 Hz, 1H), 7.11-7.33 (m, 4H), 7.34-7.46 (m, 1H). LC/MS; ESI(+) m/z: 444 (M+H)⁺.

Example 183

2-[4-(2-tert-Butylphenyl)piperazin-1-yl]-N-[1-(methylsulfonyl)piperidin-4-yl]-2-oxoacetamide

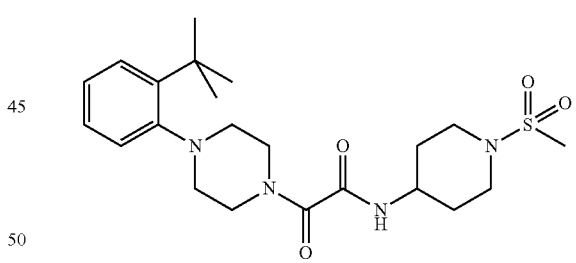

A mixture of 2-[4-(2-tert-butylphenyl)piperazin-1-yl]-2-oxo-N-piperidin-4-ylacetamide dihydrochloride (Example 182(A), 0.30 g, 0.67 mmol) and methanesulfonyl chloride (0.10 g, 0.88 mmol) in pyridine (3 mL) was stirred at room temperature for 16 h. The reaction mixture was poured into saturated NaHCO₃ solution and extracted with ethyl acetate. The extract was washed with brine, dried over anhydrous magnesium sulfate, filtered and concentrated under reduced pressure. The residue was purified by silica gel column chromatography (hexane/ethyl acetate 80:20 to 35:65) to give the title compound (0.13 g, 41%) as a white powder.

¹H NMR (300 MHz, CDCl₃) δ ppm 1.45 (s, 9H), 1.57-1.75 (m, 2H), 1.96-2.14 (m, 5H), 2.76-3.14 (m, 7H), 3.41 (ddd, J=13.0, 11.1, 3.4 Hz, 1H), 3.71-3.97 (m, 3H), 4.56 (dd, J=12.6, 2.1 Hz, 1H), 5.15 (dd, J=13.0, 2.1 Hz, 1H), 7.12-7.34 (m, 4H), 7.35-7.43 (m, 1H). LC/MS; ESI(+) m/z: 451 (M+H)⁺.

Example 184

N-(1-Acetylpiperidin-4-yl)-2-[4-(2-tert-butylphenyl)piperazin-1-yl]-2-oxoacetamide

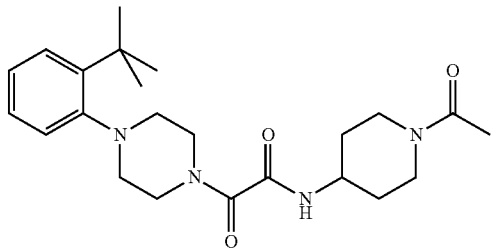 [SMILES: CC(=O)N1CCC(NC(=O)C(=O)N2CCN(c3ccccc3C(C)(C)C)CC2)CC1]

A mixture of 2-[4-(2-tert-butylphenyl)piperazin-1-yl]-2-oxo-N-piperidin-4-ylacetamide dihydrochloride (Example 182(A), 0.35 g, 0.79 mmol), acetyl chloride (72.5 mg, 1.02 mmol) and triethylamine (439 µL, 3.15 mmol) in tetrahydrofuran (4 mL) was stirred at room temperature for 16 h. The reaction mixture was poured into saturated NaHCO₃ solution and extracted with ethyl acetate. The extract was washed with brine, dried over anhydrous magnesium sulfate, filtered and concentrated under reduced pressure to give The title compound (0.34 g, quant.) as a white powder.

¹H NMR (300 MHz, CDCl₃) δ ppm 1.35-1.54 (m, 11H), 1.89-2.09 (m, 2H), 2.11 (s, 3H), 2.72-3.12 (m, 6H), 3.20 (ddd, J=14.0, 11.6, 2.6 Hz, 1H), 3.34-3.49 (m, 1H), 3.82 (dt, J=13.6, 1.5 Hz, 1H), 3.89-4.05 (m, 1H), 4.55 (dd, J=12.6, 2.1 Hz, 2H), 5.15 (d, J=12.4 Hz, 1H), 7.11-7.31 (m, 4H), 7.38 (dd, J=7.7, 1.7 Hz, 1H). LC/MS; ESI(+) m/z: 415 (M+H)⁺.

Example 185

Ethyl [4-({[4-(2-tert-butylphenyl)piperazin-1-yl](oxo)acetyl}amino)piperidin-1-yl](oxo)acetate

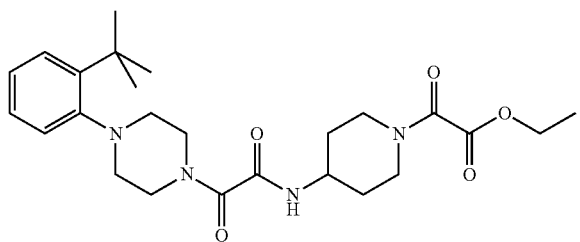 [SMILES: CCOC(=O)C(=O)N1CCC(NC(=O)C(=O)N2CCN(c3ccccc3C(C)(C)C)CC2)CC1]

A mixture of 2-[4-(2 tert-butylphenyl)piperazin-1-yl]-2-oxo-N-piperidin-4-ylacetamide dihydrochloride (Example 182-A, 0.35 g, 0.79 mmol), ethyl chloro(oxo)acetate (140 mg, 1.02 mmol) and triethylamine (439 3.15 mmol) in tetrahydrofuran (4 mL) was stirred at room temperature for 12 days. The reaction mixture was poured into saturated NaHCO₃ solution and extracted with ethyl acetate. The extract was washed with brine, dried over anhydrous magnesium sulfate, filtered and concentrated under reduced pressure. The residue was purified by silica gel column chromatography (hexane/ethyl acetate 75:25 to 25:75) to give the title compound (0.33 g, 88%) as a white amorphous.

¹H NMR (300 MHz, CDCl₃) δ ppm 1.37 (t, J=7.2 Hz, 3H), 1.45 (s, 9H), 1.49-1.64 (m, 2H), 1.99-2.12 (m, 2H), 2.82-3.13 (m, 6H), 3.17-3.31 (m, 1H), 3.34-3.49 (m, 1H), 3.71 (d, J=14.0 Hz, 1H), 3.94-4.09 (m, 1H), 4.34 (q, J=7.2 Hz, 2H), 4.46 (d, J=13.6 Hz, 1H), 4.55 (d, J=12.5 Hz, 1H), 5.11 (dd, J=13.1, 2.1 Hz, 1H), 7.12-7.30 (m, 3H), 7.38 (dd, J=7.6, 1.9 Hz, 2H). LC/MS; ESI(+) m/z: 473 (M+H)⁺.

Example 186

[4-({[4-(2-tert-Butylphenyl)piperazin-1-yl](oxo)acetyl}amino)piperidin-1-yl](oxo)acetic acid

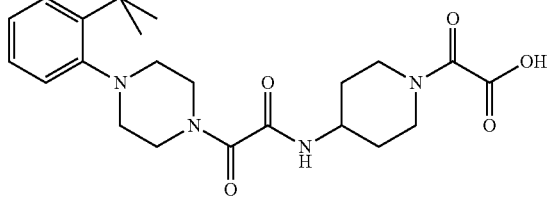

A mixture of ethyl [4-({[4-(2-tert-butylphenyl)piperazin-1-yl](oxo)acetyl}amino)piperidin-1-yl](oxo)acetate (Example 185, 0.24 g, 0.51 mmol) and 1 M LiOH solution (5 mL, 5.0 mmol) in tetrahydrofuran (5 mL) was stirred at 0° C. for 1.5 h. The reaction mixture was acidified with 1 M HCl solution and extracted with ethyl acetate. The extract was washed with brine, dried over anhydrous magnesium sulfate, filtered and concentrated under reduced pressure to give the title compound (0.21 g, 91%) as a white powder.

¹H NMR (300 MHz, DMSO-d₆) δ ppm 1.29-1.48 (m, 11H), 1.74-1.93 (m, 2H), 2.70-3.00 (m, 6H), 3.14-3.43 (m, 2H), 3.46-3.60 (m, 1H), 3.77 (d, J=13.3 Hz, 1H), 3.86-4.04 (m, 1H), 4.04-4.20 (m, 1H), 4.33 (d, J=11.4 Hz, 1H), 7.06-7.19 (m, 1H), 7.23 (td, J=7.4, 1.5 Hz, 1H), 7.28-7.40 (m, 2H), 8.79 (d, J=8.0 Hz, 1H), 14.19 (br. s., 1H). LC/MS; ESI(+) m/z: 445 (M+H)⁺.

Example 187

Methyl (4-{[4-(2-tert-butylphenyl)piperazin-1-yl]carbonyl}-1H-imidazol-1-yl)acetate

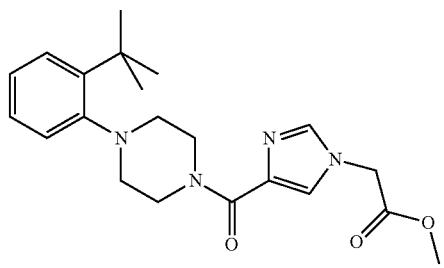 [SMILES: COC(=O)Cn1cnc(C(=O)N2CCN(c3ccccc3C(C)(C)C)CC2)c1]

A mixture of 1-(2-tert-butylphenyl)-4-(1H-imidazol-4-ylcarbonyl)piperazine (Example 3, 0.60 g, 1.92 mmol), methyl bromoacetate (0.35 g, 2.3 mmol) and potassium carbonate (0.80 g, 5.8 mmol) in N,N-dimethylformamide (6.4 mL) was stirred at room temperature for 16 h. The reaction mixture was poured into water and extracted with ethyl acetate. The extract was washed with brine, dried over anhydrous magnesium sulfate, filtered and concentrated under reduced pressure. The residue was purified by silica gel column chromatography (hexane/ethyl acetate 50:50 to 0:100 then ethyl acetate/methanol 100/0 to 90/10) to give the title compound (0.49 g, 66%) as a white powder.

$^1$H NMR (300 MHz, CDCl$_3$) δ ppm 1.47 (s, 9H), 2.81-3.21 (m, 5H), 3.43 (br. s., 1H), 3.82 (s, 3H), 4.64-4.79 (m, 3H), 5.32 (br. s., 1H), 7.10-7.18 (m, 1H), 7.18-7.24 (m, 1H), 7.27-7.32 (m, 1H), 7.38 (dd, J=7.6, 1.9 Hz, 1H), 7.47 (s, 1H), 7.61 (s, 1H). LC/MS; ESI(+) m/z: 385 (M+H)$^+$.

Example 188

(4-{[4-(2-tert-Butylphenyl)piperazin-1-yl]carbonyl}-1H-imidazol-1-yl)acetic acid

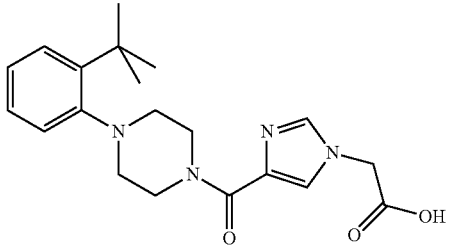 [SMILES: CC(C)(C)c1ccccc1N1CCN(C(=O)c2cn(CC(=O)O)cn2)CC1]

A mixture of methyl (4-{[4-(2-tert-butylphenyl)piperazin-1-yl]carbonyl}-1H-imidazol-1-yl)acetate (Example 187, 0.34 g, 0.87 mmol) and 1M LiOH solution (5 mL, 5.0 mmol) in tetrahydrofuran (5 mL) was stirred at 0° C. for 2 h. The reaction mixture was acidified with 1 M HCl solution and extracted with ethyl acetate. The extract was washed with brine, dried over anhydrous magnesium sulfate, filtered and concentrated under reduced pressure to give the title compound (0.34 g, quant.) as a white powder.

$^1$H NMR (300 MHz, DMSO-d$_6$) δ ppm 1.43 (s, 9H), 2.77-2.91 (m, 4H), 3.35 (br. s., 2H), 4.56 (br. s., 1H), 4.92 (s, 2H), 5.41 (br. s., 1H), 7.08-7.17 (m, 1H), 7.21 (td, J=7.4, 1.7 Hz, 1H), 7.32 (dd, J=7.9, 1.5 Hz, 1H), 7.38 (dd, J=7.7, 1.3 Hz, 1H), 7.70 (s, 2H), 13.21 (br. s., 1H). LC/MS; ESI(+) m/z: 371 (M+H)$^+$.

Example 189

5-{2-[4-(2-tert-Butyl-4-methylphenyl)piperazin-1-yl]-2-oxoethyl}imidazolidine-2,4-dione

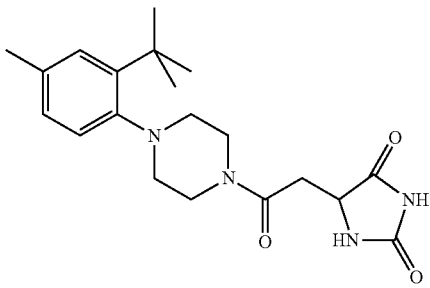 [SMILES: Cc1ccc(N2CCN(C(=O)CC3NC(=O)NC3=O)CC2)c(C(C)(C)C)c1]

A mixture of 1-(2-tert-butyl-4-methylphenyl)piperazine dihydrochloride (Reference Example 10, 0.31 g, 1.0 mmol), (2,5-dioxoimidazolidin-4-yl)acetic acid (0.19 g, 1.2 mmol), triethylamine (420 µL, 3.0 mmol), EDCI (0.23 g, 1.2 mmol) and HOBt (0.18 g, 1.2 mmol) in N,N-dimethylformamide (5 mL) was stirred at room temperature for 2 days. The reaction mixture was poured into saturated NaHCO$_3$ solution and extracted with ethyl acetate. The extract was washed with brine, dried over anhydrous magnesium sulfate, filtered and concentrated under reduced pressure to give the title compound (0.33 g, 89%) as a orange solid.

$^1$H NMR (300 MHz, DMSO-d$_6$) δ ppm 1.40 (s, 9H), 2.25 (s, 3H), 2.61-2.97 (m, 7H), 3.14-3.27 (m, 1H), 3.89 (d, J=12.9 Hz, 1H), 4.22-4.32 (m, 1H), 4.40 (d, J=11.0 Hz, 1H), 7.02 (dd, J=8.0, 1.5 Hz, 1H), 7.10 (d, J=1.5 Hz, 1H), 7.23 (dd, J=8.0, 2.7 Hz, 1H), 7.73 (d, J=9.5 Hz, 1H), 10.57 (s, 1H). LC/MS; ESI(+) m/z: 373 (M+H)$^+$.

Example 190

Methyl 1-{[4-(2-tert-butylphenyl)piperazin-1-yl](oxo)acetyl}pyrrolidine-3-carboxylate

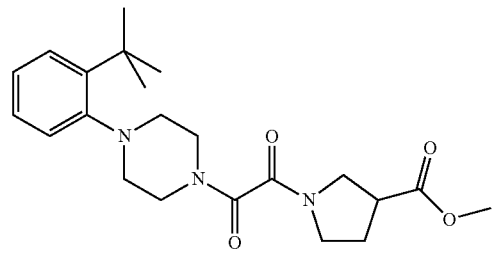 [SMILES: COC(=O)C1CCN(C(=O)C(=O)N2CCN(c3ccccc3C(C)(C)C)CC2)C1]

A mixture of 2-[4-(2-tert-butylphenyl)piperazin-1-yl]-2-oxoacetic acid (Example 44, 0.30 g, 1.03 mmol), methyl pyrrolidine-3-carboxylate hydrochloride (0.21 g, 1.2 mmol), triethylamine (215 µL, 1.6 mmol), EDCI (0.19 g, 1.2 mmol) and HOBt (0.19 g, 1.2 mmol) in N,N-dimethylformamide (5 mL) was stirred at room temperature for 2 days. The reaction mixture was poured into saturated NaHCO$_3$ solution and extracted with ethyl acetate. The extract was washed with saturated NaHCO$_3$ solution and brine, dried over anhydrous magnesium sulfate, filtered and concentrated under reduced pressure. The residue was purified by silica gel column chromatography (hexane/ethyl acetate 85:15 to 35:65) to give the title compound (0.35 g, 85%) as a pale yellow oil.

$^1$H NMR (300 MHz, CDCl$_3$) δ ppm 1.44 (s, 9H), 2.16-2.34 (m, 2H), 2.78-3.27 (m, 6H), 3.35-3.90 (m, 9H), 4.54 (d, J=12.1 Hz, 1H), 7.08-7.33 (m, 3H), 7.34-7.43 (m, 1H). LC/MS; ESI(+) m/z: 402 (M+H)⁺.

Example 191

1-{[4-(2-tert-Butylphenyl)piperazin-1-yl](oxo)acetyl}pyrrolidine-3-carboxylic acid

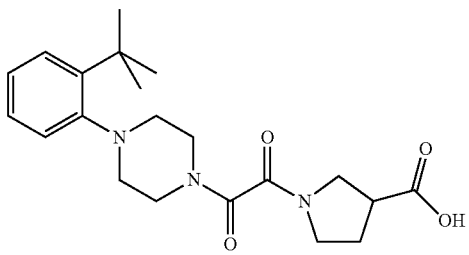 [SMILES: CC(C)(C)c1ccccc1N1CCN(C(=O)C(=O)N2CCC(C(=O)O)C2)CC1]

A mixture of methyl 1-{[4-(2-tert-butylphenyl)piperazin-1-yl](oxo)acetyl}pyrrolidine-3-carboxylate (Example 190, 0.32 g, 0.80 mmol) and 1 M LiOH solution (5 mL, 5.0 mmol) in tetrahydrofuran (5 mL) was stirred at room temperature for 3 h. The reaction mixture was acidified with 1 M HCl solution and extracted with ethyl acetate. The extract was washed with brine, dried over anhydrous magnesium sulfate, filtered and concentrated under reduced pressure to give the title compound (0.29 g, 92%) as a white amorphous. It was crystallized from diisopropyl ether-ethyl acetate.

¹H NMR (300 MHz, CDCl₃) δ ppm 1.44 (s, 9H), 2.16-2.41 (m, 2H), 2.76-3.13 (m, 5H), 3.12-3.31 (m, 1H), 3.33-3.99 (m, 6H), 4.54 (d, J=13.2 Hz, 1H), 7.11-7.29 (m, 3H), 7.38 (d, J=7.5 Hz, 1H). LC/MS; ESI(+) m/z: 388 (M+H)⁺.

Example 192

2-[4-(2-tert-Butylphenyl)piperazin-1-yl]-N-{[1-(methylsulfonyl)cyclopropyl]methyl}-2-oxoacetamide

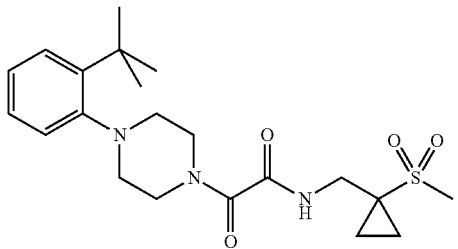 [SMILES: CC(C)(C)c1ccccc1N1CCN(C(=O)C(=O)NCC2(S(C)(=O)=O)CC2)CC1]

Sodium hydride (7.0 g, 175 mmol) was added to a solution of (methylsulfonyl)acetonitrile (20.0 g, 168 mmol) and 1,2-dibromoethane (35.7 g, 190 mmol) in N,N-dimethylformamide (200 mL) at 0° C. and stirred at 0° C. for 30 min. Sodium hydride (7.0 g, 175 mmol) was added to the mixture at 0° C. and the mixture was stirred room temperature for 2 h. Water was added to the reaction solution, and the mixture was extracted with ethyl acetate. The organic layer was washed with brine, dried over anhydrous magnesium sulfate, filtered and concentrated under reduced pressure to give oil. The oil was dissolved in tetrahydrofuran and lithium aluminium hydride (85 mL, 2.0 M tetrahydrofuran solution) was added to the mixture at 0° C. and stirred at room temperature for 2 h. Sodium sulfate decahydrate was added to the mixture, the mixture was filtered and concentrated under reduced pressure to afford oil. The oil was treated with 4 M HCl-ethyl acetate (50 mL) to afford a solid (16.3 g). A mixture of this solid (0.19 g, 1.03 mmol), 2-[4-(2-tert-butylphenyl)piperazin-1-yl]-2-oxoacetic acid (Example 44, 0.25 g, 1.03 mmol), triethylamine (180 μL, 1.29 mmol), EDCI (0.16 g, 1.03 mmol) and HOBt (0.16 g, 1.03 mmol) in N,N-dimethylformamide (5 mL) was stirred at room temperature for 4 days. The reaction mixture was poured into saturated NaHCO₃ solution and extracted with ethyl acetate. The extract was washed with saturated NaHCO₃ solution and brine, dried over anhydrous magnesium sulfate, filtered and concentrated under reduced pressure. The residue was purified by silica gel column chromatography (hexane/ethyl acetate 80:40 to 10:90) to give the title compound (0.23 g, 82%) as a white solid.

¹H NMR (300 MHz, CDCl₃) δ ppm 1.09-1.18 (m, 2H), 1.45 (s, 9H), 1.49-1.55 (m, 2H), 2.78-3.19 (m, 8H), 3.36-3.48 (m, 1H), 3.73 (d, J=6.4 Hz, 2H), 4.55 (dq, J=12.6, 2.2 Hz, 1H), 4.87 (dq, J=12.8, 2.0 Hz, 1H), 7.12-7.29 (m, 3H), 7.38 (dd, J=7.8, 1.7 Hz, 1H), 7.76 (t, J=6.1 Hz, 1H). LC/MS; ESI(+) m/z: 422 (M+H)⁺.

Example 193

2-[4-(2-tert-Butylphenyl)piperazin-1-yl]-2-oxo-N-(tetrahydro-2H-thiopyran-4-yl)acetamide

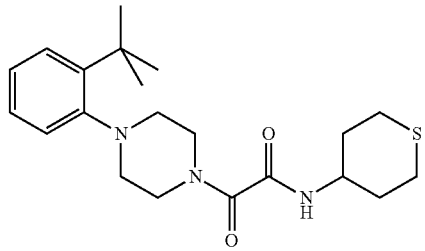 [SMILES: CC(C)(C)c1ccccc1N1CCN(C(=O)C(=O)NC2CCSCC2)CC1]

A mixture of 2-[4-(2-tert-butylphenyl)piperazin-1-yl]-2-oxoacetic acid (Example 44, 0.60 g, 2.07 mmol), tetrahydro-2H-thiopyran-4-amine hydrochloride (0.23 g, 2.48 mmol), triethylamine (433 μL, 3.11 mmol), EDCI (0.39 g, 2.48 mmol) and HOBt (0.38 g, 2.48 mmol) in N,N-dimethylformamide (10 mL) was stirred at room temperature for 4 days. The reaction mixture was poured into saturated NaHCO₃ solution and extracted with ethyl acetate. The extract was washed with saturated NaHCO₃ solution and brine, dried over anhydrous magnesium sulfate, filtered and concentrated under reduced pressure. The residue was purified by silica gel column chromatography (hexane/ethyl acetate 90:10 to 50:50) to give the title compound (0.23 g, 82%) as a white amorphous.

¹H NMR (300 MHz, CDCl₃) δ ppm 1.45 (s, 9H), 1.58-1.76 (m, 2H), 2.16-2.30 (m, 2H), 2.62-3.11 (m, 9H), 3.34-3.47 (m, 1H), 3.70-3.86 (m, 1H), 4.56 (dq, J=12.6, 2.1 Hz, 1H), 5.15

(dq, J=13.0, 2.3 Hz, 1H), 7.12-7.31 (m, 4H), 7.38 (dd, J=7.7, 1.7 Hz, 1H). LC/MS; ESI(+) m/z: 390 (M+H)+.

Example 194

2-[4-(2-tert-Butylphenyl)piperazin-1-yl]-N-(1-oxidotetrahydro-2H-thiopyran-4-yl)-2-oxoacetamide

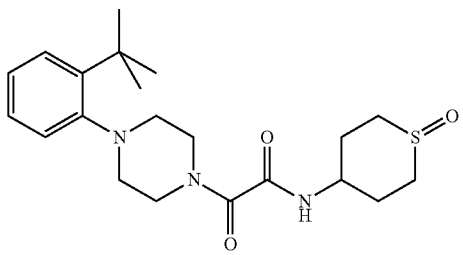 [SMILES: CC(C)(C)c1ccccc1N1CCN(C(=O)C(=O)NC2CCS(=O)CC2)CC1]

To a solution of 2-[4-(2-tert-butylphenyl)piperazin-1-yl]-2-oxo-N-(tetrahydro-2H-thiopyran-4-yl)acetamide (Example 193, 0.25 g, 0.63 mmol), in ethyl acetate (5 mL) was added m-chloroperbenzoic acid (0.19 g, 0.76 mmol) at 0° C. After stirred at 0° C. for 3 h, the mixture was poured into saturated NaHCO$_3$ solution and extracted with ethyl acetate. The extract was washed with brine, dried over anhydrous magnesium sulfate, filtered and concentrated under reduced pressure. The residue was purified by silica gel column chromatography (hexane/ethyl acetate 50:50 to 0:100 then ethyl acetate/methanol 100/0 to 70/30) to give the title compound (0.14 g, 55%) as a white solid.

$^1$H NMR (300 MHz, DMSO-d$_6$) δ ppm 1.41 (s, 9H), 1.56-1.85 (m, 2H), 1.99-2.26 (m, 2H), 2.64-2.98 (m, 8H), 3.21-3.38 (m, 3H), 3.74 (d, J=12.8 Hz, 1H), 4.33 (d, J=11.3 Hz, 1H), 7.09-7.19 (m, 1H), 7.24 (td, J=7.3, 1.5 Hz, 1H), 7.28-7.45 (m, 2H), 8.74-8.92 (m, 1H). LC/MS; ESI(+) m/z: 406 (M+H)+.

Example 195

2-[4-(2-tert-Butylphenyl)piperazin-1-yl]-N-(1,1-dioxidotetrahydro-2H-thiopyran-4-yl)-2-oxoacetamide

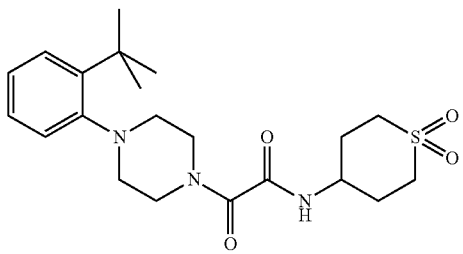 [SMILES: CC(C)(C)c1ccccc1N1CCN(C(=O)C(=O)NC2CCS(=O)(=O)CC2)CC1]

A mixture of 2-[4-(2-tert-butylphenyl)piperazin-1-yl]-2-oxo-N-(tetrahydro-2H-thiopyran-4-yl)acetamide (Example 193, 0.21 g, 0.54 mmol) and m-chloroperbenzoic acid (0.29 g, 1.13 mmol) in ethyl acetate (10 mL) was stirred at 0° C. for 2 h. Then the mixture was added saturated NaHSO$_3$ solution and stirred for 1 h. The mixture was poured into saturated NaHCO$_3$ solution and extracted with ethyl acetate. The extract was washed with brine, dried over anhydrous magnesium sulfate, filtered and concentrated under reduced pressure. The residue was purified by silica gel column chromatography (hexane/ethyl acetate 60:40 to 0:100 then ethyl acetate/methanol 100/0 to 70/30) to give the title compound (0.20 g, 88%) as a white solid.

$^1$H NMR (300 MHz, DMSO-d$_6$) δ ppm 1.41 (s, 9H), 1.86-2.19 (m, 4H), 2.67-2.97 (m, 5H), 3.01-3.15 (m, 2H), 3.19-3.37 (m, 3H), 3.74 (d, J=12.4 Hz, 1H), 3.97-4.14 (m, 1H), 4.33 (d, J=10.9 Hz, 1H), 7.11-7.19 (m, 1H), 7.24 (td, J=7.3, 1.5 Hz, 1H), 7.30-7.39 (m, 2H), 8.89 (d, J=7.9 Hz, 1H). LC/MS; ESI(+) m/z: 422 (M+H)+.

Example 196

Methyl 3-[4-({[4-(2-tert-butylphenyl)piperazin-1-yl](oxo)acetyl}amino)phenyl]propanoate

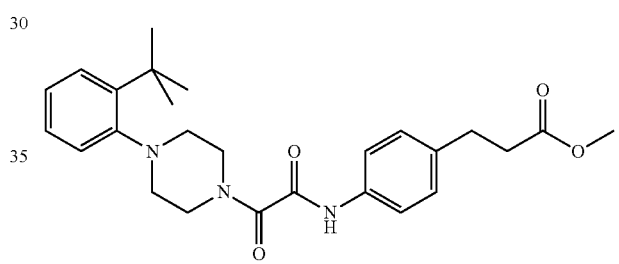

A mixture of 2-[4-(2-tert-butylphenyl)piperazin-1-yl]-2-oxoacetic acid (Example 44, 0.40 g, 1.38 mmol), methyl 3-(4-aminophenyl)propanoate (0.30 g, 1.66 mmol), EDCI (0.26 g, 1.66 mmol) and HOBt (0.25 g, 1.66 mmol) in N,N-dimethylformamide (5 mL) was stirred at room temperature for 4 days. The reaction mixture was poured into saturated NaHCO$_3$ solution and extracted with ethyl acetate. The extract was washed with saturated NaHCO$_3$ solution and brine, dried over anhydrous magnesium sulfate, filtered and concentrated under reduced pressure. The residue was purified by silica gel column chromatography (hexane/ethyl acetate 85:15 to 50:50) to give the title compound (0.56 g, 91%) as a white amorphous.

$^1$H NMR (300 MHz, CDCl$_3$) δ ppm 1.46 (s, 9H), 2.58-2.68 (m, 2H), 2.85-3.18 (m, 7H), 3.47 (ddd, J=13.2, 11.5, 3.2 Hz, 1H), 3.67 (s, 3H), 4.62 (dd, J=12.6, 2.1 Hz, 1H), 5.31 (dd, J=13.2, 2.3 Hz, 1H), 7.12-7.31 (m, 5H), 7.39 (dd, J=7.5, 1.9 Hz, 1H), 7.53 (m, 2H), 9.18 (s, 1H). LC/MS; ESI(+) m/z: 452 (M+H)+.

Example 197

3-[4-({[4-(2-tert-Butylphenyl)piperazin-1-yl](oxo)acetyl}amino)phenyl]propanoic acid

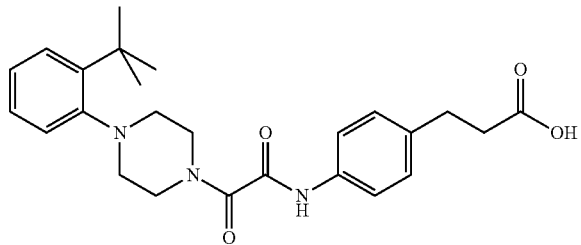 [SMILES: CC(C)(C)c1ccccc1N1CCN(C(=O)C(=O)Nc2ccc(CCC(=O)O)cc2)CC1]

A mixture of methyl 3-[4-({[4-(2-tert-butylphenyl)piperazin-1-yl](oxo)acetyl}amino)phenyl]propanoate (Example 196, 0.52 g, 1.15 mmol) and 1 M LiOH solution (5 mL, 5.0 mmol) in tetrahydrofuran (5 mL) was stirred at 0° C. for 3 h. The reaction mixture was acidified with 1 M HCl solution and extracted with ethyl acetate. The extract was washed with brine, dried over anhydrous magnesium sulfate, filtered and concentrated under reduced pressure to give the title compound (0.54 g, quant.) as a yellow amorphous.

$^1$H NMR (300 MHz, CDCl$_3$) δ ppm 1.46 (s, 9H), 2.64-2.75 (m, 2H), 2.87-3.03 (m, 6H), 3.03-3.18 (m, 1H), 3.40-3.55 (m, 1H), 4.61 (dd, J=12.4, 1.9 Hz, 1H), 5.19 (dd, J=13.0, 2.1 Hz, 1H), 7.11-7.31 (m, 5H), 7.39 (dd, J=7.7, 1.7 Hz, 1H), 7.55 (d, J=8.7 Hz, 2H), 9.39 (s, 1H). LC/MS; ESI(+) m/z: 438 (M+H)+.

Example 198

N-[4-(Benzyloxy)phenyl]-2-[4-(2-tert-butylphenyl)piperazin-1-yl]-2-oxoacetamide

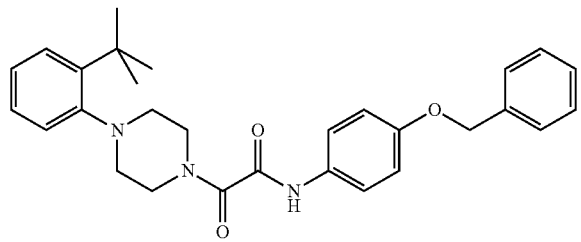 [SMILES: CC(C)(C)c1ccccc1N1CCN(C(=O)C(=O)Nc2ccc(OCc3ccccc3)cc2)CC1]

A mixture of 2-[4-(2-tert-butylphenyl)piperazin-1-yl]-2-oxoacetic acid (Example 44, 2.5 g, 8.61 mmol), 4-(benzyloxy)aniline hydrochloride (2.06 g, 10.3 mmol), triethylamine (1.8 mL, 12.9 mmol), EDCI (1.6 g, 10.3 mmol) and HOBt (1.58 g, 10.3 mmol) in N,N-dimethylformamide (10 mL) was stirred at room temperature for 16 h. The reaction mixture was poured into saturated NaHCO$_3$ solution and extracted with ethyl acetate. The extract was washed with saturated NaHCO$_3$ solution and brine, dried over anhydrous magnesium sulfate, filtered and concentrated under reduced pressure. The residue was purified by silica gel column chromatography (hexane/ethyl acetate 90:10 to 65:35) to give the title compound (3.64 g, 90%) as a white amorphous.

$^1$H NMR (300 MHz, CDCl$_3$) δ ppm 1.46 (s, 9H), 2.85-3.18 (m, 5H), 3.40-3.54 (m, 1H), 4.61 (dd, J=12.7, 2.1 Hz, 1H), 5.06 (s, 2H), 5.31 (dd, J=13.1, 2.1 Hz, 1H), 6.92-7.02 (m, 2H), 7.12-7.47 (m, 9H), 7.49-7.58 (m, 2H), 9.16 (s, 1H). LC/MS; ESI(+) m/z: 472 (M+H)+.

Example 199

2-[4-(2-tert-Butylphenyl)piperazin-1-yl]-N-(4-hydroxyphenyl)-2-oxoacetamide

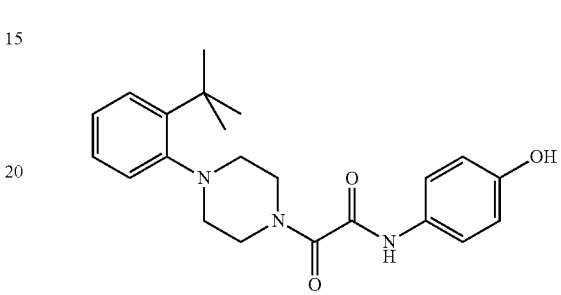

A mixture of N-[4-(benzyloxy)phenyl]-2-[4-(2-tert-butylphenyl)piperazin-1-yl]-2-oxoacetamide (Example 198, 3.64 g, 7.72 mmol) and palladium (10% on carbon, wetted with ca. 50% water, 300 mg) in ethyl acetate (10 mL) was stirred at room temperature for 24 h under hydrogen. The reaction mixture was diluted with tetrahydrofuran and filtered. The filtrate was concentrated under reduced pressure to give the title compound (2.90 g, 98%) as a white solid.

$^1$H NMR (300 MHz, DMSO-d$_6$) δ ppm 1.42 (s, 9H), 2.67-3.04 (m, 5H), 3.22-3.50 (m, 1H), 3.88 (d, J=12.4 Hz, 1H), 4.38 (d, J=11.7 Hz, 1H), 6.68-6.77 (m, 2H), 7.11-7.20 (m, 1H), 7.24 (td, J=7.5, 1.5 Hz, 1H), 7.29-7.41 (m, 2H), 7.41-7.49 (m, 2H), 9.32 (s, 1H), 10.52 (s, 1H). LC/MS; ESI(+) m/z: 382 (M+H)+.

Example 200

Methyl [4-({[4-(2-tert-butylphenyl)piperazin-1-yl](oxo)acetyl}amino)phenoxy]acetate

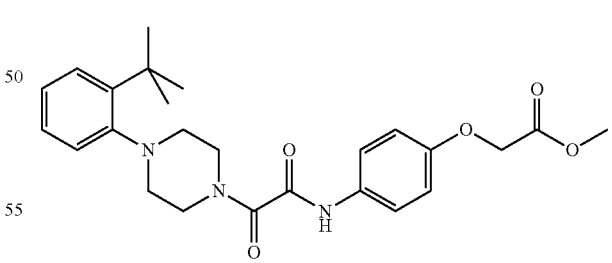

A mixture of 2-[4-(2-tert-butylphenyl)piperazin-1-yl]-N-(4-hydroxyphenyl)-2-oxoacetamide (Example 199, 0.40 g, 1.05 mmol), methyl bromoacetate (0.18 g, 1.15 mmol) and potassium carbonate (0.29 g, 2.1 mmol) in N,N-dimethylformamide (10 mL) was stirred at room temperature for 3 h. The reaction mixture was poured into water and extracted with ethyl acetate. The extract was washed with brine, dried over anhydrous magnesium sulfate, filtered and concentrated under reduced pressure. The residue was purified by silica gel column chromatography (hexane/ethyl acetate 80:20 to 35:65) to give the title compound (0.32 g, 67%) as a colorless amorphous.

$^1$H NMR (300 MHz, CDCl$_3$) δ ppm 1.46 (s, 9H), 2.85-3.19 (m, 5H), 3.40-3.54 (m, 1H), 3.81 (s, 3H), 4.54-4.69 (m, 3H), 5.31 (dd, J=12.9, 2.3 Hz, 1H), 6.87-6.98 (m, 2H), 7.12-7.33 (m, 3H), 7.39 (dd, J=7.8, 1.7 Hz, 1H), 7.51-7.61 (m, 2H), 9.18 (s, 1H). LC/MS; ESI(+) m/z: 454 (M+H)$^+$.

Example 201

[4-({[4-(2-tert-Butylphenyl)piperazin-1-yl](oxo)acetyl}amino)phenoxy]acetic acid

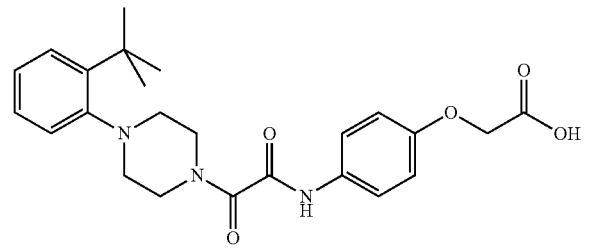

A mixture of methyl [4-({[4-(2-tert-butylphenyl)piperazin-1-yl](oxo)acetyl}amino)phenoxy]acetate (Example 200, 0.29 g, 0.64 mmol) and 1 M LiOH solution (5 mL, 5.0 mmol) in tetrahydrofuran (5 mL) was stirred at room temperature for 3 h. The reaction mixture was acidified with 1 M HCl solution and extracted with ethyl acetate. The extract was washed with brine, dried over anhydrous magnesium sulfate, filtered and concentrated under reduced pressure. The residue was crystallized from diisopropyl ether to give the title compound (0.29 g, quant.) as a white solid.

$^1$H NMR (300 MHz, DMSO-d$_6$) δ ppm 1.42 (s, 9H), 2.85 (br. s., 5H), 3.32 (br. s., 1H), 3.81-4.05 (m, 1H), 4.28-4.52 (m, 1H), 4.65 (s, 2H), 6.73-7.02 (m, 2H), 7.12-7.46 (m, 4H), 7.54-7.68 (m, 2H), 10.66 (s, 1H), 12.94 (br. s., 1H). LC/MS; ESI(+) m/z: 440 (M+H)$^+$.

Example 202

Methyl 4-[2-({[4-(2-tert-butylphenyl)piperazin-1-yl](oxo)acetyl}amino)ethyl]benzoate

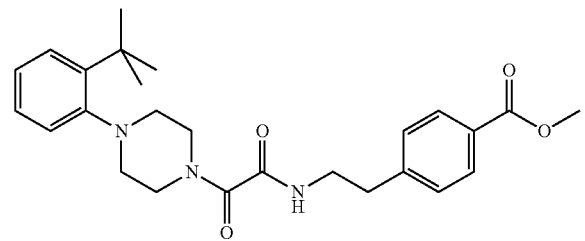 [SMILES: COC(=O)c1ccc(CCNC(=O)C(=O)N2CCN(c3ccccc3C(C)(C)C)CC2)cc1]

A mixture of 2-[4-(2-tert-butylphenyl)piperazin-1-yl]-2-oxoacetic acid (Example 44, 1.0 g, 3.44 mmol), methyl 4-(2-aminoethyl)benzoate hydrochloride (0.83 g, 4.13 mmol), triethylamine (0.72 mL, 5.16 mmol), EDCI (0.64 g, 4.13 mmol) and HOBt (0.63 g, 4.13 mmol) in N,N-dimethylformamide (10 mL) was stirred at room temperature for 16 h. The reaction mixture was poured into saturated NaHCO$_3$ solution and extracted with ethyl acetate. The extract was washed with saturated NaHCO$_3$ solution and brine, dried over anhydrous magnesium sulfate, filtered and concentrated under reduced pressure. The residue was purified by silica gel column chromatography (hexane/ethyl acetate 80:20 to 34:66) to give the title compound (1.11 g, 71%) as a white amorphous.

$^1$H NMR (300 MHz, CDCl$_3$) δ ppm 1.45 (s, 9H), 2.77-3.13 (m, 7H), 3.28-3.47 (m, 1H), 3.60 (q, J=6.9 Hz, 2H), 3.90 (s, 3H), 4.53 (dd, J=12.6, 2.1 Hz, 1H), 5.04 (dd, J=12.8, 52.3 Hz, 1H), 7.10-7.42 (m, 7H), 8.00 (d, J=8.3 Hz, 2H). LC/MS; ESI(+) m/z: 452 (M+H)$^+$.

Example 203

4-[2-({[4-(2-tert-Butylphenyl)piperazin-1-yl](oxo)acetyl}amino)ethyl]benzoic acid

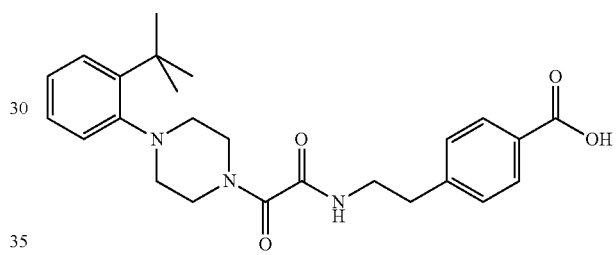

A mixture of methyl 4-[2-({[4-(2-tert-butylphenyl)piperazin-1-yl](oxo)acetyl}amino)ethyl]benzoate (Example 202, 0.51 g, 1.13 mmol) and 1 M LiOH solution (5 mL, 5.0 mmol) in tetrahydrofuran (5 mL) was stirred at room temperature for 1 h. Then to this mixture was added 8 M NaOH solution (5 mL, 40 mmol) and methanol (10 mL) and stirred at room temperature for 2 h. The reaction mixture was acidified with 1 M HCl solution and extracted with ethyl acetate. The extract was washed with brine, dried over anhydrous magnesium sulfate, filtered and concentrated under reduced pressure. The residue was purified by silica gel column chromatography (hexane/ethyl acetate 70:30 to 0:100 then ethyl acetate/methanol 100/0 to 70/30) and HPLC (Gilson Preparative HPLC System; column: YMC Combiprep ODS-A, S-5 μm, 50×20 mm; solvent: A; water containing 0.1% TFA, B; acetonitrile containing 0.1% TFA; gradient cycle: 0.00 min (A/B=90/10), 1.00 min (A/B=90/10), 4.20 min (A/B=10/90), 5.40 min (A/B=10/90), 5.50 min (A/B=90/10), 5.60 min (A/B=90/10); flow rate: 25 mL/min; detect: UV 220 nm) to give the title compound (38 mg, 8%) as a yellow amorphous.

$^1$H NMR (300 MHz, CDCl$_3$) δ ppm 1.44 (s, 9H), 2.79-3.16 (m, 7H), 3.38-3.54 (m, 1H), 3.55-3.73 (m, 2H), 4.51-4.65 (m, 1H), 4.79 (dd, J=13.0, 1.7 Hz, 1H), 7.04-7.33 (m, 5H), 7.38

(dd, J=7.5, 1.9 Hz, 1H), 7.84 (d, J=8.3 Hz, 2H), 8.32 (t, J=6.0 Hz, 1H). LC/MS; ESI(+) m/z: 438 (M+H)⁺.

Example 204

Methyl (4-{[4-(2-tert-butylphenyl)piperazin-1-yl]carbonyl}-2-methyl-1H-imidazol-1-yl)acetate

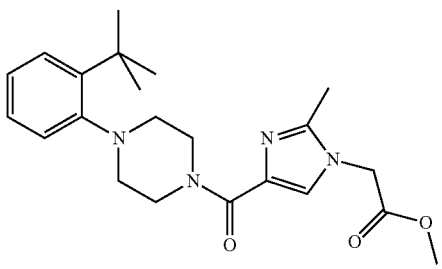 [SMILES: COC(=O)Cn1cc(C(=O)N2CCN(c3ccccc3C(C)(C)C)CC2)nc1C]

(A) 1-(2-tert-Butylphenyl)-4-[(2-methyl-1H-imidazol-4-yl)carbonyl]piperazine

A mixture of 1-(2-tert-butylphenyl)piperazine dihydrochloride (Reference Example 1, 1.63 g, 5.60 mmol), 2-methyl-1H-imidazole-4-carboxylic acid (1.0 g, 6.16 mmol), triethylamine (3.12 mL, 22.4 mmol), EDCI (0.96 g, 6.16 mmol) and HOBt (0.94 g, 6.16 mmol) in N,N-dimethylformamide (20 mL) was stirred at room temperature for 16 h. To the reaction mixture was added saturated NaHCO₃ solution and extracted with ethyl acetate. The extract was washed with saturated NaHCO₃ solution, 1 M HCl and brine, dried over anhydrous magnesium sulfate, filtered and concentrated under reduced pressure. The residue was purified by silica gel column chromatography (hexane/ethyl acetate 98:2 to 75:25) to give the title compound (1.63 g, 89%) as a white solid.

¹H NMR (300 MHz, DMSO-d₆) δ ppm 1.38 (s, 9H), 2.26 (s, 3H), 2.68-2.90 (m, 4H), 2.92-3.27 (m, 2H), 4.21-4.97 (m, 1H), 5.46 (br. s., 1H), 7.06-7.29 (m, 2H), 7.29-7.42 (m, 2H), 7.51 (s, 1H), 11.89-12.54 (m, 1H). LC/MS; ESI(+) m/z: 327 (M+H)⁺.

(B) Methyl (4-{[4-(4-(2-tert-Butylphenyl)piperazin-1-yl]carbonyl}-2-methyl-1H-imidazol-1-yl)acetate A mixture of 1-(2-tert-butylphenyl)-4-[(2-methyl-1H-imidazol-4-yl)carbonyl]piperazine (0.50 g, 1.53 mmol), methyl bromoacetate (0.28 g, 1.84 mmol) and potassium carbonate (0.63 g, 4.6 mmol) in N,N-dimethylformamide (5 mL) was stirred at 50° C. for 16 h. The reaction mixture was poured into water and extracted with ethyl acetate. The extract was washed with brine, dried over anhydrous magnesium sulfate, filtered and concentrated under reduced pressure. The residue was purified by NH-silica gel column chromatography (hexane/ethyl acetate 50:50). The residue was washed with hexane-ethyl acetate and purified by silica gel column chromatography (hexane/ethyl acetate 50:50 to 0/100 then ethyl acetate/methanol 100/0 to 90/10) to give the title compound (0.25 g, 40%) as a white solid.

¹H NMR (300 MHz, DMSO-d₆) δ ppm 1.43 (s, 9H), 2.26 (s, 3H), 2.66-2.95 (m, 4H), 3.02 (br. s., 2H), 3.72 (s, 3H), 4.59 (br. s., 1H), 4.99 (s, 2H), 5.43 (br. s., 1H), 7.06-7.17 (m, 1H), 7.21 (td, J=7.4, 1.7 Hz, 1H), 7.27-7.43 (m, 2H), 7.62 (s, 1H). LC/MS; ESI(+) m/z: 399 (M+H)⁺.

Example 205

(4-{[4-(2-tert-Butylphenyl)piperazin-1-yl]carbonyl}-2-methyl-1H-imidazol-1-yl)acetic acid

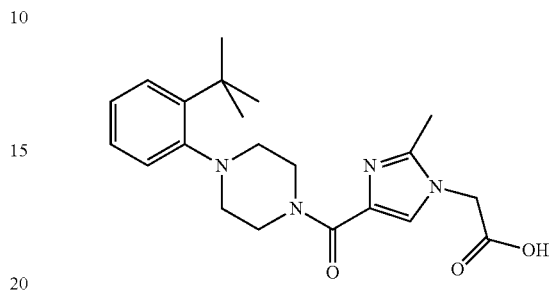

A mixture of methyl (4-{[4-(2-tert-butylphenyl)piperazin-1-yl]carbonyl}-2-methyl-1H-imidazol-1-yl)acetate (Example 204, 0.18 g, 0.44 mmol) and 1 M LiOH solution (5 mL, 5.0 mmol) in tetrahydrofuran (5 mL) was stirred at 0° C. for 3 h. The reaction mixture was acidified with 1 M HCl solution and extracted with ethyl acetate. The extract was washed with brine, dried over anhydrous magnesium sulfate, filtered and concentrated under reduced pressure to give the title compound (0.14 g, 85%) as a white solid.

¹H NMR (300 MHz, DMSO-d₆) δ ppm 1.43 (s, 9H), 2.27 (s, 3H), 2.76-3.08 (m, 4H), 3.33 (br. s., 2H), 4.35 (s, 1H), 4.88 (s, 2H), 5.29 (br. s., 1H), 7.09-7.25 (m, 2H), 7.27-7.42 (m, 2H), 7.67 (s, 1H), 13.28 (br. s., 1H). LC/MS; ESI(+) m/z: 385 (M+H)⁺.

Example 206

Ethyl 3-[4-(2-tert-butyl-4-chlorophenyl)piperazin-1-yl]-3-oxopropanoate

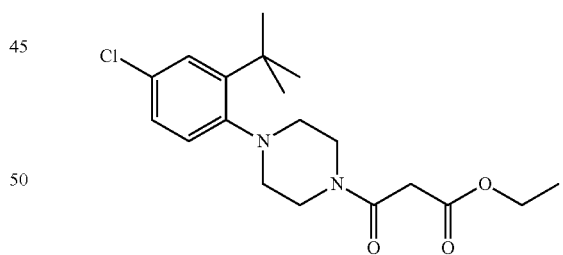

A mixture of 1-(2-tert-butyl-4-chlorophenyl)piperazine dihydrochloride (Reference Example 20, 0.40 g, 1.23 mmol), 3-ethoxy-3-oxopropanoic acid (0.19 g, 1.47 mmol), triethylamine (514 μL, 3.69 mmol), EDCI (0.23 g, 1.47 mmol) and HOBt (0.23 g, 1.47 mmol) in N,N-dimethylformamide (10 mL) was stirred at room temperature for 16 h. The reaction mixture was added to saturated NaHCO₃ solution and extracted with ethyl acetate. The extract was washed with saturated NaHCO₃ solution and brine, dried over anhydrous magnesium sulfate, filtered and concentrated under reduced pressure. The residue was purified by silica gel column chromatography (hexane/ethyl acetate 80:20 to 20:80) to give the title compound (0.39 g, 87%) as a white solid.

¹H NMR (300 MHz, CDCl₃) δ ppm 1.31 (t, J=7.2 Hz, 3H), 1.42 (s, 9H), 2.72-3.02 (m, 5H), 3.32-3.48 (m, 1H), 3.51 (s, 2H), 3.73 (dd, J=13.1, 2.1 Hz, 1H), 4.23 (q, J=7.2 Hz, 2H), 4.63 (dd, J=12.7, 1.7 Hz, 1H), 7.11-7.22 (m, 2H), 7.33 (s, 1H). LC/MS; ESI(+) m/z: 367 (M+H)⁺.

Example 207

3-[4-(2-tert-Butyl-4-chlorophenyl)piperazin-1-yl]-3-oxopropanoic acid

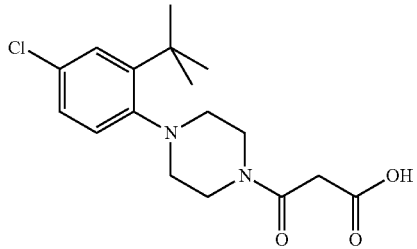 [SMILES: CC(C)(C)c1cc(Cl)ccc1N1CCN(C(=O)CC(=O)O)CC1]

A mixture of ethyl 3-[4-(2-tert-butyl-4-chlorophenyl)piperazin-1-yl]-3-oxopropanoate (Example 206, 0.35 g, 0.95 mmol) and 1 M LiOH solution (5 mL, 5.0 mmol) in tetrahydrofuran (5 mL) was stirred at 0° C. for 3 h. The reaction mixture was acidified with 1 M HCl solution and extracted with ethyl acetate. The extract was washed with brine, dried over anhydrous magnesium sulfate, filtered and concentrated under reduced pressure to give the title compound (0.32 g, 98%) as a white solid.

¹H NMR (300 MHz, CDCl₃) δ ppm 1.43 (s, 9H), 2.74-3.10 (m, 5H), 3.28-3.57 (m, 3H), 3.77 (dd, J=13.2, 2.3 Hz, 1H), 4.66 (dd, J=12.8, 2.3 Hz, 1H), 7.08-7.25 (m, 2H), 7.35 (d, J=2.3 Hz, 1H). LC/MS; ESI(+) m/z: 339 (M+H)⁺.

Example 208

6-{[4-(2-tert-Butyl-4-chlorophenyl)piperazin-1-yl]carbonyl}pyridin-3-ol

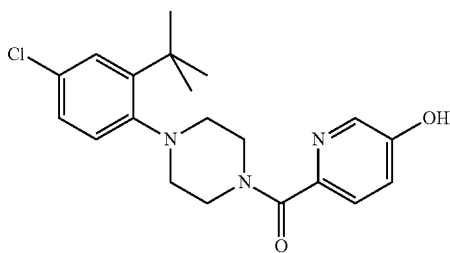 [SMILES: CC(C)(C)c1cc(Cl)ccc1N1CCN(C(=O)c2ccc(O)cn2)CC1]

A mixture of 1-(2-tert-butyl-4-chlorophenyl)piperazine dihydrochloride (Reference Example 20, 0.50 g, 1.54 mmol), 5-hydroxypyridine-2-carboxylic acid (0.26 g, 1.84 mmol), triethylamine (644 μL, 4.62 mmol), EDCI (0.29 g, 1.84 mmol) and HOBt (0.28 g, 1.84 mmol) in N,N-dimethylformamide (10 mL) was stirred at room temperature for 5 days. The reaction mixture was added to saturated NaHCO₃ solution and extracted with ethyl acetate. The extract was washed with saturated NaHCO₃ solution, brine, dried over anhydrous magnesium sulfate, filtered and concentrated under reduced pressure. The residue was purified by silica gel column chromatography (hexane/ethyl acetate 50:50 to 0:100) to give the title compound (0.30 g, 52%) as a white powder.

¹H NMR (300 MHz, DMSO-d₆) δ ppm 1.41 (s, 9H), 2.73 (br. s., 1H), 2.78-3.10 (m, 5H), 3.93-4.20 (m, 1H), 4.41-4.71 (m, 1H), 7.22-7.33 (m, 3H), 7.42-7.50 (m, 1H), 7.54 (d, J=8.7 Hz, 1H), 8.10 (d, J=2.7 Hz, 1H), 10.46 (br. s., 1H). LC/MS; ESI(+) m/z: 374 (M+H)⁺.

Example 209

Methyl [(6-{[4-(2-tert-butyl-4-chlorophenyl)piperazin-1-yl]carbonyl}pyridin-3-yl)oxy]acetate

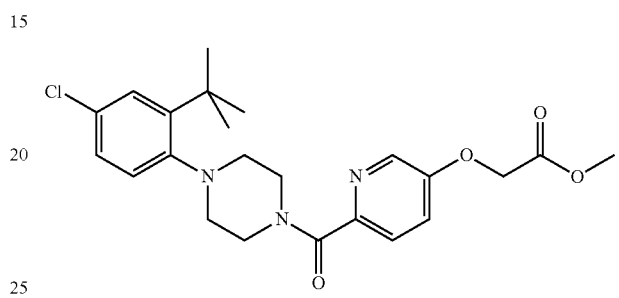

A mixture of 6-{[4-(2-tert-butyl-4-chlorophenyl)piperazin-1-yl]carbonyl}pyridin-3-ol (Example 208, 0.26 g, 0.69 mmol), methyl bromoacetate (0.13 g, 0.82 mmol) and potassium carbonate (0.19 g, 1.38 mmol) in N,N-dimethylformamide (5 mL) was stirred at room temperature for 2 h. The reaction mixture was poured into water and extracted with ethyl acetate. The extract was washed with water and brine, dried over anhydrous magnesium sulfate, filtered and concentrated under reduced pressure. The residue was filtered through NH-silica gel pad to give the title compound (0.27 g, 89%) as a white powder.

¹H NMR (300 MHz, CDCl₃) δ ppm 1.44 (s, 9H), 2.65-3.02 (m, 4H), 3.12 (br. s., 1H), 3.32-3.54 (m, 1H), 3.83 (s, 3H), 4.20 (d, J=12.9 Hz, 1H), 4.67-4.81 (m, 3H), 7.13-7.39 (m, 4H), 7.74 (d, J=8.7 Hz, 1H), 8.28 (d, J=2.7 Hz, 1H). LC/MS; ESI(+) m/z: 446 (M+H)⁺.

Example 210

[(6-{[4-(2-tert-Butyl-4-chlorophenyl)piperazin-1-yl]carbonyl}pyridin-3-yl)oxy]acetic acid

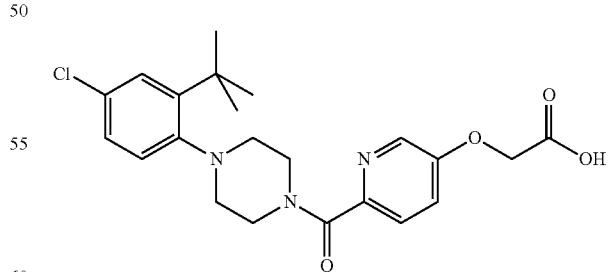

A mixture of methyl [(6-{[4-(2-tert-butyl-4-chlorophenyl)piperazin-1-yl]carbonyl}pyridin-3-yl)oxy]acetate (Example 209, 0.25 g, 0.56 mmol) and 1 M LiOH solution (5 mL, 5.0 mmol) in tetrahydrofuran (5 mL) was stirred at 0° C. for 2 h. The reaction mixture was acidified with 1 M HCl solution and extracted with ethyl acetate. The extract was washed with brine, dried over anhydrous magnesium sulfate, filtered and concentrated under reduced pressure to give the title compound (0.21 g, 87%) as a pale yellow solid.

$^1$H NMR (300 MHz, DMSO-d$_6$) δ ppm 1.41 (s, 9H), 2.60-2.75 (m, 1H), 2.83 (br. s., 3H), 2.91-3.10 (m, 1H), 3.32 (br. s., 1H), 3.98 (d, J=12.8 Hz, 1H), 4.55 (d, J=12.1 Hz, 1H), 4.85 (s, 2H), 7.23-7.32 (m, 2H), 7.41-7.53 (m, 2H), 7.64 (d, J=8.7 Hz, 1H), 8.28 (d, J=2.6 Hz, 1H), 13.19 (br. s., 1H). LC/MS; ESI(+) m/z: 432 (M+H)$^+$.

Example 211 tert-Butyl [3-(4-{[4-(2-tert-butylphenyl)piperazin-1-yl]carbonyl}phenyl)-2-oxoimidazolidin-1-yl]acetate

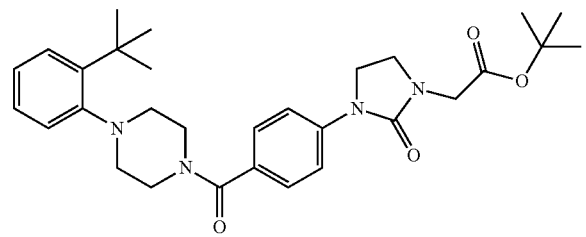 [SMILES: CC(C)(C)OC(=O)CN1CCN(c2ccc(C(=O)N3CCN(c4ccccc4C(C)(C)C)CC3)cc2)C1=O]

(A) 4-{[4-(2-tert-Butylphenyl)piperazin-1-yl]carbonyl}aniline

A mixture of 1-(2-tert-butylphenyl)piperazine dihydrochloride obtained in Reference Example 1 (1.00 g, 3.42 mmol), 4-nitrobenzoyl chloride (0.761 g, 4.1 mmol) and triethylamine (1.67 mL, 12.0 mmol) in tetrahydrofuran (25 mL) was stirred at room temperature for overnight. Water was added to the reaction solution, and the mixture was extracted with ethyl acetate. The organic layer was washed with brine, dried over anhydrous magnesium sulfate, filtered and concentrated under reduced pressure to give a solid. A mixture of the obtained solid and 10% of palladium-carbon (100 mg) in tetrahydrofuran (30 mL) and methanol (100 mL) was stirred at room temperature under hydrogen atmosphere (5 atm). After being stirred for 3 h, the reaction mixture was filtrated and concentrated to purify the residue by NH-silica gel column chromatography (hexane/ethyl acetate 0:100) and the title compound was obtained as a solid (1.28 g, quant.).

$^1$H NMR (300 MHz, CDCl$_3$) δ ppm 1.44 (s, 9H), 2.72-2.99 (m, 5H), 3.24 (br. s., 2H), 3.88 (br. s., 2H), 4.03-4.72 (m, 1H), 6.60-6.74 (m, 2H), 7.09-7.44 (m, 6H).

(B) 1-(4-{[4-(2-tert-Butylphenyl)piperazin-1-yl]carbonyl}phenyl)imidazolidin-2-one A mixture of 4-{[4-(2-tert-butylphenyl)piperazin-1-yl]carbonyl}aniline (1.1 g, 3.26 mmol) and 2-chloroethyl isocyanate (0.369 g, 3.5 mmol) in tetrahydrofuran (15 mL) was stirred at room temperature for overnight. Sodium hydride was added to the reaction mixture and the mixture was stirred at room temperature for 3 h. Water was added to the reaction solution, and the resulting solid was collected and washed with water, diethyl ether, dried over anhydrous magnesium sulfate, and dried under reduced pressure to give the title compound as a solid (1.2 g, 91%).

$^1$H NMR (300 MHz, DMSO-d$_6$) δ ppm 1.42 (s, 9H), 2.64-2.95 (m, 4H), 2.96-3.27 (m, 2H), 3.32 (s, 2H), 3.37-3.49 (m, 2H), 3.79-3.96 (m, 2H), 7.00-7.28 (m, 3H), 7.32 (d, J=8.0 Hz, 1H), 7.37-7.53 (m, 3H), 7.63 (d, J=8.3 Hz, 2H).

(C) tert-Butyl [3-(4-{[4-(2-tert-butylphenyl)piperazin-1-yl]carbonyl}phenyl)-2-oxoimidazolidin-1-yl]acetate A mixture of 1-(4-{[4-(2-tert-butylphenyl)piperazin-1-yl]carbonyl}phenyl)imidazolidin-2-one (1.0 g, 2.46 mmol) and sodium hydride (0.16 g, 4.0 mmol) in N,N-dimethylformamide (20 mL) was stirred at 0° C. for 1 h. tert-Butyl bromoacetate was added to the reaction mixture and the mixture was stirred at room temperature for 3 h. Water was added to the reaction solution, and the mixture was extracted with ethyl acetate. The organic layer was washed with brine, dried over anhydrous magnesium sulfate, filtered and concentrated under reduced pressure to give a solid (1.3 g, quant.).

$^1$H NMR (300 MHz, DMSO-d$_6$) δ ppm 1.32-1.56 (m, 18H), 2.61-2.96 (m, 5H), 2.97-3.42 (m, 3H), 3.47-3.63 (m, 2H), 3.79-4.02 (m, 4H), 7.08-7.28 (m, 2H), 7.32 (dd, J=8.0, 1.5 Hz, 1H), 7.38-7.53 (m, 3H), 7.64 (d, J=8.7 Hz, 2H).

Example 212

[3-(4-{[4-(2-tert-Butylphenyl)piperazin-1-yl]carbonyl}phenyl)-2-oxoimidazolidin-1-yl]acetic acid

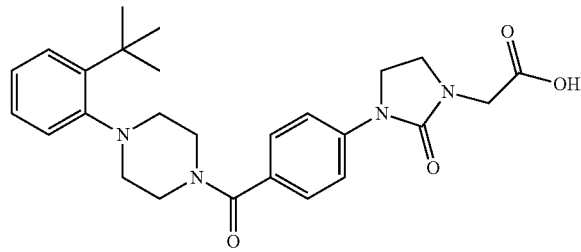 [SMILES: CC(C)(C)c1ccccc1N1CCN(C(=O)c2ccc(N3CCN(CC(=O)O)C3=O)cc2)CC1]

A mixture of tert-butyl [3-(4-{[4-(2-tert-butylphenyl)piperazin-1-yl]carbonyl}phenyl)-2-oxoimidazolidin-1-yl]acetate obtained in Example 211 (1.28 g, 2.46 mmol) and trifluoroacetic acid (5 mL) was stirred at room temperature for 4 h. Trifluoroacetic acid was removed in vacuo and water was added to the mixture. The resulting solid was collected, washed with water, diisopropyl ether and dried under reduced pressure to give a solid (1.1 g, 96%).

$^1$H NMR (300 MHz, DMSO-d$_6$) δ ppm 1.42 (s, 9H), 2.62-2.93 (m, H), 2.96-3.48 (m, 3H), 3.51-3.63 (m, 2H), 3.82-3.93

(m, 2H), 3.95 (s, 2H), 7.08-7.28 (m, 2H), 7.32 (dd, J=7.9, 1.5 Hz, 1H), 7.38-7.54 (m, 3H), 7.65 (d, J=8.7 Hz, 2H), 12.83 (br. s., 1H).

Example 213

[(3-{[4-(2-tert-Butylphenyl)piperazin-1-yl]carbonyl}-1-methyl-1H-pyrazol-5-yl)oxy]acetic acid

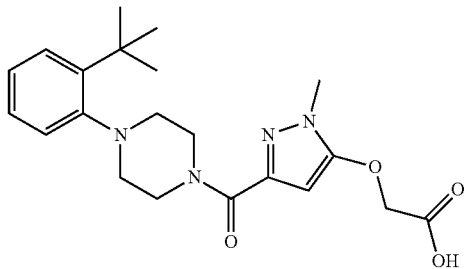 [SMILES: Cn1nc(C(=O)N2CCN(c3ccccc3C(C)(C)C)CC2)cc1OCC(=O)O]

(A) Methyl 5-(benzyloxy)-1-methyl-1H-pyrazole-3-carboxylate

A mixture of methyl 5-hydroxy-1-methyl-1H-pyrazole-3-carboxylate (10.0 g, 64.0 mmol), benzyl bromide (12.0 g, 70 mmol) and potassium carbonate (13.8 g, 100 mmol) in N,N-dimethylformamide (150 mL) was stirred at 50° C. for 16 h. Water was added to the reaction solution, and the mixture was extracted with ethyl acetate. The organic layer was washed with brine, dried over anhydrous magnesium sulfate, filtered and concentrated under reduced pressure to purify the residue by NH-silica gel column chromatography (hexane/ethyl acetate 90:10 to 50:50). Solvent was removed to obtain a solid (15.8 g, quant.).

$^1$H NMR (300 MHz, CDCl$_3$) δ ppm 3.72 (s, 3H), 3.89 (s, 3H), 5.10 (s, 2H), 6.12 (s, 1H), 7.31-7.48 (m, 5H).

(B) 5-(Benzyloxy)-1-methyl-1H-pyrazole-3-carboxylic acid

A mixture of methyl 5-(benzyloxy)-1-methyl-1H-pyrazole-3-carboxylate (15.8 g, 64.0 mmol) and 8 M sodium hydroxide solution (20 mL) in tetrahydrofuran (100 mL) and methanol (100 mL) was stirred at 40° C. for 4 h. Solvent was removed and 6 M hydrochloric acid solution added to the mixture. The mixture was extracted with ethyl acetate. The organic layer was washed with brine, dried over anhydrous magnesium sulfate, filtered and concentrated under reduced pressure to obtain a solid (13.5 g, 91%).

$^1$H NMR (300 MHz, DMSO-d$_6$) δ ppm 3.64 (s, 3H), 5.21 (s, 2H), 6.19 (s, 1H), 7.09-7.55 (m, 5H), 12.60 (br. s., 1H).

(C) 1-{[5-(Benzyloxy)-1-methyl-1H-pyrazol-3-yl]carbonyl}-4-(2-tert-butylphenyl)piperazine A mixture of 1-(2-tert-butylphenyl)piperazine dihydrochloride obtained in Reference Example 1 (1.0 g, 3.4 mmol), 5-(benzyloxy)-1-methyl-1H-pyrazole-3-carboxylic acid (0.975 g, 4.2 mmol), triethylamine (1.39 mL, 10.0 mmol), EDCI (0.978 g, 5.1 mmol) and HOBt (0.781 g, 5.1 mmol) in N,N-dimethylformamide (10 mL) was stirred at room temperature for 16 h. Water was added to the reaction solution, and the mixture was extracted with ethyl acetate. The organic layer was washed with brine, dried over anhydrous magnesium sulfate, filtered and concentrated under reduced pressure to purify the residue by NH-silica gel column chromatography (hexane/ethyl acetate 90:10 to 0:100). Solvent was removed to obtain a solid (1.75 g, quant.).

$^1$H NMR (300 MHz, CDCl$_3$) δ ppm 1.46 (s, 9H), 2.72-3.17 (m, 5H), 3.32-3.59 (m, 1H), 3.67 (s, 3H), 4.54-5.05 (m, 2H), 5.10 (s, 2H), 6.05 (s, 1H), 7.07-7.47 (m, 9H).

(D) 3-{[4-(2-tert-Butylphenyl)piperazin-1-yl]carbonyl}-1-methyl-1H-pyrazol-5-ol

A mixture of 1-{[5-(benzyloxy)-1-methyl-1H-pyrazol-3-yl]carbonyl}-4-(2-tert-butylphenyl)piperazine (1.75 g), and palladium-carbon (500 mg) in methanol (150 mL) was stirred under hydrogen atmosphere (5 atm). The mixture was filtered and concentrated under reduced pressure to purify the residue by silica gel column chromatography (ethyl acetate/methanol 100:0 to 90:10). Solvent was removed to obtain a solid (650 mg, 56%). LC/MS; ESI(+) m/z: 343 (M+H)$^+$.

(E) Methyl [(3-{[4-(2-tert-butylphenyl)piperazin-1-yl]carbonyl}-1-methyl-1H-pyrazol-5-yl)oxy]acetate A mixture of 3-{[4-(2-tert-butylphenyl)piperazin-1-yl]carbonyl}-1-methyl-1H-pyrazol-5-ol (0.65 g), methyl bromoacetate (0.38 g, 2.48 mmol), potassium carbonate (0.60 g, 4.3 mmol) in N,N-dimethylformamide (5 mL) was stirred at 40° C. for 4 h. Water was added to the reaction solution, and the mixture was extracted with ethyl acetate. The organic layer was washed with brine, dried over anhydrous magnesium sulfate, filtered and concentrated under reduced pressure to purify the residue by silica gel column chromatography (hexane/ethyl acetate 80:20 to 20:80). Solvent was removed to obtain a solid (0.573 g, 73%). LC/MS; ESI(+) m/z: 415 (M+H)$^+$.

(F) [(3-{[4-(2-tert-Butylphenyl)piperazin-1-yl]carbonyl}-1-methyl-1H-pyrazol-5-yl)oxy]acetic acid A mixture of methyl [(3-{[4-(2-tert-butylphenyl)piperazin-1-yl]carbonyl}-1-methyl-1H-pyrazol-5-yl)oxy]acetate (0.573 g, 1.38 mmol) and 1 M sodium hydroxide solution (5 mL) in tetrahydrofuran (20 mL) and methanol (20 mL) was stirred at room temperature for 3 h. Solvent was removed and 1 M hydrochloric acid solution added to the mixture. The mixture was extracted with ethyl acetate. The organic layer was washed with brine, dried over anhydrous magnesium sulfate, filtered and concentrated under reduced pressure to purify the residue by HPLC (Gilson Preparative HPLC System; column: YMC Combiprep ODS-A, S-5 μm, 50×20 mm; solvent: A; water containing 0.1% TFA, B; acetonitrile containing 0.1% TFA; gradient cycle: 0.00 min (A/B=90/10), 1.00 min (A/B=90/10), 4.20 min (A/B=10/90), 5.40 min (A/B=10/90), 5.50 min (A/B=90/10), 5.60 min (A/B=90/10); flow rate: 25 mL/min; detect: UV 220 nm). Solvent was removed to afford a solid (0.3 g, 54%).

$^1$H NMR (300 MHz, DMSO-d$_6$) δ ppm 1.42 (s, 9H), 2.65-3.04 (m, 5H), 3.19-3.38 (m, 1H), 3.64 (s, 3H), 4.44-4.64 (m, 1H), 4.80 (s, 2H), 4.84-5.00 (m, 1H), 6.04 (s, 1H), 7.08-7.27 (m, 2H), 7.28-7.43 (m, 2H), 13.22 (br. s., 1H).

Example 214

1-{[3-(Benzyloxy)isoxazol-5-yl]carbonyl}-4-(2-tert-butylphenyl)piperazine

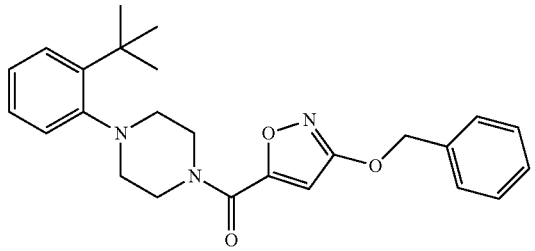 [SMILES: CC(C)(C)c1ccccc1N1CCN(C(=O)c2cc(OCc3ccccc3)no2)CC1]

(A) Methyl 3-(benzyloxy)isoxazole-5-carboxylate

A mixture of methyl 3-hydroxyisoxazole-5-carboxylate (5.0 g, 34.9 mmol), benzyl bromide (6.84 g, 40 mmol) and potassium carbonate (8.3 g, 60 mmol) in N,N-dimethylformamide (100 mL) was stirred at 50° C. for 16 h. Water was added to the reaction solution, and the mixture was extracted with ethyl acetate. The organic layer was washed with brine, dried over anhydrous magnesium sulfate, filtered and concentrated under reduced pressure to purify the residue by NH-silica gel column chromatography (hexane/ethyl acetate 95:5 to 50:50). Solvent was removed to obtain a solid (1.68 g, 21%).

$^1$H NMR (300 MHz, CDCl$_3$) δ ppm 3.94 (s, 3H), 5.31 (s, 2H), 6.57 (s, 1H), 7.31-7.53 (m, 5H).

(B) 3-(Benzyloxy)isoxazole-5-carboxylic acid

A mixture of methyl 3-(benzyloxy)isoxazole-5-carboxylate (1.68 g, 7.2 mmol) and lithium hydroxide monohydrate (0.839 g, 20 mmol) in tetrahydrofuran (20 mL) and water (20 mL) was stirred at 40° C. for 4 h. 1 M hydrochloric acid solution was added to the mixture and the mixture was extracted with ethyl acetate. The organic layer was washed with brine, dried over anhydrous magnesium sulfate, filtered and concentrated under reduced pressure to obtain a solid (1.58 g, 100%).

$^1$H NMR (300 MHz, DMSO-d$_6$) δ ppm 5.30 (s, 2H), 6.99 (s, 1H), 7.29-7.54 (m, 5H), 14.34 (br. s., 1H).

(C) 1-{[3-(Benzyloxy)isoxazol-5-yl]carbonyl}-4-(2-tert-butylphenyl)piperazine

A mixture of 1-(2-tert-butylphenyl)piperazine dihydrochloride obtained in Reference Example 1 (2.1 g, 7.2 mmol), 3-(benzyloxy)isoxazole-5-carboxylic acid (1.58 g, 7.2 mmol), triethylamine (2.79 mL, 20.0 mmol), EDCI (1.92 g, 10.0 mmol) and HOBt (1.53 g, 10.0 mmol) in N,N-dimethylformamide (20 mL) was stirred at room temperature for 16 h. Water was added to the reaction solution, and the mixture was extracted with ethyl acetate. The organic layer was washed with brine, dried over anhydrous magnesium sulfate, filtered and concentrated under reduced pressure to purify the residue by NH-silica gel column chromatography (hexane/ethyl acetate 90:10 to 50:50). Solvent was removed to obtain a solid (2.2 g, 73%).

$^1$H NMR (300 MHz, CDCl$_3$) δ ppm 1.45 (s, 9H), 2.84-3.02 (m, 4H), 3.04-3.21 (m, 1H), 3.41-3.60 (m, 1H), 4.17-4.33 (m, 1H), 4.58-4.75 (m, 1H), 5.30 (s, 2H), 6.42 (s, 1H), 7.11-7.32 (m, 3H), 7.33-7.53 (m, 6H).

Example 215 tert-Butyl [(5-{[4-(2-tert-butylphenyl)piperazin-1-yl]carbonyl}isoxazol-3-yl)oxy]acetate

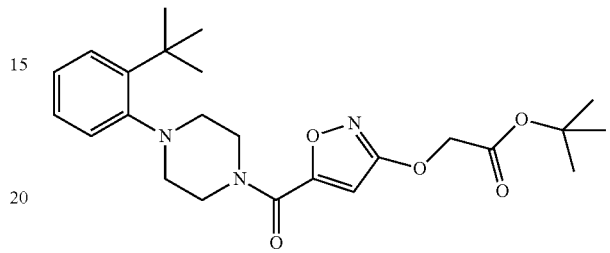

A mixture of 1-(2-tert-butylphenyl)piperazine dihydrochloride obtained in Reference Example 1 (1.13 g, 3.87 mmol), 3-hydroxyisoxazole-5-carboxylic acid (0.5 g, 3.87 mmol), triethylamine (1.39 mL, 10.0 mmol), EDCI (0.959 g, 5.0 mmol) and HOBt (0.766 g, 5.0 mmol) in N,N-dimethylformamide (15 mL) was stirred at room temperature for 16 h. Water was added to the reaction solution, and the mixture was extracted with ethyl acetate. The organic layer was washed with brine, dried over anhydrous magnesium sulfate, filtered and concentrated under reduced pressure to obtain an oil. A mixture of the obtained oil, tert-butyl bromoacetate (0.819 g, 4.2 mmol) and potassium carbonate (0.829 g, 6.0 mmol) in N,N-dimethylformamide (10 mL) was stirred at 50° C. for 16 h. Water was added to the reaction solution, and the mixture was extracted with ethyl acetate. The organic layer was washed with brine, dried over anhydrous magnesium sulfate, filtered and concentrated under reduced pressure to purify the residue by NH-silica gel column chromatography (hexane/ethyl acetate 90:10 to 40:60). Solvent was removed to afford oil (1.01 g, 59%).

$^1$H NMR (300 MHz, CDCl$_3$) δ ppm 1.45 (s, 9H), 1.50 (s, 9H), 2.82-3.02 (m, 4H), 3.04-3.23 (m, 1H), 3.41-3.58 (m, 1H), 4.16-4.28 (m, 1H), 4.58-4.70 (m, 1H), 4.73 (s, 2H), 6.48 (s, 1H), 7.12-7.33 (m, 3H), 7.39 (dd, J=7.5, 1.5 Hz, 1H).

Example 216

[(5-{[4-(2-tert-Butylphenyl)piperazin-1-yl]carbonyl}isoxazol-3-yl)oxy]acetic acid

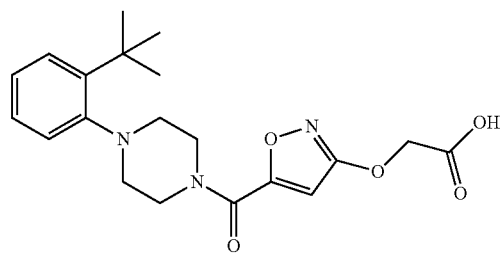 [SMILES: CC(C)(C)c1ccccc1N1CCN(C(=O)c2cc(OCC(=O)O)no2)CC1]

A mixture of tert-butyl [(5-{[4-(2-tert-butylphenyl)piperazin-1-yl]carbonyl}isoxazol-3-yl)oxy]acetate obtained in Example 215 (0.99 g, 2.23 mmol) and trifluoroacetic acid (8 mL) was stirred at room temperature for 3 h. The reaction mixture was neutralized with 1 M sodium hydroxide solution and the mixture was extracted with ethyl acetate. The organic layer was washed with brine, dried over anhydrous magnesium sulfate, filtered and concentrated under reduced pressure to afford a solid (0.74 g, 86%).

$^1$H NMR (300 MHz, DMSO-$d_6$) δ ppm 1.42 (s, 9H), 2.67-3.13 (m, 5H), 3.28-3.53 (m, 1H), 3.86-4.00 (m, 1H), 4.40-4.55 (m, 1H), 4.84 (s, 2H), 6.84 (s, 1H), 7.09-7.27 (m, 2H), 7.33 (dd, J=7.7, 1.7 Hz, 1H), 7.40 (dd, J=7.9, 1.5 Hz, 1H), 13.20 (br. s., 1H).

Example 217

Methyl {4-[(4-{[4-(2-tert-butylphenyl)piperazin-1-yl]carbonyl}phenoxy)methyl]piperidin-1-yl}(oxo)acetate

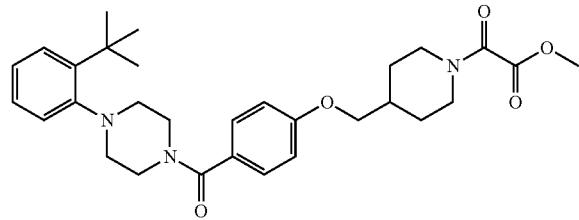 [SMILES: COC(=O)C(=O)N1CCC(COc2ccc(C(=O)N3CCN(c4ccccc4C(C)(C)C)CC3)cc2)CC1]

(A) tert-Butyl 4-{[4-(methoxycarbonyl)phenoxy]methyl}piperidine-1-carboxylate

A mixture of methyl 4-hydroxybenzoate (3.1 g, 20.4 mmol), tert-butyl 4-({[(4-methylphenyl)sulfonyl]oxy}methyl)piperidine-1-carboxylate (8.0 g, 21.7 mmol) and potassium carbonate (5.53 g, 40 mmol) in N,N-dimethylformamide (100 mL) was stirred at 60° C. for 16 h. Water was added to the reaction solution, and the mixture was extracted with ethyl acetate. The organic layer was washed with brine, dried over anhydrous magnesium sulfate, filtered and concentrated under reduced pressure to afford a solid (7.12 g, 100%).

(B) 4-{[1-(tert-Butoxycarbonyl)piperidin-4-yl]methoxy}benzoic acid

A mixture of methyl 3-(benzyloxy)isoxazole-5-carboxylate (1.68 g, 7.2 mmol) and 8 M sodium hydroxide solution (15 mL) in tetrahydrofuran (200 mL) and methanol (20 mL) was stirred at 70° C. for 4 h. 1 M hydrochloric acid solution added to the mixture at 0° C. The mixture was extracted with ethyl acetate. The organic layer was washed with brine, dried over anhydrous magnesium sulfate, filtered and concentrated under reduced pressure to obtain a solid (6.6 g, 96%).

$^1$H NMR (300 MHz, DMSO-$d_6$) δ ppm 1.09-1.22 (m, 2H), 1.40 (s, 9H), 1.73-1.77 (m, 2H), 1.90-1.98 (m, 1H), 2.70-2.80 (m, 2H), 3.90 (d, J=6.3 Hz, 2H), 3.95-4.00 (m, 2H), 6.98-7.01 (m, 2H), 7.86-7.88 (m, 2H), 12.59 (s, 1H).

(C) tert-Butyl 4-[(4-{[4-(2-tert-butylphenyl)piperazin-1-yl]carbonyl}phenoxy)methyl]piperidine-1-carboxylate A mixture of 1-(2-tert-butylphenyl)piperazine dihydrochloride obtained in Reference Example 1 (1.0 g, 3.43 mmol), 4-{[1-(tert-butoxycarbonyl)piperidin-4-yl]methoxy}benzoic acid (1.41 g, 4.2 mmol), triethylamine (1.53 mL, 11.0 mmol), EDCI (0.824 g, 4.3 mmol) and HOBt (0.659 g, 4.3 mmol) in N,N-dimethylformamide (10 mL) was stirred at room temperature for 16 h. Water was added to the reaction solution, and the mixture was extracted with ethyl acetate. The organic layer was washed with brine, dried over anhydrous magnesium sulfate, filtered and concentrated under reduced pressure to purify the residue by NH-silica gel column chromatography (hexane/ethyl acetate 10:90 to 0:100). Solvent was removed to obtain a solid (1.6 g, 87%).

$^1$H NMR (300 MHz, CDCl$_3$) δ ppm 1.20-1.40 (m, 2H), 1.45 (s, 9H), 1.47 (s, 9H), 1.80-1.85 (m, 2H), 1.92-1.98 (m, 1H), 2.71-2.95 (m, 6H), 3.10-3.30 (m, 3H), 3.82 (d, J=6.3 Hz, 2H), 4.11-4.15 (m, 2H), 4.60-4.80 (m, 1H), 6.87-6.92 (m, 2H), 7.12-7.30 (m, 3H), 7.36-7.45 (m, 3H).

(D) 1-(2-tert-Butylphenyl)-4-{[4-(piperidin-4-ylmethoxy)phenyl]carbonyl}piperazine A mixture of tert-butyl 4-[(4-{[4-(2-tert-butylphenyl)piperazin-1-yl]carbonyl}phenoxy)methyl]piperidine-1-carboxylate (1.5 g, 2.8 mmol) and 4 M hydrochloric acid-ethyl acetate solution (20 mL) in ethyl acetate (100 mL) and methanol (100 mL) was stirred at room temperature for 16 h. Solvent was removed in vacuo and 1 M sodium hydroxide solution was added to the mixture. The mixture was extracted with ethyl acetate. The organic layer was washed with brine, dried over anhydrous magnesium sulfate, filtered and concentrated under reduced pressure to obtain a solid (1.1 g, 90%).

$^1$H NMR (300 MHz, DMSO-$d_6$) δ ppm 1.08-1.21 (m, 2H), 1.41 (s, 9H), 1.66-1.70 (m, 2H), 1.74-1.81 (m, 1H), 2.21 (br. s., 1H), 2.42-2.46 (m, 2H), 2.76-2.87 (m, 4H), 2.92-2.96 (m, 2H), 3.10-3.38 (m, 3H), 3.83 (d, J=6.3 Hz, 2H), 4.38-4.44 (m, 1H), 6.97 (d, J=8.4 Hz, 2H), 7.13 (t, J=7.5 Hz, 1H), 7.19-7.24 (m, 1H), 7.29-7.34 (m, 1H), 7.40-7.43 (m, 3H).

(E) Methyl {4-[(4-{[4-(2-tert-butylphenyl)piperazin-1-yl]carbonyl}phenoxy)methyl]piperidin-1-yl}(oxo)acetate A mixture of 1-(2-tert-butylphenyl)-4-{[4-(piperidin-4-ylmethoxy)phenyl]carbonyl}piperazine (0.44 g, 1.01 mmol), methyl chloro(oxo)acetate (0.153 g, 1.25 mmol) and triethylamine (0.279 mL, 2.0 mmol) in tetrahydrofuran (10 mL) was stirred at room temperature for 16 h. Water was added to the reaction solution, and the mixture was extracted with ethyl acetate. The organic layer was washed with brine, dried over anhydrous magnesium sulfate, filtered and concentrated under reduced pressure to afford a solid (0.527 g, 100%).

$^1$H NMR (300 MHz, DMSO-$d_6$) δ ppm 1.09-1.34 (m, 3H), 1.41 (s, 9H), 1.76-1.94 (m, 2H), 2.00-2.21 (m, 1H), 2.65-2.93 (m, 5H), 2.97-3.28 (m, 3H), 3.32 (s, 1H), 3.48-3.63 (m, 1H), 3.81 (s, 3H), 3.91 (d, J=6.0 Hz, 2H), 4.19-4.36 (m, 1H), 6.99 (d, J=9.0 Hz, 2H), 7.07-7.27 (m, 2H), 7.32 (dd, J=7.7, 1.7 Hz, 1H), 7.43 (d, J=8.7 Hz, 3H).

Example 218

{4-[(4-{[4-(2-tert-Butylphenyl)piperazin-1-yl]carbonyl}phenoxy)methyl]piperidin-1-yl}(oxo)acetic acid

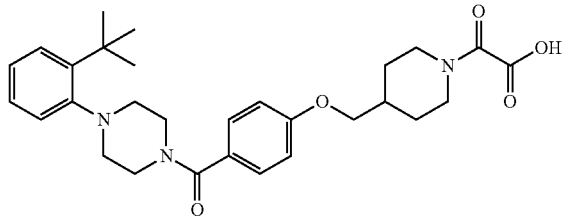 [SMILES: CC(C)(C)c1ccccc1N1CCN(C(=O)c2ccc(OCC3CCN(C(=O)C(=O)O)CC3)cc2)CC1]

A mixture of methyl {4-[(4-{[4-(2-tert-butylphenyl)piperazin-1-yl]carbonyl]phenoxy)methyl]piperidin-1-yl}(oxo)acetate (0.5 g, 0.96 mmol) and 1 M sodium hydroxide solution (15 mL) in tetrahydrofuran (100 mL) and methanol (100 mL) was stirred at room temperature for 3 h. Solvent was removed and 1 M hydrochloric acid solution added to the mixture. The mixture was extracted with ethyl acetate. The organic layer was washed with brine, dried over anhydrous magnesium sulfate, filtered and concentrated under reduced pressure to obtain a solid (0.5 g, quant.).

$^1$H NMR (300 MHz, DMSO-d$_6$) δ ppm 1.10-1.35 (m, 3H), 1.41 (s, 9H), 1.77-1.93 (m, 2H), 1.97-2.19 (m, 1H), 2.67-2.93 (m, 5H), 2.99-3.46 (m, 4H), 3.52-3.69 (m, 1H), 3.91 (d, J=6.0 Hz, 2H), 4.20-4.36 (m, 1H), 6.99 (d, J=9.0 Hz, 2H), 7.08-7.27 (m, 2H), 7.32 (dd, J=7.9, 1.5 Hz, 1H), 7.37-7.49 (m, 3H), 14.11 (br. s., 1H).

Example 219

(4'-{[4-(2-tert-Butylphenyl)piperazin-1-yl]carbonyl}biphenyl-4-yl)acetic acid

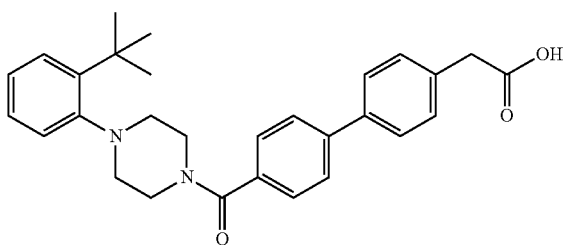 [SMILES: CC(C)(C)c1ccccc1N1CCN(C(=O)c2ccc(-c3ccc(CC(=O)O)cc3)cc2)CC1]

(A) 1-[(4-Bromophenyl)carbonyl]-4-(2-tert-butylphenyl)piperazine

A mixture of 1-(2-tert-butylphenyl)piperazine dihydrochloride obtained in Reference Example 1 (10.0 g, 34.3 mmol), 4-bromobenzoyl chloride (8.2 g, 37.4 mmol) and triethylamine (16.7 mL, 120.0 mmol) in tetrahydrofuran (200 mL) was stirred at room temperature for 16 h. Water was added to the reaction solution, and the mixture was extracted with ethyl acetate. The organic layer was washed with brine, dried over anhydrous magnesium sulfate, filtered and concentrated under reduced pressure to purify the residue by NH-silica gel column chromatography (hexane/ethyl acetate 50:50 to 0:100). Solvent was removed to obtain a solid (14.2 g, quant.).

$^1$H NMR (300 MHz, CDCl$_3$) δ ppm 1.45 (s, 9H), 2.58-3.54 (m, 6H), 3.72 (d, J=12.1 Hz, 1H), 4.72 (br. s., 1H), 7.11-7.31 (m, 3H), 7.31-7.44 (m, 3H), 7.57 (d, J=8.7 Hz, 2H).

(B) (4'-{[4-(2-tert-Butylphenyl)piperazin-1-yl]carbonyl}biphenyl-4-yl)acetic acid A mixture of 1-[(4-bromophenyl)carbonyl]-4-(2-tert-butylphenyl)piperazine (1.0 g, 2.49 mmol), [4-(4,4,5,5-tetramethyl-1,3,2-dioxaborolan-2-yl)phenyl]acetic acid (0.653 g, 2.49 mmol), 2 M sodium carbonate solution (3 mL, 6.0 mmol), and tetrakis(triphenylphosphine)palladium(0) (0.150 g, 0.13 mmol) in tetrahydrofuran (5 mL) and toluene (20 mL) was stirred at 120° C. for 16 h. 6 M hydrochloric acid solution was added and the mixture was extracted with ethyl acetate. The organic layer was washed with brine, dried over anhydrous magnesium sulfate, filtered and concentrated under reduced pressure to afford a solid. The solid was dissolved in ethanol-ethyl acetate and recrystallized to obtain a solid (0.3 g, 26%).

$^1$H NMR (300 MHz, DMSO-d$_6$) δ ppm 1.42 (s, 9H), 2.58-4.12 (m, 10H), 4.56 (br. s., 1H), 7.08-7.28 (m, 2H), 7.28-7.49 (m, 4H), 7.49-7.82 (m, 6H).

Experimental Example 1

The action of the compound of the present invention to inhibit binding of RBP4 and retinol and TTR was evaluated using the Retinol-RBP4-TTR ELISA system shown below.

1A: Cloning of Human RBP4 Gene and Human TTR Gene

Human RBP4 gene was cloned by PCR using human Universal cDNA (Clontech, QUICK-Clone cDNA) as a template and the following primer set.

```
RBPU:
                                  (SEQ ID NO: 1)
5'-ATATGGATCCACCATGAAGTGGGTGTGGGCGCTC-3'
```

```
RBPL:
                                  (SEQ ID NO: 2)
5'-ATATGCGGCCGCCTACAAAAGGTTTCTTTCTGATCTGC-3'
```

PCR reaction was performed according to the protocol attached to Pyrobest polymerase (TAKARA BIO INC., LTD.). The obtained PCR product was subjected to agarose gel (1%) electrophoresis, an about 0.6 kb DNA fragment containing RBP4 gene was recovered from the gel, and digested with restriction enzymes BamHI and NotI. The DNA fragment treated with the restriction enzymes was subjected to agarose gel (1%) electrophoresis, an about 0.6 kb DNA fragment was recovered and ligated to plasmid pcDNA3.1(+) (Invitrogen) digested with restriction enzymes BamHI and NotI to give an expression plasmid pcDNA3.1(+)/hRBP4. The DNA sequence of the inserted fragment was confirmed to have matched with the object sequence.

Human TTR gene was cloned by a PCR reaction using human small intestine cDNA (Clontech, QUICK-Clone cDNA) as a template and the following primer set.

```
TTRU:
                                  (SEQ ID NO: 3)
5'-ATATGGATCCACCATGGCTTCTCATCGTCTGCTCC-3'
```

```
TTRL:
                                  (SEQ ID NO: 4)
5'-ATATGCGGCCGCTCATTCCTTGGGATTGGTGACGA-3'
```

The PCR reaction was performed according to the protocol attached to Pyrobest polymerase (TAKARA BIO INC., LTD.). The obtained PCR product was subjected to agarose gel (1%) electrophoresis, a 0.5 kb DNA fragment containing TTR gene was recovered from the gel, and digested with restriction enzymes BamHI and NotI. The DNA fragment treated with the restriction enzymes was subjected to agarose gel (1%) electrophoresis, an about 0.5 kb DNA fragment was recovered and ligated to plasmid pcDNA3.1(+) (Invitrogen) digested with restriction enzymes BamHI and NotI to give an expression plasmid pcDNA3.1(+)/hTTR. The DNA sequence of the inserted fragment was confirmed to have matched with the object sequence.

1B: Construction of Human RBP4-His Expression Plasmid

EcoRI site was introduced into the 3' end of hRBP4 gene by PCR using the expression plasmid pcDNA3.1(+)/hRBP4 prepared in the above-mentioned 1A as a template and the following primer set.

```
CMPV:
                                         (SEQ ID NO: 5)
5'-TGGGAGGTCTATATAAGCAGAGCTCG-3'

RBPECO:
                                         (SEQ ID NO: 6)
5'-ATATGAATTCTTCCTTGGGATTGGTGAC-3'
```

The PCR was performed according to the protocol attached to Z-Taq polymerase (TAKARA BIO INC., LTD.). The obtained PCR product was purified using QIAquick PCR purification Kit (QIAGEN), and digested with restriction enzymes BamHI and EcoRI. The DNA fragment treated with the restriction enzymes was subjected to agarose gel (1%) electrophoresis, the obtained about 0.6 kb DNA fragment was recovered and ligated to plasmid pcDNA3.1(+) (Invitrogen) digested with restriction enzymes BamHI and EcoRI to give pcDNA3.1(+)/hRBP4-Eco having EcoRI site at the 3' end of hRBP4 gene.

EcoRI site was introduced into the hTTR gene 3' end by PCR using expression plasmid pcDNA3.1(+)/hTTR prepared in the above-mentioned 1A as a template and CMVP and TTRECO primer set.

```
TTRECO:
                                         (SEQ ID NO: 7)
5'-ATATGAATTCCAAAAGGTTTCTTTCTGATC-3'
```

PCR reaction was performed according to the protocol attached to Z-Taq polymerase (TAKARA BIO INC., LTD.). The obtained PCR product was purified using QIAquick PCR purification Kit (QIAGEN), and digested with restriction enzymes BamHI and EcoRI. The DNA fragment treated with the restriction enzymes was subjected to agarose gel (1%) electrophoresis, the obtained about 0.6 kb DNA fragment was recovered and ligated to plasmid pcDNA3.1(+) (Invitrogen) digested with restriction enzymes BamHI and EcoRI to give pcDNA3.1(+)/hTTR-Eco having EcoRI site at the 3' end of hTTR gene.

TTR-His expression plasmid pcDNA3.1(+)/hTTR-His having His tag added to the C-terminal of human TTR was prepared by inserting a synthetic DNA fragment containing His tag sequence prepared by annealing the following oligo DNA to the EcoRI and NotI sites of pcDNA3.1(+)/hTTR-Eco prepared above.

```
HISENU:
                                         (SEQ ID NO: 8)
5'-AATTCCATCATCATCATCATCACTAGGC-3'

HISENL:
                                         (SEQ ID NO: 9)
5'-GGCCGCCTAGTGATGATGATGATGATGG-3'
```

HISENU and HISENL were each dissolved at a concentration of 25 pmole/uL, heated at 94° C. for 5 min and annealed by cooling to room temperature to give a synthetic DNA fragment containing His tag sequence. pcDNA3.1(+)/hTTR-Eco was digested with EcoRI and NotI, the DNA fragment treated with the restriction enzyme was subjected to agarose gel (1%) electrophoresis, the obtained about 5.9 kb DNA fragment was recovered, the synthetic DNA fragment containing the His tag sequence was ligated thereto to give TTR-His expression plasmid pcDNA3.1(+)/hTTR-His having His tag added to the C-terminal of human TTR.

RBP4-His expression plasmid pcDNA3.1(+)/hRBP4-His having His tag added to the C-terminal of human RBP4 was prepared as follows. pcDNA3.1(+)/hRBP4-Eco was digested with restriction enzymes EcoRI and DraIII, subjected to agarose gel (1%) electrophoresis and the obtained about 6.0 kb DNA fragment was recovered. pcDNA3.1(+)/hTTR-His was digested with restriction enzymes EcoRI and DraIII and subjected to agarose gel (1%) electrophoresis, and the obtained about 0.6 kb DNA fragment was recovered. Both fragments were ligated to give RBP4-His expression plasmid pcDNA3.1(+)/hRBP4-His having His tag added to the C-terminal of human RBP4.

1C: Preparation of Human RBP4-His

Human RBP4-His was expressed using FreeStyle293 expression system (Invitrogen) and expression plasmid pcDNA3.1(+)/hRBP4-His prepared in the above-mentioned 1B. According to the protocol attached to the FreeStyle293 expression system, 600 mL of culture medium was used for the expression. After transfection and culture for 3 days, the culture supernatant containing secreted hRBP4-His was recovered. The culture supernatant was repeatedly concentrated using VIVACELL250 (molecular weight cut off 10K, VIVASCIENCE) and diluted with 20 mM Tris (pH 8), whereby the buffer was substituted. The liquid was passed through TOYOPEARL DEAE-650M column (1 cm ID×10 cm, Tosoh Corporation) equilibrated with 20 mM Tris buffer (pH 8) at a flow rate of 2.5 mL/min to allow adsorption and human RBP4-His fraction was obtained by elution with 0-0.35M NaCl gradient. The fractions were concentrated to about 5 mL using Vivaspin 20 (molecular weight cut off 10K, VIVASCIENCE). The concentrated solution was passed through HiLoad 26/60 Superdex 200 pg column (2.6 cm ID×60 cm, GE Healthcare) equilibrated with TBS (pH 7.4) and eluted with TBS (pH 7.4). The fractions containing human RBP4-His were collected and concentrated to about 8 mL using Vivaspin 20 (molecular weight cut off 10K, VIVASCIENCE). About 8 mg of human RBP4-His was obtained from 600 mL of the culture medium.

1D: Preparation of Human TTR

Human TTR was expressed using FreeStyle293 expression system (Invitrogen) and expression plasmid pcDNA3.1(+)/hTTR prepared in the above-mentioned 1A. According to the protocol attached to the FreeStyle293 expression system, 600 mL of culture medium was used for the expression. After transfection and culture for 3 days, the culture supernatant containing secreted human TTR was recovered. The culture supernatant was repeatedly concentrated using VIVACELL250 (molecular weight cut off 10K, VIVASCIENCE)

and diluted with 20 mM Tris (pH 8), whereby the buffer was substituted. The liquid was passed through TOYOPEARL DEAE-650M column (1 cm ID×10 cm, Tosoh Corporation) equilibrated with 20 mM Tris buffer (pH 8) at a flow rate of 2.5 mL/min to allow adsorption and human TTR fraction was obtained by elution with 0-0.55M NaCl gradient. This fraction was repeatedly concentrated using Vivaspin 20 (molecular weight cut off 10K, VIVASCIENCE) and diluted with 20 mM Tris (pH 8), whereby the buffer was substituted. The liquid was passed through HiLoad Q Sepharose HP column (1.6 cm ID×10 cm, GE Healthcare) equilibrated with 20 mM Tris buffer (pH 8) at a flow rate of 1.0 mL/min to allow adsorption and human TTR fraction was obtained by elution with 0-0.4M NaCl gradient. The fractions were concentrated to about 5 mL using Vivaspin 20 (molecular weight cut off 10K, VIVASCIENCE). The concentrated solution was passed through HiLoad 26/60 Superdex 75 pg column (2.6 cm ID×60 cm, GE Healthcare) equilibrated with PBS (pH 7.4) and eluted with PBS (pH 7.4). The fractions containing human TTR were collected and concentrated to about 5 mL using Vivaspin 20 (molecular weight cut off 10K, VIVASCIENCE). About 6 mg of human TTR was obtained from 600 mL of the culture medium.

1E: Preparation of Human TTR-Biotin

Human TTR prepared in the above-mentioned 1D was labeled with biotin using Biotinylation Kit (Sulfo-Osu) (DOJINDO LABORATORIES) according to the attached protocol, whereby human TTR-biotin was prepared. Human TTR 5.0 mg was repeatedly concentrated using Vivaspin 6 (molecular weight cut off 10K, VIVASCIENCE) and diluted with 50 mM $NaHCO_3$, whereby the buffer was substituted. The solution was diluted with 50 mM $NaHCO_3$ to human TTR concentration of 2.0 mg/mL, then aqueous Biotin-(AC5)2 Sulfo-OSu solution (10 mg/mL) (9.9 uL) was added and reacted at 25° C. for 2 hr. The solution after the reaction was passed through NAP-25 column (GE Healthcare) equilibrated with PBS (pH 7.4), eluted with PBS (pH 7.4) and an eluate (3.5 mL) containing human TTR-biotin was collected.

1F: Binding Assay by Retinol-RBP4-TTR ELISA

This ELISA system detects a complex of RBP4 and TTR based on a retinol-dependent binding of RBP4 to TTR.

His-tagged human RBP4 used was prepared in the above-mentioned 1C.

Biotinylate human TTR used was prepared in the above-mentioned 1E.

Streptavidin (20 µl) (10 µg/ml Streptavidin type II (Wako Pure Chemical Industries, Ltd.), 10 mM Tris-HCl (pH 7.5), 10 mM NaCl) was added to a 384 well black plate (Nunc MaxiSorp, Thermo Fisher Scientific Inc.), and the plate was subjected to centrifugation (1000 rpm, 1 min) and coated overnight at 4° C. The plate was washed twice with PBST (PBS, 0.05% Tween 20, 100 µl/well) and blocked with 25% Block Ace (Snow Brand Milk Products Co., Ltd., PBS, 100 µl/well). The plate was subjected to centrifugation (1000 rpm, 1 min) and incubated at room temperature for 4 hr or overnight at 4° C. The plate was washed twice with PBST (PBS, 0.05% Tween 20, 100 µl/well), and biotinylate human TTR (stock solution concentration 1.0 mg/ml) diluted 750-fold with PBST was added at 20 µl/well. The plate was subjected to centrifugation (1000 rpm, 1 min) and stood still at room temperature for 1.5 hr or overnight at 4° C. The plate was washed 3 times with PBST (100 µl/well), and His-tagged human RBP4 (stock solution concentration 0.96 mg/ml) diluted 4000-fold with a reaction buffer (50 mM Tris-HCl, 150 mM NaCl, 0.005% Tween 20, 1 mM DTT, 0.1% BSA) was added at 10 µl/well. The dilution series (8 doses from 10 mM, 200-fold concentration) of the compound was prepared with DMSO, and 1 µl of each was added to a reaction buffer (200 µl) containing retinol (50 nM) (Sigma-Aldrich Co.). A reaction buffer (200 µl) containing retinol and added with DMSO was used as a positive control, and reaction buffer (200 µl) free of retinol and added with DMSO was used as a negative control. Mixed solutions of retinol and the compound were added to the plate at 15 µl/well. The plate was stirred in a platemixer subjected to centrifugation (1000 rpm, 1 min) and reacted at room temperature for 2 hr. A 35% Block Ace solution diluted with the reaction buffer was added at 10 µl/well, centrifuged (1000 rpm, 1 min) and reacted at room temperature for 30 min. The plate was washed 3 times with PBST (100 µl/well) and SuperSignal ELISA Femto Maximum Sensitivity Substrate reagent (PIERCE, Thermo Fisher Scientific Inc.) was added at 30 µl/well, and the luminescence was measured by a platereader (Wallac).

The binding inhibitory activity of the compound was determined by 100×(positive control value-test compound value)/(positive control value-negative control value). The binding activity ($IC_{50}$) was calculated from the binding inhibitory rate at each compound concentration using a graph drawing software, GraphPad Prism (GraphPad Software Inc.). The results are shown in Tables 1 and 2.

TABLE 1

| Example No. | human RBP4 binding inhibitory activity ($IC_{50}$ nM) |
|---|---|
| 1 | 95 |
| 3 | 3.8 |
| 6 | 540 |
| 9 | 54 |
| 19 | 49 |
| 34 | 480 |
| 39 | 430 |
| 41 | 250 |
| 44 | 38 |
| 55 | 64 |
| 56 | 58 |
| 58 | 300 |
| 59 | 15 |
| 69 | 30 |
| 71 | 150 |
| 90 | 34 |
| 110 | 330 |

TABLE 2

| Example No. | human RBP4 binding inhibitory activity(% at 10 µM) |
|---|---|
| 24 | 100 |
| 25 | 100 |
| 39 | 97 |
| 44 | 100 |
| 53 | 100 |
| 67 | 100 |
| 69 | 99 |
| 71 | 100 |
| 82 | 99 |
| 87 | 100 |
| 89 | 99 |
| 94 | 100 |
| 178 | 100 |
| 180 | 100 |
| 191 | 100 |
| 197 | 100 |
| 201 | 99 |
| 203 | 100 |
| 205 | 100 |
| 207 | 100 |
| 210 | 99 |
| 216 | 100 |

TABLE 2-continued

| Example No. | human RBP4 binding inhibitory activity(% at 10 μM) |
|---|---|
| Reference Example 26 | 100 |

From the foregoing results, it was clarified that the compound of the present invention inhibits binding of RBP4, and retinol and TTR.

Experimental Example 2

The action of the compounds of the present invention to lower plasma RBP4 level was evaluated using the animal model shown below.

2A: Animals

Male Wistar fatty rats (fa/fa) were bred in Takeda Pharmaceutical Company Limited and maintained on normal diet (CE2, CLAE Japan, Inc.) and tap water. Animals were housed in a temperature-controlled room adjusted to a 12-hour light/12-hour dark cycle beginning at 7:00 and 19:00, respectively. All procedures were conducted according to the experimental animal care use committee of Takeda Pharmaceutical Company.

2B: Single Administration Test in Wistar Fatty Rats

Male 13-43-week-old Wistar fatty rats were divided into groups randomly. Compounds were suspended in 0.5% (w/v) methylcellulose in water and given orally to Wistar fatty rats at a dose of 10 mg/10 mL/kg of body weight (3-5 rats per group). Blood samples were obtained from tail vein with sodium heparin as an anticoagulant at time 0 hr (just before the administration), 4 hr, 7 hr, and 24 hr after the administration, followed by plasma separation by centrifugation. Plasma RBP4 levels were measured by enzyme-linked immunosorbent assay described in the following section.

2C: Measurement of Plasma Levels of RBP

Plasma samples were analyzed in duplicate for RBP4 by an enzyme-linked immunosorbent assay. Mouse recombinant RBP4 (Takeda Pharmaceutical Company Limited) was used as standards, and the assay range was 0.313-20 ng/ml. Samples were diluted 10,000-fold with phosphate-buffered saline (PBS) (Sigma) containing 10% (w/v) BlockAce (Dainippon Sumitomo Pharma Co., Ltd). Rabbit anti-RBP4 polyclonal antibody (100 μL/well of 50 μg/mL, Hokudo Co, Ltd) was incubated in a 96-well plate (Nalge Nunc International K.K.) for overnight at 4° C. Subsequently, the plates were washed with PBS-T (Wako Pure Chemical Industries, Ltd.) and blocked with PBS containing 25% BlockAce for 1 hr at room temperature. After another washing with PBS-T, samples and standards were applied to the well, and the plates were incubated for 2 hr at room temperature. After a washing the wells, peroxidase-labeled (Dojindo Laboratories) anti-RBP4 (100 μL/well) was added to the wells, and then the plates were incubated for 1 hr at room temperature. After a final washing with PBS-T, substrate solution 3,3,5,5-tetramethylbenzidine (Sigma) was added to the wells, and the plates were placed in the dark for 5-20 min at room temperature. The reaction was stopped with 0.5 M sulphuric acid and the optical density was measured with a spectrophotometer at 450 nm. The changes in plasma RBP4 levels were expressed as % of initial/Control. All data are presented as mean±SD. The results are shown in Table 3.

TABLE 3

| Example No. | RBP4 (% of initial/Control) | | | |
|---|---|---|---|---|
| | 0 hr | 4 hr | 7 hr | 24 hr |
| 6 | 100 ± 14.1 | 36.2 ± 5.0 | 27.4 ± 5.9 | 104.5 ± 4.4 |
| 9 | 100.0 ± 8.5 | 49.6 ± 1.3 | 49.2 ± 1.9 | 114.3 ± 6.0 |
| 44 | 100.0 ± 13.8 | 59.6 ± 14.5 | 58.5 ± 5.6 | 106.0 ± 16.1 |
| 55 | 100.0 ± 5.3 | 36.8 ± 5.8 | 31.6 ± 7.7 | 54.4 ± 14.3 |
| 58 | 100.0 ± 8.7 | 76.2 ± 11 | 89.1 ± 15.4 | 97.9 ± 10.4 |
| Reference Example 26 | 100 ± 22.9 | 34.7 ± 13.7 | 24.9 ± 10.6 | 9.2 ± 6.1 |

All compounds decreased plasma RBP4 levels 4 hr and 7 hr after the administration in Wistar fatty rats. These data indicated that these compounds have plasma RBP4-lowering activity.

Experimental Example 3

The action of the compounds of the present invention to reduce plasma RBP4 level was evaluated using the animal model shown below.

3A: Animals

Male C57BL/6J and ICR mice were purchased from Charles River (Japan) and maintained on a normal diet (CE2, CLAE Japan, Inc.) and tap water. Animals were housed in a temperature-controlled room adjusted to a 12-hour light/12-hour dark cycle beginning at 7:00 and 19:00, respectively. All procedures were conducted according to the experimental animal care use committee of Takeda Pharmaceutical Company.

3B: Single Administration Test in Mice

Male 6-12-week-old C57BL/6J or ICR mice were housed individually and fed CE2 for 4-6 days. After acclimatization, mice were divided into groups based on their body weight. Compounds were suspended in 0.5% (w/v) methylcellulose in water and given orally to mice at a dose of 50 mg/10 mL/kg of body weight (three to five mice per group). Blood samples were obtained from orbital vein with sodium heparin as an anticoagulant at time 0 hr (just before the administration), 4 hr, 7 hr, and 24 hr after the administration, followed by plasma separation by centrifugation. Plasma RBP4 levels were measured by enzyme-linked immunosorbent assay described in the following section.

3C: Measurement of Plasma Levels of RBP4

Plasma samples were analyzed in duplicate for RBP4 by an enzyme-linked immunosorbent assay. Mouse recombinant RBP4 (Takeda Pharmaceutical Company) was used as standards, and the assay range was 0.313-20 ng/ml. Samples were diluted 10,000-fold with phosphate-buffered saline (PBS) (Sigma) containing 10% (w/v) BlockAce (Dainippon Sumitomo Pharma Co., Ltd). Rabbit anti-RBP4 polyclonal antibody (100 μL/well of 50 μg/mL, Hokudo Co, Ltd) was incubated in a 96-well plate (Nalge Nunc International K.K.) for overnight at 4° C. Subsequently, the plates were washed with PBS-T (Wako Pure Chemical Industries, Ltd.) and blocked with PBS containing 25% BlockAce for 1 hr at room temperature. After another washing with PBS-T, samples and standards were applied to the well, and the plates were incubated for 2 hr at room temperature. After a washing the wells, peroxidase-labeled (Dojindo Laboratories) anti-RBP4 (100 μL/well) was added to the wells, and then the plates were incubated for 1 hr at room temperature. After a final washing with PBS-T, substrate solution 3,3,5,5-tetramethylbenzidine (Sigma) was added to the wells, and the plates were placed in the dark for 5-20 min at room temperature. The reaction was stopped with 0.5 M sulphuric acid and the optical density was measured with a spectrophotometer at 450 nm. The changes in plasma RBP4 levels were expressed as % of initial/Control. All data are presented as mean±SD. The results are shown in Table 4.

TABLE 4

| Example No. | RBP4 (% of initial/Control) | | | |
|---|---|---|---|---|
| | 0 hr | 4 hr | 7 hr | 24 hr |
| 24 | 100.0 ± 36.4 | 30.9 ± 2.7 | 32.2 ± 2.2 | 73.1 ± 25.6 |
| 25 | 100.0 ± 7.3 | 45.0 ± 1.9 | 57.6 ± 5.6 | 75.8 ± 6.0 |
| 39 | 100.0 ± 5.8 | 37.1 ± 1.9 | 45.1 ± 6.2 | 86.6 ± 12.4 |
| 44 | 100.0 ± 25.0 | 52.4 ± 2.8 | 50.2 ± 0.9 | 145.9 ± 19.6 |
| 53 | 100.0 ± 29.7 | 39.9 ± 3.4 | 30.2 ± 1.3 | 93.6 ± 15.1 |
| 67 | 100.0 ± 26.6 | 44.8 ± 2.9 | 40.3 ± 1.6 | 94.9 ± 22.6 |
| 69 | 100.0 ± 13.8 | 47.7 ± 2.7 | 44.4 ± 0.7 | 50.0 ± 2.4 |
| 71 | 100.0 ± 17.1 | 51.2 ± 1.0 | 56.7 ± 2.4 | 120.9 ± 9.0 |
| 82 | 100.0 ± 12.5 | 54.6 ± 4.1 | 74.2 ± 15.5 | 101.5 ± 9.7 |
| 87 | 100.0 ± 13.6 | 36.6 ± 1.0 | 38.1 ± 1.3 | 80.3 ± 18.4 |
| 89 | 100.0 ± 34.2 | 42.5 ± 6.0 | 46.6 ± 4.3 | 105.9 ± 27.6 |
| 94 | 100.0 ± 21.7 | 45.7 ± 0.8 | 58.9 ± 5.1 | 89.2 ± 11.6 |
| 178 | 100.0 ± 12.8 | 70.1 ± 1.8 | 67.0 ± 2.6 | 123.3 ± 14.2 |
| 180 | 100.0 ± 23.0 | 63.0 ± 2.0 | 61.0 ± 2.2 | 93.0 ± 9.6 |
| 191 | 100.0 ± 8.0 | 65.0 ± 2.2 | 61.2 ± 2.3 | 127.6 ± 40.9 |
| 197 | 100.0 ± 22.3 | 72.2 ± 3.6 | 67.0 ± 1.8 | 91.3 ± 15.9 |
| 201 | 100.0 ± 9.8 | 65.0 ± 0.7 | 60.3 ± 1.0 | 100.2 ± 13.6 |
| 203 | 1000 ± 28.2 | 43.4 ± 1.8 | 37.2 ± 1.0 | 107.9 ± 15.6 |
| 205 | 100.0 ± 18.9 | 66.3 ± 5.7 | 75.0 ± 10.8 | 125.7 ± 20.9 |
| 207 | 100.0 ± 27.4 | 43.1 ± 1.7 | 37.6 ± 0.7 | 52.0 ± 2.8 |
| 210 | 100.0 ± 10.5 | 55.3 ± 4.0 | 54.9 ± 8.8 | 97.6 ± 24.5 |
| 216 | 100.0 ± 16.6 | 43.4 ± 4.7 | 36.9 ± 1.0 | 66.4 ± 28.1 |

All compounds decreased plasma RBP4 levels 4 hr and 7 hr after the administration in mice. These data indicated that these compounds have plasma RBP4-lowering activity.

Experimental Example 4

The effect of the compound of the present invention on plasma levels of glucose and glycosylated hemoglobin were evaluated using the animal model shown below.

4A: Animals

Male Zucker fatty rats (fa/fa) and their lean littermates (Fa/?) were bred in Takeda Pharmaceutical Company Limited and maintained on normal diet (CE2, CLAE Japan, Inc.) and tap water. Animals were housed in a temperature-controlled room adjusted to a 12-hour light/12-hour dark cycle beginning at 7:00 and 19:00, respectively. All procedures were conducted according to the experimental animal care use committee of Takeda Pharmaceutical Company Limited.

4B: Repeated Drug Administration Test in Zucker Fatty Rats

From 8 weeks of age, Zucker fatty rats were maintained on a high fat diet (D06110702, 20 kCal % fat) (LSG Corporation, Japan). A compound was suspended in 0.5% (w/v) methylcellulose in water and given orally to rats at a volume of 5 mL/kg of body weight. After 4 days of pre-administration of 0.5% (w/v) methylcellulose, rats were divided based on body weight, glycosylated hemoglobin, and plasma glucose (PG) (n=6 each). Drug administration was started at 15 weeks of age and a drug (10 mg/kg) was administered once a day for 28 days.

4C: Measurement of Plasma Levels of Glucose and Glycocylated Hemoglobin

Before and 28 days after the administration, blood samples were obtained from tail vein with sodium heparin as an anticoagulant, followed by plasma separation by centrifugation. Plasma glucose (PG) levels were measured enzymatically by an Autoanalyzer 7180 (Hitachi, Japan). Glycosylated hemoglobin levels were analyzed by a high performance liquid chromatography-based method using an automated analyzer HLC-723 or HLC-723 G7 (Tosoh, Japan). The changes in glycosylated hemoglobin were calculated by subtracting the initial value from final value. The results are shown in Table 5.

TABLE 5

| | Glycosylated hemoglobin (%) | PG (% of initial/Vehicle) |
|---|---|---|
| Vehicle | 1.28 ± 0.79 | 100.0 ± 24.24 |
| Example 6 | 0.95 ± 0.67 | 70.0 ± 19.7 |

All data are presented as the mean±SD. The 28 days repeated administration of Example 6 (10 mg/kg) tended to decrease glycosylated hemoglobin (not significant), and decreased PG significantly.

Experimental Example 5

The effect of the compound on retinol level in retina was evaluated using the animal model shown below.

5A: Animals

Male CD (SD) rats were purchased from Charles River (Japan) and maintained on normal diet (CR-LPF) (Oriental Yeast Co., Ltd.) and tap water. Animals were housed in a temperature-controlled room adjusted to a 12-hour light/12-hour dark cycle beginning at 7:00 and 19:00, respectively. All procedures were conducted according to the experimental animal care use committee of Takeda Pharmaceutical Company.

5B: Repeated Drug Administration Test in CD (SD) Rats

A compound was suspended in 0.5% (w/v) methylcellulose in water and given orally to rats at a volume of 10 mL/kg of body weight. Drug administration was started at 6 weeks of age and a drug (10 mg/kg) was administered once a day for 14 days. After repeated administration, blood samples were obtained from tail vein. Rats were dissected under anesthesia with ethyl ether and eyes were isolated.

5C: Retinol Extraction and HPLC Analysis

Retina was isolated from the eye of the rats mentioned 5B with stereoscopic microscope and sonicated. Retinol was extracted into n-hexane and samples were taken to dryness under nitrogen gas. Samples residues were resuspended into 2-propanol and analyzed by HPLC. Chromatographic separations were achieved on TSKgel ODS120T Column (4.6× 250 mm) (Tosoh) using Alliance series reverse phase HPLC (Waters). The mobile phase contained acetonitrile/methanol (3/1) at 4° C. and detected at UV 325 nm. Retinol in retina was corrected by total protein detected by BCA protein assay (Pierce). The results are shown in Table 6.

TABLE 6

| | Retinol in plasma (µg/mL) | Retinol in retina (µg/mg) |
|---|---|---|
| Control | 0.87 ± 0.10 | 0.10 ± 0.02 |
| Reference Example 26 | Not detected | 0.06 ± 0.01 |

All data are presented as the mean±SD. The 14 days repeated administration of Reference Example 26 (10 mg/kg) decreased retinol in plasma and retina significantly.

Formulation Example 1

Production of Capsule

| 1) compound of Example 1 | 30 mg |
|---|---|
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablet

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2), 3) and 30 g of 4) are kneaded with water, vacuum dried and sieved. The sieved powder is mixed with 14 g of 4) and 1 g of 5) and the mixture is punched by a tableting machine. In this way, 1000 tablets each containing 30 mg of the compound of Example 1 are obtained.

INDUSTRIAL APPLICABILITY

The compound of the present invention has a superior RBP4-lowering action and is useful as a pharmaceutical agent for the prophylaxis or treatment of a disease or condition mediated by an increase in RBP4, such as diabetes, obesity, age-related macular degeneration and the like.

This application is based on application Nos. 61/202,886 filed in USA, the contents of which are incorporated hereinto by reference.

SEQUENCE LISTING

SEQ ID NO: 1: PCR primer (RBPU)
SEQ ID NO: 2: PCR primer (RBPL)
SEQ ID NO: 3: PCR primer (TTRU)
SEQ ID NO: 4: PCR primer (TTRL)
SEQ ID NO: 5: PCR primer (CMVP)
SEQ ID NO: 6: PCR primer (RBPECO)
SEQ ID NO: 7: PCR primer (TTRECO)
SEQ ID NO: 8: oligonucleotide (HISENU) for producing synthesis gene segment containing His tag sequence
SEQ ID NO: 9: oligonucleotide (HISENL) for producing synthesis gene segment containing His tag sequence

The invention claimed is:
1. A compound represented by the formula

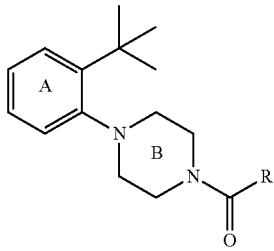

wherein
ring A is a benzene ring optionally substituted by 1 to 3 substituents selected from the group consisting of (a) a halogen atom, and (b) a $C_{1-6}$ alkyl group;
ring B is a piperazine ring optionally substituted by 1 to 3 substituents selected from the group consisting of (a) a halogen atom, (b) a $C_{1-6}$ alkyl group optionally substituted by 1 to 3 halogen atoms, and (c) a $C_{1-6}$ alkoxy group optionally substituted by 1 to 3 halogen atoms; and
R is
(1) a $C_{1-10}$ alkyl group optionally substituted by 1 to 3 substituents selected from the group consisting of:
 (a) a carbamoyl group optionally mono- or di-substituted by
  (i) a $C_{1-6}$ alkylsulfonyl group, and
  (ii) a sulfamoyl group optionally substituted by a $C_{1-6}$ alkyl group optionally substituted by $C_{3-10}$ cycloalkyl,
 (b) a 5- or 6-membered aromatic heterocyclic group optionally substituted by 1 to 3 substituents selected from the group consisting of:
  (i) a carboxy group, and
  (ii) a $C_{1-6}$ alkyl group,
 (c) a 5- or 6-membered nonaromatic heterocyclic group optionally substituted by 1 to 3 carboxy groups, and
 (d) a carboxy group;
(2) a $C_{6-14}$ aryl group optionally substituted by 1 to 3 substituents selected from the group consisting of:
 (a) a carboxy group,
 (b) a $C_{1-6}$ alkoxy group optionally substituted by 1 to 3 carboxy groups, and
 (c) a 5- or 6-membered nonaromatic heterocyclic group optionally substituted by 1 to 3 carboxy groups, and
 (d) a $C_{6-14}$ aryl group optionally substituted by a carboxy-$C_{1-6}$ alkyl group;
(3) a 5- or 6-membered aromatic heterocyclic group optionally substituted by 1 to 3 substituents selected from the group consisting of:
 (a) a $C_{1-6}$ alkyl group optionally substituted by 1 to 3 carboxy groups, and
 (b) a $C_{1-6}$ alkoxy group optionally substituted by 1 to 3 carboxy groups;
(4) an amino group optionally mono- or di-substituted by substituents selected from the group consisting of:
 (a) a $C_{6-14}$ aryl group optionally substituted by 1 to 3 carboxy-$C_{1-6}$ alkoxy groups,
 (b) a $C_{1-6}$ alkyl group optionally substituted by 1 to 3 carboxy groups, and
 (c) a 5- or 6-membered aromatic heterocyclic group optionally substituted by 1 to 3 substituents selected from the group consisting of:
  (i) a hydroxy group, and
  (ii) a carbamoyl group;
(5) a carboxy group; and
(6) a carbamoyl group optionally mono- or di-substituted by substituents selected from the group consisting of:
 (a) a $C_{1-6}$ alkyl group optionally substituted by 1 to 3 substituents selected from the group consisting of:
  (i) a $C_{6-14}$ aryl group optionally substituted by 1 to 3 substituents selected from the group consisting of:
   (A) a carboxy group, and
   (B) a carboxy-$C_{1-6}$ alkyl group,
  (ii) a carboxy group, and
  (iii) a $C_{1-6}$ alkyl-sulfonyl group, and
 (b) a 5- or 6-membered nonaromatic heterocyclic group optionally substituted by 1 to 3 substituents selected from the group consisting of:
  (i) a carboxy group,
  (ii) a carboxy-carbonyl group, and
  (iii) a carboxy-$C_{1-6}$ alkoxy group,
or a salt thereof.
2. The compound or salt of claim 1, wherein
ring A is a benzene ring optionally substituted by 1 to 3 substituents selected from the group consisting of (a) a halogen atom, and (b) a $C_{1-6}$ alkyl group;
ring B is a piperazine ring; and
R is
(1) a $C_{1-10}$ alkyl group optionally substituted by 1 to 3 substituents selected from the group consisting of:
 (a) a carbamoyl group optionally mono- or di-substituted by
  (i) a $C_{1-6}$ alkylsulfonyl group, and
  (ii) a sulfamoyl group optionally substituted by a $C_{1-6}$ alkyl group optionally substituted by $C_{3-10}$ cycloalkyl,
 (b) a 5- or 6-membered aromatic heterocyclic group optionally substituted by 1 to 3 substituents selected from the group consisting of:
  (i) a carboxy group, and
  (ii) a $C_{1-6}$ alkyl group,
 (c) a 5- or 6-membered nonaromatic heterocyclic group optionally substituted by 1 to 3 carboxy groups, and
 (d) a carboxy group;
(2) a $C_{6-14}$ aryl group optionally substituted by 1 to 3 substituents selected from the group consisting of:
 (a) a carboxy group,
 (b) a $C_{1-6}$ alkoxy group optionally substituted by 1 to 3 carboxy groups, and
 (c) a 5- or 6-membered nonaromatic heterocyclic group optionally substituted by 1 to 3 carboxy groups, and
 (d) a $C_{6-14}$ aryl group optionally substituted by a carboxy-$C_{1-6}$ alkyl group;
(3) a 5- or 6-membered aromatic heterocyclic group optionally substituted by 1 to 3 substituents selected from the group consisting of:
 (a) a $C_{1-6}$ alkyl group optionally substituted by 1 to 3 carboxy groups, and
 (b) a $C_{1-6}$ alkoxy group optionally substituted by 1 to 3 carboxy groups;
(4) an amino group optionally mono- or di-substituted by substituents selected from the group consisting of:
 (a) a $C_{6-14}$ aryl group optionally substituted by 1 to 3 carboxy-$C_{1-6}$ alkoxy groups,
 (b) a $C_{1-6}$ alkyl group optionally substituted by 1 to 3 carboxy groups, and
 (c) a 5- or 6-membered aromatic heterocyclic group optionally substituted by 1 to 3 substituents selected from the group consisting of:

(i) a hydroxy group, and
(ii) a carbamoyl group;
(5) a carboxy group; and
(6) a carbamoyl group optionally mono- or di-substituted by substituents selected from the group consisting of:
  (a) a $C_{1-6}$ alkyl group optionally substituted by 1 to 3 substituents selected from the group consisting of:
    (i) a $C_{6-14}$ aryl group optionally substituted by 1 to 3 substituents selected from the group consisting of:
      (A) a carboxy group, and
      (B) a carboxy-$C_{1-6}$ alkyl group,
    (ii) a carboxy group, and
    (iii) a $C_{1-6}$ alkyl-sulfonyl group, and
  (b) a 5- or 6-membered nonaromatic heterocyclic group optionally substituted by 1 to 3 substituents selected from the group consisting of:
    (i) a carboxy group,
    (ii) a carboxy-carbonyl group, and
    (iii) a carboxy-$C_{1-6}$ alkoxy group.

3. N-{[4-(2-tert-Butylphenyl)piperazin-1-yl]carbonyl}glycine or a salt thereof.

4. 3-[4-(2-tert-Butylphenyl)piperazin-1-yl]-3-oxopropanoic acid or a salt thereof.

5. [4-(2-tert-Butyl-4-chlorophenyl)piperazin-1-yl](oxo)acetic acid or a salt thereof.

6. A pharmaceutical composition comprising the compound or salt of claim 1, and a pharmacologically acceptable carrier.

7. 5-{2-[4-(2-tert-Butylphenyl)piperazin-1-yl]-2-oxoethyl}imidazolidine-2,4-dione or a salt thereof.

8. [(5-{[4-(2-tert-Butylphenyl)piperazin-1-yl]carbonyl}isoxazol-3-yl)oxy]acetic acid or a salt thereof.

* * * * *